United States Patent
Efimov et al.

(10) Patent No.: US 6,962,906 B2
(45) Date of Patent: Nov. 8, 2005

(54) OLIGONUCLEOTIDE ANALOGUES, METHODS OF SYNTHESIS AND METHODS OF USE

(75) Inventors: Vladimir Efimov, Moscow (RU); Joseph Fernandez, Carlsbad, CA (US); Dorothy Archdeacon, Carlsbad, CA (US); John Archdeacon, Carlsbad, CA (US); Oksana Chakhmakhcheva, Moscow (RU); Alla Buryakova, Moscow (RU); Mikhail Choob, Carlsbad, CA (US); Kyle Hondorp, Carlsbad, CA (US)

(73) Assignee: Active Motif, Carlsbad, CA (US)

( * ) Notice: Subject to any disclaimer, the term of this patent is extended or adjusted under 35 U.S.C. 154(b) by 0 days.

(21) Appl. No.: 10/072,975

(22) Filed: Feb. 9, 2002

(65) Prior Publication Data

US 2003/0059789 A1 Mar. 27, 2003

Related U.S. Application Data

(63) Continuation-in-part of application No. PCT/US01/08111, filed on Mar. 13, 2001, which is a continuation-in-part of application No. 09/805,296, filed on Mar. 13, 2001.
(60) Provisional application No. 60/189,190, filed on Mar. 14, 2000, and provisional application No. 60/250,334, filed on Nov. 30, 2000.

(51) Int. Cl.[7] .................. A01N 43/04; A01N 61/00; C07H 21/00; C12Q 1/68
(52) U.S. Cl. ..................... 514/44; 514/1; 536/23.1; 536/24.3; 435/6
(58) Field of Search ............... 536/23.1, 24.3; 514/1, 44; 435/6

(56) References Cited

U.S. PATENT DOCUMENTS 5,432,272 A 7/1995 Benner
5,508,178 A 4/1996 Rose et al.

(Continued)

FOREIGN PATENT DOCUMENTS

WO  WO 92/002258  2/1992
WO  WO 92/20702  11/1992

(Continued)

OTHER PUBLICATIONS

Uhlmann et al. Chemical Reviews vol. 90, No. 4, pp. 543–584.*

(Continued)

*Primary Examiner*—Jezia Riley
(74) *Attorney, Agent, or Firm*—Edward O. Kreusser; Bio Technology Law Group

(57) ABSTRACT

The present invention relates generally to oligonucleotide analogues that include novel protein nucleic acid molecules (PNAs), particularly monomers, dimers, oligomers thereof and methods of making and using these oligonucleotide analogues. The PNAs of the present invention are characterized as including a variety of classes of molecules, such as, for example, hydroxyproline peptide nucleic acids (HypNA), and serine peptide nucleic acids (SerNA). The invention includes monomers, homodimers, heterodimers, homopolymers and heteropolymers of these and other oligonucleotide analogues. The present invention includes methods of using these oligonucleotide analogues in the detection and separating of nucleic acid molecules, including uses that include the utilization of oligonucleotide analogues on a solid support. The present invention also includes methods for purifying or separating nucleic acids, such as mRNA molecules, by hybridization with the oligonucleotides of the present invention. The present invention also includes the use of oligonucleotides of the present invention in antisense and homologous recombination constructs and methods.

28 Claims, 9 Drawing Sheets

U.S. PATENT DOCUMENTS

| | | | |
|---|---|---|---|
| 5,539,082 A | 7/1996 | Nielsen et al. | |
| 5,641,625 A | 6/1997 | Ecker et al. | |
| 5,656,461 A | 8/1997 | Demers | |
| 5,714,331 A | 2/1998 | Buchardt et al. | |
| 5,719,262 A | 2/1998 | Buchardt et al. | |
| 5,736,336 A | 4/1998 | Buchardt et al. | |
| 5,760,201 A | 6/1998 | Glazer et al. | |
| 5,766,855 A | 6/1998 | Buchardt et al. | |
| 5,773,571 A | 6/1998 | Nielsen et al. | |
| 5,783,687 A | 7/1998 | Glazer et al. | |
| 5,786,461 A | 7/1998 | Buchardt et al. | |
| 5,837,459 A | 11/1998 | Berg et al. | |
| 5,861,250 A | 1/1999 | Stanley et al. | |
| 5,864,010 A | 1/1999 | Cook et al. | |
| 5,874,553 A | 2/1999 | Peyman et al. | |
| 5,888,733 A | 3/1999 | Hyldig-Nielson et al. | |
| 5,932,711 A | 8/1999 | Boles et al. | |
| 5,972,610 A | 10/1999 | Buchardt et al. | |
| 5,977,296 A | 11/1999 | Nielson et al. | |
| 6,004,750 A | 12/1999 | Frank-Kamenetskii et al. | |
| 6,015,887 A | 1/2000 | Teng | |
| 6,020,124 A | 2/2000 | Sorenson | |
| 6,020,126 A | 2/2000 | Carlsson et al. | |
| 6,025,140 A | 2/2000 | Langel et al. | |
| 6,025,482 A | 2/2000 | Cook et al. | |
| 6,045,995 A | 4/2000 | Cummins et al. | |
| 6,054,272 A | 4/2000 | Glazer et al. | |
| 6,060,242 A | 5/2000 | Nielson et al. | |
| 6,063,571 A | 5/2000 | Uhlmann et al. | |
| 6,107,470 A | 8/2000 | Nielson et al. | |
| 6,110,676 A | 8/2000 | Coull et al. | |
| 6,110,678 A | 8/2000 | Weisburg et al. | |
| 6,150,510 A | 11/2000 | Seela et al. | |
| 6,165,720 A | 12/2000 | Felgner et al. | |
| 6,180,767 B1 | 1/2001 | Wickstrom et al. | |
| 6,180,770 B1 | 1/2001 | Boles et al. | |
| 6,232,066 B1 | 5/2001 | Felder et al. | |
| 6,280,946 B2 | 8/2001 | Hyldig-Nielsen et al. | |
| 6,312,956 B1 | 11/2001 | Lane | |
| 6,326,479 B1 | 12/2001 | Gildea et al. | |

FOREIGN PATENT DOCUMENTS

| | | |
|---|---|---|
| WO | WO 93/10820 | 6/1993 |
| WO | WO 94/22892 | 10/1994 |
| WO | WO 94/24144 | 10/1994 |
| WO | WO 99/14266 | 3/1999 |
| WO | WO 00/56746 | 9/2000 |
| WO | WO 00/56748 | 9/2000 |
| WO | WO 00/56916 | 9/2000 |
| WO | WO 00/56920 | 9/2000 |

OTHER PUBLICATIONS

Adams et al., J. Am. Chem. Soc. 105:661–663 (1983).
Beaucage and Caruthers, Tthahedron Lett. 22:1859–1862 (1981).
Briepohl et al., Bioorg. & Med. Chem. Lett. 6:665 (1996).
Buchardt et al., PNAs and their Potential Applications in Biotechnology, Tibtech 11: 384–386 (1993).
Chandler et al., Affinity Capture and Recovery of DNA at Femtomolar Concentrations with PNA Probes, Analytical Biochemistry 283:241–249 (2000).
Chow et al., Nucl. Acids Res 9:2807–2817 (1981).
Cochet et al., Selective PCR Amplification of Functional Immunoglobulin Light Chain from Hybridoma Containing the Aberrant MOPC21–Derived Vκ by PNA–Mediated PCR Clamping, Biotechniques 26:818–822 (1999).
Coste et al., Tetrahedron Lett. 31:669–672 (1990).
Crea and Horn, Nucl. Acids Res. 8:2331–2348 (1980).
Domling et al., A Novel Method to Highly Versatile Monomeric PNA Building Blocks by Multi Component Reactions, Bioorganic & Medicinal Chemistry Letters 9: 2871–2874 (1999).
Efimov et al., Nucl. Acids Res 11:8369–8387 (1983).
Efimov et al., Nucl. Acids Res. 13:3651–3666 (1985).
Efimov et al., Application of new catalytic phosphate protecting groups for the highly efficient phophotriester oligonucleotide synthesis, *Nucl. Acids Res.* 14:6525–6540 (1986).
Efinov et al., Abstracts of Protein Engineering Symposium, Groningen, May 4–7, 1986, Groningen, The Netherlands, Drenth, ed. p. 9 (1986).
Efimov et al., Collect. Czech. Chem. Commun. 61:S262–S264 (1996).
Efimov et al., Bioorg. Khim. 24:696–709 (1998) abstract only in English.
Efimov et al., Synthesis and evaluatin of some properties of chimeric oligomers containing PNA and phophono–PNA residues, *Nucl. Acids Res.* 26:566–575 (1998).
Efimov et al., Synthesis of polyacrylamides N–substituted with PNA–like oligonucleotide mimics for molecular diagnostic applications, *Nucl. Acids Res.* 27:4416–4426 (1999).
Efimov et al., Peptide Nucleic Acids and Their Phosphonate Analogues: II. Synthesis and Physiochemical Properties of Hybrids Containing Serine and 4–Hydroxyproline Residues, *Russian Journal of Bioorganic Chemistry* 25:545–555 (1999).
Efimov et al., Polyacrylamide Conjugates with Oligonucleotides and Their Mimics for Diagnostics, *Russian Journal of Bioorganic Chemistry* 25:752–758 (1999).
Efimov et al., Phosponate Analogues of Peptide Nucleic Acids and Related Compounds: Synthesis and Hybridization Properties, *Nucleosides & Nucleotides* 18:1393–1396 (1999).
Efimov et al., Novel Oligonucleotide Analogues Derived from Serine and 4–Hydroxyproline, Nucleosides & Nucleotides 18(6&7): 1425–1426 (1999).
Efimov et al., Polyester and N–Methyl Analogues of Peptide Nucleic Acids: Synthesis and Hybridization Properties, Nucleosides & Nucleotides 18(11&12): 2533–2549 (1999).
Efimov and Chakhmakhcheva, Solid Phase Synthesis of PNA–Like Oligonucleotide Mimics and their Use for Polyacrylamide–Based Molecular Diagnostic Assays, Shemyakin & Ovchinnikov Institute of Bioorganic Chemistry, 10 pgs.
Egholm et al., Peptide Nucleic Acids Oligonucleotide Analogues with an Achiral Backbone, J. Am. Chem. Soc. 114: 1895–1897 (1992).
Egholm et al., Recognition of Guanine and Adenine in DNA by Cytosine and Thymine Containing Peptide Nucleic Acids (PNA), J. Am. Chem. Soc. 114:9677–9678 (1992).
Egholm et al., PNA Hybridizes to Complimentary Oligonucleotides Obeying the Watson–Crick Hydrogen–Bonding Rules, Nature 365: 566–568 (1993).
Falkiewicz et al., Synthesis and Characterization of New PNA Monomers, Nucleic Acids Symposium Series 42:29–30 (1999).
Fahrlander and Klausner, Amplifying DNA Probe Signals: A 'Christmas Tree ' Approach, Biotechnology 6: 1165–1168 (1988).
Finn et al., Nucl. Acids Res. 24:3357–3364 (1996).
Froehler et al., J. Am. Chem. Soc. 107:278–279 (1985).

Gait et al., Nucl. Acids Res. 8:1081–1096 (1980).
Gait et al. Nucl. Acids Res. 10:6243–6254 (1982).
Gao et al., Tetrahedron Lett. 32:5477–5480 (1991).
Goodchild, J. Bioconjugate Chem. 1:165 (1990).
Hanvey et al., Antisense and Antigene Properties of PNAs, Science 258: 1481–1485 (1992).
Heinklein et al., In Girault and Andreu (eds.) The Peptides, 21$^{st}$ European Peptide Symposium, ESCOM, Leiden pp. 67–77.
Igloi, Automated Detection of Point Mutations by Electrophoresis in PNA–containing Gels, BioTechniques 27:798–808 (1999).
Ishihara and Corey, Strand Invasion by DNA–Peptide Conjugates and Peptide Nucleic Acids, Nucleic Acids Symposium Series 42: 141–142 (1999).
Izvolsky et al., Sequence–Specific Protection of Duplex DNA against Restriction and Methylation Enzymes by Pseudocomplementary PNAs, Biochemistry 39: 10908–10913 (2000).
Kenney et al., Mutation Typing Using Electrophoresis and Gel–Immobilized Acrydite Probes, Biotechniques 25: 516–521 (1998).
Knudsen and Nielsen, Antisense Properties of Duplex– and Triplex–Forming PNAs, Nucl. Acids Res. 24(3):494–500 (1996).
Koster et al., Tetrahedron Lett. 24:747–750 (1983).
Koysynkina et al., Tetrahedron Lett. 35:5173–5176 (1994).
Kuwahara et al., Synthesis of Oxy–Peptide Nucleic Acids with Mixed Sequences, Nucleic Acids Symposium Series 42: 31–32 (1999).
Lohse et al., Double Duplex Invasion by Peptide Nucleic Acid: A General Principle for Sequence–Specific Targeting of Double–Stranded DNA, Proc. Natl. Acad. Sci. 96(21): 11804–11808 (1999).
Mayfield and Corey, Automated Synthesis of Peptide Nucleic Acids and Peptide Nucleic Acid–Peptide Conjugates, Analytical Biochemistry 268: 401–404 (1999).
McCollum and Andrus, Tetrahedron Lett. 32:4069–4072 (1991).
Mollegaard et al., PNA/DNA Strand Displacement Loops as Artificial Transcription Promoters, Proc. Natl. Acad. Sci. 91: 3892–3895 (1994).
Nielsen et al., Sequence–Selective Recognition of DNA by Strand Displacement with a Thymine–Substituted Polyamide, Science 254: 1497–1500 (1991).
Nielsen, Applications of Peptide Nucleic Acids, Current Opinion in Biotechnology 10:71–75 (1999).

Nielsen, Antisense Properties of Peptide Nucleic Acid, Methods in Enzymology 313: 156–164 (1999).
Orum et al., Nucl. Acids Res. 21:5332–5336 (1993).
Orum, et al., Sequence–Specific Purification of Nucleic Acids by PNA–Controlled Hybrid Selection, Biotechniques 19(3): 472–480 (1995).
Pain et al., Cells Tissues Organs 165:212–219 (1999).
Proudnikov et al., Immobilization of DNA in PolyAcrylamide Gel for the Manufacture of DNA and DNA–Oligonucleotide Microchips, Analytical Biochemistry 259: 34–41 (1998).
Rehman et al., Immobilization of Acrylamide–modified Oligonucleotides by Co–Polymerization, Nucl. Acids Res. 27(2): 649–655 (1999).
Sproat et al., Nucl. Acids Res. 14:1811–1824 (1986).
Sugimoto et al., Comparison of Thermodynamic Stabilities between PNA/DNA Hybrid Duplexes and DNA/DNA Duplexes, Nucleic Acids Symposium Series 42: 93–94 (1999).
Sugimoto et al., Positional Effect of Single Bulge Nucleotide on PNA/DNA Hybrid Stability, Nucleic Acids Symposium Series 42: 95–96 (1999).
Takeuchi et al., Chem. Pharm. Bull. 22:832–840 (1974).
van der Laan et al., An Approach Towards the Synthesis of Oligomers Containing a N–2–Hydroxyethyl–aminomethylphosphonate Backbone: A Novel PAN Analogue, *Tetrahedron Lett.* 37:7857–7860 (1996).
von Wintzingerode et al., PNA–Mediated PCR Clamping as a Useful Supplement in the Determination of Microbial Diversity, Applied and Env. Microbiology 66(2): 549–557 (2000).
Wang et al., PNA Binding–Mediated Induction of Human γ–globin Gene Expression, Nucl. Acids. Res. 27(13): 2806–2813 (1999).
Will et al., The Synthesis of Polyamide Nucleic Acids using a Novel Monomethoxytrityl Protecting–Group Strategy, *Tetrahedron Lett.* 51:12069–12082 (1995).
Zhong et al., Detection of Apolipoprotein B mRNA Editing by PNA mediated PCR Clamping, Biochem. and Biophys. Res. Comm 259: 311–313 (1999).
Advertisement for 'mVader', Biotechniques 28 (4): (2000).

* cited by examiner (XII)

(XIII)

Formula 1

Formula 2

OLIGONUCLEOTIDE ANALOGUES, METHODS OF SYNTHESIS AND METHODS OF USE

This application claims benefit of priority to U.S. provisional application No. 60/189,190, filed Mar. 14, 2000, herein incorporated by reference, from U.S. provisional application No. 60/250,334, filed Nov. 30, 2000, also herein incorporated by reference, this application is a continuation in part of PCT application US01/08111, WO 01/68673, filed Mar. 13, 2001, incorporated by reference, and a continuation in part of U.S. application Ser. No. 09/805,296, entitled "Oligonucleotide Analogues, Methods of Synthesis, and Methods of Use" filed Mar. 13, 2001, herein incorporated by reference.

TECHNICAL FIELD

The present invention relates to the field of nucleotide and oligonucleotide analogues, their synthesis and use.

BACKGROUND

The use of oligonucleotides for use as probes, primers, linkers, adapters, and antisense agents has been a core element in the field of molecular biology over the past twenty years. Modifications of oligonucleotides have been made to enhance their use as capture and detection probes (for example, the incorporation of biotin, digoxigenen, radioisotopes, fluorescent labels such as fluorescein, reporter molecules such as alkaline phosphatase, etc.). Modifications have also been made to the phosphodiester backbone of nucleic acid molecules to increase their stability. Such modifications involve the use of methyl phosphonates, phosphorothioates, phophorodithioates, 2'-methyl ribose, etc. Other modifications of oligonucleotides have been attempted to increase their cellular uptake or distribution.

A growing class of molecules known as "peptide nucleic acids" (PNAs) resulted from a modification that substituted an amide-linked backbone for the phosphodiester-sugar backbone. One such amide-linked backbone is based on N-(2-aminoethyl) glycine, in which each naturally or non-naturally occurring nucleobase is attached to a N-(2-aminoethyl) glycine unit, and the N-(2-aminoethyl) glycine units are linked together through peptide bonds (see, for example, WO 92/20702; U.S. Pat. No. 5,773,571 issued Jun. 30, 1998 to Nielsen et al. and U.S. Pat. No. 5,539,082 issued Jul. 23, 1996 to Nielsen et al.). The polyamide backbone of PNAs is resistant to both nucleases and proteases.

These nucleic acid analogues can bind both DNA and RNA by Watson-Crick base. pairing to form PNA/DNA or PNA/RNA duplexes that have greater thermal stability than corresponding DNA/DNA or DNA/RNA duplexes. Unlike the stability of DNA/DNA or DNA/RNA duplexes, the stability of PNA/DNA or PNA/RNA duplexes is nearly independent of salt concentration. In addition, PNAs bind nucleic acid molecules with greater affinity than DNA or RNA. This is apparent by an 8 to 20 degree drop in melting temperature when a single mismatch is introduced into a PNA/DNA duplex.

An additional feature of PNAs is that homopyrimidine PNAs have been shown to bind complementary DNA or RNA to form $(PNA)_2/DNA(RNA)$ triple helices of high thermal stability. Homopyrimidine PNAs can bind to both single-stranded and double-stranded DNA (or RNA). The binding of two single-stranded pyrimidine PNAs to a double-stranded DNA takes place via strand displacement. When PNA strands invade double-stranded DNA, one strand of the DNA is displaced and forms a loop on the side of the $(PNA)_2/DNA$ complex area. The other strand of the DNA is locked up in the $(PNA)_2/DNA$ triplex structure. The loop area (known as a D loop), being single-stranded, is susceptible to cleavage by enzymes or reagents that can cleave single-stranded DNA.

One drawback of PNAs is their reduced solubility with respect to naturally occurring nucleic acids. Modifications to PNAs to increase their solubility, binding affinity, and specificity have been introduced (see, for example, U.S. Pat. Nos. 5,714,331; 5,736,336; 5,766,855; 5,719,262; 5,786,461; 5,977,296; 6,015,887; and 6,107,470). One such modification is the use of phosphoester bonds in the backbone of nucleic acid analogues, as disclosed by (Efimov, et al. (1996) *Collect. Czech. Chem. Commun.* 61: S262–S264; van der Laan et al., *Tetrahedron Lett.* 37: 7857–7860 (1996)). However, these "phosphono PNAs" or "pPNAs" is that they exhibit reduced binding affinity with respect to polyamide or "classical" PNAs.

A common goal in discovery research is identifying genes that are expressed under particular conditions and determining their function. Identification of expressed genes can be used to discover pharmaceutical targets or develop therapeutic strategies. These objectives are often frustrated by the difficulties encountered in isolating RNA transcripts and in obtaining corresponding cDNA clones to particular RNA transcripts that are underrepresented in preparations of messenger RNA and cDNA libraries. Such under-representation can be due to the difficulty in isolating RNA molecules that have short poly A tails or lack poly A tails, or that have secondary structure at their 3' ends, all of which can confound capture of the RNA molecules by hybridization to oligo T probes. In other cases, the inability to identify a cDNA corresponding to an expressed RNA transcript can be due to the low frequency of cDNA clones corresponding to nonabundant RNAs in cDNA libraries.

There is a need to provide nucleic acid analogues that are stable to nucleases and proteases, that have high binding affinity, binding specificity, and solubility, that are relatively simple to synthesize, and can be used in a variety of applications. In particular, improved methods for the isolation of RNA transcripts and corresponding cDNAs would increase the efficiency of identifying genes that participate in a wide variety of biological functions. The present invention provides these and other benefits.

FIG. 3 depicts some preferred oligonucleotide analogue oligomers of the present invention: a) pPNA-HypNA (XII) and pPNA-SerNA (XIII), and b) acrylamide-coupled pPNA-HypNA (XIV) and acrylamide-coupled pPNA-SerNA (XV).

Figure 4:
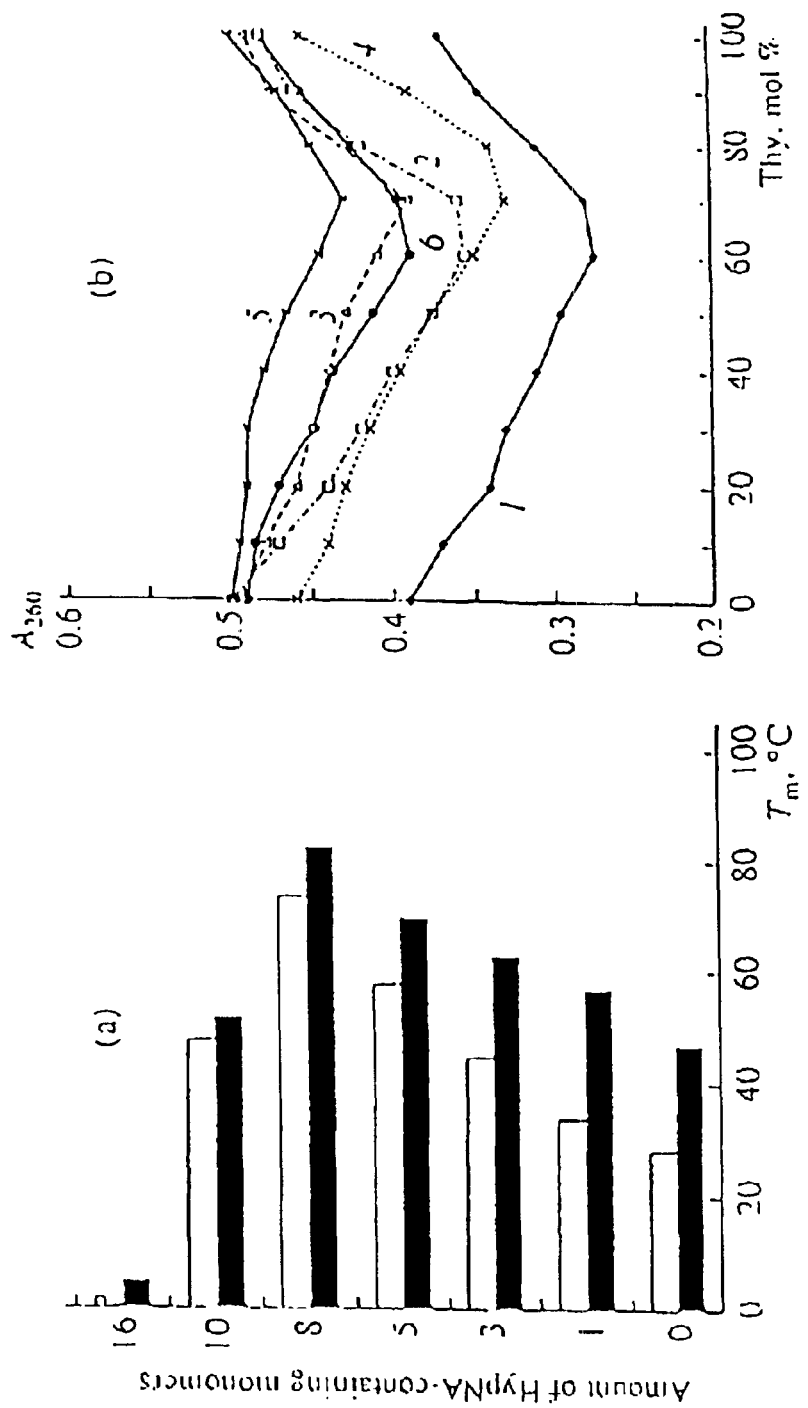

FIG. 4 depicts hybridization properties of oligonucleotide analogues of the present invention. a) shows the variation in melting temperature (Tm, x-axis) with the number of HypNA monomers (y-axis) in a HypNA-pPNA poly T 16-mer of the present invention. b) shows the formation of triple helices with a poly dA 16-mer by adding increasing amounts of oligonucleotide analogues of the present invention poly T 16-mers, monitored by the change in absorbance at 260 nm (y-axis). Oligonucleotide analogues 1) pPNA-HypNA (1:1); 2, pPNA-SerNA (1:1); 3, pPNA; 4, PNA-pPNA (1:1); 5, PNA; and 6) PNA-HypNA (1:1) were in 0.1 M NaCl, 20 mM Tris-HCl, pH 7, 10 mM $MgCl_2$.

Figure 5:
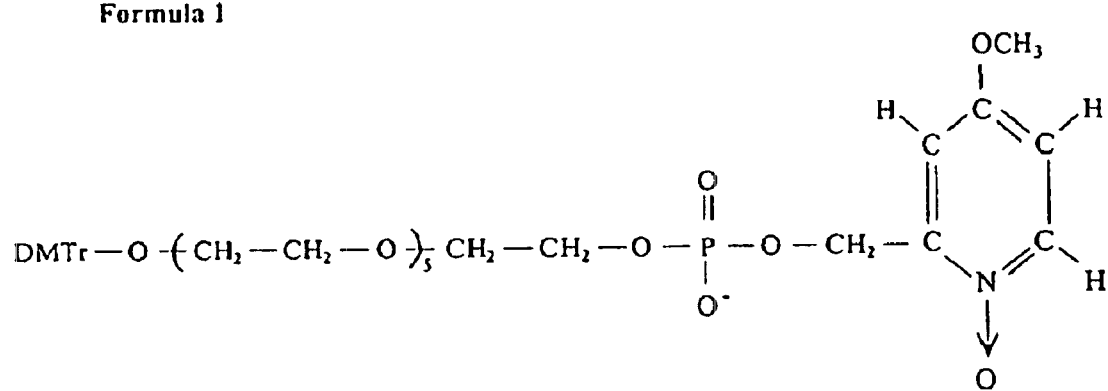
Figure 5:
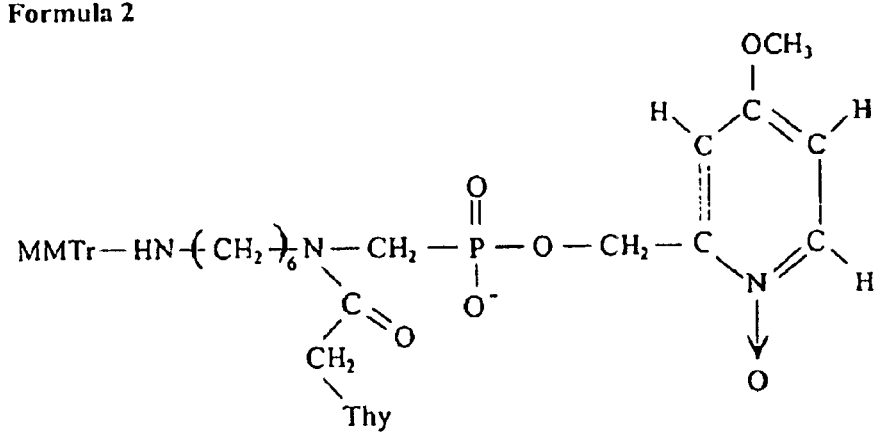

FIG. 5 depicts linkers used in some preferred clamping oligonucleotides of the present invention.

Figure 6:
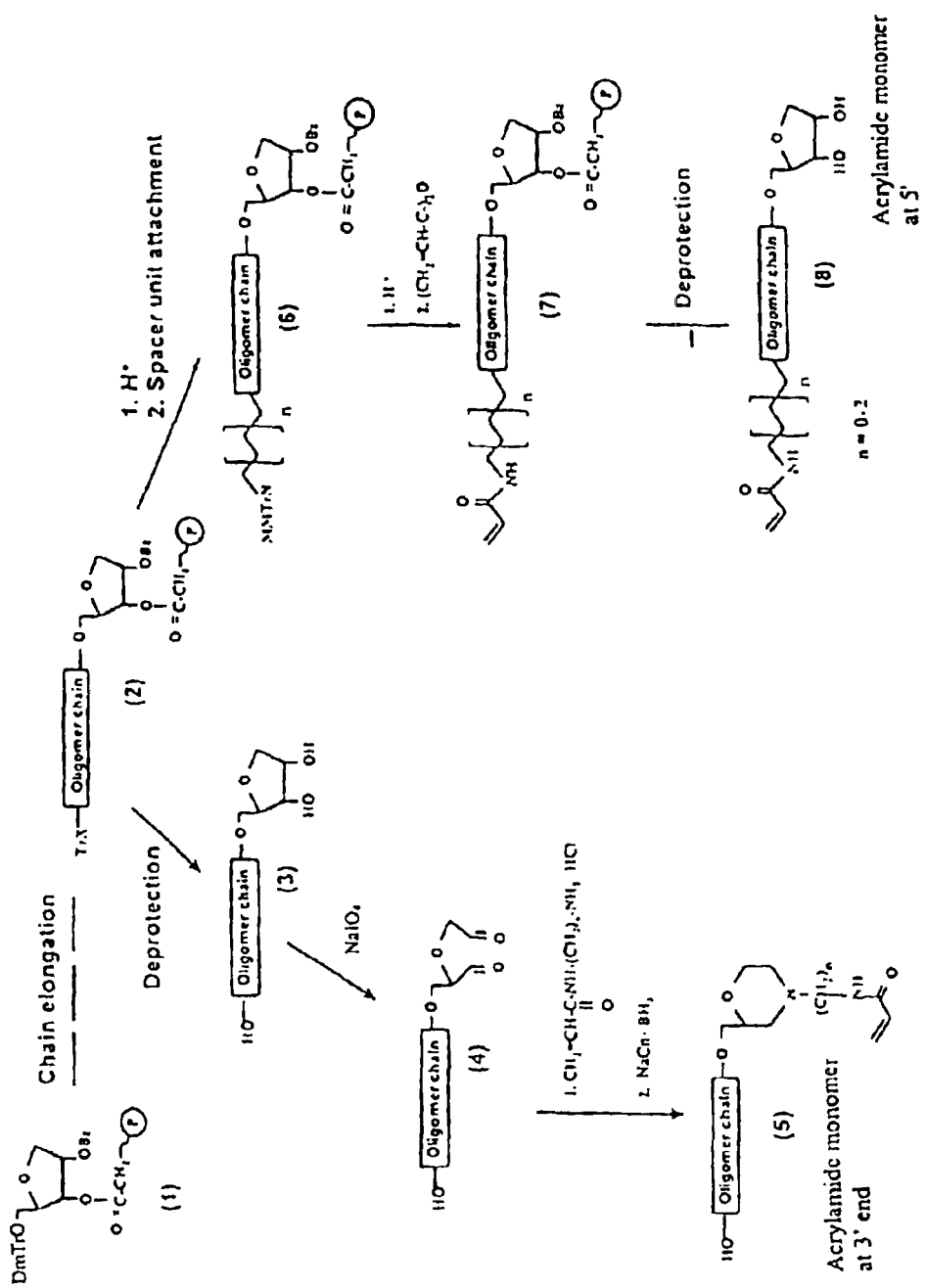

FIG. 6 depicts schemes for synthesizing an oligonucleotide analogue of the present invention coupled to polyacrylamide.

Figure 7:
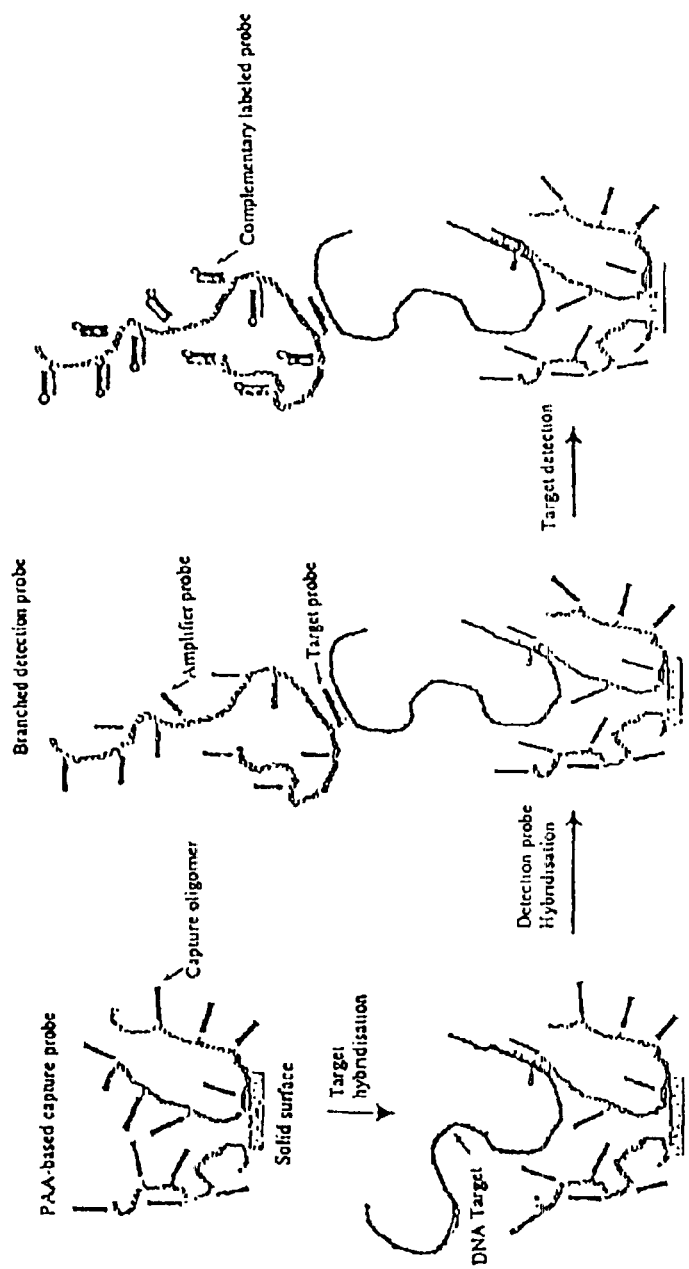

FIG. 7 depicts a method for detecting a nucleic acid sequence using an oligonucleotide analogues of the present invention coupled to acylamide using sandwich hybridization.

Figure 8:
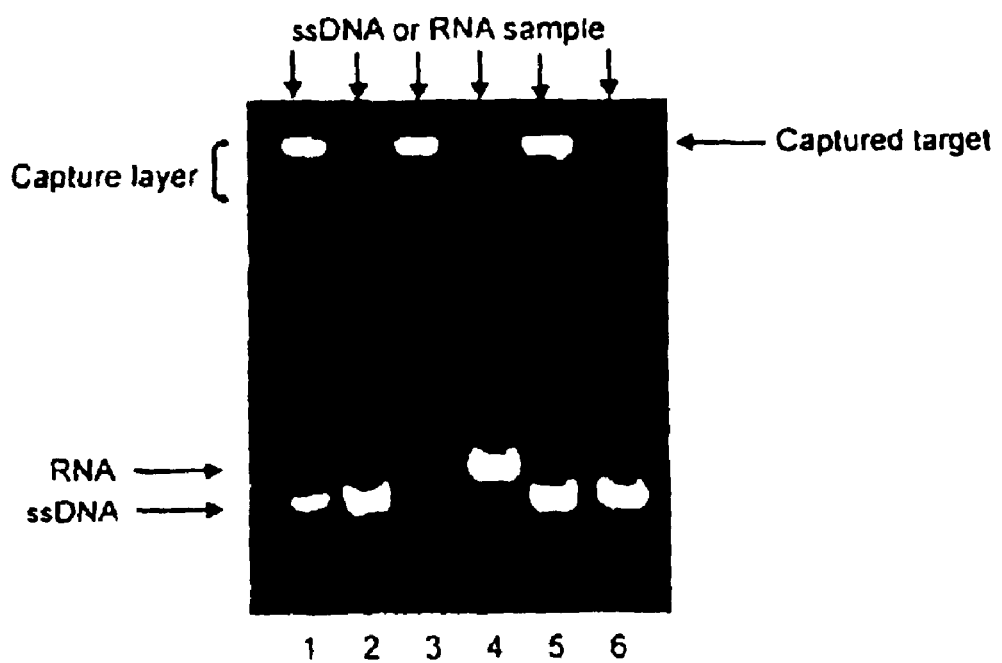

FIG. 8 depicts an acrylamide gel having incorporated oligonucleotide analogues used for capture of nucleic acid molecules. The following nucleic acids were electrophoresed through the gel: Lane 1, complementary target deoxyribooligonucleotide, Lanes 2 and 6: mismatched target deoxyribonucleotide, Lane 3: complementary target ribooligonucleotide, Lane 4: mismatched target ribooligonucleotide, Lane 5: mixture of complementary and mismatched target deoxyribooligonucleotides.

SUMMARY

The present invention relates generally to oligonucleotide analogues that include novel protein nucleic acid molecules (PNAs), particularly monomers, dimers, oligomers thereof and methods of making and using these oligonucleotide analogues. The PNAs of the present invention are characterized as including a variety of classes of molecules, such as, for example, hydroxyproline peptide nucleic acids (HypNA), and serine peptide nucleic acids (SerNA). The invention includes monomers, homodimers, heterodimers, homopolymers and heteropolymers of these and other oligonucleotide analogues. The present invention includes methods of using these oligonucleotide analogues in the detection and separating of nucleic acid molecules, including uses that include the utilization of oligonucleotide analogues on a solid support. The present invention also includes methods for purifying or separating nucleic acids, such as mRNA molecules, by hybridization with the oligonucleotides of the present invention. The present invention also includes the use of oligonucleotides of the present invention in antisense and homologous recombination constructs and methods.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the laboratory procedures in organic chemistry, chemistry, molecular biology, microbiology, cell biology, and cell culture described below are well known and commonly employed in the art. Conventional methods are used for these procedures, such as those provided in the art and various general references (Sambrook et al., *Molecular Cloning: A Laboratory Manual,* 2nd edition, Cold Spring Harbor Press, Cold Spring Harbor, N.Y. (1989); Ausubel et al., *Current Protocols in Molecular Biology,* John Wiley and Sons (1998); Harlowe and Lane, *Antibodies, a Laboratory Manual,* Cold Spring Harbor Press (1988)); Agrawal, ed. Methods in Molecular Biology, Vol. 20: Protocols for Oligonucleotides and Analogues, Humana Press (1994); and Agrawal, ed. Methods in Molecular Biology, Vol. 26: Protocols for Oligonucleotide Conjugates, Humana Press (1994). Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings:

An "organism" can be any prokaryote or eukaryote, and includes viruses, protozoans, and metazoans. Metazoans include vertebrates and invertebrates. "Organism" can also refer to more than one species that are found in association with one another, such as mycoplasm-infected cells, a plasmodium-infected animal, etc.

A "sample" is any fluid from which components are to be separated or analyzed. A sample can be from any source, such as an organism, group of organisms from the same or different species, from the environment, such as from a body of water or from the soil, or from a food source or an industrial source. A sample can be an unprocessed or a processed sample. A sample can be a gas, a liquid, or a semi-solid, and can be a solution or a suspension. A sample can be an extract, for example a liquid extract of a soil or food sample, an extract of a throat or genital swab, or an extract of a fecal sample.

"Subject" refers to any organism, such as an animal or a human. An animal can include any animal, such as a feral animal, a companion animal such as a dog or cat, an agricultural animal such as a pig or a cow, or a pleasure animal such as a horse.

A "nucleic acid molecule" is an oligonucleotide. A nucleic acid molecule can be DNA, RNA, or a combination of both. A nucleic acid molecule can also include sugars other than ribose and deoxyribose incorporated into the backbone, and thus can be other than DNA or RNA. A nucleic acid can comprise nucleobases that are naturally occurring or that do not occur in nature, such as xanthine, derivatives of nucleobases such as 2-aminoadenine and the like. A nucleic acid molecule of the present invention can have linkages other than phosphodiester linkages. A nucleic acid molecule can be of any length, and can be single-stranded or double-stranded, or partially single-stranded and partially double-stranded.

A "probe oligonucleotide analogue" is an oligonucleotide analogue that is at least partially single-stranded, and that is at least partially complementary, or at least partially substantially complementary, to a target sequence or sequence of interest. A probe oligonucleotide analogue can comprise detectable labels or specific binding members, and can be directly or indirectly bound to other moieties, for example a polymer or a solid support.

A single-stranded nucleic acid molecule is "complementary" to another single-stranded nucleic acid molecule when it can base-pair (hybridize) with all or a portion of the other nucleic acid molecule to form a double helix (double-stranded nucleic acid molecule), based on the ability of guanine (G) to base pair with cytosine (C) and adenine (A) to base pair with thymine (T) or uridine (U). For example, the nucleotide sequence 5'-TATAC-3' is completely complementary to the nucleotide sequence 5'-GTATA-3'.

"Substantially complementary" refers to nucleic acids that will selectively hybridize to one another under particular conditions, or to an oligonucleotide analogue and a nucleic acid molecule that will selectively hybridize to one another under particular conditions, but may contain mismatched bases at one or more positions.

"Partially complementary" or "complementary in part" refers to a pair of nucleic acid molecules that have stretches of sequence that are complementary and at least one of the nucleic acid molecules has at least one stretch of sequence that is not complementary to the other nucleic acid molecule of the pair.

"Selectively hybridize" refers to detectable specific binding. Polynucleotides, oligonucleotides, oligonucleotide analogues, and fragments thereof selectively hybridize to target nucleic acid strands, under hybridization and wash conditions that minimize appreciable amounts of detectable binding to nonspecific nucleic acids. High stringency conditions can be used to achieve selective hybridization conditions as known in the art. Generally, the nucleic acid sequence complementarity between the polynucleotides, oligonucleotides, oligonucleotide analogues, and fragments thereof and a nucleic acid sequence of interest will be at least 30%, and more typically and preferably of at least 40%, 50%, 60%, 70%, 80%, 90%, and can be 100%. Conditions for hybridization such as salt concentration, temperature, detergents, and denaturing agents such as formamide can be varied to increase the stringency of hybridization, that is, the requirement for exact matches of C to base pair with G, and A to base pair with T or U, along the strand of nucleic acid.

"Corresponds to" refers to an oligonucleotide sequence or oligonucleotide analogue sequence that shares identity (for example is identical) to all or a portion of a reference oligonucleotide or oligonucleotide analogue sequence. In contradistinction, the term "complementary to" is used herein to mean that the complementary sequence will base pair with all or a portion of a reference oligonucleotide or oligonucleotide analogue sequence. For illustration, the nucleotide sequence 5'-TATAC-3' corresponds to a reference sequence 5'-TATAC-3' and is complementary to a reference sequence 5'-GTATA-3'.

"Sequence identity" or "identical" means that two oligonucleotide or oligonucleotide analogue nucleobase sequences are identical (for example, on a nucleotide [or nucleotide analogue]-by-nucleotide [or nucleotide analogue] basis) over the window of comparison. "Partial sequence identity" or "partial identity" means that a portion of the nucleobase sequence of a nucleic acid molecule or oligonucleotide analogue molecule is identical to at least a portion of the sequence of another nucleic acid molecule or oligonucleotide analogue molecule.

"Substantial identity" or "substantially identical" as used herein denotes a characteristic of an oligonucleotide or oligonucleotide analogue nucleobase sequence, wherein the oligonucleotide or oligonucleotide analogue comprises a sequence that has at least 30 percent sequence identity, preferably at least 50 to 60 percent sequence identity, more usually at least 60 percent sequence identity as compared to a reference sequence over a comparison window of at least 20 nucleotide positions, frequently over a window of at least 25 to 50 nucleotides, wherein the percentage of sequence identity is calculated by comparing the reference sequence to the oligonucleotide or oligonucleotide analogue sequence that may include deletions or addition which total 20 percent or less of the reference sequence over the window of comparison. "Substantial partial sequence identity" or "substantially partially identical" is used when a portion of a nucleic acid molecule or oligonucleotide analogue is substantially identical to at least a portion of another nucleic acid molecule or oligonucleotide analogue. As used herein "identity" or "identical" refers to the base composition of nucleic acids and oligonucleotide analogues, and not to the composition of other components, such as the backbone.

A "detectable label" or "label" is a compound or molecule that can be detected, or that can generate a readout, such as fluorescence, radioactivity, color, chemiluminescence or other readouts known in the art or later developed. The readouts can be based on fluorescence, such as by fluorescent labels, such as but not limited to, ethidium bromide, ethidium homodimer, SYBR Green II, acridine orange, pyrene, 4-nitro-1,8-naphthalimide, TOTO-1, YOYO-1, cyanine 3 (Cy3), cyanine 5 (Cy5), phycoerythrin, phycocyanin, allophycocyanin, FITC, rhodamine, fluorescein, 5(6)-carboxyfluorescein, or lanthamides; by flourescent proteins such as red fluorescent protein drFP583 (DsRed) and its variants, blue fluorescent protein from Vibrio vulnificus (BFPVV) and its variants, green fluorescent protein (GFP) and its variants, etc., can be based on enzymatic or chemical activity, such as, but not limited to, the activity of beta-galactosidase, beta-lactamase, horseradish peroxidase, alkaline phosphatase, luciferase, or solutions that precipitate metal salts, such as silver salts (e.g., silver nitrate); or can be based on radioisotopes (such as $^{33}P$, $^{3}H$, $^{14}C$, $^{35}S$, $^{125}I$, $^{32}P$ or $^{131}I$). A label optionally can be a base with modified mass, such as, for example, pyrimidines modified at the C5 position or purines modified at the N7 position. Mass modifying groups can be, for examples, halogen, ether or polyether, alkyl, ester or polyester, or of the general type XR, wherein X is a linking group and R is a mass-modifying group. One of skill in the art will recognize that there are numerous possibilities for mass-modifications useful in modifying nucleic acid molecules and oligonucleotides, including those described in Oligonucleotides and Analogues: A Practical Approach, Eckstein, ed. (1991) and in PCT/US94/001 93.

"Label" or "labeled" refers to incorporation of a detectable marker, for example by incorporation of a fluorescent or radiolabled compound or attachment of moieties such as biotin that can be detected by the binding of a second moiety, such as marked avidin. Various methods of labeling nucleic acids, peptides, proteins, and peptide nucleic acids are known in the art.

A "mutation" is a change in the genome with respect to the standard wild-type sequence. Mutations can be deletions, insertions, or rearrangements of nucleic acid sequences at a position in the genome, or they can be single base changes at a position in the genome, referred to as "point mutations". Mutations can be inherited, or they can occur in one or more cells during the lifespan of an individual.

"Operably linked" refers to a juxtaposition wherein the components so described are in a relationship permitting them to function in their intended manner. For example, a control sequence operably linked to a coding sequence is positioned in such a way that expression of the coding sequence is achieved under conditions compatible with control sequences.

A "sequence of interest" or "target nucleic acid molecule" is a nucleic acid sequence that can be separated, isolated, or purified, or whose presence or amount can be detected in one or more subjects, samples, or populations of nucleic acid molecules, by the methods of the present invention.

A "population of nucleic acid molecules" is a population of at least two nucleic acid molecules that are to be tested for the presence or amount (including relative amount) of a sequence of interest or from which a sequence of interest can be separated, isolated, or purified. A population of nucleic acid molecules can be DNA, RNA, or both. A survey population of nucleic acid molecules can be from any source, such as a human source, animal source, plant source, or microbial source. The survey population can be isolated from tissue (including but not limited to hair, blood, serum, amniotic fluid, semen, urine, saliva, throat or genital swabs, biopsy samples, or autopsy samples) or cells, including cells grown in culture, and can be isolated from living or non-living samples or subjects. The survey population can be isolated from inanimate material, remnants or artifacts, including fossilized material.

"Hybridization" is the process of base-pairing of single-stranded nucleic acids or nucleic acid analogues, or single-stranded portions of nucleic acids or nucleic acid analogues, to create double-stranded or triplex nucleic acids or nucleic acid analogues (or mixtures thereof) or double-stranded or triplex portions of nucleic acid molecules or nucleic acid analogues (or mixtures thereof).

A "nucleolytic activity" or "nucleolytic agent" is an activity that can cleave nucleosidic bonds to degrade nucleic acid molecules. Nucleolytic activities or agents can be enzymes, such as, for example, Dnase I, Exonuclease III, Mung Bean Nuclease, S1 Nuclease, RNAse H, or Rnase A, or can be chemical compounds, such as hydrogen peroxide, osmium tetroxide, hydroxylamine, or potassium permanganate, or can be chemical conditions, such as high or low pH.

An "immobilized oligonucleotide analogue" is an oligonucleotide analogue that is bound to a solid support. An immobilized oligonucleotide analogue can be of any length, can be single-stranded or part of a molecule that is double-stranded, or part of a molecule that is partially single-stranded and partially double-stranded. The immobilized oligonucleotide analogue can be reversibly or irreversibly bound to the solid support. The binding to the solid support can be direct or indirect.

A "signal oligonucleotide analogue" is a oligonucleotide analogue molecule that is at least partially single-stranded, and that is at least partially complementary, or at least partially substantially complementary, or at least partially identical, or at least partially substantially identical to a sequence of interest or target nucleic acid molecule. A signal oligonucleotide analogue preferably comprises a detectable label.

A "single nucleotide polymorphism" or "SNP" is a position in a nucleic acid sequence that differs in base composition in nucleic acids isolated from different individuals of the same species.

A "solid support" is a solid material having a surface for attachment of molecules, compounds, cells, or other entities. The surface of a solid support can be flat or not flat. A solid support can be porous or non-porous. A solid support can be a chip or array that comprises a surface, and that may comprise glass, silicon, nylon, polymers, plastics, ceramics, or metals. A solid support can also be a membrane, such as a nylon, nitrocellulose, or polymeric membrane, or a plate or dish and can be comprised of glass, ceramics, metals, or plastics, such as, for example, a 96-well plate made of, for example, polystyrene, polypropylene, polycarbonate, or polyallomer. A solid support can also be a bead or particle of any shape, and is preferably spherical or nearly spherical, and preferably a bead or particle has a diameter or maximum width of 1 millimeter or less, more preferably of between 0.1 to 100 microns. Such particles or beads can be comprised of any suitable material, such as glass or ceramics, and/or one or more polymers, such as, for example, nylon, polytetrafluoroethylene, TEFLON™, polystyrene, polyacrylamide, sepaharose, agarose, cellulose, cellulose derivatives, or dextran, and/or can comprise metals, particularly paramagnetic metals, such as iron.

"Specific binding member" is one of two different molecules having an area on the surface or in a cavity that specifically binds to and is thereby defined as complementary with a particular spatial and polar organization of the other molecule. A specific binding member can be a member of an immunological pair such as antigen-antibody, biotin-avidin, hormone-hormone receptor, nucleic acid duplexes, IgG-protein A, DNA-DNA, DNA-RNA, and the like.

"Substantially linear" means that, when graphed, the increase in the product with respect to time conforms to a linear progression, or conforms more nearly to an arithmetic progression than to a geometric progression.

An "oligonucleotide" is a nucleic acid molecule composed of at least two nucleotide residues, or monomers.

An "oligonucleotide analogue" is a molecule that is not a naturally occurring nucleic acid such as DNA or RNA, but that comprises at least two nucleobases attached to a backbone comprised of repeating units that can be linked together by one or more phosphodiester, phosphoester, amide, ester, or other linkages. An oligonucleotide analogue can have any base composition, and can comprise intercalators, reporter groups, detectable labels, or specific binding members.

A "peptide nucleic acid" or "PNA" is a nucleic acid analogue having nucleobases such as those of DNA or RNA, or analogues or derivatives thereof, and a backbone that comprises amino acids or derivatives or analogues thereof. A peptide amino acid can have a backbone based on N-(2-aminoethyl)glycine ("classical PNA" or "classical" PNA or "classical" peptide nucleic acid) or derivatives thereof, wherein monomer units of the PNA are linked by peptide bonds, or can comprise other amino acids and amino acid derivatives in its backbone structure that may or may not comprise amide bonds.

A "phosphono-peptide nucleic acid" or "pPNA" is a peptide nucleic acid in which the backbone comprises amino acid analogues, such as N-(2-hydroxyethyl) phosphonoglycine or N-(2-aminoethyl)phosphonoglycine, and the linkages between monomer units are through phosphonoester or phosphonoamide bonds.

A "serine nucleic acid" or "SerNA" is a peptide nucleic acid in which the backbone comprises serine residues. Such residues can be linked through amide or ester linkages.

A "hydroxyproline nucleic acid" or "HypNA" is a peptide nucleic acid in which the backbone comprises 4-hydroxyproline residues. Such residues can be linked through amide or ester linkages.

A "peptide nucleic acid-phosphono-peptide nucleic acid" or "PNA-pPNA" or "pPNA-PNA" is a peptide nucleic acid that comprises both "classical" peptide nucleic acid and phosphono-peptide nucleic acid backbone residues. A peptide nucleic acid-phosphono-peptide nucleic acid can comprise amide and phosphonoester backbone linkages.

A "peptide nucleic acid-hydroxyproline nucleic acid" or "PNA-HypNA" or "HypNA-PNA" is a peptide nucleic acid that comprises both "classical" peptide nucleic acid and hydroxyproline nucleic acid backbone residues. A peptide nucleic acid-hydroxyproline nucleic acid can comprise amide and ester backbone linkages.

A "hydroxyproline nucleic acid-phosphono-peptide nucleic acid" or "pPNA-HypNA" or "HypNA-pPNA" is a peptide nucleic acid that comprises both phoshono-peptide nucleic acid and hydroxyproline nucleic acid backbone residues. A hydroxyproline nucleic acid-phosphono-peptide nucleic acid can comprise amide and phosphonoester backbone linkages.

A "serine nucleic acid-peptide nucleic acid" or "PNA-SerNA" or "SerNA-PNA" is a peptide nucleic acid that comprises both "classical" peptide nucleic acid and serine nucleic acid backbone residues. A serine nucleic acid-peptide nucleic acid can comprise amide and ester backbone linkages.

A "serine nucleic acid-phosphono-peptide nucleic acid" or "pPNA-SerNA" or "SerNA-pPNA" is a peptide nucleic acid that comprises both phosphono-peptide nucleic acid and serine nucleic acid backbone residues. A serine nucleic acid-phosphono-peptide nucleic acid can comprise amide and phosphonoester backbone linkages.

A "monomer" of a nucleic acid analogue is a unit comprising a nucleobase, or a derivative or analogue thereof (or, in some instances, moieties such as labels, intercalators, or nucleobase binding moieties) covalently linked to a backbone molecule that is capable of covalently linking to other backbone molecules to form a polymer. The monomer unit of a nucleic acid is a nucleotide or nucleoside, in which a nucleobase is attached to a sugar-phosphate backbone moiety. The monomer unit of a peptide nucleic acid is a nucleobase (or nucleobase analogue, nucleobase-binding group, ligand, intercalator, reporter group, or label) that is covalently attached to an amino acid or amino acid derivative or analogue.

A "dimer" is a unit of two covalently linked monomers. Where the monomers comprise different backbone moieties, a dimer can be, for example, a "HypNA-PNA dimer", or a "SerNA-pPNA dimer".

A "protecting group" is a chemical group, that when bound to a second chemical group on a moiety, prevents the second chemical group from entering into particular chemical reactions. A wide range of protecting groups are known in synthetic organic and bioorganic chemistry that are suitable for particular chemical groups and are compatible with particular chemical processes, meaning that they will protect particular groups during those processes.

A "nucleobase" is a heterocyclic base such as adenine, guanine, cytosine, thymine, uracil, inosine, xanthine, hypoxanthine, or a heterocyclic derivative, analogue, or tautomer thereof. A nucleobase can be naturally occurring or non-naturally occurring. Nonlimiting examples of nucleobases are adenine, guanine, thymine, cytosine, uracil, xanthine, hypoxanthine, 8-azapurine, purines substituted at the 8 position with methyl or bromine, 9-oxo-$N^6$-methyladenine, 2-aminoadenine, 7-deazaxanthine, 7-deazaguanine, 7-deazaadenine, $N^4$, $N^4$-ethanocytosine, 2,6-diaminopurine, $N^6$, $N^6$-ethano-2,6-diaminopurine, 5-methylcytosine, 5-($C^3$–$C^6$)-alkynylcytosine, 5-fluorouracil, 5-bromouracil, thiouracil, pseudoisocytosine, 2-hydroxy-5-methyl-4-triazolopyridine, isocytosine, isoguanine, inosine, 7,8-dimethylalloxazine, and the non-naturally occurring nucleobases described in U.S. Pat. Nos. 5,432,272 and 6,150,510 and PCT applications WO 92/002258, WO 93/10820, WO 94/22892, and WO 94/24144, all herein incorporated by reference in their entireties.

As used herein, "backbone molecule" or "backbone moiety" is a molecule or moiety to which nucleobases, nucleobase derivatives or analogues, intercalators, specific binding members, labels, or nucleobase binding molecules can be covalently attached, and that when covalently joined in a linear fashion to other backbone molecules, can form an oligomer. Backbone molecules of naturally occurring nucleic acids include pentose-phospate units linked together by phosphodiester bonds. Backbone molecules of "classical PNAs" include N-(2-aminoethyl)glycine, and backbone molecules of "phosphonoPNAs" include N-(2-hydroxyethyl)phosphonoglycine or N-(2-aminoethyl)phosphonoglycine. Backbone molecules of "HypNAs" include L-hydoxyproline, of serine nucleic acids include L-serine, etc. Backbone molecules of nucleic acid analogues can be linked together by any of a number of types of covalent bonds, including, but not limited to, ester, phosphoester, phosponoester, phosponamide, and amide bonds.

A "linker" is a molecule or moiety that joins two molecules or moieties of interest. Preferably, a linker provides spacing between the two molecules or moieties of interest such that they are able to function in their intended manner. For example, a linker can comprise a hydrocarbon chain that is covalently bound through a reactive group on one end to an oligonucleotide analogue molecule and through a reactive group on another end to a solid support, such as, for example, a glass surface. In this way the oligonucleotide analogue is not directly bound to the glass surface but can be positioned at some distance from the glass surface. A linker can also join two oligonucleotide analogue sequences in a linear fashion to provide optimal spacing between the two oligonucleotide analogue sequences such that they can form a "clamping" oligonucleotide analogue, as described in U.S. Pat. No. 6,004,750 issued Dec. 21, 1999 to Frank-Kamenetskii et al. Preferably, where a linker is attached to an oligonucleotide analogue, a linker is nonreactive with an oligonucleotide analogue and another molecule or moiety to which the linker is attached. Linkers can be chosen and designed based on the conditions under which they will be used, for example, soluble linkers will be preferred in many aspects of the present invention. Nonlimiting examples of linkers that can be useful in the present invention are dioxaoctanoic acid and its derivatives and analogues, and the linkers depicted in FIGS. 5 and 6. Linkers can be used to attach oligonucleotide analogue to a variety of molecules or substrates of interest, including, but not limited to, glass, silicon, nylon, cellulose, polymers, peptides, proteins (including antibodies and fragments of antibodies), lipids, carbohydrates, nucleic acids, molecular complexes, specific binding members, reporter groups, detectable labels, and even cells. The coupling of linkers to oligonucleotides and to molecules and substrates of interest can be through a variety of groups on the linker, for example, hydroxyl, aldehyde, amino, sulfhydryl, etc. Molecules and substrates can optionally be derivatized in a variety of ways for attachment to linkers. Oligonucleotide analogues can optionally be derivatized for attachment to linkers as well, for example by the addition of phosphate, phosphonate, carboxyl, or amino groups. Coupling of linkers to oligonucleotide analogues, molecules of interest, and substrates of interest can be accomplished through the use of coupling reagents that are known in the art (see, for example Efimov et al., *Nucleic Acids Res.* 27: 4416–4426 (1999)). Methods of derivatizing and coupling organic molecules are well known in the arts of organic and bioorganic chemistry.

An "intercalator" is a chemical moiety that can bind a nucleic acid molecule or a nucleic acid analogue molecule by inserting between adjacent nucleobases. Non-limiting examples of intercalators include acridines, anthracene, anthracyclines, anthracyclinone, methylene blue, indole, anthraquinone, quinoline, isoquinoline, dihydroquinones, tetracyclines, psoralens, coumarins, ethidium halides, ethidium homodimer, homodimeric oxazole yellow (YOYO), thiazole orange (TOTO), dynemicin, 1,10-phenanthroline-copper, calcheamicin, porphyrins, distamycin, netropcin, and viologen.

A "reporter group" is a chemical moiety that is directly or indirectly detectable. Examples of functional parts of reporter groups are biotin; digoxigenin; fluorescent proteins or groups such as dansyl (5-dimethylamino-1-naphthalenesulfonyl), DOXYL (N-oxyl-4,4-dimethyloxazolidine), PROXYL (N-oxyl-2,2,5,5-tetramethylpyrrolidine), TEMPO(N-oxyl-2,2,6,6-tetramethylpiperidine), dinitrophenyl, acridines, coumarins, Cy3 and Cy5 (Biological Detection Systems, Inc.), erytrosine, coumaric acid, umbelliferone, texas red rhodaine, tetramethyl rhodamin, Rox, 7-nitrobenzo-1-oxa-1-diazole (NBD), oxazole, thiazole, pyrene, fluorescein, ethidium, Europium, Ruthenium, and Samarium; radioisotopes, chemiluminescent labels, spin labels, enzymes (such as peroxidases, alkaline phosphatases, beta-galactosidases, and oxidases), antigens, antibodies, haptens, etc.

A "capture probe" is an oligonucleotide or oligonucleotide analogue that can bind a target nucleic acid molecule and can also directly or indirectly bind an immobilized moiety or a moiety bound to a solid support.

An "overhang" is a single-stranded region at a terminus of an otherwise double-stranded or substantially double-stranded nucleic acid molecule.

"Substantially purified" refers to the state of a species or activity that is the predominant species or activity present (for example on a molar basis it is more abundant than any other individual species or activities in the composition) and preferably a substantially purified fraction is a composition wherein the object species or activity comprises at least about 50 percent (on a molar, weight or activity basis) of all macromolecules or activities present. Generally, a substantially pure composition will comprise more than about 80 percent of all macromolecular species or activities present in a composition, more preferably more than about 85%, 90%, or 95%.

A "cellular activity" refers to an activity that occurs within a cell, including activities catalyzed by one or more enzymes, such as, but not limited to, transcription, splicing, translation, the folding or unfolding of proteins or nucleic acids, transport of nucleic acids, RNA, lipids, or proteins within the cell, cytoskeletal activity such as contractile activity, polymerization activities such as nucleic acid, fatty acid, or carbohydrate synthetic activities, etc.

Introduction

The present invention relates generally to oligonucleotide analogues that include novel protein nucleic acid molecules (PNAs), particularly monomers, dimers, oligomers thereof and methods of making and using these oligonucleotide analogues. The PNAs of the present invention are characterized as including a variety of classes of molecules, such as, for example, hydroxyproline peptide nucleic acids (HypNA), and serine peptide nucleic acids (SerNA). The invention includes monomers, homodimers, heterodimers, homopolymers and heteropolymers of these and other oligonucleotide analogues. The present invention includes methods of using these oligonucleotide analogues in the detection and separating of nucleic acid molecules, including uses that include the utilization of oligonucleotide analogues on a solid support. The present invention also includes methods for purifying or separating nucleic acids, such as mRNA molecules, by hybridization with the oligonucleotides of the present invention. The present invention also includes the use of oligonucleotides of the present invention in antisense and homologous recombination constructs and methods.

1. Nucleotide and Oligonucleotide Analogues

Monomer Compositions

The present invention comprises monomer compositions that can be incorporated into oligonucleotides and oligonucleotide analogues.

One monomer of the present invention, herein referred to as a hydroxyproline peptide nucleic acid monomer or "HypNA" monomer, comprises the structure given by the formula:

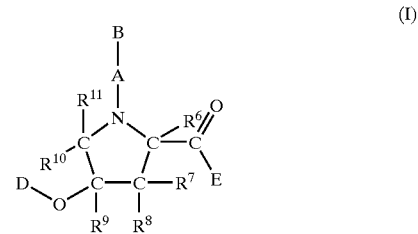

(I)

where B is H, a naturally occurring nucleobase, a non-naturally occurring nucleobase, an aromatic moiety, a DNA intercalator, a nucleobase-binding group, a heterocyclic moiety, or a reporter group, wherein amino groups are, optionally, protected by amino protecting groups;

where A is a group of formula (Ia), (Ib), or (Ic);

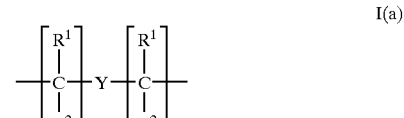

I(a)

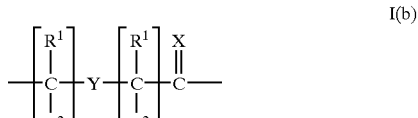

I(b)

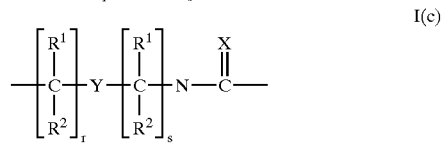

I(c)

where r and s are, for I(a) and I(b), independently of one another, values from 0 to 5 and are, for I(c), independently of one another, values from 1 to 5;

where each $R^1$ and each $R^2$ is, independently, hydrogen, $(C_1–C_6)$alkyl, hydroxy-, alkoxy-, amino-, or alkythio-substituted $(C_1–C_6)$alkyl, hydroxy, alkoxy, alkylthio, amino, or halogen;

where each of $R^3$, $R^4$, and $R^5$, is, independently, hydrogen, $(C_1-C_6)$alkyl, hydroxy-, alkoxy-, amino-, or alkythio-substituted $(C_1-C_6)$alkyl, hydroxy, amino, alkoxy, aryl, aralkyl, heteroaryl, or an amino acid side chain;

Y is a single bond, O, S, or $NR^4$; and

X is O, S, Se, $NR^5$, $CH_2$, or $C(CH_3)_2$;

where $R^6$ is hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where $R^7$ is hydrogen, hydroxy, alkoxy, $(C_1-C_6)$alkyl, hydroxy-, alkoxy-, amino-, or alkythio-substituted $(C_1-C_6)$ alkyl, alkylthio, aryl, aralkyl, heteroaryl, amino, or halogen, and $R^8$ is hydrogen, $(C_1-C_6)$alkyl, hydroxy-, alkoxy-, amino-, or alkythio-substituted $(C_1-C_6)$alkyl, aryl, aralkyl, heteroaryl;

or $R^7$ is hydrogen, $(C_1-C_6)$alkyl, hydroxy-, alkoxy-, amino-, or alkythio-substituted $(C_1-C_6)$alkyl, alkoxy, aryl, aralkyl, or heteroaryl, and $R^8$ is hydrogen, hydroxy, alkoxy, alkthio, amino, $(C_1-C_6)$alkyl, hydroxy-, alkoxy-, amino-, or alkythio-substituted $(C_1-C_6)$alkyl, aryl, aralkyl, heteroaryl, or halogen;

where $R^9$ is hydrogen, alkoxy, $(C_1-C_6)$alkyl, hydroxy-, alkoxy-, amino-, or alkythio-substituted $(C_1-C_6)$alkyl, aryl, arylkyl, or heteroaryl;

where each of $R^{10}$ and each $R^{11}$ is, independently, hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where D is a protecting group compatible with the conditions of ester, amide, or phosphonoester bond formation, $R^{18}$, or $NR^{18}R^{19}$;

where E is $O^-$, $OCH_3$, a protecting or activating group compatible with ester, phosphoester, or phosphonoester bond formation, $R^{20}$, $NR^{20}R^{21}$, or $OR^{20}$; and each $R^{18}$, $R^{19}$, $R^{20}$, and $R^{21}$ is, independently, hydrogen, alkyl, an amino protecting group, a reporter group, an intercalator, a linker, a chelator, a peptide, a protein, a carbohydrate, a lipid, a steroid, a nucleotide or oligonucleotide, or a soluble or nonsoluble polymer;

Another monomer of the present invention, herein referred to as a hydroxyproline-1 phosphono peptide nucleic acid monomer or "Hyp-1NA" monomer, comprises the structure given by the formula:

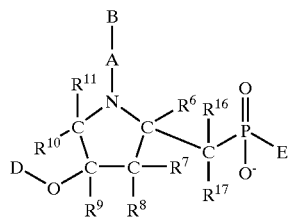

(II)

where B is H, a naturally occurring nucleobase, a non-naturally occurring nucleobase, an aromatic moiety, a DNA intercalator, a nucleobase-binding group, a heterocyclic moiety, or a reporter group, wherein amino groups are, optionally, protected by amino protecting groups;

where A is a group of formula (Ia), (Ib), or (Ic);

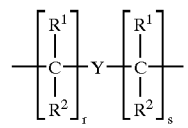

I(a)

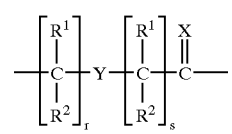

I(b)

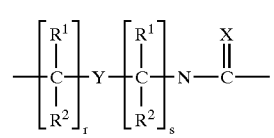

I(c)

where r and s are, for I(a) and I(b), independently of one another, values from 0 to 5 and are, for I(c), independently of one another, values from 1 to 5;

where each $R^1$ and each $R^2$ is, independently, hydrogen, $(C_1-C_6)$alkyl, hydroxy-, alkoxy-, amino-, or alkythio-substituted $(C_1-C_6)$alkyl, hydroxy, alkoxy, alkylthio, amino, or halogen;

where each of $R^3$, $R^4$, and $R^5$, is, independently, hydrogen, $(C_1-C_6)$alkyl, hydroxy-, alkoxy-, amino-, or alkythio-substituted $(C_1-C_6)$alkyl, hydroxy, amino, alkoxy, aryl, aralkyl, heteroaryl, or an amino acid side chain;

Y is a single bond, O, S, or $NR^4$; and

X is O, S, Se, $NR^5$, $CH_2$, or $C(CH_3)_2$;

where $R^6$ is hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where $R^7$ is hydrogen, hydroxy, alkoxy, $(C_1-C_6)$alkyl, hydroxy-, alkoxy-, amino-, or alkythio-substituted $(C_1-C_6)$ alkyl, alkylthio, aryl, aralkyl, heteroaryl, amino, or halogen, and $R^8$ is hydrogen, $(C_1-C_6)$alkyl, hydroxy-, alkoxy-, amino-, or alkythio-substituted $(C_1-C_6)$alkyl, aryl, aralkyl, heteroaryl;

or $R^7$ is hydrogen, $(C_1-C_6)$alkyl, hydroxy-, alkoxy-, amino-, or alkythio-substituted $(C_1-C_6)$alkyl, alkoxy, aryl, aralkyl, or heteroaryl, and $R^8$ is hydrogen, hydroxy, alkoxy, alkthio, amino, $(C_1-C_6)$alkyl, hydroxy-, alkoxy-, amino-, or alkythio-substituted $(C_1-C_6)$alkyl, aryl, aralkyl, heteroaryl, or halogen;

where $R^9$ is hydrogen, alkoxy, $(C_1-C_6)$alkyl, hydroxy-, alkoxy-, amino-, or alkythio-substituted $(C_1-C_6)$alkyl, aryl, arylkyl, or heteroaryl;

where each of $R^{10}$ and $R^{11}$ is, independently, hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where each each of $R^{16}$ and $R^{17}$ is, independently, hydrogen, $(C_1-C_6)$alkyl, hydroxy-, alkoxy-, amino-, or alkythio-substituted $(C_1-C_6)$alkyl, hydroxy, alkoxy, alkythio, aryl, aralkyl, or heteroaryl;

where D is a protecting group compatible with the conditions of phosphoester, phosphonoester, or phosphonamide bond formation, $R^{18}$, or $NR^{18}R^{19}$;

where E is a protecting or activating group compatible with ester, phosphoester, phosphonoester, or phosphonamide bond formation, $O^-$, $R^{20}$, $NR^{20}R^{21}$, or $OR^{20}$; and each $R^{18}$, $R^{19}$, $R^{20}$, and $R^{21}$ is, independently, hydrogen, alkyl, an amino protecting group, a reporter group, an intercalator, a linker, a chelator, a peptide, a protein, a carbohydrate, a lipid, a steroid, a nucleotide or oligonucleotide, or a soluble or nonsoluble polymer;

Another monomer of the present invention, herein referred to as a hydroxyproline-2 phosphono peptide nucleic acid monomer or "Hyp-2NA" monomer, comprises the structure given by the formula:

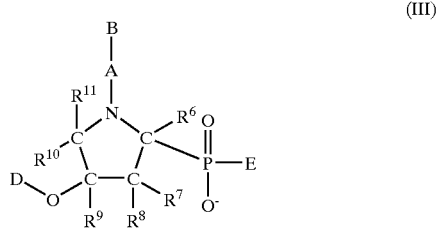
(III)

where B is H, a naturally occurring nucleobase, a non-naturally occurring nucleobase, an aromatic moiety, a DNA intercalator, a nucleobase-binding group, a heterocyclic moiety, or a reporter group, wherein amino groups are, optionally, protected by amino protecting groups;

where A is a group of formula (Ia), (Ib), or (Ic);

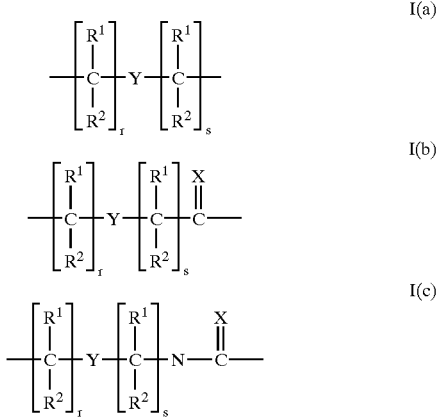

where r and s are, for I(a) and I(b), independently of one another, values from 0 to 5 and are, for I(c), independently of one another, values from 1 to 5;

where each $R^1$ and each $R^2$ is, independently, hydrogen, $(C_1-C_6)$alkyl, hydroxy-, alkoxy-, amino-, or alkythio-substituted $(C_1-C_6)$alkyl, hydroxy, alkoxy, alkylthio, amino, or halogen;

where each of $R^3$, $R^4$, and $R^5$, is, independently, hydrogen, $(C_1-C_6)$alkyl, hydroxy-, alkoxy-, amino-, or alkythio-substituted $(C_1-C_6)$alkyl, hydroxy, amino, alkoxy, aryl, aralkyl, heteroaryl, or an amino acid side chain;

Y is a single bond, O, S, or $NR^4$; and

X is O, S, Se, $NR^5$, $CH_2$, or $C(CH_3)_2$;

where $R^6$ is hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where $R^7$ is hydrogen, $(C_1-C_6)$alkyl, hydroxy-, alkoxy-, amino-, or alkythio-substituted $(C_1-C_6)$alkyl, hydroxy, alkoxy, alkylthio, aryl, aralkyl, heteroaryl, amino, or halogen, and $R^8$ is hydrogen, $(C_1-C_6)$alkyl, hydroxy-, alkoxy-, amino-, or alkythio-substituted $(C_1-C_6)$alkyl, aryl, aralkyl, heteroaryl;

or $R^7$ is hydrogen, $(C_1-C_6)$alkyl, hydroxy-, alkoxy-, amino-, or alkythio-substituted $(C_1-C_6)$alkyl, alkoxy, aryl, aralkyl, or heteroaryl, and $R^8$ is hydrogen, hydroxy, alkoxy, alkylthio, amino, $(C_1-C_6)$alkyl, hydroxy-, alkoxy-, amino-, or alkythio-substituted $(C_1-C_6)$alkyl, aryl, aralkyl, heteroaryl, or halogen;

where $R^9$ is hydrogen, alkoxy, $(C_1-C_6)$alkyl, hydroxy-, alkoxy-, amino-, or alkythio-substituted $(C_1-C_6)$alkyl, aryl, arylkyl, or heteroaryl;

where each of $R^{10}$ and $R^{11}$ is, independently, hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where each of $R^{16}$ and each $R^{17}$ is, independently, hydrogen, $(C_1-C_6)$alkyl, hydroxy-, alkoxy-, amino-, or alkythio-substituted $(C_1-C_6)$alkyl, hydroxy, alkoxy, alkylthio, amino, aryl, aralkyl, heteroaryl, or an amino acid side chain;

where D is a protecting group compatible with the conditions of ester, amide, phosphoester, or phosphonoester bond formation, $R^{18}$, or $NR^8R^{19}$;

where E is a protecting or activating group compatible with ester, phosphoester, phosphonoester, or phosphonamide bond formation, $O^-$, OH, $R^{20}$, $NR^{20}R^{21}$, or $OR^{20}$; and where each $R^{18}$, $R^{19}$, $R^{20}$, and $R^{21}$ is, independently, hydrogen, alkyl, an amino protecting group, a reporter group, an intercalator, a chelator, a peptide, a protein, a carbohydrate, a lipid, a steroid, a nucleotide or oligonucleotide, or a soluble or nonsoluble polymer.

Another monomer of the present invention, herein referred to as an aryl phosphono peptide nucleic acid monomer or "pPNA-Ar-1" monomer, comprises the structure given by the formula:

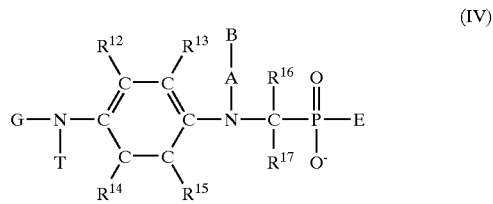
(IV)

where B is H, a naturally occurring nucleobase, a non-naturally occurring nucleobase, an aromatic moiety, a DNA intercalator, a nucleobase-binding group, a heterocyclic moiety, or a reporter group, wherein amino groups are, optionally, protected by amino protecting groups;

where A is a group of formula (Ia), (Ib), or (Ic);

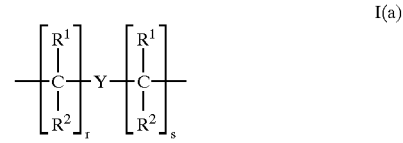
I(a)

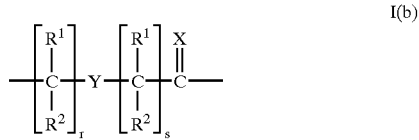
I(b)

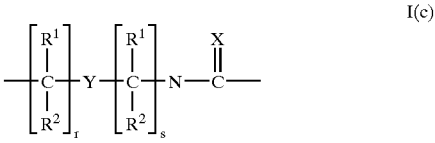
I(c)

where r and s are, for I(a) and I(b), independently of one another, values from 0 to 5 and are, for I(c), independently of one another, values from 1 to 5;

where each $R^1$ and each $R^2$ is, independently, hydrogen, $(C_1-C_6)$alkyl, hydroxy-, alkoxy-, amino-, or alkythio-substituted $(C_1-C_6)$alkyl, hydroxy, alkoxy, alkylthio, amino, or halogen;

where each of $R^3$, $R^4$, and $R^5$, is, independently, hydrogen, $(C_1-C_6)$alkyl, hydroxy-, alkoxy-, amino-, or alkythio-substituted $(C_1-C_6)$alkyl, hydroxy, amino, alkoxy, aryl, aralkyl, heteroaryl;

Y is a single bond, O, S, or $NR^4$; and

X is O, S, Se, $NR^5$, $CH_2$, or $C(CH_3)_2$;

where each of $R^{12}$, $R^{13}$, $R^{14}$, and $R^{15}$, is, independently, hydrogen, $(C_1-C_6)$alkyl, hydroxy-, alkoxy-, amino-, or alkythio-substituted $(C_1-C_6)$alkyl, hydroxy, alkoxy, alkylthio, amino, aryl, aralkyl, heteroaryl, or halogen;

where each of $R^{16}$ and $R^{17}$, is, independently, hydrogen, $(C_1-C_6)$alkyl, hydroxy-, alkoxy-, amino-, or alkythio-substituted $(C_1-C_6)$alkyl, aryl, aralkyl, or heteroaryl;

where E is a protecting or activating group compatible with the conditions of amide, phosphonoamide, or phosphonoester bond formation, O⁻, $R^{20}$, $NR^{20}R^{21}$, or $OR^{20}$;

where G is a protecting group compatible with the conditions of phosphonoester, phospho- or phosphonoamide bond formation, or $R^{20}$;

where T is hydrogen, hydroxy, alkoxy, $(C_1-C_6)$alkyl, hydroxy-, alkoxy-, amino-, or alkythio-substituted $(C_1-C_6)$alkyl, alkylthio, aryl, aralkyl, heteroaryl, or amino; and where each $R^{18}$, $R^{19}$, $R^{20}$, and $R^{21}$ is, independently, hydrogen, alkyl, an amino protecting group, a reporter group, an intercalator, a linker, a chelator, a peptide, a protein, a carbohydrate, a lipid, a steroid, a nucleotide or oligonucleotide, or a soluble or nonsoluble polymer.

Another monomer of the present invention, herein referred to as a serine peptide nucleic acid monomer or "SerNA" monomer, comprises the structure given by the formula:

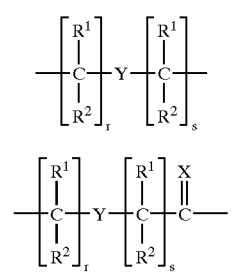

(V)

where B is H, a naturally occurring nucleobase, a non-naturally occurring nucleobase, an aromatic moiety, a DNA intercalator, a nucleobase-binding group, a heterocyclic moiety, or a reporter group, wherein amino groups are, optionally, protected by amino protecting groups;

where A is a group of formula (Ia), (Ib), or (Ic);

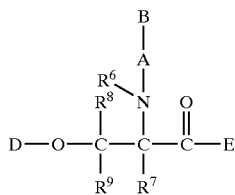

I(a)

I(b)

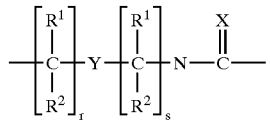

I(c)

where r and s are, for I(a) and I(b), independently of one another, values from 0 to 5 and are, for I(c), independently of one another, values from 1 to 5;

where each $R^1$ and each $R^2$ is, independently, hydrogen, $(C_1-C_6)$alkyl, hydroxy-, alkoxy-, amino-, or alkythio-substituted $(C_1-C_6)$alkyl, hydroxy, alkoxy, alkylthio, amino, or halogen;

where each of $R^3$, $R^4$, and $R^5$, is, independently, hydrogen, $(C_1-C_6)$alkyl, hydroxy-, alkoxy-, amino-, or alkythio-substituted $(C_1-C_6)$alkyl, hydroxy, amino, alkoxy, aryl, aralkyl, heteroaryl;

Y is a single bond, O, S, or $NR^4$; and

X is O, S, Se, $NR^5$, $CH_2$, or $C(CH_3)_2$;

where $R^6$ is hydrogen, $(C_1-C_6)$alkyl, hydroxy-, alkoxy-, amino-, or alkythio-substituted $(C_1-C_6)$alkyl, hydroxy, alkoxy, alkylthio, amino, aryl, aralkyl, heteroaryl, or an amino acid side chain;

where each of $R^7$, $R^8$, and $R^9$ is, independently, hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where D is a protecting group compatible with the conditions of ester, amide, or phosphonoester bond formation, $R^{18}$, or $NR^8R^{19}$;

where E is O⁻, a protecting group compatible with ester, phosphoester, or phosphonoester bond formation, $R^{20}$, $NR^{20}R^{21}$, or $OR^{20}$; and where each $R^{18}$, $R^{19}$, $R^{20}$, and $R^{21}$ is, independently, hydrogen, alkyl, an amino protecting group, a reporter group, an intercalator, a chelator, a linker, a peptide, a protein, a carbohydrate, a lipid, a steroid, a nucleotide or oligonucleotide, or a soluble or nonsoluble polymer.

A base position (B in formulas (I), (II), (III), (IV), and (V)) of a nucleotide analogue of the present invention preferably includes a nucleobase, where a nucleobase can be a naturally occurring nucleobase, such as, but not limited to, adenine, guanine, cytosine, thymine, uracil, inosine, 5-methylcytosine, xanthine, and hypoxanthine, or can be a non-naturally occurring nucleobase or nucleobase analogue, such as, but not limited to azaadenine, azacytosine, azaguanine, 5-bromo-uracil, thiouracil, bromothymine, 7,8-dimethyl alloxazine, and 2,6-diaminopurine. Alternatively or in addition, a nucleotide analogue monomer of the present invention can optionally comprise at a base position (B) at least one reporter group, aromatic ring, or intercalator, such as for example, fluorescamine, OPA, NDA, JOE, FAM, rhodamine, pyrene, 4-nitro-1,8-naphthylamide, ethidium bromide, acridine orange, thiazole orange, TOTO-1, YOYO-1, psoralen, actinomycin D, or angelicin (see, for example, Goodchild, J. Bioconjugate Chemistry 1: 165 (1990)). A nucleotide analogue of the present invention can also optionally comprise at the base position H, OH, an alkynoyl, an alkyl, an aromatic group, or nucleobase-binding moiety. Moieties at a base position of an oligonucleotide analogue monomer can also be specific binding members, such as hapten, biotin, polyhistidine, etc. Moieties at the base position of an oligonucleotide analogue momomer of the present invention can incorporate detectable labels, such as, but not limited to, fluorescent labels, radioisotope labels, spin labels, or mass-altered labels.

A moiety at a base position of an oligonucleotide analogue monomer can optionally comprise one or more protecting groups. Such protecting groups can optionally but preferably be removed when synthesis of an oligonucleotide analogue diner or oligomer is complete. Protecting groups for protecting various chemical groups that are compatible with the conditions of oligonucleotide analogue synthesis are known in the art (see, for example, Sonveaux, *Protecting Groups in Oligonucleotide Synthesis* in Methods in Molecular Biology: Protocols for Oligonucleotide Conjugates, S. Agrawal, ed. Humana Press (1994)). Of particular relevance are protecting groups, such as, but not limited to, acyl groups, that can be used to protect the extracyclic amino groups of nucleobases such as adenine, cytosine, and guanine.

In selecting moieties for base positions in nucleic acid analogue monomers, one can be guided by the principal that any moiety that will permit the hybridization of the single-stranded oligonucleotide analogue comprising the monomer to specifically bind to a single or double-stranded nucleic acid molecule (by Watson-Crick base-pairing in the first instance, and by Hoogsteen base-pairing in the second instance) is permissible. Thus, it is possible to synthesize oligonucleotide analogue monomers of the present invention with moieties at B positions that have desirable properties (as ligands or labels, for example) and screen for the ability of oligonucleotide analogue oligomers incorporating one or more such monomers to hybridize to DNA or RNA using methods known in the art, for example, by monitoring the formation of double-stranded molecules by UV spectrometry, or by detecting binding of labeled nucleic acid molecules to oligonucleotide analogues fixed to a solid support. In this regard, it can also be recognized that certain conditions that determine, at least in part, the hybridization of synthetic oligonucleotide analogues of the present invention to nucleic acid molecules can be altered, such as for example, by making longer probes, or altering temperature or salt conditions, to permit hybridization of oligonucleotide analogues that incorporate one or more monomers of the present invention at the B position. It is also possible to position one or more monomers with one or more moieties of interest at the B position so that the effect on hybridization of the moiety or moieties at one or more B positions is minimal, for example, at one or more terminuses of an oligonucleotide analogue oligomer, or by positioning one or more monomers in the center of a sequence with high binding affinity for a nucleic acid sequence of interest. Thus, a great number and variety of groups can potentially be incorporated in the B position of a monomer of the present invention.

Similarly, a wide variety of side groups represented by "R" and (in the case of Monomer (IV)) "T" can be chosen and selected based on the ability of oligomers comprising monomers of the present invention to hybridize to nucleic acid sequences under the desired conditions.

Other important considerations in the selection and testing of R, T, and B groups and moieties include the stability and reactivity of resulting monomer that includes a given group or moiety at a given R position or B position. The stability of monomers, and of dimers and oligomers that incorporate monomers can be tested by methods known in the art, including, but not limited to, spectrometry and NMR. The stability of monomers of the present invention and of dimers and oligomers that incorporate monomers can be influenced by the addition of, for example, salts, reducing agents, acids, bases, or buffers, to solutions that comprise such oligonucleotide analogue compounds of the present invention, where achieving stability of a compound that comprises a particular group or moiety at an R or B position is desirable.

Monomers of the present invention can comprise protecting groups. Monomers of the present invention that can be used in synthesis of oligonucleotide analogue dimers and oligomers preferably have protecting groups at the D position. Preferably, a protecting group at the D position is a hydroxyl protecting group compatible with amide, ester, phosphoester or phoshoester bond formation, such that it is able to prevent chemical reaction of the oxygen it is bound to during one or more reactions that forms at least one of these bonds, but that is not a requirement of the present invention. Preferred protecting groups for the D position include, but are not limited to, dimethoxytrityl (DMTr), monomethoxytrityl (MMTr), trityl (Tr), tert-butyl dimethyl silyl (TBDMS), 9-fluorenylmethyloxycarbonyl (Fmoc) and tetrahydropyranyl. Monomers of the present invention that have at the D position a wide variety of R groups, including complex molecules such as linkers, polymers, labels, reporter groups, nucleic acids, peptides, proteins, carbohydrates, lipids, steroids, specific binding members, and the like are also within the scope of the present invention. Monomers comprising such moieties can optionally be incorporated at a terminus of an oligonucleotide analogue or oligonucleotide.

The E position of a monomer of the present invention can be $O^-$, OH, or can comprise protecting or activating groups. Preferably, a protecting group at the E position of monomers (I) and (V) is a carboxy protecting group that is compatible with ester, phosphoester, or phosphonoester bond formation, such that it is able to prevent chemical reactions of the carboxyl group it is bound to during one or more reactions that forms at least one of these bonds (such as at the D positions of these monomers), but that is not a requirement of the present invention. Preferred protecting groups for the E position of monomers (I) and (V) include, but are not limited to, $CH_3$, tert-butyl dimethyl silyl (TBDMS), 9-fluorenylmethyl, 2-cyanoethyl, 2-(4-nitrophenyl)ethyl and tetrahydropyranyl.

Preferably, a protecting group at the E position of monomers (II), (III), (IV) is a phosphonate protecting group compatible with phosphonamide and amide bond formation, such that the protecting groups are able to prevent chemical reactions of the phosphate during reactions that form these bonds at the D position, but that is not a requirement of the present invention. Where the E position of a monomer of the present invention comprises an activating group, an activating group preferably can also be a protecting group. For example, in certain preferred embodiments of the present invention, the E position of monomers (II), (III), and (IV) can comprise a protecting/activating group that prevents reaction of the phosphate during the formation of bonds at the D position (such as ester, phosphoester, phosphonamide, or amide bonds) and activates the phosphate for the formation of phosphonoester or phosphonamide bonds. Preferred protecting groups for the E position of monomers (II), (III), and (IV) include, but are not limited to, $CH_3$, tert-butyl dimethyl silyl (TBDMS), 9-fluorenylmethyl, 2-cyanoethyl, 2-(4-nitrophenyl)ethyl and tetrahydropyranyl. Preferred protecting/activating groups for the E position of monomers (II), (III), and (IV) include, but are not limited to, derivatives of 1-oxido-4-alkoxy-2-picolyl derivatives such as 1-oxydo-4-methoxy-2-picolyloxy, phenoxy, 2-methylphenoxy, and 2-cyanoethoxy.

Monomers of the present invention can also have at the D position a wide variety of R groups, including simple and complex molecules such as linkers, polymers, labels, reporter groups, nucleic acids, peptides, proteins, carbohydrates, lipids, steroids, specific binding members, and the like. Monomers comprising such moieties can optionally be incorporated at a terminus of an oligonucleotide analogue or oligonucleotide.

Monomers of the present invention that conform to formula (IV) can also have protecting groups at the G position. The G position preferably comprises an amino protecting group, more preferably an amino protecting group that is compatible with reactions that form phosphonoester or phosphonamide bonds, for example, DMTr, MMTr, Tr, or Fmoc. In the alternative, a monomer of the present invention can have at the G position a wide variety of R groups, including simple or complex molecules such as linkers, polymers, labels, reporter groups, nucleic acids, peptides, proteins, carbohydrates, lipids, steroids, specific binding members, and the like. Monomers comprising such moieties can optionally be incorporated at a terminus of an oligonucleotide analogue or oligonucleotide.

Preferred monomers of the present invention that conform to the formula of monomer (I) include 4-O-Monomethoxytrityl-N-(thymin-1-ylacetyl)-L-hydroxyproline, 4-O-Monomethoxytrityl-N-(N(4)-benzoylcytosinyl-N(1)-acetyl)-L-hydroxyproline, 4-O-Monomethoxytrityl-N-(N(6)-benzoyladenyl-N(9)-acetyl)-L-hydroxyproline, and 4-O-Monomethoxytrityl-N-(N(6)-isobutanoylguanine-N(9)-acetyl)-L-hydroxyproline, and other monomers based on L-4-trans-hydroxyproline that comprise other nucleobases.

Preferred monomers of the present invention that conform to the formula of monomer (V) include 4-O-Monomethoxytrityl-N-(thymin-1-ylacetyl)-L-serine, 4-O-Monomethoxytrityl-N-(N(4)-benzoylcytosinyl-N(1)-acetyl)-L-serine, 4-O-Monomethoxytrityl-N-(N(6)-benzoyladenyl-N(9)-acetyl)-L-serine, and 4-O-Monomethoxytrityl-N-(N(6)-isobutanoylguanine-N(9)-acetyl)-L-serine, and other monomers based on L-4-trans-serine that comprise other nucleobases.

Monomers of the present invention can be synthesized by any appropriate methods known in the arts of organic and bioorganic chemistry. For example, a heterocyclic base can be introduced into the methyl ester of a backbone moiety such as L-4-trans-hydroxyproline (or a derivative of hydroxyproline) for monomers conforming to the formulas (I), (II), or (III); L-serine (or a derivative of serine) for monomers conforming to formula (V); or the aryl-based molecule of monomer (IV); using a methylene carboxylic acid of the appropriate base, where bases such as, but not limited to, adenine, cytosine, or guanine, that comprise exocyclic amino groups preferably have their exocyclic amino groups protected (for example, $N^4$-benzoyl-cytosine, $N^2$-isobutyrylguanine or $N^6$-benzoyladenine). Protection of the exocyclic amino groups can be effected by acylation or alkylation using groups such as, but are not limited to benzoyl, butyryl, benzyloxycarbonyl, anisoyl, 4-tert-butylbenzoyl (Will et al., *Tetrahedron* 51: 12069 (1995)), or 4-monomethoxytrityl (Briepohl et al., *Bioorg. & Med. Chem. Lett.* 6: 665 (1996)).

A coupling agent can be used to condense the nucleobase carboxylic acid with a backbone molecule using methods such as those described in Efimov et al., Bioorg. Khim. 24: 696–709 (1998); Finn et al., Nucleic Acids Res. 24: 3357–3364 (1996); and Efimov, et al., Nucleic Acids Res. 26: 566–575 (1998). Coupling agents that can be used to condense a carboxylic acid with an amino group to form an amide bond between a carboxylic acid substituted with a heterocyclic base and an amino acid (including a modified or derivatized amino acid) or backbone moiety of the present invention include, but are not limited to, N,N'-dicyclohexylcarbodiimide (DCC) (Sheehan and Hess (1955) *J. Amer. Chem. Soc.* 77: 1067), TOTU (Briepohl et al., *Bioorg. & Med. Chem. Lett.* 6: 665 (1996), TopPipU (Heinklein et al., in Girault and Andreu (eds.) *The Peptides, 21st European Peptide Symposium*, ESCOM, Leiden, pp. 67–77 (1990) and Finn et al., Nucleic Acids Res. 24: 3357–3364 (1996)) PyBroP (Coste et al., Tetrahedron Lett. 31: 669–672 (1990), DCC/HOBT, or a mixture of triphenylphosphine and $CCl_4$ (Takeuchi et al., Chem. Pharm. Bull. 22: 832–840 (1974).

For the synthesis of monomers (I), (II), (III), and (V), the free hydroxyl group of the hydroxyproline or serine backbone moiety can be protected, for example with a group such as dimethoxytrityl (DMTr), monomethoxytrityl (MMTr), trityl (Tr), tert-butyl dimethyl silyl (TBDMS), 9-fluorenylmethyloxycarbonyl (Fmoc), or tetrahydropyranyl. The ester protecting group can be removed, for example, with NaOH, DBU, $DBU/H_2O$, $NBu_4F \times nH_2O$.

The synthesis of 4-O-4,4'-monomethoxytrityl-N-(thymin-1-ylacetyl)-L-hydroxyproline, a monomer of the present invention described by formula (I), is described in Example 1. The synthesis of 4-O-4,4'-monomethoxytrityl-N-(N(6)-benzoyladenin-(9-ylacetyl)-L-hydroxyproline, another monomer of the present invention described by formula (I), is described in Example 2. The synthesis of 4-O-4,4'-monomethoxytrityl-N-(N(4)-benzoylcytosin-9-ylacetyl)-L-hydroxyproline, another monomer of the present invention described by formula (I), is described in Example 3. The synthesis of 4-O-4,4'-monomethoxytrityl-N-(N(2)-isobutyrylguanin-9-ylacetyl)-L-hydroxyproline, another monomer of the present invention described by formula (I), is described in Example 4.

The synthesis of 4-O-4,4'-monomethoxytrityl-N-(thymin-1-ylacetyl)-L-serine, a monomer described by formula (IV), is described in Example 5. The synthesis of 4-O-4,4'-monomethoxytrityl-N-(N(6)-benzoyladenin-9-ylacetyl)-L-serine, another monomer described by formula (II), is described in Example 6. The synthesis of 4-O-4,4'-monomethoxytrityl-N-(N(4)-benzoylcytosin-9-ylacetyl)-L-serine, another monomer described by formula (II), is described in Example 7. The synthesis of 4-O-4,4'-monomethoxytrityl-N-(N(2)-isobutyrylguanin-9-ylacetyl)-L-serine, another monomer described by formula (II), is described in Example 8. Dimer compositions The present invention also comprises dimer compositions that can be incorporated into oligonucleotides and oligonucleotide analogues.

One dimer of the present invention, herein referred to as a hydroxyproline peptide nucleic acid-peptide nucleic acid dimer or "HypNA-PNA" dimer, comprises the structure given by the formula:

(VI)

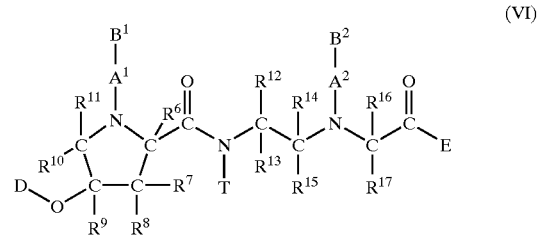

where each of $B^1$ and $B^2$ is, independently selected from the group of H, naturally occurring nucleobases, non-naturally occurring nucleobases, aromatic moieties, DNA intercalators, nucleobase-binding groups, heterocyclic moieties, and reporter ligands, wherein amino groups are, optionally, protected by amino protecting groups;

where each of $A^1$ and $A^2$ is, independently, a group of formula (Ia), (Ib), or (Ic);

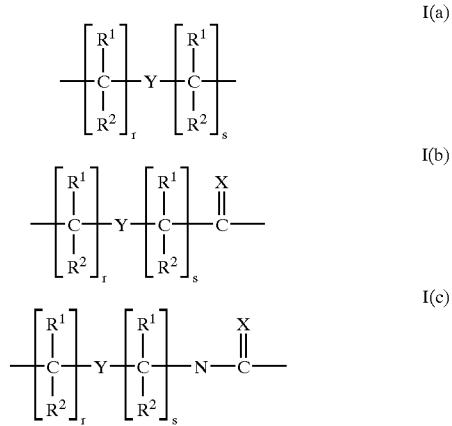

where r and s are, for I(a) and I(b), independently of one another, values from 0 to 5 and are, for I(c), independently of one another, values from 1 to 5;

where each $R^1$ and each $R^2$ is, independently, hydrogen, $(C_1-C_6)$alkyl, hydroxy-, alkoxy-, amino-, or alkythio-substituted $(C_1-C_6)$alkyl, hydroxy, alkoxy, alkylthio, amino, or halogen;

where each $R^3$, $R^4$, and $R^5$, is, independently, hydrogen, $(C_1-C_6)$alkyl, hydroxy-, alkoxy-, amino-, or alkythio-substituted $(C_1-C_6)$alkyl, hydroxy, amino, alkoxy, aryl, aralkyl, heteroaryl, or an amino acid side chain;

Y is a single bond, O, S, or $NR^4$; and

X is O, S, Se, $NR^5$, $CH_2$, or $C(CH_3)_2$;

where $R^6$ is hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where $R^7$ is hydrogen, hydroxy, alkoxy, $(C_1-C_6)$alkyl, hydroxy-, alkoxy-, amino-, or alkythio-substituted $(C_1-C_6)$alkyl, alkylthio, aryl, aralkyl, heteroaryl, amino, or halogen, and $R^8$ is hydrogen, $(C_1-C_6)$alkyl, hydroxy-, alkoxy-, amino-, or alkythio-substituted $(C_1-C_6)$alkyl, aryl, aralkyl, heteroaryl;

or $R^7$ is hydrogen, $(C_1-C_6)$alkyl, hydroxy-, alkoxy-, amino-, or alkythio-substituted $(C_1-C_6)$alkyl, alkoxy, aryl, aralkyl, or heteroaryl, and $R^8$ is hydrogen, hydroxy, alkoxy, alkthio, amino, $(C_1-C_6)$alkyl, hydroxy-, alkoxy-, amino-, or alkythio-substituted $C_1-C_6$)alkyl, aryl, aralkyl, heteroaryl, or halogen;

where $R^9$ is hydrogen, alkoxy, $(C_1-C_6)$alkyl, hydroxy-, alkoxy-, amino-, or alkythio-substituted $(C_1-C_6)$alkyl, aryl, arylkyl, or heteroaryl;

where each of $R^{10}$ and each $R^{11}$ is, independently, hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where each $R^{12}$, $R^3$, $R^{14}$, $R^{15}$, $R^{16}$, and $R^{17}$ is, independently, hydrogen, $(C_1-C_6)$alkyl, hydroxy-, alkoxy-, amino-, or alkythio-substituted $(C_1-C_6)$alkyl, hydroxy, amino, alkoxy, alkylthio, aryl, aralkyl, heteroaryl, or an amino acid side chain;

where D is a protecting group compatible with the conditions of ester, amide, or phosphonoester bond formation, $R^{18}$, or $NR^{18}R^{19}$;

where E is $O^-$, a protecting or activating group compatible with ester, phosphoester, or phosphonoester bond formation, $R^{20}$, $NR^{20}R^{21}$, or $OR^{20}$;

where T is hydrogen, hydroxy, alkoxy, $(C_1-C_6)$alkyl, hydroxy-, alkoxy-, amino-, or alkythio-substituted $(C_1-C_6)$ alkyl, alkylthio, aryl, aralkyl, heteroaryl, or amino; and where each $R^{18}$, $R^{19}$, $R^{20}$, and $R^{21}$ is, independently, hydrogen, alkyl, an amino protecting group, a reporter group, an intercalator, a linker, a chelator, a peptide, a protein, a carbohydrate, a lipid, a steroid, a nucleotide or oligonucleotide, or a soluble or nonsoluble polymer.

Another dimer of the present invention, herein referred to as a peptide nucleic acid-hydroxyproline peptide nucleic acid dimer or "PNA-HypNA" dimer, comprises the structure given by the formula:

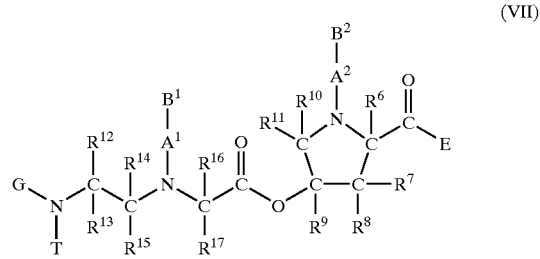

where each of $B^1$ and $B^2$ is, independently, selected from the group of H, naturally occurring nucleobases, non-naturally occurring nucleobases, aromatic moieties, DNA intercalators, nucleobase-binding groups, heterocyclic moieties, and reporter ligands, wherein amino groups are, optionally, protected by amino protecting groups;

where each of $A^1$ and $A^2$ is, independently, a group of formula (Ia), (Ib), or (Ic);

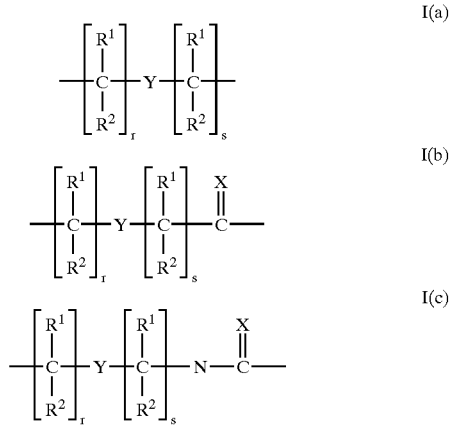

where r and s are, for I(a) and I(b), independently of one another, values from 0 to 5 and are, for I(c), independently of one another, values from 1 to 5;

where each $R^1$ and each $R^2$ is, independently, hydrogen, $(C_1-C_6)$alkyl, hydroxy-, alkoxy-, amino-, or alkythio-substituted $(C_1-C_6)$alkyl, hydroxy, alkoxy, alkylthio, amino, or halogen;

where each of $R^3$, $R^4$, and $R^5$, is, independently, hydrogen, $(C_1-C_6)$alkyl, hydroxy-, alkoxy-, amino-, or alkythio-substituted $(C_1-C_6)$alkyl, hydroxy, amino, alkoxy, aryl, aralkyl, heteroaryl, or an amino acid side chain;

Y is a single bond, O, S, or $NR^4$; and

X is O, S, Se, $NR^5$, $CH_2$, or $C(CH_3)_2$;

where $R^6$ is hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where $R^7$ is hydrogen, hydroxy, alkoxy, $(C_1-C_6)$alkyl, hydroxy-, alkoxy-, amino-, or alkythio-substituted $(C_1-C_6)$ alkyl, alkylthio, aryl, aralkyl, heteroaryl, amino, or halogen, and $R^8$ is hydrogen, $(C_1-C_6)$alkyl, hydroxy-, alkoxy-, amino-, or alkythio-substituted $(C_1-C_6)$alkyl, aryl, aralkyl, heteroaryl;

or $R^7$ is hydrogen, $(C_1-C_6)$alkyl, hydroxy-, alkoxy-, amino-, or alkythio-substituted $(C_1-C_6)$alkyl, alkoxy, aryl, aralkyl, or heteroaryl, and $R^8$ is hydrogen, hydroxy, alkoxy, alkythio, amino, $(C_1-C_6)$alkyl, hydroxy-, alkoxy-, amino-, or alkythio-substituted $C_1-C_6$)alkyl, aryl, aralkyl, heteroaryl, or halogen;

where $R^9$ is hydrogen, alkoxy, $(C_1-C_6)$alkyl, hydroxy-, alkoxy-, amino-, or alkythio-substituted $(C_1-C_6)$alkyl, aryl, arylkyl, or heteroaryl;

where each $R^{10}$ and each $R^{11}$ is, independently, hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where each of $R^2$, $R^{13}$, $R^{14}$, $R^{15}$, $R^{16}$, and $R^{17}$ is, independently, hydrogen, $(C_1-C_6)$alkyl, hydroxy-, alkoxy-, amino-, or alkythio-substituted $(C_1-C_6)$alkyl, hydroxy, amino, alkoxy, alkylthio, aryl, aralkyl, heteroaryl, or an amino acid side chain;

where G is an amino protecting group compatible with the conditions of phosphonoester, phospho- or phosphonoamide bond formation or $R^{20}$;

where E is $O^-$, $OCH_3$, a protecting or activating group compatible with ester, phosphoester, or phosphonoester bond formation, $R^{20}$, $NR^{20}R^{21}$, or $OR^{20}$;

T is hydrogen, hydroxy, alkoxy, $(C_1-C_6)$alkyl, hydroxy-, alkoxy-, amino-, or alkythio-substituted $(C_1-C_6)$alkyl, alkylthio, aryl, aralkyl, heteroaryl, or amino; and where each $R^{18}$, $R^{19}$, $R^{20}$, and $R^{21}$ is, independently, hydrogen, alkyl, an amino protecting group, a reporter group, an intercalator, a linker, a chelator, a peptide, a protein, a carbohydrate, a lipid, a steroid, a nucleotide or oligonucleotide, or a soluble or nonsoluble polymer.

Another dimer of the present invention, herein referred to as a hydroxyproline peptide nucleic acid-phosphono peptide nucleic acid dimer or "HypNA-pPNA" dimer, comprises the structure given by the formula:

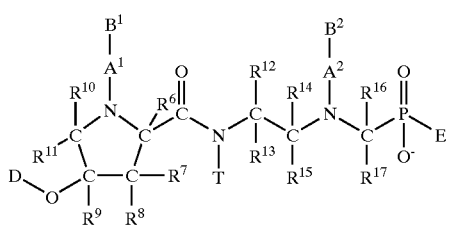

(VIII)

where each of $B^1$ and $B^2$ is, independently, H, a naturally occurring nucleobase, a non-naturally occurring nucleobase, an aromatic moiety, a DNA intercalator, a nucleobase-binding group, a heterocyclic moiety, or a reporter group, wherein amino groups are, optionally, protected by amino protecting groups;

where each of $A^1$ and $A^2$ is, independently, a group of formula (Ia), (Ib), or (Ic);

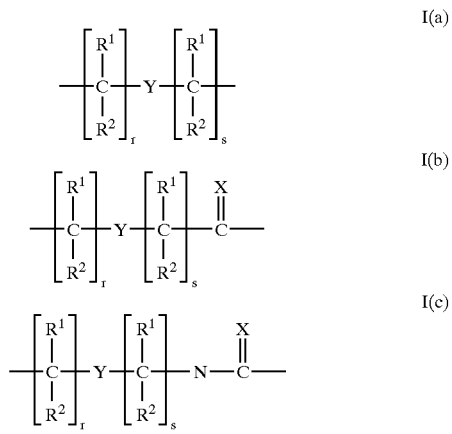

where r and s are, for I(a) and I(b), independently of one another, values from 0 to 5 and are, for I(c), independently of one another, values from 1 to 5;

where each $R^1$ and each $R^2$ is, independently, hydrogen, $(C_1-C_6)$alkyl, hydroxy-, alkoxy-, amino-, or alkythio-substituted $(C_1-C_6)$alkyl, hydroxy, alkoxy, alkylthio, amino, or halogen;

where each of $R^3$, $R^4$, and $R^5$, is, independently, hydrogen, $(C_1-C_6)$alkyl, hydroxy-, alkoxy-, amino-, or alkythio-substituted $(C_1-C_6)$alkyl, hydroxy, amino, alkoxy, aryl, aralkyl, heteroaryl, or an amino acid side chain;

Y is a single bond, O, S, or $NR^4$; and

X is O, S, Se, $NR^5$, $CH_2$, or $C(CH_3)_2$;

where $R^6$ is hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where $R^7$ is hydrogen, hydroxy, alkoxy, $(C_1-C_6)$alkyl, hydroxy-, alkoxy-, amino-, or alkythio-substituted $(C_1-C_6)$ alkyl, alkylthio, aryl, aralkyl, heteroaryl, amino, or halogen, and $R^8$ is hydrogen, $(C_1-C_6)$alkyl, hydroxy-, alkoxy-, amino-, or alkythio-substituted $(C_1-C_6)$alkyl, aryl, aralkyl, heteroaryl;

or $R^7$ is hydrogen, $(C_1-C_6)$alkyl, hydroxy-, alkoxy-, amino-, or alkythio-substituted $(C_1-C_6)$alkyl, alkoxy, aryl, aralkyl, or heteroaryl, and $R^8$ is hydrogen, hydroxy, alkoxy, alkthio, amino, $(C_1-C_6)$alkyl, hydroxy-, alkoxy-, amino-, or alkythio-substituted $(C_1-C_6)$alkyl, aryl, aralkyl, heteroaryl, or halogen;

where $R^9$ is hydrogen, alkoxy, $(C_1-C_6)$alkyl, hydroxy-, alkoxy-, amino-, or alkythio-substituted $(C_1-C_6)$alkyl, aryl, arylkyl, or heteroaryl; where each of $R^{10}$ and $R^{11}$ is, independently, hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where each of $R^2$, $R-R^{14}$, $R^{15}$, $R^6$, and $R^{17}$ is, independently, hydrogen, $(C_1-C_6)$alkyl, hydroxy-, alkoxy-, amino-, or alkythio-substituted $(C_1-C_6)$alkyl, hydroxy, amino, alkoxy, alkylthio, aryl, aralkyl, heteroaryl, or an amino acid side chain;

where D is a protecting group compatible with the conditions of ester, amide, or phosphonoester bond formation, $R^{18}$, or $NR^{18}R^{19}$;

where E is $O^-$, $OCH_3$, a protecting or activating group compatible with ester, phosphoester, phosphonoester or phosphonamide bond formation, $R^{20}$, $NR^{20}R^{21}$, or $OR^{20}$;

T is hydrogen, hydroxy, alkoxy, $(C_1-C_6)$alkyl, hydroxy-, alkoxy-, amino-, or alkythio-substituted $(C_1-C_6)$alkyl, alkylthio, aryl, aralkyl, heteroaryl, or amino; and where each $R^{18}$, $R^{19}$, $R^{20}$, and $R^{21}$ is, independently, hydrogen, alkyl, an amino protecting group, a reporter group, an intercalator, a linker, a chelator, a peptide, a protein, a carbohydrate, a lipid, a steroid, a nucleotide or oligonucleotide, or a soluble or nonsoluble polymer.

Another dimer of the present invention, herein referred to as a phosphono peptide nucleic acid-hydroxyproline peptide nucleic acid dimer or "pPNA-HypNA" dimer, comprises the structure given by the formula:

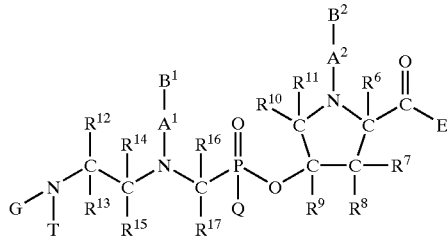

(IX)

where each of $B^1$ and $B^2$ is, independently, H, a naturally occurring nucleobase, a non-naturally occurring nucleobase, an aromatic moiety, a DNA intercalator, a nucleobase-binding group, a heterocyclic moiety, or a reporter group, wherein amino groups are, optionally, protected by amino protecting groups;

where each of $A^1$ and $A^2$ is, independently, a group of formula (Ia), (Ib), or (Ic);

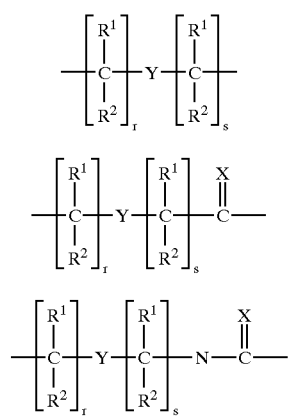

I(a)

I(b)

I(c)

where r and s are, for I(a) and I(b), independently of one another, values from 0 to 5 and are, for I(c), independently of one another, values from 1 to 5;

where each $R^1$ and each $R^2$ is, independently, hydrogen, $(C_1-C_6)$alkyl, hydroxy-, alkoxy-, amino-, or alkythio-substituted $(C_1-C_6)$alkyl, hydroxy, alkoxy, alkylthio, amino, or halogen;

where each of $R^3$, $R^4$, and $R^5$, is, independently, hydrogen, $(C_1-C_6)$alkyl, hydroxy-, alkoxy-, amino-, or alkythio-substituted $(C_1-C_6)$alkyl, hydroxy, amino, alkoxy, aryl, aralkyl, heteroaryl, or an amino acid side chain;

Y is a single bond, O, S, or $NR^4$; and

X is O, S, Se, $NR^5$, $CH_2$, or $C(CH_3)_2$;

where $R^6$ is hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where $R^7$ is hydrogen, hydroxy, alkoxy, $(C_1-C_6)$alkyl, hydroxy-, alkoxy-, amino-, or alkythio-substituted $(C_1-C_6)$ alkyl, alkylthio, aryl, aralkyl, heteroaryl, amino, or halogen, and $R^8$ is hydrogen, $(C_1-C_6)$alkyl, hydroxy-, alkoxy-, amino-, or alkythio-substituted $(C_1-C_6)$alkyl, aryl, aralkyl, heteroaryl;

or $R^7$ is hydrogen, $(C_1-C_6)$alkyl, hydroxy-, alkoxy-, amino-, or alkythio-substituted $(C_1-C_6)$alkyl, alkoxy, aryl, aralkyl, or heteroaryl, and $R^8$ is hydrogen, hydroxy, alkoxy, alkthio, amino, $(C_1-C_6)$alkyl, hydroxy-, alkoxy-, amino-, or alkythio-substituted $(C_1-C_6)$alkyl, aryl, aralkyl, heteroaryl, or halogen;

where $R^9$ is hydrogen, alkoxy, $(C_1-C_6)$alkyl, hydroxy-, alkoxy-, amino-, or alkythio-substituted $(C_1-C_6)$alkyl, aryl, arylkyl, or heteroaryl;

where each of $R^{10}$ and $R^{11}$ is, independently, hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where each of $R^{12}$, $R^{13}$, $R^{14}$, $R^{15}$, $R^{16}$, and $R^{17}$ is, independently, hydrogen, $(C_1-C_6)$alkyl, hydroxy-, alkoxy-, amino-, or alkythio-substituted $(C_1-C_6)$alkyl, hydroxy, amino, alkoxy, alkylthio, aryl, aralkyl, heteroaryl, or an amino acid side chain;

where G is a protecting group compatible with the conditions of phosphonoester, phospho- or phosphonoamide bond formation or $R^{20}$;

where E is $O^-$, $OCH_3$, a protecting or activating group compatible with ester, phosphoester, or phosphonoester bond formation, $R^{20}$, $NR^{20}R^{21}$, or $OR^{20}$;

where Q is a protecting or activating group compatible with the conditions of amide, ester, phosphonoester, phosphonoamide bond formation;

T is hydrogen, hydroxy, alkoxy, $(C_1-C_6)$alkyl, hydroxy-, alkoxy-, amino-, or alkythio-substituted $(C_1-C_6)$alkyl, alkylthio, aryl, aralkyl, heteroaryl, or amino; and where each $R^{18}$, $R^{19}$, $R^{20}$, and $R^{21}$ is, independently, hydrogen, alkyl, an amino protecting group, a reporter group, an intercalator, a linker, a chelator, a peptide, a protein, a carbohydrate, a lipid, a steroid, a nucleotide or oligonucleotide, or a soluble or nonsoluble polymer.

Another dimer of the present invention, herein referred to as a serine peptide nucleic acid-phosphono peptide nucleic acid dimer or "SerNA-pPNA" dimer, comprises the structure given by the formula:

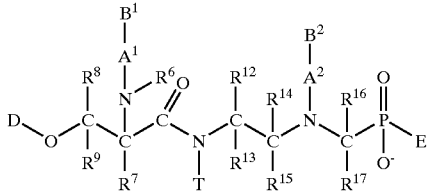

(X)

where each of $B^1$ and $B^2$ is, independently, H, a naturally occurring nucleobase, a non-naturally occurring nucleobase, an aromatic moiety, a DNA intercalator, a nucleobase-binding group, a heterocyclic moiety, or a reporter group, wherein amino groups are, optionally, protected by amino protecting groups;

where each of $A^1$ and $A^2$ is, independently, a group of formula (Ia), (Ib), or (Ic);

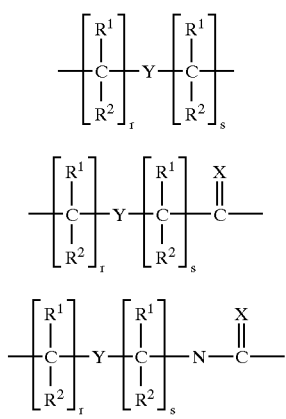

I(a)

I(b)

I(c)

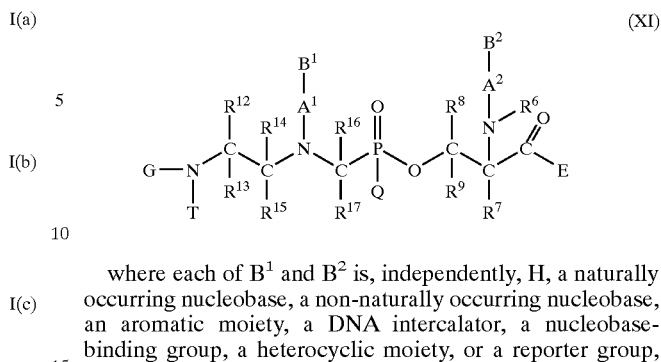

(XI)

where each of $B^1$ and $B^2$ is, independently, H, a naturally occurring nucleobase, a non-naturally occurring nucleobase, an aromatic moiety, a DNA intercalator, a nucleobase-binding group, a heterocyclic moiety, or a reporter group, wherein amino groups are, optionally, protected by amino protecting groups;

where each of $A^1$ and $A^2$ is, independently, a group of formula (Ia), (Ib), or (Ic);

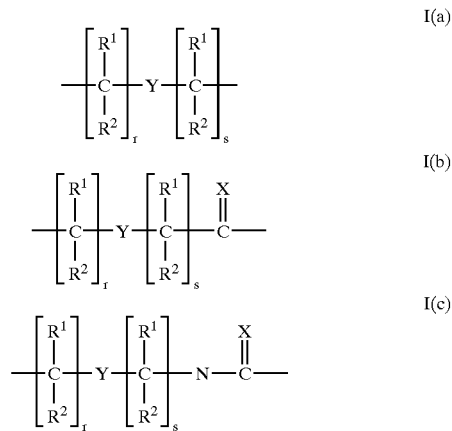

I(a)

I(b)

I(c)

where r and s are, for I(a) and I(b), independently of one another, values from 0 to 5 and are, for I(c), independently of one another, values from 1 to 5;

where each $R^1$ and each $R^2$ is, independently, hydrogen, $(C_1-C_6)$alkyl, hydroxy-, alkoxy-, amino-, or alkythio-substituted $(C_1-C_6)$alkyl, hydroxy, alkoxy, alkylthio, amino, or halogen;

where each of $R^3$, $R^4$, and $R^5$, is, independently, hydrogen, $(C_1-C_6)$alkyl, hydroxy-, alkoxy-, amino-, or alkythio-substituted $(C_1-C_6)$alkyl, hydroxy, amino, alkoxy, aryl, aralkyl, heteroaryl;

Y is a single bond, O, S, or $NR^4$; and

X is O, S, Se, $NR^5$, $CH_2$, or $C(CH_3)_2$;

where $R^6$ is hydrogen, $(C_1-C_6)$alkyl, hydroxy-, alkoxy-, amino-, or alkythio-substituted $(C_1-C_6)$alkyl, hydroxy, alkoxy, alkylthio, amino, aryl, aralkyl, heteroaryl, or an amino acid side chain;

where each of $R^7$, $R^8$, and $R^9$ is, independently, hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where each of $R^{12}$, $R^{13}$, $R^{14}$, $R^{15}$, $R^{16}$, and $R^{17}$ is, independently, hydrogen, $(C_1-C_6)$alkyl, hydroxy-, alkoxy-, amino-, or alkythio-substituted $(C_1-C_6)$alkyl, hydroxy, alkoxy, alkylthio, aryl, aralkyl, heteroaryl, or an amino acid side chain;

where D is hydrogen, a protecting group compatible with the conditions of ester, phosphoester or phosphonoester bond formation, $R^{18}$, or $NR^{18}R^{19}$;

where E is $O^-$, $OCH_3$, a protecting or activating group compatible with amide or ester bond formation, $R^{20}$, $NR^{20}R^{21}$, or $OR^{20}$;

T is hydrogen, hydroxy, alkoxy, $(C_1-C_6)$alkyl, hydroxy-, alkoxy-, amino-, or alkythio-substituted $(C_1-C_6)$alkyl, alkylthio, aryl, aralkyl, heteroaryl, or amino; and where each $R^{18}$, $R^{19}$, $R^{20}$, and $R^{21}$ is, independently, hydrogen, alkyl, an amino protecting group, a reporter group, an intercalator, a chelator, a peptide, a protein, a carbohydrate, a lipid, a steroid, a nucleotide or oligonucleotide, or a soluble or nonsoluble polymer.

Another dimer of the present invention, herein referred to as a phosphono peptide nucleic acid-serine peptide nucleic acid dimer or "pPNA-SerNA" dimer, comprises the structure given by the formula:

where r and s are, for I(a) and I(b), independently of one another, values from 0 to 5 and are, for I(c), independently of one another, values from 1 to 5;

where each $R^1$ and each $R^2$ is, independently, hydrogen, $(C_1-C_6)$alkyl, hydroxy-, alkoxy-, amino-, or alkythio-substituted $(C_1-C_6)$alkyl, hydroxy, alkoxy, alkylthio, amino, or halogen;

where each of $R^3$, $R^4$, and $R^5$, is, independently, hydrogen, $(C_1-C_6)$alkyl, hydroxy-, alkoxy-, amino-, or alkythio-substituted $(C_1-C_6)$alkyl, hydroxy, amino, alkoxy, aryl, aralkyl, heteroaryl;

Y is a single bond, O, S, or $NR^4$; and

X is O, S, Se, $NR^5$, $CH_2$, or $C(CH_3)_2$;

where each of $R^7$, $R^8$, and $R^9$ is, independently, hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where each of $R^{12}$, $R^{13}$, $R^{14}$, $R^{15}$, $R^{16}$, and $R^{17}$ is, independently, hydrogen, $(C_1-C_6)$alkyl, hydroxy-, alkoxy-, amino-, or alkythio-substituted $(C_1-C_6)$alkyl, hydroxy, amino, alkoxy, alkylthio, aryl, aralkyl, heteroaryl, or an amino acid side chain;

where G is a protecting group compatible with the conditions of phosphonoester, phospho- or phosphonoamide bond formation or $R^{20}$;

where E is $O^-$, $OCH_3$, a protecting or activating group compatible with ester, phosphoester, or phosphonoester bond formation, $R^{20}$, $NR^{20}R^{21}$, or $OR^{20}$;

where Q is a protecting or activating group compatible with the conditions of amide, ester, phosphonoester, phosphonoamide bond formation;

where T is hydrogen, hydroxy, alkoxy, $(C_1-C_6)$alkyl, hydroxy-, alkoxy-, amino-, or alkythio-substituted $(C_1-C_6)$ alkyl, alkylthio, aryl, aralkyl, heteroaryl, or amino; and where each $R^{18}$, $R^{19}$, $R^{20}$, and $R^{21}$ is, independently, hydrogen, alkyl, an amino protecting group, a reporter group, an intercalator, a linker, a chelator, a peptide, a protein, a carbohydrate, a lipid, a steroid, a nucleotide or oligonucleotide, or a soluble or nonsoluble polymer.

At least one base position ($B^1$ and $B^2$ in formulas (VI) through (XI)) of an oligonucleotide analogue dimer of the present invention preferably includes a nucleobase, where a nucleobase can be a naturally occurring nucleobase, such as, but not limited to, adenine, guanine, cytosine, thymine, uracil, inosine, 5-methylcytosine, xanthine, and hypoxanthine, or can be a non-naturally occurring nucleobase or nucleobase analogue, such as, but not limited to, azaadenine, azacytosine, azaguanine, 5-bromo-uracil, thiouracil, bromothymine, 7,8-dimethylalloxazine, and 2,6-diaminopurine. An oligonucleotide analogue dimer of the present invention can optionally comprise at at least one base position at least one reporter group, aromatic ring, or intercalator, such as for example, fluorescamine, OPA, NDA, JOE, FAM, rhodamine, pyrene, 4-nitro-1,8-naphthylamide, ethidium bromide, acridine orange, thiazole orange, TOTO-1, YOYO-1, psoralen, actinomycin D, or angelicin (see, for example, Goodchild, J. Bioconjugate Chemistry 1: 165 (1990). A dimer of the present invention can optionally comprise at at least one base position H, OH, an alkynoyl, an alkyl, an aromatic group, or nucleobase-binding moiety. Moieties at a base position of an oligonucleotide analogue dimer can also be specific binding members, such as hapten, biotin, polyhistidine, etc. Moieties at the base position of an oligonucleotide analogue dimer of the present invention can incorporate detectable labels, such as, but not limited to, fluorescent labels, radioisotope labels, spin labels, or mass-altered labels.

One or more moieties at one or more base positions of an oligonucleotide analogue dimer can optionally comprise one or more protecting groups. Such protecting groups can optionally but preferably be removed when synthesis of an oligonucleotide analogue dimer or oligomer is complete. Protecting groups for protecting various chemical groups that are compatible with the conditions of oligonucleotide analogue synthesis are known in the art (see, for example, Sonveaux, Protecting Groups in Oligonucleotide Synthesis in Methods in Molecular Biology: Protocols for Oligonucleotide Conjugates, S. Agrawal, ed. Humana Press (1994)). Of particular relevance are protecting groups that can be used to protect the extracyclic amino groups of nucleobases such as adenine, cytosine, and guanine. Protection of the exocyclic amino groups can be effected by acylation or alkylation using groups such as, but are not limited to benzoyl, butyryl, benzyloxycarbonyl, anisoyl, 4-tert-butylbenzoyl (Will et al., Tetrahedron 51: 12069 (1995)), or 4-monomethoxytrityl (Briepohl et al., Bioorg. & Med. Chem. Lett. 6: 665 (1996)).

In selecting groups for "B" positions in nucleic acid analogue dimers, one can be guided by the principal that any group that will permit the hybridization of the single-stranded oligonucleotide analogue comprising the dimer to specifically bind to a single or double-stranded nucleic acid molecule (by Watson-Crick base-pairing in the first instance, and by Hoogsteen base-pairing in the second instance) is permissible. Thus, it is possible to synthesize the oligonucleotide analogue dimers of the present invention having one or more moieties at one or more B positions that have desirable properties (as ligands or labels, for example) and screen for the ability of oligonucleotide analogue oligomers incorporating such dimers to hybridize to DNA or RNA using methods known in the art, for example, by monitoring the formation of double-stranded molecules by UV spectrometry, or by detecting binding of labeled nucleic acid molecules to oligonucleotide analogues fixed to a solid support. In this regard, it can also be recognized that certain conditions that determine, at least in part, the hybridization of synthetic oligonucleotide analogues of the present invention to nucleic acid molecules can be altered, such as for example, by making longer probes, or altering temperature or salt conditions, to permit hybridization of oligonucleotide analogues incorporating various moieties at one or more B positions. It is also possible to position one or more dimer with one or more moieties of interest at one or more B positions so that the effect on hybridization is minimal, for example, by positioning one or more dimers at one or more terminuses of an oligonucleotide analogue oligomer, or in the center of a sequence with high binding affinity for a nucleic acid sequence of interest. Thus, a great number and variety of moieties can potentially be incorporated in one or more B positions of a dimer of the present invention.

Similarly, a wide variety of side groups represented by "R" and "T" can be chosen and selected based on the ability of oligomers comprising dimers of the present invention to hybridize to nucleic acid sequences under the desired conditions.

Other important considerations in the selection and testing of R, T, and B groups and moieties include the stability and reactivity of resulting dimer that includes a particular group or moiety at a given R position, T position, or B position. The stability of dimers of the present invention, and of oligomers that incorporate dimers of the present invention, can be tested by methods known in the art, including, but not limited to, spectrometry and NMR. The stability of dimers of the present invention and of oligomers that incorporate dimers of the present invention can be influenced by the addition of, for example, salts, reducing agents, acids, bases, or buffers, to solutions that comprise such oligonucleotide analogue compounds of the present invention, where achieving stability of a compound that comprises a particular group or moiety at an R, T, or B position is desirable.

Dimers of the present invention can comprise protecting groups. Dimers that conform to formulas (VI), (VIII), and (X) that are to be used in the synthesis of oligonucleotide analogue oligomers preferably have protecting groups at the D position. Preferably, a protecting group at the D position of dimers (VI), (VIII), and (X) is a hydroxyl protecting group compatible with at least one reaction that can result in at least one amide, ester, phosphoester, phosphonoester, or phosphonamide bond, such that it is able to prevent chemical reactions of the oxygen it is bound to during reactions that can form at least one of these bonds. Preferred protecting groups for the D position include, but are not limited to, dimethoxytrityl (DMTr), monomethoxytrityl (MMTr), trityl (Tr), tert-butyl dimethyl silyl (TBDMS), 9-fluorenylmethyloxycarbonyl (Fmoc) and tetrahydropyranyl. Dimers of the present invention can also have at the D position a wide variety of R groups, including complex molecules such as linkers, polymers, labels, reporter groups, nucleic acids, peptides, proteins, carbohydrates, lipids, steroids, specific binding members, and the like, particularly where dimers comprising such R groups can be incorporated at a terminus of an oligonucleotide analogue or oligonucleotide.

The E position of dimers of the present invention can be $O^-$, OH, or can comprise protecting or activating groups. Preferably, a protecting group at the E position of dimers (VI), (VIII), and (X) is compatible with at least one reaction that can result in an ester, phosphoester, or phosphonoester bond, such that the protecting group is able to prevent a chemical reactions of a phosphonate or carbonyl group during at least one reaction that form can form at least one or these bonds, such as at the D position. Preferably, a protecting group at the E position of dimers (VII), (IX), and (XI) is compatible with at least one reaction that can result in phosphonamide and amide bond formation, such that the protecting group is able to prevent a chemical reaction of the phosphonate or carbonyl group during reactions that can form at least one of these bonds, such as at the D position. Preferably, a protecting group at the E position of dimers (VI), (VII), (IX), and (XI) is a carboxyl protecting group, such as, but not limited to, Preferably, a protecting group at the E position of dimers (VI), (VII), (VIII), (IX), (X), and (XI) is a phosphonate or carboxyl protecting group, such as, but not limited to, $CH_3$, tert-butyl dimethyl silyl (TBDMS), 9-fluorenylmethyl, 2-cyanoethyl, 2-(4-nitrophenyl)ethyl and tetrahydropyranyl. Where an E position of monomer (VIII) or (X) comprises an activating group, the activating group is preferably also a protecting group that prevents reaction of a phosphate during one or more reactions that result in the formation of a bond, such as at the D position (such as, but not limited to, an ester or a phosphoester bond) and in one or more other reactions can activate the phosphate it is bound to for the formation of a phosphonoester or phosphonamide bond. Preferred protecting/activating groups for the E position of monomers (VII)and (X) include, but are not limited to, derivatives of 1-oxido-4-alkoxy-2-picolyl derivatives such as 1-oxydo-4-methoxy-2-picolyloxy, phenoxy, 2-methylphenoxy, and 2-cyanoethoxy.

The Q position of a dimer of the present invention can be O⁻, OH, or can comprise a protecting or activating group. Preferably, a protecting group at the Q position of dimers (IX) and (XI) is a phosphonate protecting group compatible with ester, phosphoester, phosphonoester, phosphonamide, or amide bond formation, such that it is able to prevent chemical reaction of the oxygen it is bound to during at least one reaction that can form at least one of these bonds (such as at the D positions of these monomers), but this is not a requirement of the present invention. Preferred protecting groups at the Q position of a dimer of the present invention include, but are not limited to, derivatives of 1-oxido-4-alkoxy-2-picolyl derivatives such as 1-oxydo-4-methoxy-2-picolyloxy, phenoxy, 2-methylphenoxy, and 2-cyanoethoxy.

An oligonucleotide analogue dimer of the present invention can optionally comprise or be conjugated to one or more detectable labels, specific binding members, polymers, peptides, polypeptides, nucleic acids, carbohydrates, lipids, steroids, enzymes, small molecules, or coupling agents. Coupling of oligonucleotide analogues to various organic molecules can be achieved by those skilled in the art of bioorganic synthesis. Methods of coupling oligonucleotide analogues to amino acids, peptides, and polypeptides can be through synthesis of a peptide (amide) bond as disclosed for the synthesis of peptide nucleic acids in, for example, Efimov, et al. *Russian Journal of Bioorganic Chemistry* 25: 545–555 (1999), or by using a linker, for example, as disclosed in U.S. Pat. No. 6,165,720 issued Dec. 26, 2000 to Felgner et al. The coupling of oligonucleotide analogues of the present invention to nucleic acid molecules can also optionally be achieved through the use of a linker that can be added to an oligonucleotide analogue oligomer coupled to a solid support. Nucleic acid molecules or nucleotides can be coupled to the linker attached to an oligonucleotide analogue (Efimov, et al. *Russian Journal of Bioorganic Chemistry* 25: 545–555 (1999); Finn et al., *Nucleic Acids Res.* 24: 3357–3364 (1996)). Dimers of the present invention can also be coupled to linkers that are in turn coupled to detectable labels, specific binding members, polymers, peptides, polypeptides, nucleic acids, carbohydrates, lipids, steroids, enzymes, small molecules, or coupling agents. Dimers can optionally be derivatized, for example, by the addition of amino or phosphono groups, for the direct or indirect attachment of other molecules.

Compounds of formulas (VI) ("HypNA-PNA dimer"), (VIII) ("HypNA-pPNA dimer"), and (X) ("SerNA-pPNA dimer") can be synthesized by any appropriate methods known in the arts of organic and bioorganic chemistry. Preferably, the synthesis of compound (VI) is performed by forming an amide bond between a compound of formula (I) and an appropriate peptide nucleic acid monomer, and the synthesis of compound (VIII) is performed by forming an amide bond between a compound of formula (I) and an appropriate phosphono peptide nucleic acid monomer. Preferably, the synthesis of compound (X) is performed by forming an amide bond between a compound of formula (V) and an appropriate phosphono peptide nucleic acid monomer.

In preferred methods for the synthesis of compounds (VI), (VIII), and (X), the hydroxyl groups of compounds of formulas (I) and (V) are protected with protecting groups such as, but not limited to, dimethoxytrityl (DMTr), monomethoxytrityl (MMTr), trityl (Tr), tert-butyl dimethyl silyl (TBDMS), 9-fluorenylmethyloxycarbonyl (Fmoc) and tetrahydropyranyl. Where compounds of formulas (I) and (V) are protected with carboxyl protecting groups, such protecting groups can be removed prior to the formation of the amide bond, for example, by treating a compound having the $CH_3$ carboxyl protecting group with base.

Preferably, the terminal carboxyl group of a peptide nucleic acid monomer that can be coupled to a compound of formula (I) for the synthesis of a compound of formula (VI) is protected with a protecting group such as, but not limited to, $CH_3$, tert-butyl dimethyl silyl (TBDMS), 9-fluorenylmethyl, 2-cyanoethyl, 2-(4-nitrophenyl)ethyl or tetrahydropyranyl. Preferably, the terminal phosphate group of a phosphono peptide nucleic acid monomer that can be coupled to a compound of formula (I) or (V) for the synthesis of compounds of formulas (VIII) and (X) is protected with at least one protecting group such as, but not limited to phenyl, 2-methylphenyl, 2-cyanoethyl, 2-chlorophenyl, 4-chlorophenyl, 2-(1-methylimidazole-2-yl) phenyl (Froehler et al. J. Am. Chem. Soc. 107:278–279 (1985); Sproat et al. Nucleic Acids Res. 14: 1811–1824 (1986)), 1-oxido-4-alkoxy-2-picolyl, 4-alkoxy-2-picolyl, or 1-oxido-2-picolyl (Efimov et al., in Abstracts of Protein Engineering Symposium, Groningen, May 4–7, 1986, Drenth, ed. p. 9 (1986)). The addition of one of these preferred protecting groups, 1-oxydo-4-methoxy-2-picolyl, to a pPNA monomer is described in van der Laan et al., Tetrahedron Lett. 37: 7857–7860 (1996). Where a peptide nucleic acid monomer or phosphono peptide nucleic acid monomer is protected with amino protecting groups, such protecting groups can be removed prior to the reaction that forms the amide bond. For example, removal of an amino-protecting MMTr group can be accomplished by treating the compounds with 0.2 M picric acid in 5% acetonitrile.

A compound of formula (I) can be coupled to a PNA monomer to form a compound of formula (VI), or a compound of formula (I) can be coupled to a pPNA monomer to form a compound of formula (VIII), or a compound of formula (V) can be coupled to a pPNA monomer to form a compound of formula (X), by a condensation reaction that results in the formation of an amide bond. Coupling agents that can be used include TOTU, TopPipU, BOP, PyBroP, $Ph_3P/CCl_4$. A preferred coupling agent is dicyclohexylcarbodiimide (DCC).

For example, to synthesize dimers described by formulas (VIII) and (X), monomers of formulas (I) and (V), respectively, can preferably be coupled to a phosphono PNA monomer 1-oxydo-4-methoxy-2-picolylphenyl diester or diphenyl ester synthesized by methods, such as those disclosed in Efimov et al., Nucleic Acids Res. 26: 566–575 (1998), herein incorporated by reference. Monomers (I) and (V) can be coupled to a phosphono PNA monomer in a presence of, for example, oxygen nucleophilic catalysts such as 4-substituted derivatives of pyridine N-oxide such as those described in Efimov et al., Nucleic Acids Res. 13: 3651–3666 (1985) and in Efimov et al., Nucleic Acids Res. 14: 6525–6540 (1986), both herein incorporated by reference.

A compound of formula (VII) ("PNA-HypNA dimer") can be synthesized by any appropriate methods known in the arts of organic and bioorganic chemistry. Preferably, the synthesis of compound (VII) is performed by forming an ester bond between an appropriate peptide nucleic acid monomer and a compound of formula (I).

In preferred methods for the synthesis of a compound of formula (VII), the carbonyl group of a compound of formula (I) is protected with a protecting group such as, but not limited to, $CH_3$, tert-butyl dimethyl silyl (TBDMS), 9-fluorenylmethyl, 2-cyanoethyl, 2-(4-nitrophenyl)ethyl or tetrahydropyranyl. Where a compound of formulas (I) is protected with a hydroxyl protecting group, the protecting group can be removed prior to the formation of the ester bond. For example, DMTr or MMTr can be removed from the terminal hydroxyl by treating with 5% dichloroacetic acid in dichloromethane.

Preferably, the terminal amino group of a peptide nucleic acid monomer that can be coupled to a compound of formula (I) for the synthesis of a compound of formula (VII) is protected with a protecting group such as, but not limited to, DMTr, MMTr, Tr, or Fmoc. Where a peptide nucleic acid monomer is protected with a carboxyl protecting group, the protecting group can be removed prior to the reaction that forms the amide bond, for example, by treating a compound having the $CH_3$ carboxyl protecting group with base.

A PNA monomer can be coupled to a compound of formula (I) to form a compound of formula (VII) by a condensation reaction that results in the formation of an ester bond. To catalyze the synthesis of an ester bond, coupling agents such as, for example, 2,4,6-triisopropylbenzenesulfonyl-3-nitro-1,2,4-triazolide (TPS-NT) or 2,4,6-triisopropylbenzenesulfonyl-3-nitro-1,2,4-chloride (TPS-Cl) and 1-methylimidazole can be used (Efimov et al., Nucleic Acids Res. 11: 8369–8387 (1983)).

Compounds of formulas (IX) ("pPNA-HypNA dimer") and (XI) ("pPNA-SerNA dimer") can be synthesized by any appropriate methods known in the arts of organic and bioorganic chemistry. Preferably, the synthesis of compounds (IX) and (XI) is performed by forming an phosphonoester bond between a compound of formula (I) (for the synthesis of compound (IX) or a compound of formula (V) (for the synthesis of compound (XI)) and a phosphono peptide nucleic acid monomer.

In preferred methods for the synthesis of compounds of formulas (IX) and (XI), the carbonyl groups of compounds of formulas (I) and (V) are protected with protecting groups such as, but not limited to, $CH_3$, tert-butyl dimethyl silyl (TBDMS), 9-fluorenylmethyl, 2-cyanoethyl, 2-(4-nitrophenyl)ethyl or tetrahydropyranyl. Where compounds of formulas (I) and (V) are protected with hydroxyl protecting groups, such protecting groups can be removed prior to performing reactions that result in the formation of the phosphonoester bond, for example, by treating a compound having the [X]protecting group with [X].

Preferably, the terminal amino group of a phosphono peptide nucleic acid monomer that can be coupled to a compound of formula (I) for the synthesis of a compound of formula (IX) or to a compound of formula (V) for the synthesis of a compound of formula (XI) is protected with a protecting group such as, but not limited to DMTr, MMTr, Tr, or Fmoc.

Preferably, the terminal phosphate group of a phosphono peptide nucleic acid monomer that can be coupled to a compound of formula (I) or (V) for the synthesis of compound of formulas (IX) and (XI) is bound to at least one protecting/activating group such as, but not limited to phenyl, 2-methylphenyl, 2-cyanoethyl, 2-chlorophenyl, 4-chlorophenyl, 2-(1-methylimidazole-2-yl) phenyl (Froehler et al. J. Am. Chem. Soc. 107:278–279 (1985); Sproat et al. Nucleic Acids Res. 14: 1811–1824 (1986)), 1-oxido-4-alkoxy-2-picolyl, 4-alkoxy-2-picolyl, or 1-oxido-2-picolyl (Efimov et al., in Abstracts of Protein Engineering Symposium, Groningen, May 4–7, 1986, Drenth, ed. p. 9 (1986)). The addition of one of these preferred protecting groups, 1-oxydo-4-methoxy-2-picolyl, to a pPNA monomer is described in van der Laan et al., Tetrahedron Lett. 37: 7857–7860 (1996).

A phosphono PNA monomer can be coupled to a compound of formula (I) or a compound of formula (V) to form compounds of formulas (IX) or (XI), respectively, by a condensation reaction that results in the formation of a phosphonoester bond. Coupling agents such as, but not limited to, 1-(2,4,6-triisopropylbenzenesulfonyl)-3-nitro-1,2,4-triazole (TPSNT) can be used to catalyze the formation of the phosphonoester bond.

For example, to synthesize dimers described by formulas (IX) and (XI), monomers of formulas (I) and (V), respectively, can be preferably be coupled to a phosphono PNA monomer 1-oxydo-4-methoxy-2-picolylphenyl diester, or diphenyl ester synthesized by methods, such disclosed in Efimov et al., Nucleic Acids Res. 26: 566–575 (1998), and Efimov, et al. Russian Journal of Bioorganic Chemistry 25: 545–555 (1999). both herein incorporated by reference. Monomers (I) and (V) can be coupled to a phosphono PNA monomer in a presence of, for example, oxygen nucleophilic catalysts such as 4-substituted derivatives of pyridine N-oxide such as those described in Efimov et al., Nucleic Acids Res. 13: 3651–3666 (1985) and in Efimov et al., Nucleic Acids Res. 14: 6525–6540 (1986) herein incorporated by reference.

Oligomer Compositions

The present invention also comprises oligomer compositions that can be used in a variety of applications.

One oligomer composition, herein referred to as a hydroxyproline nucleic acid-phosphono peptide nucleic acid oligomer or "HypNA-pPNA oligomer", comprises the structure given by the formula:

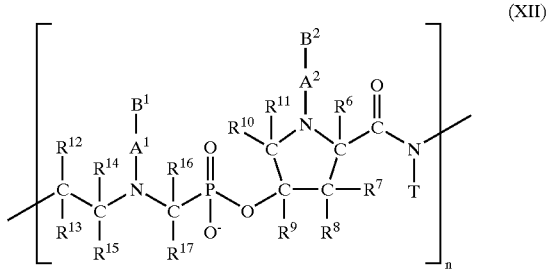

(XII)

where each of $B^1$ and $B^2$ is, independently, H, a naturally occurring nucleobase, a non-naturally occurring nucleobase, an aromatic moiety, a DNA intercalator, a nucleobase-binding group, a heterocyclic moiety, or a reporter group, wherein amino groups are, optionally, protected by amino protecting groups;

where each of $A^1$ and $A^2$ is, independently, a group of formula (Ia), (Ib), or (Ic);

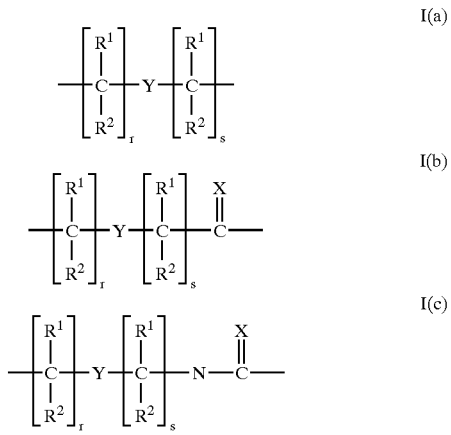

I(a)

I(b)

I(c)

where r and s are, for I(a) and I(b), independently of one another, values from 0 to 5 and are, for I(c), independently of one another, values from 1 to 5;

where each $R^1$ and each $R^2$ is, independently, hydrogen, $(C_1-C_6)$alkyl, hydroxy-, alkoxy-, amino-, or alkythio-substituted $(C_1-C_6)$alkyl, hydroxy, alkoxy, alkylthio, amino, or halogen;

where each of $R^3$, $R^4$, and $R^5$, is, independently, hydrogen, $(C_1-C_6)$alkyl, hydroxy-, alkoxy-, amino-, or alkythio-substituted $(C_1-C_6)$alkyl, hydroxy, amino, alkoxy, aryl, aralkyl, heteroaryl, or an amino acid side chain;

Y is a single bond, O, S, or $NR^4$; and

X is O, S, Se, $NR^5$, $CH_2$, or $C(CH_3)_2$;

where $R^6$ is hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where $R^7$ is hydrogen, hydroxy, alkoxy, $(C_1-C_6)$alkyl, hydroxy-, alkoxy-, amino-, or alkythio-substituted $(C_1-C_6)$ alkyl, alkylthio, aryl, aralkyl, heteroaryl, amino, or halogen, and $R^8$ is hydrogen, $(C_1-C_6)$alkyl, hydroxy-, alkoxy-, amino-, or alkythio-substituted $(C_1-C_6)$alkyl, aryl, aralkyl, heteroaryl;

or $R^7$ is hydrogen, $(C_1-C_6)$alkyl, hydroxy-, alkoxy-, amino-, or alkythio-substituted $(C_1-C_6)$alkyl, alkoxy, aryl, aralkyl, or heteroaryl, and $R^8$ is hydrogen, hydroxy, alkoxy, alkthio, amino, $(C_1-C_6)$alkyl, hydroxy-, alkoxy-, amino-, or alkythio-substituted $(C_1-C_6)$alkyl, aryl, aralkyl, heteroaryl, or halogen;

where $R^9$ is hydrogen, alkoxy, $(C_1-C_6)$alkyl, hydroxy-, alkoxy-, amino-, or alkythio-substituted $(C_1-C_6)$alkyl, aryl, arylkyl, or heteroaryl;

where each of $R^{10}$ and $R^{11}$ is, independently, hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where each of $R^{12}$, $R^{13}$, $R^{14}$, $R^{15}$, $R^{16}$, and $R^{17}$ is, independently, hydrogen, $(C_1-C_6)$alkyl, hydroxy-, alkoxy-, amino-, or alkythio-substituted $(C_1-C_6)$alkyl, hydroxy, amino, alkoxy, alkylthio, aryl, aralkyl, heteroaryl, or an amino acid side chain;

where T is hydrogen, hydroxy, alkoxy, $(C_1-C_6)$alkyl, hydroxy-, alkoxy-, amino-, or alkythio-substituted $(C_1-C_6)$ alkyl, alkylthio, aryl, aralkyl, heteroaryl, or amino; and n is 1 or greater.

Another oligomer composition, herein referred to as a serine nucleic acid-phosphono peptide nucleic acid oligomer of "SerNA-pPNA oligomer", comprises the structure given by the formula:

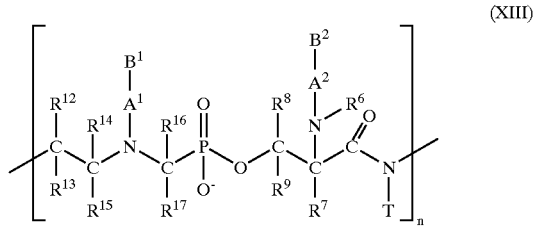

(XIII)

where each of $B^1$ and $B^2$ is, independently, H, a naturally occurring nucleobase, a non-naturally occurring nucleobase, an aromatic moiety, a DNA intercalator, a nucleobase-binding group, a heterocyclic moiety, or a reporter group, wherein amino groups are, optionally, protected by amino protecting groups;

where each of $A^1$ and $A^2$ is, independently, a group of formula (Ia), (Ib), or (Ic);

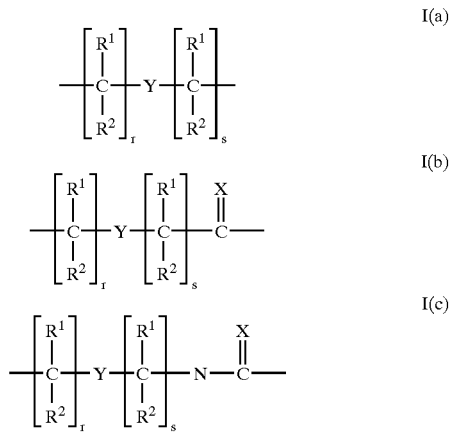

I(a)

I(b)

I(c)

where r and s are, for I(a) and I(b), independently of one another, values from 0 to 5 and are, for I(c), independently of one another, values from 1 to 5;

where each $R^1$ and each $R^2$ is, independently, hydrogen, $(C_1-C_6)$alkyl, hydroxy-, alkoxy-, amino-, or alkythio-substituted $(C_1-C_6)$alkyl, hydroxy, alkoxy, alkylthio, amino, or halogen;

where each of $R^3$, $R^4$, and $R^5$, is, independently, hydrogen, $(C_1-C_6)$alkyl, hydroxy-, alkoxy-, amino-, or alkythio-substituted $(C_1-C_6)$alkyl, hydroxy, alkoxy, amino, aryl, aralkyl, heteroaryl, or an amino acid side chain.

Y is a single bond, O, S, or $NR^4$; and

X is O, S, Se, $NR^5$, $CH_2$, or $C(CH_3)_2$;

where each of $R^7$, $R^8$, and $R^9$ is, independently, hydrogen, $(C_1-C_6)$alkyl, hydroxy-, alkoxy-, amino-, or alkythio-substituted $(C_1-C_6)$alkyl, aryl, aralkyl, heteroaryl, or an amino acid side chain;

where each of $R^{12}$, $R^{13}$, $R^{14}$, $R^{16}$, and $R^{17}$ is, independently, hydrogen, $(C_1-C_6)$alkyl, hydroxy-, alkoxy-, amino-, or alkythio-substituted $(C_1-C_6)$alkyl, hydroxy, amino, alkoxy, alkylthio, aryl, aralkyl, heteroaryl, or an amino acid side chain;

where T is hydrogen, hydroxy, alkoxy, $(C_1-C_6)$alkyl, hydroxy-, alkoxy-, amino-, or alkythio-substituted $(C_1-C_6)$ alkyl, alkylthio, aryl, aralkyl, heteroaryl, or amino; and n is one or greater.

Oligomers comprising the structures of formulas (XII) and (XIII) can be made by any appropriate methods known in the arts of organic and bioorganic chemistry. The backbone of an oligonucleotide analogue oligomer of the present invention can comprise at least two different amino acid or amino acid derivatives. Preferably, an oligonucleotide analogue of the present invention can comprise one or more amino acids based on L-4-trans-hydroxyproline or L-serine. More than one amino acid based on L-4-trans-hydroxyproline in an oligonucleotide analogue can be the same or different amino acids, that is, they can optionally comprise different R groups. More than one amino acid based on L-serine in an oligonucleotide analogue can be the same or different amino acids, that is, they can optionally comprise different R groups. An oligonucleotide analogue of the present invention can comprise a plurality of amino acids or amino acid derivatives that are the same or different from one another.

At least one base position ($B^1$ and $B^2$ in formulas (XII) and (XIII)) preferably includes a nucleobase, where a nucleobase can be a naturally occurring nucleobase, such as, but not limited to, adenine, guanine, cytosine, thymine, uracil, inosine, 5-methylcytosine, xanthine, and hypoxanthine, or can be a non-naturally occurring nucleobase or nucleobase analogue, such as, but not limited to, 2-aminoadenosine, azaadenine, azacytidine, azaguanine, 5-bromo-uracil, thiouracil, bromothymine, 7,8-dimethylalloxazine, and 2,6-diaminopurine. An oligonucleotide analogue of the present invention can optionally comprise at at least one base position at least one reporter group, aromatic ring, or intercalator, such as for example, fluorescamine, OPA, NDA, JOE, FAM, rhodamine, pyrene, 4-nitro-1,8-naphthylamide, ethidium bromide, acridine orange, thiazole orange, TOTO-1, YOYO-1, psoralen, actinomycin D, or angelicin (see, for example, Goodchild, J. Bioconjugate Chemistry 1: 165 (1990)). An oligonucleotide analogue of the present invention can optionally comprise at at least one base position H, OH, an alkynoyl, an alkyl, an aromatic group, or nucleobase-binding moiety. Moieties at a base position of an oligonucleotide analogue can also be specific binding members, such as hapten, biotin, polyhistidine, etc. Moieties at the base position of an oligonucleotide analogue of the present invention can incorporate detectable labels, such as, but not limited to, fluorescent labels, radioisotope labels, spin labels, or mass-altered labels.

One or more moieties at one or more base positions of an oligonucleotide analogue oligomer of the present invention can optionally comprise protecting groups. Such protecting groups can optionally but preferably be removed when synthesis of an oligonucleotide analogue oligomer is complete. Protecting groups for various groups that are compatible with the conditions of oligonucleotide analogue synthesis are known in the art (see, for example, Sonveaux, *Protecting Groups in Oligonucleotide Synthesis* in Methods in Molecular Biology: Protocols for Oligonucleotide Conjugates, S. Agrawal, ed. Humana Press (1994)). Of particular relevance are protecting groups that can be used to protect the extracyclic amino groups of nucleobases such as adenine, cytosine, and guanine.

In selecting moieties for "B" positions in nucleic acid analogue oligomers, one can be guided by the principal that any moiety that will permit the hybridization of the single-stranded oligonucleotide analogue comprising the dimer to specifically bind to a single or double-stranded nucleic acid molecule (by Watson-Crick base-pairing in the first instance, and by Hoogsteen base-pairing in the second instance) is permissible. Thus, it is possible to synthesize oligonucleotide analogue oligomers of the present invention having one or more moieties at one or more B positions that has desirable properties (as a ligand or label, for example) and screen for the ability of such oligonucleotide analogue oligomers to hybridize to DNA or RNA using methods known in the art, for example, by monitoring the formation of double-stranded molecules by UV spectrometry, or by detecting binding of labeled nucleic acid molecules to oligonucleotide analogues fixed to a solid support. In this regard, it can also be recognized that certain conditions that determine, at least in part, the hybridization of synthetic oligonucleotide analogues of the present invention to nucleic acid molecules can be altered, such as for example, by making longer probes, or altering temperature or salt conditions, to permit hybridization of oligonucleotide analogues incorporating various moieties at one or more B positions. It is also possible to position a monomer or dimer with one or moieties of interest at one or more B positions so that its effect on hybridization of the oligomer incorporating the monomer or dimer is minimal, for example, by positioning it at a terminus of an oligonucleotide analogue oligomer, or in the center of an oligomer sequence with high binding affinity for a nucleic acid sequence of interest. Thus, a great number and variety of moieties can potentially be incorporated in at least one B position of an oligomer of the present invention.

Similarly, a wide variety of side groups represented by "R" and "T" can be chosen and selected based on the ability of oligonucleotide analogue oligomers of the present invention to hybridize to nucleic acid sequences under the desired conditions.

Other important considerations in the selection and testing of R, T, and B groups or moieties include the stability and reactivity of resulting oligomer that includes a particular group or moiety at a given R position, T position, or B position. The stability of of oligomers of the present invention that incorporate particular R, T, or B groups or moieties, can be tested by methods known in the art, including, but not limited to, spectrometry and NMR. The stability of oligomers that incorporate dimers of the present invention can be influenced by the addition of, for example, salts, reducing agents, acids, bases, or buffers, to solutions that comprise such oligonucleotide analogue compounds of the present invention, where achieving stability of a compound that comprises a particular group or moiety at an R, T, or B position is desirable.

An oligonucleotide analogue oligomer of the present invention can optionally comprise or be conjugated to one or more detectable labels, specific binding members, polymers, peptides, polypeptides, nucleic acids, carbohydrates, lipids, steroids, enzymes, small molecules, protecting groups, or coupling agents. Coupling of oligonucleotide analogues to various organic molecules can be achieved by those skilled in the art of bioorganic synthesis. Coupling of oligonucleotide analogues to various organic molecules can be achieved by those skilled in the art of bioorganic synthesis. Methods of coupling oligonucleotide analogues to amino acids, peptides, and polypeptides can be through synthesis of a peptide (amide) bond as disclosed for the synthesis of peptide nucleic acids in, for example, Efimov, et al. *Russian Journal of Bioorganic Chemistry* 25: 545–555 (1999), or by using a linker, for example, as disclosed in U.S. Pat. No. 6,165,720 issued Dec. 26, 2000 to Felgner et al. The coupling of oligonucleotide analogues of the present invention to nucleic acid molecules can also optionally be achieved through the use of a linker that can be added to an oligonucleotide analogue oligomer coupled to a solid support (Efimov, et al. *Russian Journal of Bioorganic Chemistry* 25: 545–555 (1999); Finn et al., *Nucleic Acids Res.* 24: 3357–3364 (1996)). Oligomers of the present invention can also be coupled to linkers that are in turn coupled to detectable labels, specific binding members, polymers, small molecules, matrices, polymers, and the like.

An oligonucleotide analogue of the present invention can be of any length. Preferably, an oligonucleotide analogue of the present invention is from between two and about 1,000 residues long, more preferably between about six and about 200 residues long, and most preferably between about ten and about 60 residues long.

An oligonucleotide analogue oligomer of the present invention can optionally comprise at least one deoxyribonucleotide or deoxyribonucleoside residue and/or at least one ribonucleotide or ribonucleoside residue. A deoxyribonucleotide, deoxyribonucleoside, ribonucleotide or ribonucleoside residue or that is a part of an oligonucleotide analogue of the present invention can comprise naturally or non-naturally occurring nucleobases, nucleobase binding moieties, detectable labels, or specific binding members. An oligonucleotide analogue of the present invention can also include one or more other oligonucleotide analogue residues, such as, but not limited to, one or more of the oligonucleotide analogue residues described in U.S. Pat. Nos. 5,714,331; 5,736,336; 5,766,855; 5,719,262; 5,786,461; 5,977,296; 6,015,887; and 6,107,470.

In a preferred aspect of the present invention, a HypNA-pPNA oligomer (XII) of the present invention can comprise HypNA residues and pPNA residues in any ratio. Preferably, the ratio of HypNA residues to pPNA residues in a HypNA-pPNA oligomer of the present invention is from between about 1:99 to about 99:1, more preferably from about 1:20 to about 20:1, and most preferably from about 1:5 to about 5:1. In some preferred aspects of the invention, the ratio of HypNA residues to pPNA residues in a oligonucleotide analogue of the present invention is from between about 1:4 to about 1:1.

In another preferred aspect of the present invention, a SerNA-pPNA oligomer (XIII) of the present invention can comprise SerNA residues and pPNA residues in any ratio. Preferably, the ratio of SerNA residues to pPNA residues in a SerNA:pPNA oligonucleotide analogue of the present invention is from between about 1:99 to about 99:1, more preferably from about 1:20 to about 20:1, and most preferably from about 1:5 to about 5:1. In some preferred aspects of the invention, the ratio of SerNA residues to pPNA residues in a SerNA-pPNA oligonucleotide analogue of the present invention is from between about 1:4 to about 1:1.

Oligonucleotide analogue oligomers of the present invention can be made by the formation of amide, phosphonoester, or ester bonds between monomers and the growing oligomer chain or made by the formation of amide, ester, or phosphonoester bonds between dimers and the growing oligomer chain. Oligonucleotide analogue oligomer synthesis can therefore employ a variety of protection, coupling, and deprotection strategies depending on the monomer composition of the oligonucleotide analogue being synthesized.

Synthesis of oligonucleotide analogue oligomers of the present invention can be performed by any appropriate methods known in the arts of organic or bioorganic chemistry, including the phosphoramidite, H-phosphonate, and phosphotriester methods developed for nucleic acid synthesis (Beaucage and Caruthers, *Tetrahedron Lett.* 22:1859–1862 (1981); Gait et al., *Nucl. Acids Res.* 8: 1081–1096 (1980)), and can be performed in solution or in solid phase. Preferably, synthesis of oligonucleotide analogue oligomers of the present invention is performed in solid phase using, at least in part, the phosphotriester method as described in Efimov et al., *Nucleic Acids Res.* 26: 566–575 (1998), Efimov, et al. *Russian Journal of Bioorganic Chemistry* 25: 545–555 (1999).

Supports for solid phase synthesis are known in the art and include, but are not limited to, high cross-linking polystyrene (McCollum and Andrus, Tetrahedron Lett. 32: 4069–4072 (1991), polystyrene/PEG copolymer (Gao et al. Tetrahedron Lett. 32: 5477–5480 (1991), silica gel (Chow et al., Nucl. Acids Res. 9: 2807–2817 (1981)), polyamide bonded silica gel (Gait et al. Nucl. Acids Res. 10: 6243–6254 (1982)), cellulose (Crea and Horn, Nucl. Acids Res. 8: 2331–2348 (1980)), (and controlled pore glass (CPG) (Koster, et al. Tetrahedron Lett. 24: 747–750 (1983). A preferred solid support is CPG beads. CPG beads can be derivatized for the attachment of oligonucleotide analogues in a variety of ways. For example, CPG beads can be treated with 3-aminopropyltriethoxysilane to add an amino propyl linker handle for the attachment of oligonucleotide analogue monomers or dimers (Koster, et al. Tetrahedron Lett. 24: 747–750 (1983), or, preferably, a long-chain alkylamine group, most preferably including a terminal nucleoside, can be attached to CPG (Adams et al. J. Am. Chem. Soc. 105: 661–663 (1983)). Supports for oligonucleotide synthesis or peptide synthesis, for example dT-LCAA-CPG (Applied Biosystems), are commercially available.

In a preferred method of synthesis of oligonucleotide analogue oligomers (XII) and (XIII) of the present invention, the HypNA:pPNA dimer (VIII) or SerNA:pPNA dimer (X), respectively, can be used as a unit of synthesis. The first monomer or dimer added attached to the solid support can be any group, and can be attached by any means. Preferably, however, a monomer or dimer comprising a "3'" or "carboxy" terminal phosphonate or phosphate group groups, for example, a HypNA:pPNA dimer (VIII), a SerNA: pPNA dimer (X), a pPNA monomer, a dimer or oligomer comprising a terminal pPNA monomer, a monomer of formula (II), a monomer of formula (III), a monomer of formula (IV), or a nucleotide is coupled to a derivatized solid support having terminal OH groups (such as, but not limited to, dT-LCAA-CPG). Where a derivatized solid support has protected OH groups to be used for the attachment of monomers or dimers, the protective groups are preferably removed prior to the coupling reaction. For example a DMTr-protected derivatized support can be treated with acid to remove DMTr groups. Preferably, the terminal 3' phosphonate or phosphate of the monomer, dimer, or nucleotide to be attached to the solid support comprises a protecting group, such as, but not limited to, 1-oxydo-4-methoxy-2-picolyloxy, phenoxy, 2-methylphenoxy, or 2-cyanoethoxy, most preferably 1-oxydo-4-methoxy-2-picolyloxy.

The coupling reaction can use any reagents and conditions that catalyze the formation of a bond between the "3'" or "carboxy" terminal phosphonate or phosphate of an oligonucleotide dimer or monomer of the present invention or a pPNA monomer or pPNA-containing dimer or a nucleotide and the derivatized solid support, for example, MSNT in pyridine solution, optionally including 1-methylimidazole, 4-morpholino-pyridine-1-oxide, or, preferably, by treatment with triisopropylbenzenesulfonyl chloride (TPSCI). Subsequent monomers, dimers, or nucleotides having 5' terminal phosphates or phosphonates carrying appropriate protecting groups can be added by the same coupling reaction. Appropriate washes are performed between synthesis cycles to remove unicorporated precursors. For synthesis of the oligonucleotide analogue oligomers of the present invention, the addition of HypNA-pPNA or SerNA-pPNA dimers by phosphotriester synthesis is preferred. However, the choice of dimers and monomers used at each cycle of the synthesis oligonucleotide analogue oligomers of the present invention will be determined by the composition of the desired oligomer, most particularly, by the ratio and order of HypNA and pPNA or SerNA and pPNA monomers in the oligonucleotide analogue monomer to be synthesized. In addition, the oligonucleotide analogue oligomers can optionally comprise other moieties, such as, but not limited to, nucleotide residues and PNA monomers, including, but not limited to "classical" PNA monomers and the novel PNA and pPNA monomers disclosed herein. The synthesis of oligonucleotide analogues of the present invention can therefore include phosphotriester synthesis steps as well as coupling and washing steps designed for the formation of, for example amide and ester bonds, as described in Efimov, et al. *Russian Journal of Bioorganic Chemistry* 25: 545–555 (1999). For example, amide and ester bonds can be formed between synthesis units using TPS-NT and 1-methylimidazole in $CH_3CN$. These reactions can be combined in a solid phase synthesis that also uses the phophotriester method for adding synthesis units by the formation of phosphonoester (and, optionally, phosphoester) bonds.

As nonlimiting examples, coupling of an L-serine based monomer or an L-trans-hydroxyproline based monomer to a free hydroxyl of a growing oligonucleotide analogue oligomer can be through the formation of an ester bond or amide bond. In another case, a "classical" PNA or phosphono PNA can be coupled to a free hydroxyl of a growing oligonucleotide analogue oligomer can be through the formation of an ester bond or a phosphonoester bond. A "classical" PNA can also be coupled to a free amino of a growing oligonucleotide analogue oligomer can be through the formation of an amide bond.

An oligonucleotide can be freed from a solid support by hydrolysis of the linker, such as by treatment with ammonia. Terminal trityl protecting groups can be removed before cleavage during synthesis cycle or after cleavage by treatment with 80% acetic acid and the oligomers can optionally be purified using, for example, polyacrylamide gel electrophoresis, HPLC, FPLC.

In an alternative method of solid phase synthesis, the pPNA: HypNA dimer (IX) or pPNA:SerNA dimer (XI) can be used as a unit of synthesis, and synthesis can be through the formation of amide bonds between dimers. In this case, attachment to a derivatized solid support can be as described for solid phase phosphotriester synthesis, above, and the terminal amino group of a pPNA: HypNA dimer or pPNA: SerNA dimer is preferably protected, for example with DMTr, MMTr, Tr, TMDMS, or tetrahydropyranyl. The phosphate group of a pPNA: HypNA dimer or pPNA:SerNA dimer is preferably protected, for example with, 1-oxydo-4-methoxy-2-picolyloxy, phenoxy, 2-methylphenoxy, or 2-cyanoethoxy, most preferably with 1-oxydo-4-methoxy-2-picolyloxy. pPNA:HypNA dimer or pPNA:SerNA dimers are added to the solid support carrying, for example, a linker with a free amino group, as described for the phosphotriester method, above. Coupling can be performed using reagents that can catalyze the formation of an amide bond, for example, TPSNT. Additional pPNA: HypNA dimer or pPNA: SerNA dimers carrying appropriate protecting groups, can be coupled to the growing oligomer by the formation of amide bonds. Additional dimers, or optionally monomers, including but not limited to dimers and monomers of the present invention, optionally including nucleic acid monomers, carrying appropriate protecting groups, can be coupled to the growing oligomer by the formation of amide, ester, or phosphoester or phosphonoester bonds using catalytic reagents known in the art. Appropriate washes are performed between synthesis cycles to remove unincorporated precursors. When synthesis of the oligomer is complete, phosphate protecting groups can be removed, for example, by treatment with thiophenol-triethylamine dioxane. Any N-protecting groups can also be removed, for example by treatment with ammonia. Cleavage of a completed oligonucleotide analogue oligomer from a solid support can also be accomplished by treatment with ammonia. Oligomers can optionally be purified using, for example, polyacrylamide gel electrophoresis, HPLC, FPLC.

Oligonucleotide Analogues Coupled to a Polymerizable Compound

The present invention also includes oligonucleotide analogues of the present invention coupled to polymerizable compounds. Preferred oligonucleotide analogues that can be coupled to a polymerizable compound include oligonucleotide analogues oligomers of formulas (XII) and (XIII) of the present invention, described herein, and compounds comprising the oligomers of formulas (XII) and (XIII). Such oligomers and compounds comprising oligomers can be of any length or base composition, and can optionally include other moieties, such as, but not limited to, nucleotides, nucleic acid molecules, detectable labels, or specific binding members.

Preferably, an oligonucleotide analogue is bound to a monomer of a polymerizable compound. Preferred oligonucleotide analogues of the present invention coupled to monomers of a polymerizable compound are compounds (XIV) and (XV) depicted in FIG. 3b. Preferably, a monomer with an oligonucleotide analogue covalently attached to it can form a polymer with other monomers of the polymerizable compound under polymerizing conditions. A polymerizable compound of the present invention can be any polymerizable compound, but preferably is a polymerizable compound that can be polymerized without the use of very high temperatures or extremes of pH that can affect the structure of oligonucleotide analogues that are bound to the polymerizable compound. Preferred polymerizable compounds for use in the present invention include ethylene-containing monomer units, including acrylamide, methacrylamide, and other acrylamide derivatives, acrylic acid, methacrylic acid, and other derivatives of acrylic acid.

A polymerizable compound can be coupled to an oligonucleotide analogue of them present invention by any appropriate means. The coupling can be direct or indirect and can be at either terminus of the oligonucleotide analogue, or at any position along the oligonucleotide analogue. Direct coupling of a polymerizable compound to an oligonucleotide analog of the present invention can occur by covalent binding of the polymerizable compound to the backbone or to a nucleobase or other ligand. An oligonucleotide analogue can be derivatized to add groups, such as thiols or amines, to which a polymerizable compound can be coupled.

Preferably, however, coupling of a polymerizable compound of the present invention can be through a linker that provides spacing between the oligonucleotide analogue and the polymerizable compound. The linker is preferably an organic molecule, and can be of any length, which can be selected depending on the application in which the coupled oligonucleotide is to be used. Longer linkers can, for example, allow the oligonucleotide to extend outward from a polymer that can coat a surface. Linkers can be selected based on knowledge of chemical structures and their properties using criteria such as polarity, which confers water solubility, their lack of interaction (either specific or non-specific binding or strong repulsion) with the oligonucleotide analogues of the present invention, their flexibility, and their stability under conditions of high temperature that can be used during hybridization of oligonucleotide analogues. Chemical linkers should also be stable and unreactive under conditions of polymerization of the polymerizable compound and conditions of oligonucleotide hybridization. However, in some aspects it can be preferable to employ a linker that is cleavable under specific and controllable conditions. For example, a linker can comprise disulfide bonds that can be chemically cleaved with dithiothreitol (Mattson et al. (1993) *Molecular Biology Reports* 17: 167–183), and particular linkers can also be cleavable with enzymes or chemical agents. Preferred linkers of the present invention include polyethylene glycol, polyvinyl alcohol, polyvinyl pyrrolidone, and the linkers depicted in FIG. 6.

Coupling of a linker to an oligonucleotide analog of the present invention can occur by covalent binding of the polymerizable compound to the backbone or to a nucleobase or other ligand. An oligonucleotide analogue can be derivatized to add groups, such as thiols or amines, to which a linker can be coupled. Coupling of a polymerizable compound to a linker can be by any means that results in the formation of a covalent bond, and can optionally be through functional groups that can be added on the polymerizable compound, the linker, or both.

In a preferred embodiment, a monomer of a polymerizable compound is coupled to an oligonucleotide analogue of the present invention while the oligonucleotide analogue is coupled to a solid support. In one aspect of this preferred embodiment depicted in FIG. 6 and exemplified in Example 19, an oligonucleotide analogue of the present invention is made by solid phase synthesis on a solid support, and after completion of the synthesis of the oligonucleotide analogue, an acrylamide monomer is covalently attached to the "5' end" of the oligonucleotide analogue while the oligonucleotide analogue is still on the solid support. Preferably, the attachment occurs through a linker. Following the addition of the acrylamide monomer, the oligonucleotide analogue can be released from the solid support.

In another preferred embodiment, also depicted in FIG. 6 and exemplified in Example 18, an oligonucleotide analogue of the present invention is synthesized on a solid support and the attachment of the oligonucleotide analogue to the solid support is through an abasic ribose unit. After the completion of chain elongation, the oligonucleotide plus a "3"end" ribose unit is released from the solid support by treatment with ammonia, the ribose unit is derivatized dialdehyde and an acrylamide monomer is coupled to the oligonucleotide through the substituted N-alkylmorpholine linker.

Oligonucleotide analogues coupled to polymerizable compounds can optionally be purified by any suitable method known in the art (for example, PAGE, HPLC, or FPLC). The oligonucleotide analogues coupled to polymerizable compounds can be polymerized with at least one polymerizable unit that is not coupled to an oligonucleotide or oligonucleotide analogue under conditions that promote polymerization. In preferred embodiments of the invention, one or more oligonucleotide analogues of the present invention that are coupled to acrylamide or derivatized acrylamide monomers are polymerized with acrylamide or derivatized acrylamide monomers that are not coupled to oligonucleotide analogues.

Depending upon the polymerizable compound, polymerization can be initiated by heat, light, chemical agents, ionizing radiation, or combinations thereof (Sandler and Karo (1992) Polymer Synthesis Vol. 1, Academic Press; Sandler and Karo (1994) Polymer Synthesis Vol. 2, Academic Press). For example, photosensitizing polymerizing agents such as benzophenone, camphoquinone, riboflavin, benzoin, or benzoin ethyl ether can be used. Initiators such as 2,2'azobis(isobutyronitrile) and dibenzoyl peroxide decompose at temperatures above 50 degrees C. to form free radicals that promote polymerization of ethylene-containing polymers. A preferred initiator for use in the present invention is a combination of ammonium persulfate and N,N,N', N'-tetramethylethylenediamine (TEMED) that are able to polymerize acrylamide and its derivatives. Cross-linking reagents such as bis-acrylamide can also be added to the polymerization reaction to increase the strength of the resulting polymer. The present invention includes oligonucleotide analogues coupled to polymerizable compounds in polymerized matrices, including oligonucleotide analogues coupled to polymerizable compounds in polymerized matrices that are hybridized to nucleic acid molecules.

II Methods of Detecting Nucleic Acids Using Oligonucleotide Analogues

Oligonucleotide analogues of the present invention can also be used for detection of nucleic acids. Such detection methods include: providing a sample, contacting at least one oligonucleotide analogue of the present invention with the sample under conditions that allow hybridization of oligonucleotide analogues to nucleic acid molecules, and detecting one or more nucleic acid molecules of the sample that have hybridized to one or more oligonucleotide analogues of the present invention.

A sample can be from any source, and can be a biological sample, such as a sample from an organism or a group of organisms from the same or different species. A biological sample can be a sample of bodily fluid, for example, a blood sample, serum sample, lymph sample, a bone marrow sample, ascites fluid, pleural fluid, pelvic wash fluid, ocular fluid, urine, semen, sputum, or saliva. A biological sample can also be an extract from cutaneous, nasal, throat, or genital swabs, or extracts of fecal material. Biological samples can also be samples of organs or tissues, including tumors. Biological samples can also be samples of cell cultures, including both cell lines and primary cultures of both prokaryotic and eukaryotic cells.

A sample can be from the environment, such as from a body of water or from the soil, or from a food, beverage, or water source, an industrial source, workplace area, public area, or living area. A sample can be an extract, for example a liquid extract of a soil or food sample. A sample can be a solution made from washing or soaking, or suspending a swab from, articles such as tools, articles of clothing, artifacts, or other materials.

A sample can be an unprocessed or a processed sample, where processing can involve steps that increase the purity, concentration, or accessibility of components of the sample to facilitate the analysis of the sample. As nonlimiting examples, processing can include steps that reduce the volume of a sample, remove or separate components of a sample, solubilize a sample or one or more sample components, or disrupt, modify, expose, release, or isolate components of a sample. Nonlimiting examples of such procedures are centrifugation, precipitation, filtration, homogenization, cell lysis, binding of antibodies, cell separation, etc. For example, in some preferred embodiments of the present invention, the sample is a blood sample that is at least partially processed, for example, by the removal of red blood cells, by concentration, by selection of one or more cell or virus types (for example, white blood cells or pathogenic cells), or by lysis of cells, etc.

Another preferred sample is a solution of at least partially purified nucleic acid molecules. The nucleic acid molecules can be from a single source or multiple sources, and can comprise DNA, RNA, or both. For example, a solution of nucleic acid molecules can be a sample that was subjected to any of the steps of cell lysis, concentration, extraction, precipitation, nucleic acid selection (such as, for example, poly A RNA selection or selection of DNA sequences comprising Alu elements), or treatment with one or more enzymes. The sample can also be a solution that comprises synthetic nucleic acid molecules.

An oligonucleotide analogue of the present invention can be any oligonucleotide analogue disclosed herein, or any oligonucleotide analogue comprising a monomer or dimer disclosed herein. An oligonucleotide analogue used in the methods of the present invention can be of any length and of any base composition, and can comprise one or more nucleic acid moieties, peptides, proteins lipids, carbohydrates, steroids, and other biochemical and chemical moieties. An oligonucleotide analogue of the present invention can be provided in solution or bound to a solid support. In some preferred embodiments of the present invention, the oligonucleotide analogues comprise HypNA and pPNA residues, and can comprise HypNA and pPNA residues in ratios from about 2:1 to about 1:3. More preferably, the oligonucleotide analogues used in the methods of the present invention comprise ratios of HypNA to pPNA residues from about 1:1 to about 1:2.

Conditions that favor hybridization between oligonucleotide analogues of the present invention and target nucleic acid molecules can be determined empirically by those skilled in the art, and can include optimal incubation temperatures, salt concentrations, length and base compositions of oligonucleotide analogue probes, and concentrations of oligonucleotide analogues and nucleic acid molecules of the sample. Preferably, hybridization is performed in the presence of at least one millimolar magnesium and at a pH that is above 6.0. In some embodiments, it may be necessary or desirable to treat a sample to render nucleic acid molecules in the sample single-stranded prior to hybridization. Examples of such treatments include, but are not limited to, treatment with base (preferably followed by neutralization), incubation at high temperature, or treatment with nucleases.

Of particular relevance in carrying out the methods of the present invention is the ability to manipulate the ratios of oligonucleotide monomer types in an oligonucleotide analogue probe to achieve particular binding affinities of oligonucleotide analogues. For example, oligonucleotide analogue probes that comprise HypNA and pPNA residues in different proportions can hybridize to the same target nucleic acid molecule with different affinities (see FIG. 4a).

In addition, because the salt dependence of hybridization to nucleic acids is largely determined by the charge density of the backbone of a hybridizing oligonucleotide analogue, increasing the ratio of pPNA monomers in a HypNA-pPNA oligomer or a SerNA-pPNA oligomer of the present invention can increase the salt dependence of hybridization. This can be used to advantage in the methods of the present invention where it can in some aspects be desirable to be able to increase the stringency of hybridization by changing salt conditions, for example, or release a hybridized nucleic acid by reducing the salt concentration. In yet other aspects of the present invention, it can be desirable to have high-affinity binding of an oligonucleotide analogue of the present invention to a nucleic acid in very low salt. In this case, maintaining a ratio of close to 1:1 of HypNA to pPNA monomers in an oligonucleotide analogue of the present invention is advantageous.

The high degree of specificity of oligonucleotide analogues of the present invention in binding to nucleic acid molecules allow the practitioner to select hybridization conditions that can favor discrimination between nucleic acid sequences that comprise a stretch of sequence that is completely complementary to at least a portion of one or more oligonucleotide analogues and nucleic acid molecules that comprise a stretch of sequence that comprises a small number of non-complementary bases within a substantially complementary sequence. For example, hybridization or wash temperatures can be selected that permit stable hybrids between oligonucleotide analogues of the present invention and nucleic acid molecules that are completely complementary along a stretch of sequence but promote dissociation of hybrids between oligonucleotide analogues of the present invention and nucleic acid molecules that are not completely complementary, including those that comprise one or two base mismatches along a stretch of complementary sequence. (See, for example, Examples 20, 27, 28, and 29). The selection of a temperature for hybridization and washes can be dependent, at least in part, on other conditions, such as the salt concentration, the concentration of oligonucleotide analogues and nucleic acid molecules, the relative proportions of oligonucleotide analogues to nucleic acid molecules, the length of the oligomers to be hybridized, the base composition of the oligonucleotide analogues and nucleic acid molecules, the monomer composition of the oligonucleotide analogue molecules, etc. In addition, when selecting for conditions that favor stable hybrids of completely complementary molecules and disfavor stable hybrids between oligonucleotide analogues and nucleic acid molecules that are mismatched by one or more bases, additional conditions can be taken into account, and, where desirable, altered, including but not limited to, the length of the oligonucleotide analogue to be hybridized, the length of the stretch of sequence of complementarity between oligonucleotide analogues and nucleic acid molecules, the number of non-complementary bases within a stretch of sequence of complementarity, the identity of mismatched bases, the identity of bases in the vicinity of the mismatched bases, and the relative position of any mismatched bases along a stretch of complementarity. (See, for example, Examples 20, 27, 28, and 29.) Those skilled in the art of nucleic acid hybridization would be able to determine favorable hybridization and wash conditions in using oligonucleotide analogues of the present invention for hybridization to nucleic acid molecules, depending on the particular application. "Favorable conditions" can be those favoring stable hybrids between oligonucleotide analogues and nucleic acid molecules that are, at least in part, substantially complementary, including those that comprise one or more mismatches.

"Favorable conditions" can be those favoring stable hybrids between oligonucleotide analogues and nucleic acid molecules that are, at least in part, completely complementary and disfavor or destabilized hybrids between molecules that are not completely complementary.

Using methods such as those disclosed herein, the melting temperature of oligonucleotide analogues of the present invention hybridized to nucleic acid molecules of different sequences can be determined and can be used in determining favorable conditions for a given application. It is also possible to empirically determine favorable hybridization conditions by, for example, hybridizing nucleic acid molecules to oligonucleotide analogues that are attached to a solid support and detecting hybridized complexes.

Target nucleic acid molecules that are bound to oligonucleotide analogue probes of the present invention can be conveniently and efficiently separated from unbound nucleic acid molecules of the survey population by the direct or indirect attachment of oligonucleotide analogue probes to a solid support. A solid support can be washed at high stringency to remove nucleic acid molecules that are not bound to oligonucleotide analogue probes. However, the attachment of oligonucleotide analogue probes to a solid support is not a requirement of the present invention. For example, in some applications bound and unbound nucleic acid molecules can be separated by centrifugation through a matrix or by phase separation or some by other forms of separation (for example, differential precipitation) that can optionally be aided by chemical groups incorporated into the oligonucleotide analogue probes (see, for example, U.S. Pat. No. 6,060,242 issued May 9, 2000, to Nie et al.).

Detection methods for bound nucleic acids are well known in the art, and can include the use of a detectable label that is attached to or incorporated into nucleic acid molecules of the survey population or that becomes bound to or incorporated into a hybridized target nucleic acid molecule or hybridized target nucleic acid molecule complex. Detectable labels for nucleic acid molecules are well-known in the art, and comprise fluorescent molecules such as Cy3 and Cy5, radioisotopes, mass-altered chemical groups, specific binding members such as biotin that can be detected by signal-generating molecules, and the like. Detectable labels can also be incorporated into or attached to oligonucleotide analogues of the present invention, for example, in cases where sandwich hybridization using a signal oligonucleotide analogue is used for detection, or detection is performed using a specific binding member such as an antibody that recognizes oligonucleotide analogue/nucleic acid molecule complexes. Solid supports can be scanned, exposed to film, visually inspected, etc. to determine the presence of a detectable label and thereby determine the binding of a target nucleic acid molecule.

A preferred detection method for nucleic acids bound to oligonucleotide analogues includes staining of hybridized nucleic acids/oligonucleotide analogues with nucleic acid stains, such as intercalating dyes. Because of the different backbone structure of PNAs with respect to nucleic acids, nucleic acid intercalating dyes that bind to nucleic acids do not substantially bind to PNAs. Hybridized complexes that comprise certain oligonucleotide analogues of the present invention that comprise pPNA residues, such as, for example, HypNA-pPNA oligomers, hybridized to nucleic acid molecules, however, are able to bind intercalating nucleic acid dyes. This is in contrast to hybridized complexes of "classical" PNAs and nucleic acid molecules that do not stain appreciably with intercalating nucleic acid stains such as ethidium bromide (Wittung et al. Nucleic Acids Research 22: 5371–5377 (1994)). In particular, intercalating fluorescent nucleic acid stains such as, for example, ethidium stains and cyanine dyes, such as, not limited to, ethidum bromide; ethidium homodimers; 1-ethyl-2-[3-(1-ethylnapthol[1,2-d]thiazolin-2-ylidine)-2-methylpropenyl]napthol[1,2-d]thiazolium bromide ("Stains all"); the cyanine dyes "PicoGreen", "OliGreen", Ribogreen", SYBR Fold, SYBR Green 1, SYBR Green 11, SYBR DX, and CyQUANT GR, all available from Molecular Probes, Eugene, Oreg.; the TO-PRO family of monomeric cyanine dyes (including PO-PRO-1, BO-PRO-1, YO-PRO-1, TO-PRO-1, JO-PRO-1, PO-PRO-3, LO-PRO-1, BO-PRO-3, YO-PRO-3, TO-PRO-3, TO-PRO-5); and the TOTO family of cynanine dimers, including POPO-1, BOB-1, YOYO-1, JOJO-1, POPO-3, LOLO-1, BOBO-3, YOYO-3, and TOTO-3), can be useful in the present invention due to their ability to stain nucleic acid molecules hybridized to oligonucleotide analogues of the present invention, but not unhybridized oligonucleotide analogues. Use of these stains can therefore preclude conjugative chemical or enzymatic labeling of the survey population of nucleic acid molecules, or of the target nucleic acid molecules, or of the hybridized complexes to be detected.

Certain dimeric intercalating nucleic acid stains, such as, for example, ethidium homodimers and dimeric cyanine dyes such as TOTO and its derivatives (Molecular Probes, Eugene, Oreg.), can be especially useful in the methods of the present invention. These dyes are highly sensitive, stable to electrophoresis, and bind quantitatively. Thus, dimeric intercalating dyes such as ethidium dimers and cyanine dimers, as they are known in the art or become known in the art, can be used to rapidly detect the presence of nucleic acid molecules hybridized to oligonucleotide analogues, such as nucleic acid molecules hybridized to oligonucleotide analogues attached to a solid support, with little or no background staining in the absence of hybridization. The use of intercalating dyes to detect the presence of nucleic acids is known in the art (see, for example, Rye et al. Nucleic Acids Research 20: 2803–2812 (1992)), and many of these dyes are commercially available from, for example, Molecular Probes (Eugene, Oreg.). It is contemplated that intercalating nucleic acid dyes that are developed in the future, such as, but not limited to, those with new spectral properties, can also be used in the methods of the present invention.

Oligonucleotide Analogue Probes on Solid Supports

For detection of nucleic acids, one or more oligonucleotide analogues of the present invention can be provided on a solid support. Because of their greatly increased stability with respect to natural nucleic acids, oligonucleotide analogues are particularly well suited to being attached to solid supports, as the solid supports can be used repeatedly without degradation of the immobilized probes. Preferably, an oligonucleotide analogue of the present invention that is attached to a solid support is from about six to about 1,000 residues in length, more preferably from about 12 to about 60 residues in length. An oligonucleotide analogue of the present invention can be covalently or noncovalently, reversibly or irreversibly, bound to a solid support. Reversible binding of an oligonucleotide analogue of the present invention to a solid support can be through specific binding members or other means, for example, by electrostatic interactions (see, for example, WO 00/34521, herein incorporated by reference in its entirety). A solid support can comprise a membrane, such as a nitrocellulose or nylon membrane; paper (filter paper, cellulose); a bead, such as a magnetic bead; a polymer such as sepharose or polyacrylamide; a glass, silicon, metal, ceramic, plastic, or polymeric surface structure, or any combination of these. A preferred solid support is a chip or array comprised of any suitable material (for example, a nylon membrane, a glass slide, an acrylamide layer, a plastic multiwell plate, etc.) to which a plurality of oligonucleotide analogues are directly or indirectly coupled.

A solid support can also be a particle or bead that can comprise glass, can comprise one or more plastics or polymers, such as, for example, polystyrene, polyacrylamide, sepaharose, agarose, cellulose or dextran, and/or can comprise metals, particularly paramagnetic metals, such as iron.

One preferred solid support of the present invention is a chip or array that comprises a flat surface, and that may comprise glass, silicon, nylon, polymers, plastics, ceramics, or metals. Oligonucleotide analogues of the present invention are attached to the surface, such that the attached oligonucleotide analogue molecules are preferably at least partially complementary to one or more target nucleic acid sequences, such as sequences comprising single nucleotide polymorphisms (SNPs) or sequences comprising at least a portion of identified or unidentified genes (such as expressed sequence tags (ESTs)), and are arranged on the array at known locations so that positive hybridization events may be correlated to the presence of a nucleic acid molecule of a particular sequences in a sample from which the survey nucleic acid population is derived.

A number of different array configurations for nucleic acids, peptides, and peptide nucleic acids and methods for their production are known to those of skill in the art and disclosed in U.S. Pat. Nos. 5,445,934; 5,242,974; 5,384,261; 5,405,783; 5,412,087; 5,429,807; 5,436,327; 5,472,672; 5,527,681; 5,545,531; 5,554,501; 5,571,639; 5,624,711; 5,658,734; 5,700,637; and 6,280,946; WO 99/60156, WO 01/38565, WO 99/60156, and WO 01/01144; the disclosures of which are herein incorporated by reference in their entireties. The processes of attachment and, where applicable, synthesis, of polymers on a solid support can be modified to those compatible with oligonucleotides analogues of the present invention.

Direct coupling of oligonucleotide analogues of the present invention to a solid support can be achieved by, for example, UV crosslinking, or by chemical attachment using a derivatized surface and functional groups on the oligonucleotide analogue. For example, the functional group on the oligonucleotide analogue can be an amine, such as the amine of a terminal oligonucleotide analogue moiety, or, for example, an arylamine that is part of a derivatized terminal monomer. The surface of the solid support can comprise activated carboxylic acid groups, for example, N-hydroxysuccinimidyl esters. Alternatively, the oligonucleotide analogue can comprise an activated carboxylic acid group, and the surface of the solid support can comprise amine groups. Methods for producing condensation reactions to produce amide bonds between activated carboxyl and amines, such as those using N,N'-dicyclohexylcarbodiimide (DCC) or 1-(3-dimethylaminopropyl)-3-ethylcarbodiimide hydrochloride (EDC) are known in organic chemistry and in the attachment of polymers to other compounds, moieties, or surfaces. Other groups can also be used for covalent attachment of oligonucleotide analogues of the present invention to a solid support, such as, but not limited to, thiol, thiolester thio urea, isothiocyanate, isocyanate, ether, carbamate, maleimide, or aldehyde groups.

Indirect coupling of oligonucleotide analogues of the present invention to solid supports can include the use of linkers that can be coupled to oligonucleotide analogues and to a solid support. The linker can be an organic molecule that can be attached to the oligonucleotide analogue during synthesis of the oligonucleotide analogue, or a linker can be attached to the oligonucleotide analogue after its synthesis. Linkers are preferably hydrophilic and nonreactive with the solid support and nucleic acids, and can include, as nonlimiting examples, dioxaoctanoic acid and derivatives thereof, polyethylene glycol and derivatives thereof, polyvinyl alcohol and derivatives thereof, and polyvinyl pyrrolidone and derivatives thereof. Other means of indirect attachment of an oligonucleotide analogue to a solid support can be noncovalent, and can include specific binding members, such as, for example, biotin and avidin. For example, a biotin moiety can be coupled to an oligonucleotide analogue oligomer, and a solid support can be coated with avidin.

One form of array is a glass slide to which oligonucleotide analogues of the present invention can be bound. Another preferred solid support is a dish or multi-well plate made of polymeric plastic, such as polystyrene. In a preferred aspect of the present invention, oligonucleotide analogues of the present invention can be coupled to acrylamide monomers and incorporated into polymers that comprise derivatized polyacrylamide monomers, that can provide a means for coupling the oligomer-acrylamide-polyacrylamide co-polymer to a derivatized solid support having, for example, isothiocyanate, aldehyde or thiol groups (Efimov et al., *Nucleic Acids Res.* 22, 4416–4426).

Yet another preferred solid support of the present invention is a particle that comprises a spherical or nonflat surface, and that may comprise glass, polymers (such as, but not limited to, polyacrylamide, agaroses, dextrans, cellulose, or plastics), ceramics, or metals. Nucleic acid molecules can be attached to the particles, which may or may not be porous. Such particles can be used, for example, to capture nucleic acid molecules by hybridization to oligonucleotide analogues of the present invention that are bound to the particle or particles. Binding of an oligonucleotide analogue of the present invention to a particle can be direct or indirect, covalent or noncovalent.

It is also possible to synthesize one or more oligonucleotide analogue polymers on a solid support that can also be used in the detection methods of the present invention. For example, one or more oligonucleotide analogues of the present invention can be synthesized on a glass support (optionally attached to the support through a linker) using methods disclosed herein, and the final oligonucleotide analogue products can be deprotected but not cleaved from the solid support.

In some preferred embodiments of the present invention, an oligonucleotide analogue of the present invention is provided attached to a solid support, and contacted with a population of nucleic acid molecules under conditions that permit hybridization of oligonucleotide analogues and target nucleic acid sequences. (It is also within the scope of the present invention to hybridize oligonucleotide analogues and nucleic acid molecules in solution, and subsequently attach oligonucleotide analogue moieties to a solid support, such as through the use of specific binding members.) Hybridized oligonucleotide analogue/nucleic acid molecule complexes can be detected by staining with intercalating dyes, such as but not limited to, ethidium bromide, ethidium homodimer, TOTO, and YOYO.

In other embodiments, nucleic acid molecules of the survey population are labeled using any of a number of methods well known in the art of detection of nucleic acids. By labeling nucleic acid molecules of the survey population, the detection of nucleic acid molecules to a solid support comprising oligonucleotide analogues can be detected by detection of the label. More than one population of nucleic acid molecules can be labeled with one or more types of label. For example, one population of nucleic acid molecules can be labeled with, for example, Cy3, and another population of nucleic acid molecules can be labeled with, for example, Cy5. Both populations can be hybridized to the same solid support comprising oligonucleotide analogues of the present invention, either concurrently or sequentially, and the hybridization patterns of the survey populations can be compared.

In yet another alternative, a second "signal oligonucleotide" or, optionally, "signal oligonucleotide analogue" that can be hybridized to a target nucleic acid molecule is detectably labeled. The signal oligonucleotide can bind a target nucleic acid molecule before or after the target nucleic acid molecule binds a capture probe. In one aspect, the signal oligonucleotide can be a high affinity oligonucleotide analogue probe that binds the target molecule, and subsequently the target nucleic acid molecule binds an immobilized oligonucleotide analog, optionally at lower stringency than the solution hybridization of the signal oligonucleotide binding. (In some aspects of the present invention, the stringency of hybridization can optionally be determined by the ratio of monomers, for example, HypNA to pPNA residues in the immobilized probe oligonucleotide analogue and the signal oligonucleotide analogue.) In other aspects, the target nucleic acid molecule can bind an immobilized oligonucleotide analogue probe, and in a second step a signal oligonucleotide, or preferably, oligonucleotide analogue, that comprises a detectable label can bind the bound target nucleic acid molecule, in a "sandwich" type hybridization.

Other labeling systems can include incorporating label into a target nucleic acid molecule-oligonucleotide analogue probe complex that is immobilized on a solid support using, for example, nucleic acid polymerases in reactions that incorporate detectably labeled nucleotides into the target nucleic acid molecule or oligonucleotide analog probe. Preferably, an oligonucleotide analog probe used in these methods comprises at least one deoxyribonucleotide or ribonucleotide at its 3' terminus. In these aspects, it is preferable that hybridization of the target nucleic acid molecule-oligonucleotide analog probe leaves an overhang of the target nucleic acid molecule or of the oligonucleotide analog probe that can act as a template for nucleic acid synthesis.

Oligonucleotide Analogue Probes in Solution

An oligonucleotide analogue of the present invention used as a probe for the detection of target sequences in a sample can also be provided in solution. An oligonucleotide analogue of the present invention used as a probe for the detection of target sequences that is provided in solution can comprise a specific binding member, but that is not a requirement of the present invention. Preferred specific binding members are biotin, binding domains of proteins (for example, a calmodulin binding domain or a chitin binding domain), and a plurality of histidine residues, such that an oligonucleotide analogue probe can be captured by high affinity binding, for example, on an avidin, calmodulin, chitin, or nickel-NTA-coated surface of a solid support.

In embodiments where an oligonucleotide analogue of the present invention that is provided in solution comprises a specific binding member and is used to capture complementary or substantially complementary nucleic acid molecules of the present invention, the nucleic acid molecules of the survey population are preferably labeled.

In some preferred embodiments of the present invention, after hybridizing oligonucleotide analogues and nucleic acid molecules in solution, and subsequently capturing oligonucleotide analogue moieties to a solid support, such as through the use of specific binding members, the hybridized oligonucleotide analogue/nucleic acid molecule complexes can be detected by staining with intercalating dyes, such as but not limited to, ethidium bromide, ethidium homodimers, cyanine monomeric and cynanine dimeric stains such as, for example TOTO-1 and YOYO-1. Such intercalating dyes will not stain oligonucleotide analogues, but will stain nucleic acid molecules hybridized to oligonucleotide analogues with high sensitivity, providing a simple and reliable way of detecting hybridized nucleic acid molecules.

It is also possible to hybridize oligonucleotide analogues and nucleic acid molecules in solution, and electrophorese the hybridized complexes on a gel or matrix (for example an acrylamide or agarose gel). The gel or matrix can then be stained with an intercalating dye such as, for example, ethidium homodimer, TOTO, or YOYO. These compounds bind HypNA-pPNA/nucleic acid complexes quantitively and with high affinity. It is also possible to stain the hybridized complexes in solution, prior to electrophoresis, with dyes such as ethidium homodimer, TOTO-1, and YOYO-1, whose binding is stable to electrophoresis. In this way it is possible to label the products of two or more hybridizations with different survey populations or two or more hybridizations with different probes, stained with different dimeric intercalating fluorescent dyes having different fluorescence spectra, and electrophoreses on the same gel or captured on the same solid support.

In an alternative method, an oligonucleotide analogue of the present invention that is provided in solution to be used as a probe for the detection of target sequences preferably comprises a specific binding member. An oligonucleotide analogue probe comprising a specific binding member can be hybridized to unlabeled target nucleic acid molecules, the target nucleic acid molecule/oligonucleotide analogue probe complexes can be captured on a solid support comprising a complementary specific binding member, and subsequently the bound target nucleic acid molecules can be detected by hybridization of a labeled signal oligonucleotide, or signal oligonucleotide analogue, or by binding of a specific binding member such as an antibody that can recognize nucleic acid molecule/oligonucleotide analogue complexes.

In yet other embodiments, target nucleic acid molecules can be captured to a solid support using an oligonucleotide analogue probe that comprises a specific binding member, and polymerase reactions can be performed using captured target nucleic acid molecules as templates. Such polymerase reactions may or may not incorporate a detectable label into their products. (For example, non-labeled amplification products may be electrophoresed on gels, and subsequently detected by staining, or may be sequenced, etc.). Such polymerase reactions can be done on a solid support or following release from a solid support, and can use one or more primers that are provided after the capture of the target nucleic acid molecules.

Applications of the Method

The present invention can be directed to detection of nucleic acids in a sample, such as, but not limited to, the detection of sequences used for identification or genotyping of a subject, or the detection of pathogen or contaminant sequences in biological or environmental samples. The methods of the present invention can also be used to provide quantitative information of the copy number of a gene in one or more cells, such as a malignant cell. The methods of the present invention can be directed toward pre-natal screening, paternity testing, forensics, crime suspect investigation, genotyping, screening for genetically-based diseases, etc. The methods of the present invention can also be directed toward detecting contaminants or pathogens in food, beverages, water, pharmaceutical products, mail, in public or private living, working, or transportation areas, etc.

The methods and compositions of the present invention can also be directed to the detection of mutations or SNPs. In this regard, the high degree of sequence specificity of oligonucleotide analogues of the present invention can be exploited, such that hybridization conditions used in the detection methods do not permit the formation of stable duplexes between oligonucleotide analogue probes and survey nucleic acid molecules that have, for example, single base pair mismatches (see, for example, Examples 20, 27, 28, and 29). SNP or mutation detection can optionally be performed on arrays, to which one or more oligonucleotide analogues have been attached in an ordered fashion to a plurality of loci, such that the detection of hybridization of a nucleic acid molecule of a survey population to a position on the array can be indicative of the presence of a particular sequence in the population of nucleic acid molecules. For example, an array used for SNP or mutation detection can comprise, as nonlimiting examples, a nylon membrane, a glass surface, or a multiwell plastic dish, that comprises a plurality of oligonucleotide analogues, each with a particular sequence that is at least partially complementary to a target sequence. A population of nucleic acid molecules can be contacted with the array under conditions that promote hybridization between oligonucleotide analogues and nucleic acid molecules. Preferably, the array is washed using conditions that discriminate between complementary and mismatched oligonucleotide analogue/nucleic acid molecule complexes (for example, at a temperature that destabilizes mismatched complexes), and hybridized complexes are detected by staining with an intercalating dye, or by the use of labels incorporated into or attached to nucleic acid molecules of the survey population, or by the use of labels incorporated into or attached to signal oligonucleotide analogues, nucleic acid molecules that are subsequently contacted with the array. Other directly or indirectly labeled specific binding members, such as antibodies that recognize nucleic acid/oligonucleotide analogue complexes, can also be used for detection).

Because of the high degree of sequence specificity of oligonucleotide analogues for nucleic acid molecules under a wide range of salt concentrations, SNP detection can be performed rapidly and reliably using temperature adjustments to achieve the desired hybridization stringency.

In some embodiments, a set of one or more oligonucleotide analogues is fixed in a plurality of positions on the array, and two or more populations of nucleic acid molecules can be contacted with the same array to obtain data on more than one sample from a single hybridization. (For example, different populations of nucleic acid molecules can be applied to different wells of a microtiter dish.) In other embodiments, a single array that can comprise from one to thousands of oligonucleotide analogues, each with a different sequence of nucleobases, can be contacted with a single nucleic acid population.

The methods of the present invention can also be directed to expression profiling, such as by the use of arrays comprising oligonucleotide analogues that comprise EST sequences or sequences of identified or unidentified genes or gene fragments. Expression profiling can be directed toward identifying genes expressed by one or more organisms at a particular time, at a particular stage of development, in a particular state (such as a disease state), or under particular conditions.

It is recognized that the present invention can also be used to detect portions of genes, and thus the present invention can detect a region of a gene that is common to different gene transcripts and/or can detect more than one region of a single gene transcript. In these aspects probe nucleic acid molecules of the present invention can be designed such that they are at least partially complementary or at least partially substantially complementary to one or more than one region of a particular gene, and/or to one or more regions of a gene that may be shared among different gene transcripts, such as splice variants ("isoforms") of gene transcripts, gene transcripts originating from different members of a gene family, or variant gene transcripts produced by viruses.

The methods of the present invention can also be used to detect or identify pathogens or contaminants. ("Identify" can mean determining the species, strain, type, or subtype or a pathogen or contaminant.) The pathogens or contaminants can be viruses, bacteria, parasites, or fungi. For example, the viruses detected using the methods of the present invention can be influenza, rubella, varicella-zoster, hepatitis A, hepatitis B, hepatitis C, herpes simplex, polio, smallpox, human immunodeficiency virus, vaccinia, rabies, Epstein Barr, retroviruses, or rhinoviruses. The pathogens or contaminants can also be bacteria such as, but not limited to, *Bacillus anthracis, Escherichia coli, Mycobacterium tuberculosis, Salmonella, Staphylococcus, Chlamydia* or *Streptococcus*. The pathogens can be parasites such as *Plasmodium, Trypanosoma, Toxoplasma gondii*, or *Onchocerca*.

In these detections methods, the survey population of nucleic acid molecules or nucleic acid molecules synthesized therefrom, can optionally be labeled. For example, for expression profiling, a label such as a fluorophore or a radioisotope can be incorporated into cDNA molecules that are synthesized from a population of RNA molecules in a sample using reverse transcriptase. In another example, DNA molecules of a sample can be used as templates for amplification reactions or "fill-in" polymerase reactions (where the sample DNA has been digested with a restriction nuclease that results in overhangs) that incorporate labeled monomers. A nucleic acid population from a sample can also be labeled without the use of polymerases, for example, by biotinylation or by kinasing with a radiolabeled phosphate moiety.

Oligonucleotide analogues of the present invention can also be used as probes in detection methods such as Northern and Southern blots, dot blots, in situ RNA detection performed on cells or tissues, fluorescence in situ hybridization (FISH) on cells or chromosome preparations, etc. (See, for example, U.S. Pat. No. 6,280,946, herein incorporated by reference in its entirety.) Such oligonucleotide analogue probes can comprise labels, such as, but not limited to, radiolabels and fluorescent labels, as described herein.

Kits

The present invention includes compositions in the form of oligonucleotide analogues linked to solid supports, where a solid support can be a bead or particle, a membrane, or a surface comprising at least in part, plastic, a polymers, glass, ceramic, or metal. The present invention also includes oligonucleotide analogues conjugated to polymerizable compounds. Oligonucleotide analogues of the present invention coupled to solid supports or to polymerizable compounds can be provided in a kit that can optionally include one or more buffers, solutions, reagents, enzymes, or nucleic acid molecules. Kits can also include instructions for use.

The present invention also includes arrays comprised of any suitable material comprising at least two oligonucleotide analogue molecules of the present invention, and kits comprising at least one array that comprises oligonucleotide analogue molecules comprising at least two different nucleobase sequences. Kits comprising oligonucleotide analogues can also optionally include one or more comprise buffers, solutions, reagents, enzymes, or nucleic acid molecules. Kits can also include instructions for use.

III. Methods of Separating, Isolating, and Purifying Nucleic Acid Molecules Using Oligonucleotide Analogues Another aspect of the invention provides for the separation, isolation or purification of at least one nucleic acid molecule using at least one oligonucleotide analogue of the present invention. In these aspects of the invention, an oligonucleotide analogue of the present invention can be used as a capture probe that can hybridize to one or more target nucleic acid molecules of a population of nucleic acid molecules and thereby be used to separate the one or more target nucleic acid molecules from the remaining population. In some aspects of the present invention, the separated nucleic acid molecules are retained for further detection, analysis, or biochemical and molecular biological procedures, such as, but not limited to, amplification; ligation; chemical, nuclease, or restriction enzyme cleavage; reverse transcription; transcription; translation; and the like. In some other aspects of the present invention, the separated nucleic acid molecule are removed from the population of nucleic acid molecules, and the remaining population of nucleic acid molecules can be used for further detection, analysis, or biochemical and molecular biological procedures, such as, but not limited to, hybridization detection assays (including, but not limited to Southern, Northern, slot or dot blot, and array hybridization), nuclease protection assays, binding assays (such as, for example, DNA binding protein assays or RNA binding protein assays), amplification, ligation, restriction enzyme digestion, reverse transcription, in vivo or in vitro assays, in vitro or in vivo transcription, in vivo or in vitro translation, and the like.

The method includes: providing a population of nucleic acid molecules, contacting the population of nucleic acid molecules with one or more capture probes that comprises one or more oligonucleotide analogues of the present invention under conditions that allow hybridization of oligonucleotide analogues and nucleic acid molecules, and separating at least one target nucleic acid that is hybridized to the one or more capture probes from the members of the population of nucleic acid molecules that are not hybridized to the one or more capture probes.

The population of nucleic acid molecules can be from a sample, where a sample can be a sample from an organism, from a group of organisms of the same or different species, or from the environment, for example, a water or soil sample. The sample can be a bodily fluid, such as blood, lymph, cerebrospinal fluid, amniotic fluid, semen, urine, or saliva, or can be an extract of for example, a nasal swab, fecal sample, or material extracted from clothing, tools, upholstery, etc.

The population of nucleic acid molecules can also be from one or more organisms or from a culture, such as a bacterial culture, fungal culture, plant tissue or cell culture, or from vertebrate or invertebrate tissue or cell culture (from primary cells or cell lines).

The population of nucleic acid molecules can be not purified, partially purified, or substantially purified from a sample, one or more organisms, or one or more cultures. Purification procedures for nucleic acids are well known in the art, and can include, for example, lysis of cells, pulverization, homogenization, or maceration of tissue, extraction of nucleic acid from solid or porous surfaces with buffers, centrifugation, precipitation, extraction with organic solvents, enzymatic digestion, etc.

Preferably, a capture probe comprises at least a portion of an oligonucleotide analogue of the present invention. A capture probe of the present invention can be of any length, but preferably a capture probe is at least six residues in length. Preferably, at least a portion of a capture probe is provided in the single stranded state, and preferably, at least a portion of a capture probe that is provided in the single stranded state is complementary to or substantially complementary to at least one nucleic acid molecule known to be or suspected of being in the nucleic acid population. Preferably, the portion of a capture probe that is provided in the single stranded state that is complementary to or substantially complementary to at least one nucleic acid molecule known to be or suspected of being in the nucleic acid population is at least six residues in length, more preferably between about eight and about 120 residues in length, and most preferably between about ten and about 60 residues in length.

A capture probe preferably includes at least one specific binding member, but this is not a requirement of the present invention. Examples of specific binding members useful in a capture probe of the present invention include nucleic acid or nucleic acid analogue sequences, biotin, a plurality of histidine residues, a peptide sequence such as the hemagglutin tag sequence, the myc tag sequence, or the FLAG tag sequence, or other peptide or non-peptide specific binding members that are known or become known in the art. Preferably, the specific binding member that is comprised by a capture probe of the present invention is recognized by a specific binding member that is directly or indirectly attached to a solid support, such as a bead, column matrix, gel matrix, membrane, or a glass, silicon, metal, or polymeric surface, such as, but not limited to, a chip or array. Capture probes can optionally include a detectable label, such as a reporter group.

One or more capture probes comprising one or more sequence of bases can be provided for hybridization to one or more nucleic acid molecules of the population. For example, two or more capture probes can be provided, wherein each capture probe has a different sequence of bases and can hybridize to a different sequence of the same target nucleic acid molecule. Alternatively or in addition, two or more capture probes can be provided wherein at least one capture probe can hybridize to a target nucleic acid molecule that is different from a target nucleic acid molecule that another capture probe can hybridize to. Where more than one capture probe is utilized, the capture probes can have the same or different compositions, for example, both may comprise oligonucleotides analogues with a 1:1 ratio of HypNA to pPNA residues, or one may comprise HypNA and PNA residues and another may comprise HypNA and pPNA residues, or they may have different ratios of HypNA residues to pPNA residues, or they may have different ratios of HypNA residues to PNA residues, or they may comprise different reporter groups, specific binding members, etc.

In one embodiment of this method, a capture probe is provided free in solution. In embodiments where capture probes are provided free in solution, they preferably comprise at least one specific binding member that allows a target nucleic acid molecule bound to a capture probe to be retained, such as by binding of the capture probe to a specific binding member that is attached to a solid support, although this is not a requirement of the present invention. For example, it is possible to separate nucleic acid molecules that are bound to capture probes of the present invention by means such as, but not limited to, electrophoresis (in solution or through a matrix), phase separation, passing the hybridized solution through a filter or column (see, for example, U.S. Pat. No. 6,060,242 issued May 9, 2000, to Nie et al.). Such methods can rely on the differential behavior of hybridized and nonhybridized nucleic acid molecules of the population, relying on, for example, the different properties of single and double-stranded nucleic acid molecules that can optionally be enhanced by using capture probes that incorporate particular moieties.

In another embodiment of the method, one or more capture probes is provided that is bound to a solid support. The binding of a capture probe to a solid support can be direct or indirect. Method for direct coupling of nucleic acids and nucleic acid analogues to derivatized surfaces are known in the art and can include specific binding members, linkers, and the use of derivatized groups on the solid support and oligonucleotide analogue.

Optimal conditions for hybridization of capture probes to target nucleic acids can be determined empirically using hybridization and detection methods known in the art. Parameters such as the temperature of hybridization and the length, monomer composition, and nucleobase sequence of the capture probe can be varied to optimize hybridization conditions for the particular application. Preferably, hybridization is performed in the presence of at least one millimolar magnesium and at a pH that is above 6.0. Of particular utility is the potential to alter the ratios of HypNA to PNA residues, or HypNA to pPNA residues, in capture probes of the present invention, thereby altering the binding affinity of the capture probes. In applications where more than one capture probe is used, different capture probes can have different affinities for their target sequences.

For example, in many cases, solution hybridization of nucleic acids is more efficient than hybridization of nucleic acids (or nucleic acid analogues) to target sequences attached to a solid support. In some applications the separation of one or more target nucleic acid molecules can be done in more than one hybridization step, where a first step uses a first oligonucleotide analogue as a capture probe to bind a target nucleic acid molecule in solution, and a second step results in the hybridization of the capture probe that is hybridized to the target nucleic acid molecule to an immobilized oligonucleotide analogue that is bound to a solid support. The hybridization of the second step can be performed at a lower stringency than that of the first step, to promote more efficient hybridization to an immobilized probe. The compositions of the present invention are well suited to two-step hybridization methods, as capture probes and immobilized probes can be designed to have different affinities by altering the ratios of, for example HypNA residues to pPNA residues in capture probes and immobilized probes. In this way, hybridization conditions such as salt concentration and temperature do not have to be altered during the procedure.

Nucleic acid molecules that have hybridized to oligonucleotide analogue capture probes can be separated from unhybridized nucleic acid molecules by, for example, physically removing the unbound nucleic acids from the solid support to which the hybridized nucleic acid molecules are bound. This can be performed through pouring or pipeting the nucleic acid solution from the solid support, or through electrophoresis (for example, where the solid support is a gel or polymer), gravity, centrifugation, etc. Preferably but optionally, the separation process utilizes washes, which are performed under conditions that do not disrupt complexes comprising oligonucleotides and nucleic acid molecules that are at least partially complementary, but do not promote the formation or can disrupt complexes between oligonucleotides and nucleic acid molecules that are not at least partially complementary. Wash conditions that give optimal yield and purity of target nucleic acid molecules can be determined empirically. Such factors as salt concentration, temperature, and the presence of denaturants and detergents are among the conditions that can be varied to optimize separation protocols.

The methods of the present invention can be used for the isolation of any nucleic acid molecule whose sequence is at least partially known. For example, plasmid DNA can be isolated from bacterial culture be passing a bacterial lysate over a column comprising a matrix to which an oligonucleotide analogue that is at least partially complementary or at least partially substantially complementary to a sequence found in the plasmid, has been coupled. Partially purified or substantially purified nucleic acids, including nucleic acids that have been amplified, transcribed in vitro, digested with restriction enzymes, etc., can be purified by electrophoresis through a matrix such as polyacrylamide to which a complementary or substantially complementary oligonucleotide analogue has been coupled. The inherent stability of the oligonucleotide analogues of the present invention, and their high affinity for complementary sequences at a range of temperatures and salt conditions, and their ability to bind double-stranded DNA through strand displacement, such that hybridization to target nucleic acid molecules does not rely on the single strandedness of the target nucleic acid molecules, makes them particularly useful in such applications.

Reducing the Occurrence of Abundant RNAs

In one preferred aspect of the present invention, an oligonucleotide analogue of the present invention can be used for reducing the occurrence of one or more RNA molecules in a population of RNA molecules to be used for the synthesis of cDNA. The method includes: providing a population of RNA molecules, contacting the population of RNA molecules with one or more capture probes comprising oligonucleotides of the present invention under conditions that allow hybridization of oligonucleotide analogues to nucleic acid molecules, and separating at least one RNA molecule of the population of RNA molecules that is bound to the one or more capture probes of the present invention from the unbound members of the population of RNA molecules.

In one aspect of the embodiment, the unbound RNA molecules are used for cDNA synthesis. In one example, one or more capture probes comprise a HypNA-PNA oligonucleotide or a HypNA-PNA oligonucleotide that is at least partially complementary or at least partially substantially complementary to an RNA molecule that is known to be or suspected of being abundant in the population of nucleic acid molecules. By "abundant" is meant that the RNA molecule represents at least 10%, at least 20%, at least 30%, at least 40%, at least 50%, at least 60%, or at least 70% of the population of RNA molecules. An abundant RNA molecule can be a transcript that is highly expressed in the organism or tissue from which the population of RNA molecules is derived, for example, a globin transcript from an RNA population isolated from blood cells, an actin transcript from HeLa cells, or a light harvesting chlorophyll binding protein transcript from leaf tissue of a plant. Using the methods of the present invention, transcripts from highly expressed genes can be depleted from the population of RNA molecules that can be used to synthesize cDNA, including cDNA that can be cloned into a library and screened for RNA molecules of interest. The representation of cDNAs derived from non-abundant RNA transcripts is greater in the cDNA library than in the original population of RNA molecules, increasing the chances of obtaining such a cDNA from a non-abundant RNA transcript by screening.

These methods can also be used to separate ribosomal RNAs from a population of RNA molecules, where the population of RNA molecules can be from a prokaryotic or eukaryotic cell. The population of RNA that is depleted of ribosomal RNA molecules can be used to synthesize DNA, using oligo T priming (where the population is from eukaryotic cells), random priming (where the RNA transcripts of interest are not polyadenylated, such as prokaryotic RNA transcripts and nonpolyadenylated eukaryotic transcripts), or priming with specific sequence primers.

In other aspects, the method described above can be used to separate abundant RNA molecules from a population of RNA molecules, and the unbound RNA molecules of the population of RNA molecules can be optionally used for purposes other than cDNA synthesis, such as nucleic acid hybridization, e.g. "dot blot" or "Northern" hybridization, Rnase protection experiments, in vitro or in vivo experiments that include translation of at least one of the unbound RNA molecules of the population, and/or reverse transcription, including, but not limited to, reverse transcription followed by amplification reactions.

Isolation of Poly(A) RNA Molecules

Another preferred embodiment of the invention is a method for isolating polyadenylated (poly A) RNA molecules from a population of RNA molecules. The method includes: providing a population of RNA molecules, adding to the population of RNA molecules one or more oligonucleotide analogues of the present invention that comprise an oligo T sequence of at least six residues, allowing the one or more oligonucleotide analogues of the present invention to bind to one or more RNA molecules of the population of RNA molecules, and separating the polyadenylated RNA molecules of the population of RNA molecules that are bound to the one or more oligonucleotide analogues of the present invention from the unbound RNA molecules of the population of RNA molecules.

The population of RNA molecules can be partially purified or substantially purified from a sample, one or more organisms, or culture. Purification procedures for RNA are well known in the art, and can include, for example, lysis of cells, pulverization, homogenization, or maceration of tissue, denaturation of proteins, centrifugation, precipitation, extraction with organic solvents, enzymatic digestion, etc. In certain aspects of the invention, the RNA population is provided in a crude lysate of cells or tissue, that can optionally be treated, for example, with RNAse-free DNAse to remove DNA from the population that might otherwise hybridize to an oligo T capture probe of the present invention.

An oligo T capture probe of the present invention can comprise any oligonucleotide analogue of the present invention. Preferably, an oligonucleotide analogue used as an oligo T capture probe of the present invention comprises, at least in part, HypNA-PNA or Hyp-pPNA oligonucleotides.

An oligonucleotide analogue used as an oligo T capture probe can have any ratio of Hyp residues to PNA residues or of Hyp residues to pPNA residues, but preferably, the ratio of Hyp residues to PNA residues or of Hyp residues to pPNA residues in at least one region of an oligonucleotide analogue used as an oligo T capture probe is from about 2:1 to about 1:4, most preferably from about 1:1 to about 1:3. Preferably, at least one region of an oligonucleotide analogue used as an oligo T capture probe comprises at least six consecutive thymine (T)-containing, more preferably at least eight thymine (T)-containing residues. In certain preferred aspects of the present invention, at least one oligo T capture probe used in the disclosed methods can include a sequence of at least ten T residues joined to another sequence of at least ten T residues by a linker. This clamp structure can form triple helix structures with RNA sequences that may have secondary structure around the poly A sequence, including secondary structure that cause the poly A sequence to be inaccessible to capture by conventional oligo T capture probes.

An oligonucleotide analogue oligo T capture probe of the present invention preferably comprises a specific binding member, but that is not a requirement of the present invention. Preferred specific binding members are biotin, polyhistidine, and peptide binding domains (such as, but not limited to, calmodulin binding domain and chitin binding domain). Preferably, a specific binding member that is attached to an oligonucleotide analogue oligo T capture probe is attached to a terminus of an oligonucleotide analogue oligo T capture probe, but this is not required.

Preferably, following addition of one or more oligonucleotide analogue oligo T capture probes of the present invention to a population of RNA molecules, the population of RNA molecules-oligonucleotide capture probe mixture is incubated at a temperature and salt concentration that allows hybridization of an oligo T capture probe to members of the RNA population that comprise poly A sequences. In some aspects, the mixture of oligo T capture probes and population of RNA molecules can optionally be heated for a period of time at the initial stages of the hybridization, for example to a temperature above 40 degrees C. and less than 100 degrees C., more preferably to a temperature greater than 50 degrees C. and less than 90 degrees C., to allow unfolding of secondary structure that may be present in RNA molecules of the population. The length of the high temperature incubation can vary, for example, from about thirty seconds to over 24 hours, but more conveniently can be from about five to about fifteen minutes at about 70 degrees C. Preferably, hybridization is performed in the presence of at least one millimolar magnesium and at a pH that is above 6.0. The temperature and salt concentration used will depend, at least in part, on the ratio of HypNA:pPNA residues in the oligo T capture probe. Optimal salt concentrations and temperatures for hybridization of a given capture probe can be determined by hybridization/denaturation experiments, using methods known in the art. In many cases (optionally following an initial high temperature incubation), hybridization can be performed at room temperature for a period of at least ten minutes, preferably for a period of at least fifteen minutes, in the presence of from 0.05 to 0.5 molar salt.

The mixture of the RNA population with one or more oligonucleotide analogue oligo T capture probes can be added to a solid support that comprises at least one specific binding member that can bind the one or more oligonucleotide analogue oligo T capture probes. Preferred solid supports are beads, such as paramagnetic beads that can be captured with a magnet, the surface of plates, such as multiwell plates comprised of a polymer such as polystyrene, and column matrices, such as, for example sepharose. The specific binding member can be a nucleic acid or nucleic acid analogue, an antibody, an antigen, a protein (such as avidin), a ligand (such as nitriloacetic acid-nickel), etc. In certain preferred aspects of the invention, the oligo T capture probe comprises biotin, and the solid support comprises avidin or streptavidin.

In the alternative, one or more oligonucleotide analogue oligo T capture probes may or may not comprise a specific binding member and is directly or indirectly coupled to a solid support, such as, but not limited to, a bead, the surface of a dish, or a column matrix. In this case, the RNA population is added to the solid support that comprises the oligonucleotide analogue oligo T capture probe (for example, is added to the column or dish, or added to a tube containing beads).

After allowing the specific binding member of the oligonucleotide analogue oligo T capture probe to bind the specific binding member of the solid support (where the capture probe is not already bound to a solid support), unbound nucleic acid molecules of the population can be washed off, such as by repeated rinses with a buffer compatible with oligo T capture probe binding and specific binding member binding. Preferably, washing takes place in low (less than 50 millimolar) salt, or in the absence of salt. temperature can be elevated, preferably to less than 70 degrees C., but this will depend on other conditions, such Preferably, the wash buffer includes at least 50 micromolar magnesium, more preferably, at least 1 millimolar magnesium. Optionally, the wash buffer can include Dnase to eliminate any residual DNA. Washes can be performed at room temperature, or at elevated temperatures. Temperatures selected for washes can depend on such factors as the salt concentration of the wash buffer, the length and composition of the PNA probe, etc.

Captured poly A RNA molecules can be eluted from the solid support, for example, with water. Elution can also be performed in the presence of denaturing agents or formamide (from 5 to 20%) or DMSO (from 1 to 20 percent). In some preferred aspects of this method, elution is performed using a low salt buffer or water at a temperature below the Tm of the oligonucleotide analogue oligo T capture probe hybridized to DNA, such as at room temperature. This can prevent the elution of DNA molecules that may be bound to the capture probes. The elution temperature can also be higher than room temperature, such as, for example at temperatures up to 90 degrees or even higher. The elution time can vary as well, for example, from about one minute in duration to about fifteen minutes or even longer. In some preferred aspects of the invention, elution is performed in water at 75 degrees C. for two minutes.

It will be apparent to those skilled in the art of nucleic acid hybridization and separation that many parameters of hybridization, washing, and elution, such as but not limited to, temperature, duration, salt concentration, presence of denaturants, and the length and composition of probe, can affect the yield and quality of nucleic acid isolated by hybridization, such as poly A RNA. It is within the scope of the present invention to vary these and other parameters to optimize the isolation procedures using oligonucleotide analogues of the present invention.

The present invention includes kits for poly A RNA isolation that include at least one oligonucleotide analogue of the present invention. The oligonucleotide analogue is preferably provided linked to a specific binding member. Such kits can also optionally include one or more of the following: a solid support such as beads, preferably comprising at least one specific binding member, one or more buffers or solutions, water, such as DEPC-treated or HPLC grade water, one or more enzymes, one or more precipitation reagents, plasticware (such as tubes or plates), one or more filters, and instructions for use.

IV. Methods of Enhancing or Inhibiting the Activity of an Enzyme or Cellular Activity Using Oligonucleotide Analogues of the Present Invention The present invention also provides methods for enhancing or inhibiting the activity of an enzyme or cellular activity using an oligonucleotide analogue of the present invention. The method includes: providing at least one subject, sample or solution comprising an enzyme or cellular activity and an enzyme or cellular activity substrate, adding an oligonucleotide analogue of the present invention to the subject, sample, or solution, and providing conditions under which the enzyme has at least one activity in the presence or absence of the one or more oligonucleotide analogues.

A subject, sample, or solution can be an organism, including a prokaryotic or eukaryotic organism, including a human. As used herein, "at least one subject" can refer to one or more organisms or from a cell or tissue culture, such as a bacterial culture, fungal culture, plant cell or tissue culture, or from vertebrate or invertebrate tissue or cell culture (from primary cells or cell lines).

A sample can be a sample from an organism, from a group of organisms of the same or different species, or from the environment, for example, a water or soil sample. The sample can be a bodily fluid, such as blood, lymph, cerebrospinal fluid, amniotic fluid, semen, urine, or saliva, or can be an extract of for example, a nasal swab, fecal sample, or material extracted from clothing, tools, upholstery, etc.

A sample can also be an unpurified, partially purified, or substantially purified fraction or extract from a sample (including biological and nonbiological samples), one or more organisms, or culture. Purification procedures for many enzymes and activities are known in the art, and can include, for example, lysis of cells, pulverization, homogenization, or maceration of tissue, centrifugation, precipitation, extraction with organic solvents, enzymatic digestion, etc. In some cases, highly purified enzymes (such as polymerases) are available commercially.

Solutions comprising enzymes and cellular activities in crude or purified form can be used in the methods of the present invention.

An oligonucleotide analogue of the present invention can be any oligonucleotide analogue of the present invention. The addition of an oligonucleotide analogue of the present invention to a subject can be by injection, inhalation, oral administration, topical administration, implantation of a solid support comprising the nucleic acid analogue, etc. An oligonucleotide analogue of the present invention can simply be added to a cell or tissue culture or can be added along with cell transfection reagents, such as, but not limited to, calcium phosphate, polyethylene glycol, cationic lipids such as lipofectamine™ (Life Technologies), geneporter™ (Gene Therapy Systems), liposomes, etc. An oligonucleotide analogue of the present invention can also be coupled to a peptide or other molecule that promotes transport into cells such as polylysine, the HIV TAT protein, the *Drosophila anatennapedia* protein, or peptides derived from these proteins, or can be microinjected, electroporated, or introduced by bombardment of cells or tissue. An oligonucleotide analogue of the present invention can simply be added to a solution that comprises an enzyme or cellular activity.

An oligonucleotide analogue of the present invention can enhance or inhibit the activity of an enzyme or cellular activity, such as, but not limited to, a polymerase, telomerase, helicase, spliceosome, ribosome, nuclear transport factor, etc. The effects of an oligonucleotide analogue of the present invention on the activity of an enzyme or cellular activity can be determined using assays developed in the particular fields and subfields to which the enzymatic functions and cellular activities pertain. For example, the activity of a polymerase can be measured by the incorporation of labeled nucleotides into the nucleic acid product, a splicing assay can quantitate the relative amounts of alternatively spliced transcripts from an RNA molecule, etc. The design of oligonucleotide analogues to be used to enhance or inhibit an enzymatic or cellular activity can be based on, among other things, the nucleobase sequence of nucleic acid substrates of the enzyme or activity. The length, nucleobase composition, structure (i.e. presence of linkers and other groups) and monomer composition of oligonucleotide analogues can be varied to optimize the inhibition or enhancement.

The Use of Nucleotide Analogues in Enhancing the Activity of a Polymerase

In one aspect of the method, an oligonucleotide analogue can enhance the activity of an enzyme, such as, but not limited to, a polymerase. For example, oligonucleotide analogues of the present invention can be designed such that they can hybridize with one or more nucleic acid molecules in a subject, sample, or solution. The oligonucleotide analogue can promote or maintain the single-strandedness of at least a portion of the nucleic acid molecule of the population to prevent inhibition of RNA or DNA polymerase activity that can occur when there is a double-stranded region or secondary structure in the template nucleic acid. Oligonucleotides of the present invention used to promote or maintain the single-stranded state of a template nucleic acid can be displaced from the template nucleic acid by the polymerase as it synthesizes portions of a nucleic acid that are bound by the oligonucleotide analogue. Polymerases used in the methods of the present invention can be any nucleic acid polymerases, including RNA polymerases and DNA polymerases. Of particular interest are reverse transcriptases that use RNA as a template (e.g., AMV reverse transcriptase, MMLV reverse transcriptase, derivatives thereof, and Tth reverse transcriptase) and high temperature DNA polymerases such as Taq, Pfu, Tth, and the like. Methods of enhancing DNA amplification using peptide nucleic acids are disclosed in U.S. Pat. No. 5,656,461 issued Aug. 12, 1997 to Demers, herein incorporated by reference.

An oligonucleotide analogue can also promote polymerase activity by acting as a primer in a polymerase reaction. In these aspects, an oligonucleotide analogue of the present invention preferably comprises at least one nucleic acid residue, such as an RNA residue or a DNA residue, that is at at least one terminus of the oligonucleotide analogue. Preferably, the nucleic acid residue at at least one terminus of the oligonucleotide analogue used in these aspects of the invention has a free 3' hydroxyl group. Oligonucleotide analogues of the present invention that act as primers can enhance the synthesis of regions of nucleic acid molecules that have secondary structure by binding at the regions of secondary structure and priming nucleic acid synthesis Oligonucleotide analogues of the present invention can also be used to enhance transcriptional activity, such as the activity of DNA-dependent RNA polymerases. For example, oligonucleotide analogues that bind at or near the transcriptional start site of a gene or gene construct can promote an open configuration of the promoter region of a gene through strand displacement and the initiation of transcription by a polymerase, such as, but not limited to, a prokaryotic DNA-dependent RNA polymerase as described in U.S. Pat. No. 5,837,459 issued Nov. 17, 1998 to Berg et al.

The Use of Oligonucleotide Analogues in Inhibiting the Activity of a Polymerase

In other aspects of the method, an oligonucleotide analogue of the present invention can inhibit the activity of an enzyme or cellular activity, such as, but not limited to, the activity of a polymerase, telomerase, helicase, spliceosome, ribosome, nuclear transport factor, etc.

In one aspect of the invention that pertains to polymerase function, a nucleic acid analogue can bind a nucleic acid molecule and prevent the progression of a polymerase through the region of the nucleic acid molecule that is bound by the oligonucleotide analogue (Larsen et al. *Nucl. Acids Res.* 24:458–463 (1996); Good and Nielsen, *Proc. Natl. Acad. Sci. USA* 95: 2073–2076 (1998); Knudsen and Nielsen, *Nucl. Acids Res.* 24: 494–590 (1996); Faria et al. *Proc. Natl. Acad. Sci. USA* 97: 3862–3867 (2000)). Preferably, oligonucleotide analogues that are used for the inhibition of polymerase activities are "clamping" oligonucleotide analogues, that have two polypyrimidine tracts connected by a flexible linker (see, for example, U.S. Pat. No. 6,004,750 issued Dec. 21, 1999 to Frank-Kamenetskii et al.).

In one preferred aspect of these methods of the invention, clamping oligonucleotide analogues of the present invention that are complementary to a region of an abundant RNA transcript can be used to inhibit reverse transcription of the abundant message by reverse transcriptase. In this way, the frequency of the cDNA corresponding to the abundant message is "subtracted" from a population of cDNA molecules, such that its frequency in the population of cDNA generated by reverse transcription of a population of RNA that comprises the abundant message is reduced. A population of cDNA in which the frequency of sequences corresponding to one or more abundant transcripts is reduced can optionally be used to construct a cDNA that will have a correspondingly higher frequency of non-abundant RNA transcripts than a cDNA library that is not constructed using this subtractive method. Subtracted cDNA can also be used without cloning, for example, it can be used to hybridize to arrays, such as, but not limited to, arrays of nucleotide sequences corresponding to ESTs or identified genes, or the subtracted cDNA can itself be bound to an array for screening with other nucleic acid or nucleic acid analogue probes.

In another preferred aspect of these methods of the invention, clamping oligonucleotide analogues of the present invention that are complementary to a region of a DNA template can be used to inhibit DNA-dependent DNA polymerase, such as but not limited to, high temperature DNA polymerase such as Taq or Pfu polymerase. In these instances, the polymerase is unable to use the bound oligonucleotide analogue as a primer. Clamping oligonucleotide analogues can be used to inhibit amplification of sequences that might otherwise compete with the amplification of a nucleic acid molecule sequence of interest to which it has a high degree of homology. As such, clamping oligonucleotide analogues are useful in the detection of SNPs, because their high degree of binding specificity allows them to selectively bind to and inhibit amplification of a nucleic acid molecule or sequence while permitting the binding of an oligonucleotide primer to a sequence that can differ by as little as a single base pair (Orum et al. *Nucl Acids Res.* 21: 5332–5336 (1993), and see Examples 20, 27, and 28).

Oligonucleotide analogues of the present invention can be synthesized and selected for use as clamping oligonucleotide analogs based on knowledge of the target sequence and assays that identify and quantitate amplification products from one or more nucleic acid molecules. Parameters such as, but not limited to, the length, base composition, and monomer composition of a clamping oligonucleotide analogue of the present invention can be varied to obtain optimal inhibition of amplification of a nucleic acid molecule.

Oligonucleotide analogues of the present invention can also be used to inhibit transcription in vivo or in vitro. Without wishing to be bound by any mechanism, oligonucleotide analogues that can hybridize to the promoter region of a gene or gene construct can prevent the binding of transcription factors that activate transcription of a gene (Knudsen and Nielsen, *Nucl. Acids Res.* 24: 494–590 (1996); Faria et al. *Proc. Natl. Acad. Sci.* USA 97: 3862–3867 (2000)). Oligonucleotide analogues of the present invention can be synthesized and selected for use as inhibitors of transcription based on knowledge of the nucleic acid sequence and assays that identify and quantitate transcription products from one or more nucleic acid molecules. Parameters such as, but not limited to, the length, base composition, and monomer composition of an oligonucleotide analogue of the present invention can be varied to obtain optimal inhibition of transcription of a nucleic acid molecule. Of particular relevance to the present invention is the ability to alter the ratio of HypNA to pPNA residues in an oligonucleotide analogue of the present invention to achieve desirable binding affinities.

Other activities that can be inhibited by an oligonucleotide analogue of the present invention include, but are not limited to, telomerase activity (Kelland et al. *Anticancer Drugs* 11: 503–13 (2000)) and the activity of enzymes or complexes that bind nucleic acids, for example, helicases, topoisomerases, nuclear transport factors, splicing factors, polyadenylases, and nucleases. Oligonucleotide analogues of the present invention can be synthesized and selected for use as inhibitors of such activities based on knowledge of the nucleic acid sequence bound by the enzyme, factor, or complex, and assays that measure the activity of the by the enzyme, factor, or complex. Parameters such as, but not limited to, the length, base composition, and monomer composition of an oligonucleotide analogue of the present invention can be varied to obtain optimal inhibition of transcription of a nucleic acid molecule. Of particular relevance to the present invention is the ability to alter the ratio of HypNA to PNA or pPNA residues in an oligonucleotide analogue of the present invention to achieve desirable binding affinities.

Use of Oligonucleotide Analogues as Antisense Agents

Oligonucleotide analogues of the present invention can also be used as antisense agents for the inhibition of gene expression. In some preferred embodiments of the present invention, an oligonucleotide analogue used as an antisense agent is from ten to one hundred residues in length, and comprises HypNA and pPNA residues in a 1:1 ratio. Sequences for oligonucleotide analogue antisense agents can be chosen such that they are complementary to at least a portion of a gene.

Clamping oligonucleotide analogues of the present invention can also find use as antisense agents, and can comprise pyrimidine-rich sequences that can hybridize to a purine-rich tract in any portion of an RNA transcript. Preferably, a clamping oligonucleotide analogue used as an antisense agent comprises two pyrimidine-rich tracts separated by a flexible linker, such as a linker depicted in FIG. 5.

Oligonucleotide analogues of the present invention can be synthesized and selected for their ability to inhibit gene expression based on knowledge of the target sequence and assays that quantitate transcription, translation, or splicing products from one or more nucleic acid molecules. Parameters such as, but not limited to, the length, base composition, and monomer composition of a translational start site-binding or clamping oligonucleotide analogue of the present invention can be varied to obtain optimal inhibition of gene expression of a nucleic acid molecule. Of particular relevance to the present invention is the ability to alter the ratio of HypNA to PNA or pPNA residues in an oligonucleotide analogue of the present invention to be used for the inhibition of translation to achieve desirable binding affinities.

Oligonucleotide analogue antisense agents of the present invention can be administered to cells or tissues, both in vivo and ex vivo, and can be administered to cell lines as well as primary cells. Oligonucleotide analogue antisense agents of the present invention can also be administered to living organisms and subjects, including mammalian subjects, including human subjects.

Oligonucleotide analogue antisense agents can be delivered by any convenient means, including, but not limited to, addition to culture media, particle bombardment, direct injection or perfusion into tissues or organisms, topical or local adminstration, optionally with the use of implants (such as polymers). The oligonucleotide analogue antisense agents can be delivered with transfection or penetration agents of any type, including salts, alcohols, detergents, polymers, lipids, liposomes, or peptides that can be mixed with or applied with, or conjugated to, an oligonucleotide analogue transfection agent.

The effectiveness of an oligonucleotide analogue of the present invention as an inhibitor of gene expression can be assessed in many different ways, including determination of RNA levels of the targeted gene, determination of protein levels, cell expression assays using reporter genes, assays that measure downstream biochemical or cellular effects, and assays that measure phenotypic responses.

Oligonucleotide analogue antisense agents can be used for research purposes (for example, to determine a function of a targeted gene), for the creation of animal models for disease states, for target validation, or for therapeutic purposes.

Where oligonucleotide analogues of the present invention are used as therapeutic agents, they can be provided in pharmaceutical compositions, which may include carriers, thickeners, diluents, buffers, preservatives, surface active agents and the like in addition to the oligonucleotide analogue. Pharmaceutical compositions may also include one or more active ingredients such as antimicrobial agents, anti-inflammatory agents, anesthetics, and the like in addition to oligonucleotide analogues.

The pharmaceutical composition may be administered in a number of ways depending on whether local or systemic treatment is desired, and on the area to be treated. Administration may be done topically (including ophthalmically, vaginally, rectally, intranasally), orally, by inhalation, or parenterally, for example by intravenous drip or by intravenous, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms may also be useful.

Compositions for oral administration include powders or granules, suspensions or solutions in water or nonaqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated. Persons of ordinary skill can easily determine optimum dosages, dosing methodologies and repetition rates. Optimum dosages may vary depending on the relative potency of individual oligonucleotides, and can generally be calculated based on EC50's in in vitro and in vivo animal studies. For example, given the molecular weight of compound (derived from oligonucleotide sequence and chemical structure) and an effective dose such as an IC50, for example (derived experimentally), a dose in mg/kg is routinely calculated.

Thus, in the context of this invention, by "therapeutically effective amount" is meant the amount of the compound that is required to have a therapeutic effect on the treated subject. This amount, which will be apparent to the skilled artisan, will depend upon the age and weight of the subject, the type of disease to be treated, perhaps the gender of the subject, and other factors which are routinely taken into consideration when treating a subject with a disease. A therapeutic effect is assessed in the subject by measuring the effect of the compound on the disease state in the subject. For example, if the disease to be treated is psoriasis, a reduction or ablation of the skin plaque is an indication that the administered dose has a therapeutic effect. Similarly, in mammals being treated for cancer, therapeutic effects are assessed by measuring the rate of growth or the size of the tumor, or by measuring the production of compounds such as cytokines, which production is an indication of the progress or regression of the tumor.

V. Methods of Promoting Homologous Recombination Using Oligonucleotide Analogues The present invention also includes a method for promoting homologous recombination of genes or gene segments using oligonucleotide analogues. Methods of introducing genes, portions of genes, and inactivated genes, including genes or portions of genes with mutations, insertions, or deletions into cellular DNA by homologous recombination are known in the art (U.S. Pat. No. 5,998,209 issued Dec. 7, 1999 to Jakobovits, et al. and U.S. Pat. No. 6,066,778 issued May 23, 2000 to Ginsburg et al., both herein incorporated by reference). The efficiency of homologous recombination for gene targeting can be enhanced by using chimeric oligonucleotides, for example, oligonucleotides comprising DNA and RNA (Gamper et al. Biochemistry 39: 5808–5816 (2000); Xiang et al. J Mol Med. 75: 829–35 (1997); Beethem et al. Proc. Natl. Acad. Sci. USA 96:8774–8778 (1999); Zhu et al. Proc. Natl. Acad. Sci. USA 96:8768–8773 (1999)). The present invention includes gene targeting constructs that include oligonucleotide analogues.

Preferably, an oligonucleotide analog that is included in a gene targeting construct is a peptide nucleic acid, a phosphono peptide nucleic acid, a peptide nucleic acid-phosphono nucleic acid, a hydroxyproline nucleic acid-peptide nucleic acid, a hydroxyproline nucleic acid-phosphono peptide nucleic acid, a serine nucleic acid, a serine nucleic acid-peptide nucleic acid, a serine nucleic acid-phosphono peptide nucleic acid, phosphono peptide nucleic acid-aromatic-1 peptide nucleic acid, a phospono hydroxyproline-1 nucleic acid, or a phospono hydroxyproline-2 nucleic acid.

Preferably, a gene targeting construct comprises DNA and oligonucleotide analogue sequences. The portion of the gene targeting vector that comprises DNA can be made by methods well known in the art (Sambrook et al.), such as gene isolation and cloning techniques. The portion of the gene targeting vector that comprises DNA can be replicated, for example, in bacteria or yeast as a plasmid or viral construct. The portion of the gene targeting vector that comprises oligonucleotide analogue sequences can be chemically coupled to the DNA, or can be hybridized to single- or double-stranded portions of the DNA. For example, a double-stranded vector can be rendered at least partially single-stranded by enzymes, heat, denaturing agents, or high pH. Oligonucleotide analogues can be hybridized to at least a portion of the single-stranded DNA construct. Sequences that are not hybridized to the oligonucleotide analogue can be made double-stranded by, for example, polymerase reactions or renaturation conditions. Thus, a construct can be made that comprises at least one region of double-stranded DNA and at least one region of DNA hybridized to an oligonucleotide analogue. In the alternative, an oligonucleotide analogue can hybridize to at least a portion of a double-stranded DNA vector by Hoogstein base-pairing.

The targeting construct preferably comprises sequences that are homologous to the gene being targeted. Where gene expression of the targeted gene is to be ablated, the homologous sequences preferably comprise a deletion or insertion in the sequences that are homologous to the targeted gene, such that expression of the gene from that template is interrupted. The portion of a construct that comprises an oligonucleotide analogue can comprise at least a portion of a gene to be targeted. Alternatively, the portion of a construct that comprises an oligonucleotide analogue can be outside of the boundaries of a gene to be targeted.

Preferably, targeting constructs comprise at least one gene encoding a selectable marker. More preferably, targeting constructs comprise two genes encoding different selectable markers. At least one selectable marker provides for positive selection, such as by selection on media comprising an antibiotic such as neomycin or hygromycin. The replacement targeting construct may include a deletion at one site and an insertion at another site which includes a gene for a selectable marker, such as neomycin resistance. The presence of the selectable marker gene inserted into the target gene establishes the integration of the target vector into the host genome. However, DNA analysis will be required in order to establish whether homologous or non-homologous recombination occurred. This can be determined by employing probes for the insert and then sequencing the 5' and 3' regions flanking the insert for the presence of DNA extending beyond the flanking regions of the construct or identifying the presence of a deletion, when such deletion is introduced. The selectable marker may be flanked by recombinase target site sequences, such that it can be excised by supplying an appropriate recombinase after selection of the transgenic cells and conformation of the homologously inserted sequence. Methods for excision of introduced sequences in transgenic cells using the cre-lox recombinase system is described in U.S. Pat. No. 6,066,778 issued May 23, 2000 to Ginsburg et al.

Upstream and/or downstream from the target gene construct may be a gene which provides for identification of whether a double crossover has occurred. For this purpose, the Herpes simplex virus thymidine kinase gene may be employed, since cells expressing the thymidine kinase gene may be killed by the use of nucleoside analogs such as acyclovir or gancyclovir, by their cytotoxic effects on cells that contain a functional HSV-tk gene. The absence of sensitivity to these nucleoside analogs indicates the absence of the HSV-thymidine kinase gene and, therefore, where homologous recombination has occurred, that a double crossover has also occurred.

Where a selectable marker gene is involved, as an insert, and/or flanking gene, depending upon the nature of the gene, it may be from a host where the transcriptional initiation region (promoter) is not recognized by the transcriptional machinery of the avian host cell. In this case, a different transcriptional initiation region (promoter) will be required. This region may be constitutive or inducible. A wide variety of transcriptional initiation regions have been isolated and used with different genes. Of particular interest is the promoter region of rous sarcoma virus. In addition to the promoter, the wild type enhancer may be present or an enhancer from a different gene may be joined to the promoter region.

While the presence of the marker gene in the genome will indicate that integration has occurred, it will still be necessary to determine whether homologous integration has occurred. This can be achieved in a number of ways. For the most part, DNA analysis will be employed to establish the location of the integration. By employing probes for the insert and then sequencing the 5' and 3' regions flanking the insert for the presence of the target locus extending beyond the flanking region of the construct or identifying the presence of a deletion, when such deletion has been introduced, the desired integration may be established.

The polymerase chain reaction (PCR) can also be employed in detecting the presence of homologous recombination. Probes may be used which are complementary to a sequence within the construct and complementary to a sequence outside the construct and at the target locus. In this way, one can only obtain DNA segments having both the primers present in the complementary chains if homologous recombination has occurred. By demonstrating the presence of the PCR products for the expected size sequence, the occurrence of homologous recombination is supported.

In constructing the subject constructs for homologous recombination, a replication system for procaryotes, particularly E. coli, may be included, for preparing the construct, cloning after each manipulation, analysis, such as restriction mapping or sequencing, expansion and isolation of the desired sequence. Where the construct is large, generally exceeding about 50 kbp, a yeast artificial chromosome (YAC) may be used for cloning of the construct. When necessary, a different selectable marker may be employed for detecting bacterial or yeast transformations.

Once a construct has been prepared and optionally, any undesirable sequences removed, e.g., procaryotic sequences, the construct can be optionally linearized and optionally be converted to at least partially single-stranded form. The oligonucleotide analogue portion can then be joined to the DNA construct, either by hybridization or by chemical coupling, or both. The construct comprising both nucleic acid and oligonucleotide analogue sequences can then be introduced into the target cell. For introduction of the targeting construct, the construct can be provided in single-stranded form, double-stranded form, or partially single-stranded and partially double-stranded form. In addition at least a portion of a targeting construct can optionally comprise double-stranded DNA bound by oligonucleotide analogue sequences by Hoogstein base-pairing.

Any convenient technique for introducing the DNA/oligonucleotide analogue construct into the target cells may be employed. Techniques which may be used to introduce the replacement targeting construct into cells include calcium phosphate/DNA coprecipitates, microinjection into the nucleus, electroporation, bacterial protoplast fusion with intact cells, transfection, particle gun bombardment, lipofection or the like. Where avian embryonic stem cells are used as the recipient cells, the construct can be targeted to the cells using liposomes (Pain et al. *Cells Tissues Organs* 165: 212–219 (1999)). After transformation or transfection of the target cells, target cells may be selected by means of positive and/or negative markers, as previously indicated, neomycin resistance and acyclovir or gancyclovir resistance. Cells having the desired phenotype may then be further analyzed by restriction analysis, electrophoresis, Southern analysis, PCR, or the like. By identifying fragments which show the presence of the lesion(s) at the target locus, one can identify cells in which homologous recombination has occurred to inactivate a copy of the target locus.

EXAMPLES

Example 1

Synthesis of 4-O-monomethoxytrityl-N-(thymine-1-ylacetyl)-L-hydroxyproline [monomer (I)]

4-O-4-monomethoxytrityl-N-(thymin-1-ylacetyl)-L-hydroxyproline (HypNA Thy) was made by dissolving 4-hydroxyproline methyl ester hydrochloride (1.82 g, 10 mmol) in 40 ml of a 1:1 mixture of pyridine-acetonitrile containing 1.4 ml (10 mmol) of triethylamine. Thymin-1-ylacetic acid (2.02 g, II mmol) and N,N'-dicyclohexylcarbodiimide (DCC) (2.47 g, 12 mmol) were added. The reaction was terminated after 3 hours stirring by the addition of 2 ml water and incubated overnight at room temperature.

The mixture was then filtered to remove precipitated dicyclohexyl urea. The filtrate was dried by evaporation and coevaporated with pyridine (2×30 ml) and then dissolved in pyridine (40 ml). 4-Monomethoxytrityl chloride (MMTrC 1) (4.02 g, 13 mmol) and N,N-diisopropylethylamine (DIEA) (1.72 ml, 10 mmol) were added and the mixture was incubated at 70 degrees C. for 1 h., cooled to room temperature followed by addition 5% NaHCO$_3$ (60 ml). The product was extracted with methylene chloride (DCM) (2×80 ml), organic layers were dried over Na$_2$SO$_4$ then solvent was removed by evaporation and the product was coevaporated with toluene (3×50 ml). The residue was dissolved in methanol (100 ml) and 2M NaOH in the mixture methanol-water (1:1 v/v) (15 ml) was added. Pyridine (30 ml) and Dowex-50 (PyridineH$^+$) were added after 30 min to neutralize the solution. The solution was filtered to remove the Dowex resin and the resin was washed with 50% aqueous pyridine. Triethylamine (2.1 ml, 15 mmol) was added to the filtrate, which was evaporated, after which the resulting oil was evaporated with toluene.

The resulting product was chromatographed on silica gel in a gradient of 0–8% methanol in DCM containing 1% triethylamine to give 6.1 mmol (4.09 g, 61%) triethylammonium salt of the title compound. Rf 0.28 (A); $^1$H NMR: 1.20 (9H, t, CH$_3$, NHEt$_3$), 1.8 (3H, s, CH$_3$, Thy), 1.95 and 2.15 (2H, m, H3, Pro), 2.95 (6H, q, CH$_2$, NHE$_3$), 2.95 and 3.15 (2H, dd+dd, H5, Pro), 3.75 (3H, s, OCH$_3$, MMTr), 4.0 (1H, m, H4, Pro), 4.25 (1H, m, H2, Pro), 4.4–4.5 (2H, s+s, rotamers NCOCH$_2$), 6.75–7.40 (15H, m, H, Ar, and H6, Thy); mass: m/z 570 (M+H)$^+$, C$_{32}$H$_3$, N$_3$O$_7$ Another (HypNA Thy) monomer of formula (I), 4-O-4-dimethoxytrityl-N-(thymin-1-ylacetyl)-L-hydroxyproline, that may be preferred in some aspects of the invention can be made using similar methods:

4-O-4,4'-dimethoxytrityl-N-(thymin-1-ylacetyl)-L-hydroxyproline (HypNA Thy), is made by dissolving 4-hydroxyproline methyl ester hydrochloride (1.82 g, 10 mmol) in 40 ml of a 1:1 mixture of pyridine-acetonitrile containing 1.4 ml (10 mmol) of triethylamine. Thymin-1-ylacetic acid (2.02 g, 11 mmol) and N,N'-dicyclohexylcarbodiimide (DCC) (2.47 g, 12 mmol) are added. The reaction is terminated after 3 hours stirring by the addition of 2 ml water and incubated overnight at room temperature.

The mixture is then filtered to remove precipitated dicyclohexyl urea. The filtrate is dried by evaporation and coevaporated with pyridine (2×30 ml) and then dissolved in pyridine (40 ml). 4,4'-Dimethoxytrityl chloride (DMTrC 1) (4.41 g, 13 mmol) is added and the mixture is incubated at 50 degrees C. for 30 min. and cooled to room temperature, followed by the addition of 5% $NaHCO_3$ (60 ml). The product is extracted with methylene chloride (DCM) (2×80 ml), organic layers are dried over $Na_2SO_4$, and then solvent is removed by evaporation and the product is coevaporated with toluene (3×50 ml). The residue is dissolved in methanol (100 ml) and 2M NaOH in a mixture of methanol-water (1:1 v/v) (15 ml) is added. Pyridine (30 ml) and Dowex-50 (PyridineH$^+$) are added after 30 min to neutralize the solution. The solution is filtered to remove the Dowex resin and the resin is washed with 50% aqueous pyridine. Triethylamine (2.1 ml, 15 mmol) is added to the filtrate, which is evaporated, after which the resulting oil is evaporated with toluene.

The resulting product is chromatographed on silica gel in a gradient of 0–8% methanol in DCM containing 1% triethylamine to obtain the title compound.

Example 2

Synthesis of 4-O-monomethoxytrityl-N-(N-$^6$-benzoyladenine-9-ylacetyl)-L-hydroxyproline [monomer (I)]

4-O-monomethoxytrityl-N-(N$^6$-benzoyladenin-9-ylacetyl)-L-hydroxyproline (HypNA Ade) was made by dissolving 4-hydroxyproline methyl ester hydrochloride (1.82 g, 10 mmol) in 40 ml of a 1:1 mixture of pyridine-acetonitrile containing 1.4 ml (10 mmol) of triethylamine. N$^6$-Benzoyladenin-9-ylacetic acid (3.86 g, 13 mmol) and DCC (2.88 g, 14 mmol) were added. The reaction was terminated after 3 hours stirring by the addition of 2 ml water and incubated overnight at room temperature.

The mixture was then filtered to remove precipitated dicyclohexyl urea. The filtrate was dried by evaporation and coevaporated with pyridine (2×30 ml) and then dissolved in pyridine (40 ml). MMTrC 1 (4.94 g, 16 mmol) and DIEA (1.72 ml, 10 mmol) were added and the mixture was incubated at 70 degrees C. for 1 h. and then cooled to room temperature, followed by addition 5% $NaHCO_3$ (60 ml). The product was extracted with DCM (2×80 ml), organic layers were dried over $Na_2SO_4$, and then solvent was removed by evaporation and the product was coevaporated with toluene (3×50 ml). The residue was dissolved in methanol (100 ml) and 2M NaOH in a mixture of methanol-water (1:1 v/v) (15 ml) was added. Pyridine (30 ml) and Dowex-50 (PyridineH$^+$) were added after 30 min to neutralize the solution. The solution was filtered to remove the Dowex resin and the resin was washed with 50% aqueous pyridine. Triethylamine (2.1 ml, 15 mmol) was added to the filtrate, which was evaporated, after which the resulting oil was evaporated with toluene.

The resulting product was chromatographed on silica gel in a gradient of 0–8% methanol in DCM containing 1% triethylamine to give 4.6 mmol (3.60 g, 46%) triethylammonium salt of the title compound.

Another (HypNA Ade) monomer of formula (I), 4-O-4-dimethoxytrityl-N-(N$^6$-benzoyladenin-9-ylacetyl)-L-hydroxyproline, that may be preferred in some aspects of the invention can be made using similar methods:

4-O-4,4'-dimethoxytrityl-N-(N$^6$-benzoyladenin-9-ylacetyl)-L-hydroxyproline is made by dissolving 4-hydroxyproline methyl ester hydrochloride (1.82 g, 10 mmol) in 40 ml of a 1:1 mixture of pyridine-acetonitrile containing 1.4 ml (10 mmol) of triethylamine. N$^6$-Benzoyladenin-9-ylacetic acid (3.86 g, 13 mmol) and DCC (2.88 g, 14 mmol) are added. The reaction is terminated after 3 hours of stirring by the addition of 2 ml water and incubated overnight at room temperature.

The mixture is then filtered to remove precipitated dicyclohexyl urea. The filtrate is dried by evaporation and coevaporated with pyridine (2×30 ml) and then dissolved in pyridine (40 ml). DMTrC 1(5.41 g, 16 mmol) is added and the mixture is incubated at 50 degrees C. for 30 min. and cooled to room temperature, followed by the addition of 5% $NaHCO_3$ (60 ml). The product is extracted with DCM (2×80 ml), organic layers are dried over $Na_2SO_4$, and then solvent is removed by evaporation and the product is coevaporated with toluene (3×50 ml). The residue is dissolved in methanol (100 ml) and 2M NaOH in a mixture of methanol-water (1:1 v/v) (15 ml) is added. Pyridine (30 ml) and Dowex-50 (PyridineH$^+$) are added after 30 min to neutralize the solution. The solution is filtered to remove the Dowex resin and the resin is washed with 50% aqueous pyridine. Triethylamine (2.1 ml, 15 mmol) is added to the filtrate, which is evaporated, after which the resulting oil is evaporated with toluene.

The resulting product is chromatographed on silica gel in a gradient of 0–8% methanol in DCM containing 1% triethylamine to obtain the title compound.

Example 3

Synthesis of 4-O-monomethoxytrityl-N-(N$^4$-benzoylcytosin-9-ylacetyl)-L-hydroxyproline [monomer (I)]

N-tert-Butyloxycarbonyl-4-hydroxyproline (Sigma) (2.31 g, 10 mmol) was dissolved in acetonitrile (45 ml) with 3-hydroxypropionitrile (3.55 ml, 50 mmol) and 4-(dimethylamino)pyridine (0.06 g, 0.5 mmol). The mixture was cooled in an ice bath and DCC (2.27 g, 11 mmol) was added. The solution was stirred 1 hour at room temperature then was filtered to remove precipitated dicyclohexyl urea. The filtrate was evaporated, water (50 ml) was added to the residue and the product was extracted with ethyl acetate (2×50 ml), organic layers were washed by saturated NaCl and dried over $Na_2SO_4$, and then solvent was removed by evaporation. The gum was dissolved in acetonitrile (25 ml), then 4M HCl solution in 1,4-dioxane (8 ml) was added and the mixture was incubated 30 min at room temperature. Solvents were removed by evaporation and the product was coevaporated with acetonitrile (2×30 ml) and toluene (30 ml).

4-O-monomethoxytrityl-N-(N-$^4$-benzoylcytosin-9-ylacetyl)-L-hydroxyproline (HypNA Cyt), was made by dissolving crude 4-hydroxyproline 2-cyanoethyl ester hydrochloride gum, obtained as described above, in 40 ml of a 1:1 mixture of pyridine-acetonitrile containing 1.54 ml (11 mmol) of triethylamine. $N^4$-Benzoylcytosin-9-ylacetic acid (3.55 g, 13 mmol) and DCC (2.88 g, 14 mmol) were added. The reaction was terminated after 3 hours stirring by the addition of 2 ml water and incubated overnight at room temperature.

The mixture was then filtered to remove precipitated dicyclohexyl urea. The filtrate was dried by evaporation and coevaporated with pyridine (2×30 ml) and then dissolved in pyridine (40 ml). MMTrC 1(6.18 g, 20 mmol) and DIEA (1.72 ml, 10 mmol) were added and the mixture was incubated at 70 degrees C. for 1 h. and cooled to room temperature followed by addition 5% $NaHCO_3$ (60 ml). The product was extracted with DCM (2×80 ml), organic layers were dried over $Na_2SO_4$, and then solvent was removed by evaporation and coevaporated with toluene (3×50 ml). The residue was dissolved in DCM (50 ml) and 1,8-diazabicyclo[5.4.0]undec-7-ene (DBU) (2.28 ml, 15 mmol) was added. The mixture was diluted with DCM (60 ml) after 10 min. incubation and was washed with 1 M triethylammonium bicarbonate (TEAB) (60 ml), organic layer was dried over $Na_2SO_4$ then solvent was removed by evaporation.

The resulting product was chromatographed on silica gel in a gradient of 0–8% methanol in DCM containing 1% triethylamine to give 4.5 mmol (3.42 g, 45%) triethylammonium salt of the title compound.

Another (HypNA Cyt) monomer of formula (I) that may be preferred in some aspects of the invention comprises a DMTr protecting group and can be made using similar methods:

N-tert-Butyloxycarbonyl-4-hydroxyproline (Sigma) (2.31 g, 10 mmol) is dissolved in acetonitrile (45 ml) with 3-hydroxypropionitrile (3.55 ml, 50 mmol) and 4-(dimethylamino)pyridine (0.06 g, 0.5 mmol). The mixture is cooled in an ice bath and DCC (2.27 g, 11 mmol) is added. The solution is stirred 1 hour at room temperature and then filtered to remove precipitated dicyclohexyl urea. The filtrate is evaporated, water (50 ml) is added to the residue and the product is extracted with ethyl acetate (2×50 ml). Organic layers are washed by saturated NaCl, dried over $Na_2SO_4$, and then solvent is removed by evaporation. The gum is dissolved in acetonitrile (25 ml), then 4M HCl solution in 1,4-dioxane (8 ml) is added and the mixture is incubated 30 min at room temperature. Solvents are removed by evaporation and the product is coevaporated with acetonitrile (2×30 ml) and toluene (30 ml).

4-O-4,4'-dimethoxytrityl-N-(N-$^4$-benzoylcytosin-9-ylacetyl)-L-hydroxyproline (HypNA Cyt) is made by dissolving crude 4-hydroxyproline 2-cyanoethyl ester hydrochloride gum, obtained as described above, in 40 ml of a 1:1 mixture of pyridine-acetonitrile containing 1.54 ml (11 mmol) of triethylamine. $N^4$-Benzoylcytosin-9-ylacetic acid (3.55 g, 13 mmol) and DCC (2.88 g, 14 mmol) are added. The reaction is terminated after 3 hours stirring by the addition of 2 ml water and incubated overnight at room temperature.

The mixture is then filtered to remove precipitated dicyclohexyl urea. The filtrate is dried by evaporation and coevaporated with pyridine (2×30 ml) and then dissolved in pyridine (40 ml). DMTrC 1(6.76 g, 20 mmol) is added and the mixture is incubated at 50 degrees C. for 30 min. and cooled to room temperature, followed by the addition of 5% $NaHCO_3$ (60 ml). The product is extracted with DCM (2×80 ml), organic layers are dried over $Na_2SO_4$, and then solvent is removed by evaporation and the product is coevaporated with toluene (3×50 ml). The residue is dissolved in DCM (50 ml) and 1,8-diazabicyclo[5.4.0]undec-7-ene (DBU) (2.28 ml, 15 mmol) is added. The mixture is diluted with DCM (60 ml) after 10 min. incubation and is washed with 1M triethylammonium bicarbonate (TEAB) (60 ml). The organic layer is dried over $Na_2SO_4$ and solvent is removed by evaporation.

The resulting product is chromatographed on silica gel in a gradient of 0–8% methanol in DCM containing 1% triethylamine to obtain the title compound.

Example 4

Synthesis 4-O-4-monomethoxytrityl-N-($N^2$-isobutyrylguanin-9-ylacetyl)-L-hydroxyproline [monomer (I)]

N-tert-Butyloxycarbonyl-4-hydroxyproline (Sigma) (2.31 g, 10 mmol) was dissolved in acetonitrile (45 ml) with 3-hydroxypropionitrile (3.55 ml, 50 mmol) and 4-(dimethylamino)pyridine (0.06 g, 0.5 mmol). The mixture was cooled in an ice bath and DCC (2.27 g, 11 mmol) was added. The solution was stirred 1 hour at room temperature then was filtered to remove precipitated dicyclohexyl urea. The filtrate was evaporated, water (50 ml) was added to the residue and the product was extracted with ethyl acetate (2×50 ml), organic layers were washed with saturated NaCl, dried over $Na_2SO_4$ then solvent was removed by evaporation. The gum was dissolved in acetonitrile (25 ml), then 4M HCl solution in 1,4-dioxane (8 ml) was added and the mixture was incubated 30 min at room temperature. Solvents were removed by evaporation and the product was coevaporated with acetonitrile (2×30 ml) and toluene (30 ml). 4-O-4-monomethoxytrityl-N-($N^2$-isobutyrylguanin-9-ylacetyl)-L-hydroxyproline (HypNA Gua) was made by dissolving crude 4-hydroxyproline 2-cyanoethyl ester hydrochloride gum, obtained as described above, in 40 ml of a 1:1 mixture of pyridine-acetonitrile containing 1.54 ml (11 mmol) of triethylamine. $N^2$-Isobutyrylguanin-9-ylacetic acid (3.62 g, 13 mmol) and DCC (2.88 g, 14 mmol) were added. The reaction was terminated after 3 hours stirring by the addition of 2 ml water and incubated overnight at room temperature.

The mixture was then filtered to remove precipitated dicyclohexyl urea. The filtrate was dried by evaporation and coevaporated with pyridine (2×30 ml) and then dissolved in pyridine (40 ml). MMTrC 1 (6.18 g, 20 mmol) and DIEA (1.72 ml, 10 mmol) was added and the mixture was incubated at 70 degrees C. for 1 h., cooled to room temperature followed by addition 5% $NaHCO_3$ (60 ml). The product was extracted with DCM (2×80 ml), organic layers were dried over $Na_2SO_4$, and then solvent was removed by evaporation and coevaporated with toluene (3×50 ml). The residue was dissolved in DCM (50 ml) and DBU (2.28 ml, 15 mmol) was added. The mixture was diluted with DCM (60 ml) after 10 min. incubation and was washed with 1M TEAB (60 ml), organic layer was dried over $Na_2SO_4$ then solvent was removed by evaporation.

The resulting product was chromatographed on silica gel in a gradient of 0–10% methanol in DCM containing 1% triethylamine to give 3.4 mmol (2.60 g, 34%) triethylammonium salt of the title compound.

Another (HypNA Gua) monomer of formula (I) that may be preferred in some aspects of the invention comprises a DMTr protecting group and can be made using similar methods:

N-tert-Butyloxycarbonyl-4-hydroxyproline (Sigma) (2.31 g, 10 mmol) is dissolved in acetonitrile (45 ml) with 3-hydroxypropionitrile (3.55 ml, 50 mmol) and 4-(dimethylamino)pyridine (0.06 g, 0.5 mmol). The mixture is cooled in an ice bath and DCC (2.27 g, 11 mmol) is added. The solution is stirred 1 hour at room temperature then is filtered to remove precipitated dicyclohexyl urea. The filtrate is evaporated, water (50 ml) was added to the residue and the product is extracted with ethyl acetate (2×50 ml). Organic layers are washed by saturated NaCl, dried over $Na_2SO_4$, and then solvent is removed by evaporation. The gum is dissolved in acetonitrile (25 ml), then 4M HCl solution in 1,4-dioxane (8 ml) is added and the mixture is incubated 30 min at room temperature. Solvents are removed by evaporation and the product is coevaporated with acetonitrile (2×30 ml) and toluene (30 ml).

4-O-4,4'-dimethoxytrityl-N-($N^2$-isobutyrylguanin-9-ylacetyl)-L-hydroxyproline (HypNA Gua) is made by dissolving crude 4-hydroxyproline 2-cyanoethyl ester hydrochloride gum, obtained as described above, in 40 ml of a 1:1 mixture of pyridine-acetonitrile containing 1.54 ml (11 mmol) of triethylamine. $N^2$-Isobutyrylguanin-9-ylacetic acid (3.62 g, 13 mmol) and DCC (2.88 g, 14 mmol) are added. The reaction is terminated after 3 hours of stirring by the addition of 2 ml water and then incubated overnight at room temperature.

The mixture is then filtered to remove precipitated dicyclohexyl urea. The filtrate is dried by evaporation and coevaporated with pyridine (2×30 ml) and then dissolved in pyridine (40 ml). DMTrC 1 (6.76 g, 20 mmol) is added and the mixture is incubated at 50 degrees C. for 30 min. and cooled to room temperature, followed by the addition of 5% $NaHCO_3$ (60 ml). The product is extracted with DCM (2×80 ml). Organic layers are dried over $Na_2SO_4$, and then solvent is removed by evaporation and coevaporated with toluene (3×50 ml). The residue is dissolved in DCM (50 ml) and DBU (2.28 ml, 15 mmol) is added. The mixture is diluted with DCM (60 ml), and after a 10 min. incubation is washed with 1M TEAB (60 ml). The organic layer is dried over $Na_2SO_4$, and then the solvent is removed by evaporation.

The resulting product is chromatographed on silica gel in a gradient of 0–10% methanol in DCM containing 1% triethylamine to obtain the triethylammonium salt of the title compound.

Example 5

Synthesis of 4-O-4-monomethoxytrityl-N-(thymin-1-ylacetyl)-L-serine [monomer (V)]

4-O-4-monomethoxytrityl-N-(thymin-1-ylacetyl)-L-serine (SerNA Thy) was made by dissolving L-serine methyl ester hydrochloride (Sigma) (1.56 g, 10 mmol) in 40 ml of a 1:1 mixture of pyridine-acetonitrile containing 1.4 ml (10 mmol) of triethylamine. Thymin-1-ylacetic acid (2.02 g, 11 mmol) and DCC (2.47 g, 12 mmol) were added. The reaction was terminated after 2 hours of stirring by the addition of 2 ml water and incubated overnight at room temperature.

The mixture was then filtered to remove precipitated dicyclohexyl urea. The filtrate was dried by evaporation and coevaporated with pyridine (2×30 ml) and then dissolved in pyridine (40 ml). MMTrC 1(4.02 g, 13 mmol) and DIEA (1.72 ml, 10 mmol) were added and the mixture was incubated at 50 degrees C. for 1 h. and cooled to room temperature, followed by the addition of 5% $NaHCO_3$ (60 ml). The product was extracted with DCM (2×80 ml). The organic layers were dried over $Na_2SO_4$, and then solvent was removed by evaporation and coevaporated with toluene (3×50 ml). The residue was dissolved in methanol (100 ml) and 2M NaOH in a mixture of methanol-water (1:1 v/v) (15 ml) was added. Pyridine (30 ml) and Dowex-50 ($PyridineH^+$) were added after 30 min to neutralize the solution. The solution was filtered to remove the Dowex resin and the resin was washed with 50% aqueous pyridine. Triethylamine (2.1 ml, 15 mmol) was added to the filtrate, which was evaporated, after which the resulting oil was evaporated with toluene.

The resulting product was chromatographed on silica gel in a gradient of 0–8% methanol in DCM containing 1% triethylamine to give 6.8 mmol (4.38 g, 68%) triethylammonium salt of the title compound. Rf 0.25 (A); $^1$H NMR: 1.20 (9H, t, $CH_3$, $NHEt_3$), 1.82 (3H, s, $CH_3$, Thy), 2.95 (6H, q, $CH_2$, $NHE_3$), 3.35 (2H, m, $CH_2$, MMTrO); 3.75 (2H, s, $OCH_3$, MMTrO), 4.16 (1H, m, HOOC—CH—$CH_2$), 4.3 (2H, dd, $NCOCH_2$), 6.75–7.60 (15H, m, H, Ar, and H6, Thy), 9.3 (1H, br. s, NH); mass: m/z 570 $(M+H)^+$, $C_{30}H_{29}N_3O_7$.

Another (SerNA Thy) monomer of formula (V) that may be preferred in some aspects of the invention comprises a DMTr protecting group and can be made using similar methods:

4-O-4,4'-dimethoxytrityl-N-(thymin-1-ylacetyl)-L-serine, is made by dissolving L-serine methyl ester hydrochloride (Sigma) (1.56 g, 10 mmol) in 40 ml of a 1:1 mixture of pyridine-acetonitrile containing 1.4 ml (10 mmol) of triethylamine. Thymin-1-ylacetic acid (2.02 g, 11 mmol) and DCC (2.47 g, 12 mmol) are added. The reaction is terminated after 2 hours stirring by the addition of 2 ml water and incubated overnight at room temperature.

The mixture is then filtered to remove precipitated dicyclohexyl urea. The filtrate is dried by evaporation and coevaporated with pyridine (2×30 ml) and then dissolved in pyridine (40 ml). DMTrC 1 (4.41 g, 13 mmol) is added and the mixture is incubated at 50 degrees C. for 30 min. and cooled to room temperature, followed by the addition of 5% $NaHCO_3$ (60 ml). The product is extracted with DCM (2×80 ml), organic layers are dried over $Na_2SO_4$, and then solvent is removed by evaporation and coevaporated with toluene (3×50 ml). The residue is dissolved in methanol (100 ml) and 2M NaOH in a mixture of methanol-water (1:1 v/v) (15 ml) is added. Pyridine (30 ml) and Dowex-50 ($PyridineH^+$) are added after 30 min to neutralize the solution. The solution is filtered to remove the Dowex resin and the resin is washed with 50% aqueous pyridine. Triethylamine (2.1 ml, 15 mmol) is added to the filtrate, which is evaporated, after which the resulting oil is evaporated with toluene.

The resulting product is chromatographed on silica gel in a gradient of 0–8% methanol in DCM containing 1% triethylamine to give the title compound.

Example 6

Synthesis of 4-O-4-monomethoxytrityl-N-($N^6$-benzoyladenin-9-ylacetyl)-L-serine [monomer (V)]

4-O-4-monomethoxytrityl-N-($N^6$-benzoyladenin-9-ylacetyl)-L-serine (SerNA Ade) is made by dissolving serine methyl ester hydrochloride (Sigma) (1.56 g, 10 mmol) in 40 ml of a 1:1 mixture of pyridine-acetonitrile containing 1.4 ml (10 mmol) of triethylamine. $N^6$-Benzoyladenin-9-ylacetic acid (3.86 g, 13 mmol) and DCC (2.88 g, 14 mmol) were added. The reaction is terminated after 2 hours stirring by the addition of 2 ml water and incubated overnight at room temperature.

The mixture is then filtered to remove precipitated dicyclohexyl urea. The filtrate is dried by evaporation and coevaporated with pyridine (2×30 ml) and then dissolved in pyridine (40 ml). MMTrC 1(4.94 g, 16 mmol) and DIEA (1.72 ml, 10 mmol) are added and the mixture is incubated at 50 degrees C. for 1 h. and then cooled to room temperature, followed by addition 5% NaHCO$_3$ (60 ml). The product is extracted with DCM (2×80 ml), organic layers are dried over Na$_2$SO$_4$, and then solvent is removed by evaporation and coevaporated with toluene (3×50 ml). The residue is dissolved in methanol (100 ml) and 2M NaOH in a mixture of methanol-water (1:1 v/v) (15 ml) is added. Pyridine (30 ml) and Dowex-50 (PyridineH$^+$) are added after 30 min to neutralize the solution. The solution is filtered to remove the Dowex resin and the resin is washed with 50% aqueous pyridine. Triethylamine (2.1 ml, 15 mmol) is added to the filtrate, which is evaporated, after which the resulting oil is evaporated with toluene.

The resulting product is chromatographed on silica gel in a gradient of 0–8% methanol in DCM containing 1% triethylamine to give the triethylammonium salt of the title compound.

Another (SerNA Ade) monomer of formula (V) that may be preferred in some aspects of the invention comprises a DMTr protecting group and can be made using similar methods:

4-O-4,4'-dimethoxytrityl-N-(N$^6$-benzoyladenin-9-ylacetyl)-L-serine, is made by dissolving serine methyl ester hydrochloride (Sigma) (1.56 g, 10 mmol) in 40 ml of a 1:1 mixture of pyridine-acetonitrile containing 1.4 ml (10 mmol) of triethylamine. N$^6$-Benzoyladenin-9-ylacetic acid (3.86 g, 13 mmol) and DCC (2.88 g, 14 mmol) are added. The reaction is terminated after 2 hours stirring by the addition of 2 ml water and incubated overnight at room temperature.

The mixture is then filtered to remove precipitated dicyclohexyl urea. The filtrate is dried by evaporation and coevaporated with pyridine (2×30 ml) and then dissolved in pyridine (40 ml). DMTrC 1(5.41 g, 16 mmol) is added and the mixture is incubated at 50 degrees C. for 30 min. and cooled to room temperature followed by the addition of 5% NaHCO$_3$ (60 ml). The product is extracted with DCM (2×80 ml), and the organic layers are dried over Na$_2$SO$_4$, and then solvent is removed by evaporation and coevaporated with toluene (3×50 ml). The residue is dissolved in methanol (100 ml) and 2M NaOH in a mixture of methanol-water (1:1 v/v) (15 ml) is added. Pyridine (30 ml) and Dowex-50 (PyridineH$^+$) are added after 30 min to neutralize the solution. The solution is filtered to remove the Dowex resin and the resin is washed with 50% aqueous pyridine. Triethylamine (2.1 ml, 15 mmol) is added to the filtrate, which is evaporated, after which the resulting oil is evaporated with toluene.

The resulting product is chromatographed on silica gel in a gradient of 0–8% methanol in DCM containing 1% triethylamine to give the triethylammonium salt of the title compound.

Example 7

Synthesis of 4-O-4-monomethoxytrityl-N-(N$^4$-betizoylcytosin-9-ylacetyl)-L-serine [monomer (V)]

N-tert-Butyloxycarbonyl-L-serine (Sigma) (2.05 g, 10 mmol) is dissolved in acetonitrile (45 ml) with 3-hydroxypropionitrile (3.55 ml, 50 mmol) and 4-(dimethylamino)pyridine (0.06 g, 0.5 mmol). The mixture is cooled in an ice bath and DCC (2.27 g, 11 mmol) is added. The solution is stirred 1 hour at room temperature then filtered to remove precipitated dicyclohexyl urea. The filtrate is evaporated, water (50 ml) is added to the residue and the product is extracted with ethyl acetate (2×50 ml). The organic layers are washed with saturated NaCl, dried over Na$_2$SO$_4$, and then solvent is removed by evaporation. The gum is dissolved in acetonitrile (25 ml), and then 4M HCl in 1,4-dioxane (8 ml) is added and the mixture is incubated 30 min at room temperature. Solvents are removed by evaporation and the product is coevaporated with acetonitrile (2×30 ml) and toluene (30 ml). 4-O-4-monomethoxytrityl-N-(N$^4$-benzoylcytosin-9-ylacetyl)-L-serine (SerNA Cyt) is made by dissolving crude L-serine 2-cyanoethyl ester hydrochloride gum, obtained as described above, in 40 ml of a 1:1 mixture of pyridine-acetonitrile containing 1.54 ml (11 mmol) of triethylamine. N$^4$-Benzoylcytosin-9-ylacetic acid (3.55 g, 13 mmol) and DCC (2.88 g, 14 mmol) are added. The reaction is terminated after 2 hours of stirring by the addition of 2 ml water and incubated overnight at room temperature. The mixture is then filtered to remove precipitated dicyclohexyl urea. The filtrate is dried by evaporation and coevaporated with pyridine (2×30 ml) and then dissolved in pyridine (40 ml). MMTrC 1 (6.18 g, 20 mmol) and DIEA (1.72 ml, 10 mmol) are added and the mixture is incubated at 50 degrees C. for 1 h., cooled to room temperature followed by the addition of 5% NaHCO$_3$ (60 ml). The product is extracted with DCM (2×80 ml), organic layers are dried over Na$_2$SO$_4$, and then solvent is removed by evaporation and coevaporated with toluene (3×50 ml). The residue is dissolved in DCM (50 ml) and 1,8-diazabicyclo[5.4.0]undec-7-ene (DBU) (2.28 ml, 15 mmol) is added. The mixture is diluted with DCM (60 ml) after 10 min. incubation and is washed with 1M triethylammonium bicarbonate (TEAB) (60 ml). The organic layer is dried over Na$_2$SO$_4$ then solvent is removed by evaporation.

The resulting product is chromatographed on silica gel in a gradient of 0–8% methanol in DCM containing 1% triethylamine to give 4.5 mmol (3.30 g, 45%) triethylammonium salt of the title compound.

Another (SerNA Cyt) monomer of formula (V) that may be preferred in some aspects of the invention comprises a DMTr protecting group and can be made using similar methods:

N-tert-Butyloxycarbonyl-L-serine (Sigma) (2.05 g, 10 mmol) is dissolved in acetonitrile (45 ml) with 3-hydroxypropionitrile (3.55 ml, 50 mmol) and 4-(dimethylamino)pyridine (0.06 g, 0.5 mmol). The mixture is cooled in an ice bath and DCC (2.27 g, 11 mmol) is added. The solution is stirred 1 hour at room temperature and then is filtered to remove precipitated dicyclohexyl urea. The filtrate is evaporated, water (50 ml) is added to the residue, and the product is extracted with ethyl acetate (2×50 ml) ). Organic layers are washed by saturated NaCl, dried over Na$_2$SO$_4$, and then solvent is removed by evaporation. The gum is dissolved in acetonitrile (25 ml) and then a solution of 4M HCl in 1,4-dioxane (8 ml) is added and the mixture is incubated 30 min at room temperature. Solvents are removed by evaporation and the product was coevaporated with acetonitrile (2×30 ml) and toluene (30 ml).

4-O-4,4'-dimethoxytrityl-N-(N$^4$-benzoylcytosin-9-ylacetyl)-L-serine, is made by dissolving crude L-serine 2-cyanoethyl ester hydrochloride gum, obtained as described above, in 40 ml of a 1:1 mixture of pyridine-acetonitrile containing 1.54 ml (11 mmol) of triethylamine. N$^4$-Benzoylcytosin-9-ylacetic acid (3.55 g, 13 mmol) and DCC (2.88 g, 14 mmol) are added. The reaction is terminated after 2 hours stirring by the addition of 2 ml water and incubated overnight at room temperature. The mixture is then filtered to remove precipitated dicyclohexyl urea. The filtrate is dried by evaporation and the product is coevaporated with pyridine (2×30 ml) and then dissolved in pyridine (40 ml). DMTrC 1 (6.76 g, 20 mmol) is added and the mixture is incubated at 50 degrees C. for 30 min. and cooled to room temperature, followed by the addition of 5% NaHCO$_3$ (60 ml). The product is extracted with DCM (2×80 ml), organic layers are dried over Na$_2$SO$_4$, and then solvent is removed by evaporation and the product is coevaporated with toluene (3×50 ml). The residue is dissolved in DCM (50 ml) and 1,8-diazabicyclo[5.4.0]undec-7-ene (DBU) (2.28 ml, 15 mmol) is added. The mixture is diluted with DCM (60 ml) and after a 10 min. incubation is washed with 1M triethylammonium bicarbonate (TEAB) (60 ml). The organic layer was dried over Na$_2$SO$_4$ and then solvent was removed by evaporation.

The resulting product is chromatographed on silica gel in a gradient of 0–8% methanol in DCM containing 1% triethylamine to give the triethylammonium salt of the title compound.

Example 8

Synthesis of 4-O-4-monomethoxytrityl-N-(N$^2$-isobutyrylguanin-9-ylacetyl)-L-serine [monomer (V)]

N-tert-Butyloxycarbonyl-serine (Sigma) (2.05 g, 10 mmol) is dissolved in acetonitrile (45 ml) with 3-hydroxypropionitrile (3.55 ml, 50 mmol) and 4-(dimethylamino)pyridine (0.06 g, 0.5 mmol). The mixture is cooled in an ice bath and DCC (2.27 g, 11 mmol) is added. The solution is stirred 1 hour at room temperature then filtered to remove precipitated dicyclohexyl urea. The filtrate is evaporated, water (50 ml) is added to the residue and the product is extracted with ethyl acetate (2×50 ml). Organic layers are washed by saturated NaCl, dried over Na$_2$SO$_4$, and then solvent is removed by evaporation. The gum is dissolved in acetonitrile (25 ml), then 4M HCl solution in 1,4-dioxane (8 ml) is added and the mixture is incubated 30 min at room temperature. Solvents are removed by evaporation and the product is coevaporated with acetonitrile (2×30 ml) and toluene (30 ml).

4-O-4-monomethoxytrityl-N-(N$^2$-i sobutyrylguanin-9-ylacetyl)-L-serine (SerNA Gua) is made by dissolving crude L-serine 2-cyanoethyl ester hydrochloride gum, obtained as described above, in 40 ml of a 1:1 mixture of pyridine-acetonitrile containing 1.54 ml (11 mmol) of triethylamine. N$^2$-Isobutyrylguanin-9-ylacetic acid (3.62 g, 13 mmol) and DCC (2.88 g, 14 mmol) are added. The reaction is terminated after 3 hours stirring by the addition of 2 ml water and incubated overnight at room temperature. The mixture is then filtered to remove precipitated dicyclohexyl urea. The filtrate is dried by evaporation and coevaporated with pyridine (2×30 ml) and then dissolved in aqueous pyridine (40 ml). MMTrC 1(6.18 g, 20 mmol) and DIEA (1.72 ml, 10 mmol) are added and the mixture is incubated at 50 degrees C. for 1 h. and cooled to room temperature followed by the addition of 5% NaHCO$_3$ (60 ml). The product is extracted with DCM (2×80 ml), organic layers are dried over Na$_2$SO$_4$, and then solvent is removed by evaporation and coevaporated with toluene (3×50 ml). The residue is dissolved in DCM (50 ml) and DBU (2.28 ml, 15 mmol) is added. The mixture is diluted with DCM (60 ml) after a 10 min. incubation and is washed with 1M TEAB (60 ml). The organic layer is dried over Na$_2$SO$_4$, and then solvent is removed by evaporation.

The resulting product was chromatographed on silica gel in a gradient of 0–10% methanol in DCM containing 1% triethylamine to give 3.7 mmol (2.73 g, 37%) triethylammonium salt of the title compound.

Another (SerNA Gua) monomer of formula (V) that may be preferred in some aspects of the invention comprises a DMTr protecting group and can be made using similar methods:

N-tert-Butyloxycarbonyl-serine (Sigma) (2.05 g, 10 mmol) is dissolved in acetonitrile (45 ml) with 3-hydroxypropionitrile (3.55 ml, 50 mmol) and 4-(dimethylamino)pyridine (0.06 g, 0.5 mmol). The mixture is cooled in an ice bath and DCC (2.27 g, 11 mmol) is added. The solution is stirred 1 hour at room temperature then is filtered to remove precipitated dicyclohexyl urea. The filtrate is evaporated, water (50 ml) is added to the residue and the product is extracted with ethyl acetate (2×50 ml). Organic layers are washed by saturated NaCl, dried over Na$_2$SO$_4$, and then solvent is removed by evaporation. The gum is dissolved in acetonitrile (25 ml) and then a solution of 4M HCl in 1,4-dioxane (8 ml) is added and the mixture is incubated 30 min at room temperature. Solvents are removed by evaporation and the product is coevaporated with acetonitrile (2×30 ml) and toluene (30 ml). 4-O-4,4'-dimethoxytrityl-N-(N$^2$-isobutyrylguanin-9-ylacetyl)-L-serine (SerNA Gua) is made by dissolving crude L-serine 2-cyanoethyl ester hydrochloride gum, obtained as described above, in 40 ml of a 1:1 mixture of pyridine-acetonitrile containing 1.54 ml (11 mmol) of triethylamine. N$^2$-Isobutyrylguanin-9-ylacetic acid (3.62 g, 13 mmol) and DCC (2.88 g, 14 mmol) are added. The reaction is terminated after 3 hours stirring by the addition of 2 ml water and incubated overnight at room temperature. The mixture is then filtered to remove precipitated dicyclohexyl urea. The filtrate is dried by evaporation and coevaporated with pyridine (2×30 ml) and then dissolved in aqueous pyridine (40 ml). DMTrC 1 (6.76 g, 20 mmol) is added and the mixture is incubated at 50 degrees C. for 30 min. and cooled to room temperature, followed by the addition of 5% NaHCO$_3$ (60 ml). The product is extracted with DCM (2×80 ml), organic layers are dried over Na$_2$SO$_4$, and then solvent is removed by evaporation and the product is coevaporated with toluene (3×50 ml). The residue is dissolved in DCM (50 ml) and DBU (2.28 ml, 15 mmol) is added. The mixture is diluted with DCM (60 ml) after 10 min. incubation and is washed with 1M TEAB (60 ml). The organic layer is dried over Na$_2$SO$_4$, then solvent is removed by evaporation.

The resulting product was chromatographed on silica gel in a gradient of 0–10% methanol in DCM containing 1% triethylamine to give the triethylammonium salt of the title compound.

Example 9

Synthesis of a HypNA-pPNA Dimer

A Thy-Thy HypNA-pPNA dimer of formula (VIII) was synthesized using the 4-0-4,4'-dimethoxytrityl-N-(thymin-1-ylacetyl)-L-hydroxyproline monomer synthesized as in Example 1 and N-[2-monomethoxytritylaminoethyl]-N-(thymin-1-ylacetyl)aminomethylphosphonic acid 1-oxydo-4-methoxy-2-picolylphenyl diester synthesized by methods known in the art and disclosed in Efimov et al. (1998) Nucl. Acids Res. 26: 566–575.

The monomethoxytrityl group of the thymine-containing pPNA moiety was removed by dissolving 2 mmol of the monomer in 10 ml of 2.1 mmol (0.48 g) picric acid in 5% aqueous acetonitrile. After 15 min. the reaction mixture was evaporated under vacuum and coevaporated twice with 20 ml acetonitrile, before finally dissolving the residue in 15 ml of a 1:1 mixture of pyridine-acetonitrile.

To couple the thymine-containing HypNA monomer to the pPNA monomer, 1.9 mmol HypNA monomer was added to the dissolved pPNA moiety and 2.5 mmol (0.52 g) DCC was added. The mixture was incubated for 2 h. at room temperature. To remove the phenyl group, water (2 ml) and DBU (1.52 ml, 10 mmol) were added to the HypNA-pPNA dimer and incubated 1.5 h. at room temperature. Dowex-50 (PyridineH$^+$) was added to neutralize the solution. The solution was filtered to remove the Dowex resin and the resin was washed with 50% aqueous pyridine. Triethylamine (1.40 ml, 10 mmol) was added to the filtrate, which was evaporated, after which the resulting oil was coevaporated with toluene.

The resulting product was chromatographed on a silica gel in a gradient of 0–17% methanol in DCM containing 3% triethylamine to give 1.04 mmol (1.19 g, 52%) triethylammonium salt of the Thy-Thy HypNA-pPNA dimer.

Dimers comprising alternative bases (for example, C, G, or A) can also be made following the procedures of this example, using protecting groups for nucleobase groups where appropriate.

Example 10

Synthesis of a pPNA-HypNA Dimer

Thy-Thy pPNA-HypNA dimers of formula (IX) are synthesised using the 4-O-4,4'-dimethoxytrityl-N-(thymin-1-ylacetyl)-L-hydroxyproline monomer synthesized as in Example 1 and N-[2-monomethoxytritylaminoethyl]-N-(thymin-1-ylacetyl)aminomethylphosphonic acid 1-oxydo-4-methoxy-2-picolyl ester synthesized by methods known in the art and disclosed in Efimov et al. (1998) Nucl. Acids Res. 26: 566–575.

4-O-4,4'-Dimethoxytrityl-N-(thymin-1-ylacetyl)-L-hydroxyproline (2 mmol) synthesized as in Example 1 is dissolved in 15 ml acetonitrile containing 3-hydroxypropionitrile (0.43 ml, 6 mmol) and 1-methylimidazole (0.57 ml, 7 mmol) then 1-(2-mesitylenesulfonyl)-3-nitro-1,2,4-triazole (MSNT) (Aldrich) (1.04 g, 3.5 mmol) is added. The reaction is terminated after 20 min. by the addition of 30 ml 5% NaHCO$_3$ and the product is extracted with DCM (2×30 ml). The organic layers are dried over Na$_2$SO$_4$, and then solvent is removed by evaporation. The resulting product is chromatographed on a silica gel in a gradient of 0–5% methanol in DCM containing 0.5% triethylamine to give the 4-O-4,4'-dimethoxytrityl-N-(thymin-1-ylacetyl)-L-hydroxyproline 2-cyanoethyl ester.

To obtain a Thy-Thy pPNA-HypNA dimer, 2 mmol 4-O-4,4'-dimethoxytrityl-N-(thymin-1-ylacetyl)-L-hydroxyproline 2-cyanoethyl ester synthesized as described above is dissolved in 80% aqueous acetic acid and incubated for 1 h. to remove the dimethoxytrityl protecting group. The product is dried by evaporation and then coevaporated twice with 20 ml acetonitrile and once with 20 ml toluene. The residue is resuspended in 8 ml pyridine containing 2.1 mmol N-[2-monomethoxytritylaminoethyl]-N-(thymin-1-ylacetyl) aminomethylphosphonic acid 1-oxydo-4-methoxy-2-picolyl ester and 3 mmol MSNT (0.89 g) in 10 ml acetonitrile is added to condense the two monomers. After 15 min, 50 ml 5% NaHCO$_3$ is added and the mixture is extracted with DCM (3×50 ml). The combined organic phases are evaporated. To remove the carboxy-protecting group, the resulting gum is dissolved in 15 ml DCM containing 3.5 mmol (0.54 ml) DBU. The mixture is incubated for 15 min, after which the mixture is diluted with DCM (40 ml) and washed with 1 M TEAB (60 ml). The organic phase is dried over Na$_2$SO$_4$, and then solvent is removed by evaporation.

The resulting product is chromatographed on silica gel in a gradient of 0–10% methanol in DCM containing 2% triethylamine to give the triethylammonium salt of the thy-thy pPNA-HypNA dimer.

Example 11

Synthesis of a SerNA-pPNA Dimer

A Thy-Thy SerNA-pPNA dimer of formula (X) was synthesized using the 4-O-4,4'-dimethoxytrityl-N-(thymin-1-ylacetyl)-L-serine monomer synthesized as in Example 5 and N-[2-monomethoxytritylaminoethyl]-N-(thymin-1-ylacetyl)aminomethylphosphonic acid 1-oxydo-4-methoxy-2-picolylphenyl diester by methods known in the art and disclosed in Efimov et al. (1998) Nucl. Acids Res. 26: 566–575.

The monomethoxytrityl group of thymine-containing pPNA moiety was removed by dissolving 2 mmol of the monomer in 10 ml of 2.1 mmol (0.48 g) picric acid in 5% aqueous acetonitrile. After 15 min. the reaction mixture was evaporated under vacuum and coevaporated twice with 20 ml acetonitrile, before finally dissolving the residue in 15 ml of a 1:1 mixture of pyridine-acetonitrile.

To couple the thymine-containing SerNA monomer to the pPNA monomer, 1.9 mmol SerNA monomer was added to the dissolved pPNA moiety and 2.5 mmol (0.52 g) DCC was added. The mixture was incubated for 2 h. at room temperature. To remove the phenyl group, water (2 ml) and DBU (1.52 ml, 10 mmol) were added to the SerNA-pPNA dimer and incubated 1.5 h. at room temperature. Dowex-50 (PyridineH$^+$) was added to neutralize the solution. The solution was filtered to remove the Dowex resin and the resin was washed with 50% aqueous pyridine. Triethylamine (1.40 ml, 10 mmol) was added to the filtrate, which was evaporated, after which the resulting oil was coevaporated with toluene.

The resulting product was chromatographed on silica gel in a gradient of 0–17% methanol in DCM containing 3% triethylamine to give 1.16 mmol (1.19 g, 55%) triethylammonium salt of the Thy-Thy SerNA-pPNA dimer.

Example 12

Synthesis of a pPNA-SerNA Dimer

Thy-Thy pPNA-SerNA dimers of formula (XI) were synthesized using the 4-O-4,4'-dimethoxytrityl-N-(thymin-1-ylacetyl)-L-serine monomer synthesized as in Example 5 and N-[2-monomethoxytritylaminoethyl]-N-(thymin-1-ylacetyl)aminomethylphosphonic acid 1-oxydo-4-methoxy-2-picolyl ester by methods known in the art and disclosed in Efimov et al. (1998) Nucl. Acids Res. 26: 566–575.

4-O-4,4'-Dimethoxytrityl-N-(thymin-1-ylacetyl)-L-hydroxyproline (2 mmol) synthesized as in Example 5 was dissolved in 15 ml acetonitrile containing 3-hydroxypropionitrile (0.43 ml, 6 mmol) and 1-methylimidazole (0.57 ml, 7 mmol) and then 1-(2-mesitylenesulfonyl)-3-nitro-1,2,4-triazole (MSNT) (Aldrich) (1.04 g, 3.5 mmol) was added. The reaction was terminated after 20 min. by the addition of 30 ml 5% NaHCO$_3$ and the product was extracted with DCM (2×30 ml). Organic layers were dried over Na$_2$SO$_4$, and then solvent was removed by evaporation. The resulting product was chromatographed on a silica gel in a gradient of 0–5% methanol in DCM containing 0.5% triethylamine to give 1.68 mmol (1.09 g, 84%) of the 4-O-4,4'-dimethoxytrityl-N-(thymin-1-ylacetyl)-L-serine 2-cyanoethyl ester.

To obtain a Thy-Thy pPNA-SerNA dimer, 2 mmol 4-O-4,4'-dimethoxytrityl-N-(thymin-1-ylacetyl)-L-serine 2-cyanoethyl ester synthesized as described above was dissolved in 80% aqueous acetic acid and incubated for 1 h. to remove the dimethoxytrityl protecting group. The product was dried by evaporation and then coevaporated twice with 20 ml acetonitrile and once with 20 ml toluene. The residue was resuspended in 8 ml pyridine containing 2.1 mmol N-[2-monomethoxytritylaminoethyl]-N-(thymin-1-ylacetyl) aminomethylphosphonic acid 1-oxydo-4-methoxy-2-picolyl ester and 3 mmol MSNT (0.89 g) in 10 ml acetonitrile was added to condense the two monomers. After 15 min, 50 ml 5% $NaHCO_3$ was added and the mixture was extracted with DCM (3×50 ml). The combined organic phases were evaporated. To remove the carboxy-protecting group, the resulting gum was dissolved in 15 ml DCM containing 3.5 mmol (0.54 ml) DBU. The mixture was incubated for 15 min, after which the mixture was diluted with DCM (40 ml) and was washed with 1M TEAB (60 ml). The organic phase was dried over $Na_2SO_4$ and then solvent was removed by evaporation.

The resulting product was chromatographed on silica gel in a gradient of 0–10% methanol in DCM containing 2% triethylamine to give 1.50 mmol (1.61 g, 75%) triethylammonium salt of the pPNA-SerNA dimmer of formula (XI).

Example 13

Synthesis of a HypNA-pPNA Oligomer by Solid Phase Phosphotriester Synthesis Using HypNA-pPNA Dimer Synthons The synthesis of a 12-mer poly T HypNA-pPNA oligomer of formula (XII) having HypNA and pPNA residues in a 1:1 ratio was performed in 1 micromole scale using an automated model 381 A synthesizer from Applied Biosystems. The solid support was 30 mg CPG beads derivatized with 5'-DMTr-dT-3'-O-succinate (Applied Biosystems).

The HypNA-pPNA dimer was the unit of synthesis or "synthon" in which the free hydroxyl group of hydroxyproline was protected with DMTr and the pPNA phosphonate was protected with the catalytic 1-oxido-4-alkoxy-2-picolyl group. HypNA-pPNA dimers were sequentially added by the formation of phosphonoester bonds using the phophotriester synthesis to make a poly T 12-mer.

Initially, the derivatized support was treated with 3% trichloroacetic acid (TCA) in DCM for 3 min to remove the protecting group from the terminal OH-group of 5'-DMTr-dT and then washed for 1 min. with acetonitrile, followed by a 3 min wash with a 2:1 solution of acetonitrile-pyridine. In each cycle in which a dimer was added, a HypNA-pPNA dimer (0.05M phosphonate component) was coupled to the growing oligonucleotide chain using 0.15M 2,4,6-triisopropylbenzenesulfonyl chloride (TPSCl) (Aldrich) in a 2:1 solution acetonitrile-pyridine for 5 min. The support was washed for 1 min. with a 2:1 solution acetonitrile-pyridine followed by 1 min. acetonitrile washing. Then a capping step was performed in which the support was treated with a 1:1:2:6 v/v/v/v solution of acetic anhydride: 1-methylimidazole:pyridine:acetonitrile for 1 min. before washing for 1.5 min. in DCM.

When the oligomer is complete the terminal protecting group was removed using 3% trichloroacetic acid (TCA) in DCM for 3 min. The catalytic phosphonate protecting groups were removed by treatment with 2 ml of a solution 1:2:2 v/v/v thiophenol-triethylamine-dioxane for 3 h. at room temperature. The support is treated for 5 h. (55 degrees C.) with concentrated ammonia to cleave the oligomer from the support (this step also removes any N-protecting groups from nucleobases). The overall yield of the crude oligomer after a desalting step (performed by gel-filtration on Pharmacia NAP-10 column) was 0.35 micromol.

Oligomers were purified by polyacrylamide gel electrophoresis (15% polyacrylamide gel, 7M urea). Electrophoresis was performed in 0.1 M Tris-borate/EDTA buffer (pH 8.3). Oligomers can also be purified by anion-exchanged FPLC in 1 ml/min. linear gradient NaCl (0–1.2M) in 0.02M NaOH (pH 12) on a Mono-Q column.

HypNA-pPNA oligomers or varying base composition can also be synthesized using the protocol of this example, using dimers and, optionally, monomers in which nucleobase groups are protected where appropriate.

Example 14

Synthesis of a pPNA-HypNA Oligomer by Solid Phase Synthesis Using pPNA-HypNA Dimer Synthons The synthesis of a pPNA-HypNA oligomer of formula (XII) having HypNA and pPNA residues in a 1:1 ratio is performed in 1 micromol scale using an automated model 381A synthesizer from Applied Biosystems. The solid support is 30 mg CPG beads derivatized with 5'-N-MMTr-amino-dT-3'-O-succinate. The pPNA-HypNA dimer is the unit of synthesis or "synthon" in which the free terminal amino group of the pPNA is protected with MMTr and the phosphonate of the phosphono-PNA is protected with the catalytic 1-oxido-4-alkoxy-2-picolyl group. pPNA-HypNA dimers of varying base composition are sequentially added by the formation of amide bonds. The order of the dimers used in the synthesis is G-C, T-T, T-G, T-T, C-A, G-G, A-G.

Initially, the derivatized support is treated with 3% pentafluorophenol in DCM for 3 min to remove the protecting group from the terminal amino group of 5'-MMTr-amino-dT and then washed for 0.5 min. with 0.2M diisopropylethylamine in DCM, followed by a 1 min wash with a 4:1 solution of acetonitrile-pyridine. In each cycle, a pPNA-HypNA dimer (0.05M carboxyl component) is mixed with 0.06M 2,4,6-triisopropylbenzenesulfonyl-3-nitro-1,2,4-triazole (TPSNT) (Aldrich) and 0.2M 1-methylimidazole in a 2:1 v/v solution acetonitrile-pyridine is added to the support carrying dimers with unprotected amino groups. After a 5 min. coupling reaction, the support is washed for 1 min. with a 4:1 solution acetonitrile-pyridine. Then the support is then treated with a 1:1:2:6 v/v/v/v solution of acetic anhydride: 1-methylimidazole: pyridine: acetonitrile for 1 min. before washing for 1.5 min. in DCM.

When the oligomer is complete the terminal protecting group is removed using 3% pentafluorophenol in DCM for 3 min. The catalytic phosphonate protecting groups are removed by treatment with 2 ml of a solution 1:2:2 v/v/v thiophenol-triethylamine-dioxane for 3 h. at room temperature. The support is treated for 5 h. (55 degrees C.) with concentrated ammonia to remove any N-protecting group from nucleobases and to cleave the oligomer from the support. The overall yield of the crude oligomer after desalting step (performed by gel-filtration on Pharmacia NAP-10 column) should be about 0.20 micromol.

Oligomers can be purified by polyacrylamide gel electrophoresis (15% polyacrylamide gel, 7M urea). Electrophoresis is performed in 0.1 M Tris-borate/EDTA buffer (pH 8.3). Oligomers can be purified also by anion-exchanged FPLC in 1 ml/min. linear gradient NaCl (0–1.2M) in 0.02M NaOH (pH 12) on a Mono-Q column.

Example 15

Synthesis of a SerNA-pPNA Oligomer by Solid Phase Phosphotriester Synthesis Using SerNA-pPNA Dimer Synthons The synthesis of a pPNA-SerNA oligomer of formula (XIII) having SerNA and pPNA residues in a 1:1 ratio is performed in 1 micromole scale using an automated model 381A synthesizer from Applied Biosystems. The solid support is 30 mg CPG beads derivatized with 5'-DMTr-dT-3'-O-succinate (Applied Biosystems). The SerNA-pPNA dimer is the unit of synthesis or "synthon" in which the free hydroxyl group of serine is protected with DMTr and the pPNA phosphonate is protected with the catalytic 1-oxido-4-alkoxy-2-picolyl group. SerNA-pPNA dimers of varying base composition are sequentially added by the formation of phosphonoester bond using the phophotriester synthesis. The order of the dimers used in the synthesis is G-C, T-T, T-G, T-T, C-A, G-G, A-G.

Initially, the derivatized support is treated with 3% trichloroacetic acid (TCA) in DCM for 3 min to remove the protecting group from the terminal OH-group of 5'-DMTr-dT and then washed for 1 min. with acetonitrile, followed by a 3 min wash with a 2:1 solution of acetonitrile-pyridine.

In each cycle in which a dimer is added, a SerNA-pPNA dimer (0.05M phosphonate component) is coupled to the growing oligonucleotide chain using 0.1 SM 2,4,6-triisopropylbenzenesulfonyl chloride (TPSCI) (Aldrich) in a 2:1 solution acetonitrile-pyridine for 5 min. The support is washed for 1 min. with a 2:1 solution acetonitrile-pyridine followed by 1 min. acetonitrile washing. Then the support is treated with a 1:1:2:6 v/v/v/v solution of acetic anhydride:1-methylimidazole:pyridine: acetonitrile for 1 min. before washing for 1.5 min. in DCM.

When the oligomer is complete the terminal protecting group is removed using 3% trichloroacetic acid (TCA) in DCM for 3 min. The catalytic phosphonate protecting groups are removed by treatment with 2 ml of a solution 1:2:2 v/v/v thiophenol-triethylamine-dioxane for 3 h. at room temperature. The support is treated for 5 h. (55 degrees C.) with concentrated ammonia to remove any N-protecting group from nucleobases and to cleave the oligomer from the support.

Oligomers are purified by polyacrylamide gel electrophoresis (15% polyacrylamide gel, 7M urea). Electrophoresis is performed in 0.1M Tris-borate/EDTA buffer (pH 8.3). They can Iso be purified by anion-exchanged FPLC in 1 ml/min. linear gradient NaCl (0–1.2M) in 0.02M NaOH (pH 12) on a Mono-Q column.

Example 16

Synthesis of a pPNA-SerNA Oligomer by Solid Phase Synthesis using pPNA-SerNA Dimer Synthons The synthesis of a pPNA-SerNA oligomer of formula (XIII) having SerNA and pPNA residue in a 1:1 ratio is performed in 1 micromol scale using an automated model 381A synthesizer from Applied Biosystems. The solid support is 30 mg CPG beads derivatized with 5'-N-MMTr-amino-dT-3'-O-succinate. The pPNA-SerNA dimer is the unit of synthesis or "synthon" in which the free terminal amino group of the pPNA is protected with MMTr and the phosphonate of the phosphono-PNA is protected with the catalytic 1-oxido-4-alkoxy-2-picolyl group. pPNA-SerNA dimers of varying base composition are sequentially added by the formation of amide bonds. The order of the dimers used in the synthesis is G-C, T-T, T-G, T-T, C-A, G-G, A-G.

Initially, the derivatized support is treated with 3% pentafluorophenol in DCM for 3 min to remove the protecting group from the terminal amino group of 5'-MMTr-amino-dT and then washed for 0.5 min. with 0.2M diisopropylethylamine in DCM, followed by a 1 min wash with a 4:1 solution of acetonitrile-pyridine. In each cycle, a pPNA-SerNA dimer (0.05M carboxyl component) is mixed with 0.06M 2,4,6-triisopropylbenzene-sulfonyl-3-nitro-1,2,4-triazole (TPSNT) (Aldrich) and 0.2M 1-methylimidazole in a 2:1 v/v solution acetonitrile-pyridine is added to the support carrying dimers with unprotected amino groups. After a 5 min. coupling reaction, the support is washed for 1 min. with a 4:1 solution acetonitrile-pyridine. Then the support is treated with a 1:1:2:6 v/v/v/v solution of acetic anhydride: 1-methylimidazole: pyridine: acetonitrile for 1 min. before washing for 1.5 min. in DCM.

When the oligomer is complete the terminal protecting group is removed using 3% pentafluorophenol in DCM for 3 min. The catalytic phosphonate protecting groups are removed by treatment with 2 ml of a solution 1:2:2 v/v/v thiophenol-triethylamine-dioxane for 3 h. at room temperature. The support is treated for 5 h. (55 degrees C.) with concentrated ammonia to remove any N-protecting group from nucleobases and to cleave the oligomer from the support.

Oligomers are purified by polyacrylamide gel electrophoresis (15% polyacrylamide gel, 7M urea). Electrophoresis is performed in 0.1M Tris-borate/EDTA buffer (pH 8.3). They can be purified also by anion-exchanged FPLC in 1 ml/min. linear gradient NaCl (0–1.2M) in 0.02M NaOH (pH 12) on a Mono-Q column.

Example 17

Hybridization of Oligonucleotide Analogues to Nucleic Acids

Polythymine oligonucleotides and oligonucleotide analogues were synthesized according to the methods of the present invention and methods known in the art. Oligomers 4 and 5 comprised pPNA monomers alternating with HypNA and SerNA, respectively, linked by alternating phosphonoester and amide bonds, and thus are represented by oligomers (XII) and (XIII) of the present invention. Other oligomers, such as oligomers 7, 8, 9, 10, 11, and 12, comprised HypNA or SerNA monomers in combination with other monomers, and were synthesized by forming amide, phosphonoester, or ester bonds. Oligomers 10 and 11 also contained monomers having classical PNA backbones and pyridine in the base position. Homogeneous DNA oligomers, or homogeneous oligomers comprising classical PNA monomers or pPNA monomers (1, 6, and 2) or HypNA or SerNA monomers (13 and 14), were also used for comparison in hybridization experiments.

The oligomers were hybridized to poly(dA) and poly(rA) at a concentration of 3–5 mM in 150 mM NaCl, 10 mM Tis-HCl (pH 7.5), 5 mM EDTA, and 10 mM $MgCl_2$, The solution was heated to 95 degrees C. for two minutes, then cooled to 5 degrees C. at a rate of 0.5 degrees C. per minute. The absorbance at 260 nm was measured using a Gilford 250

UV VIS spectrophotometer equipped with a Gilford 2527 thermocell.

TABLE 1

Thermal Stability of Duplexes Comprising Preferred Oligomers of the Present Invention and Nucleic Acid Molecules.

| Oligomer No. | Oligomer Type | Structure | Tm (degr. C.) poly (dA) | Tm (degr. C.) poly (rA) |
|---|---|---|---|---|
| 1 | DNA | $dT_{16}$(SEQ ID NO: 9) | 45 | 43 |
| 2 | pPNA | $P^O_{15}$-T* | 52 | 41 |
| 3 | PNA-pPNA | Ac-$(T^O-P^N)_7$-$T^O$-T* | 68 | 60 |
| 4 | pPNA-HypNA | $(hT-P^N)_7$-hT-T* | 83 | 77 |
| 5 | pPNA-SerNA | $(sT-P^N)_7$-sT-T* | 40 | 36 |
| 6 | PNA | Ac-$T^N_{15}$-T* | 85 | 82 |
| 7 | PNA-HypNA | $(hT-T^N)_7$-hT-$P^{Ph}$ | 81 | 78 |
| 8 | PNA-SerNA | $(sT-T^N)_7$-sT-$P^{Ph}$ | 56 | 53 |
| 9 | pPNA-HypNA | $P^O$-$(P^O-hT-P^N)_4$-hT-T* | 66 | |
| 10 | PNA-pPNA-HypNA | Ac-$Pyr^N$-$P^N$-$(P^O$-hT-$P^N)_4$-hT-T* | 73 | 66 |
| 11 | PNA-pPNA-HypNA | Ac-$Pyr_2^N$-$P^N$-$(P^O$-hT-$P^N)_4$-hT-T* | 79 | 74 |
| 12 | pPNA-HypNA | $(hT-P^N$-$hT)_5$-T* | 52 | 48 |
| 13 | HypNA | $hT_{15}$-$P^{Ph}$ | <10 | <10 |
| 14 | SerNA | $sT_{15}$-$P^{Ph}$ | <5 | <5 |

Figure 1:
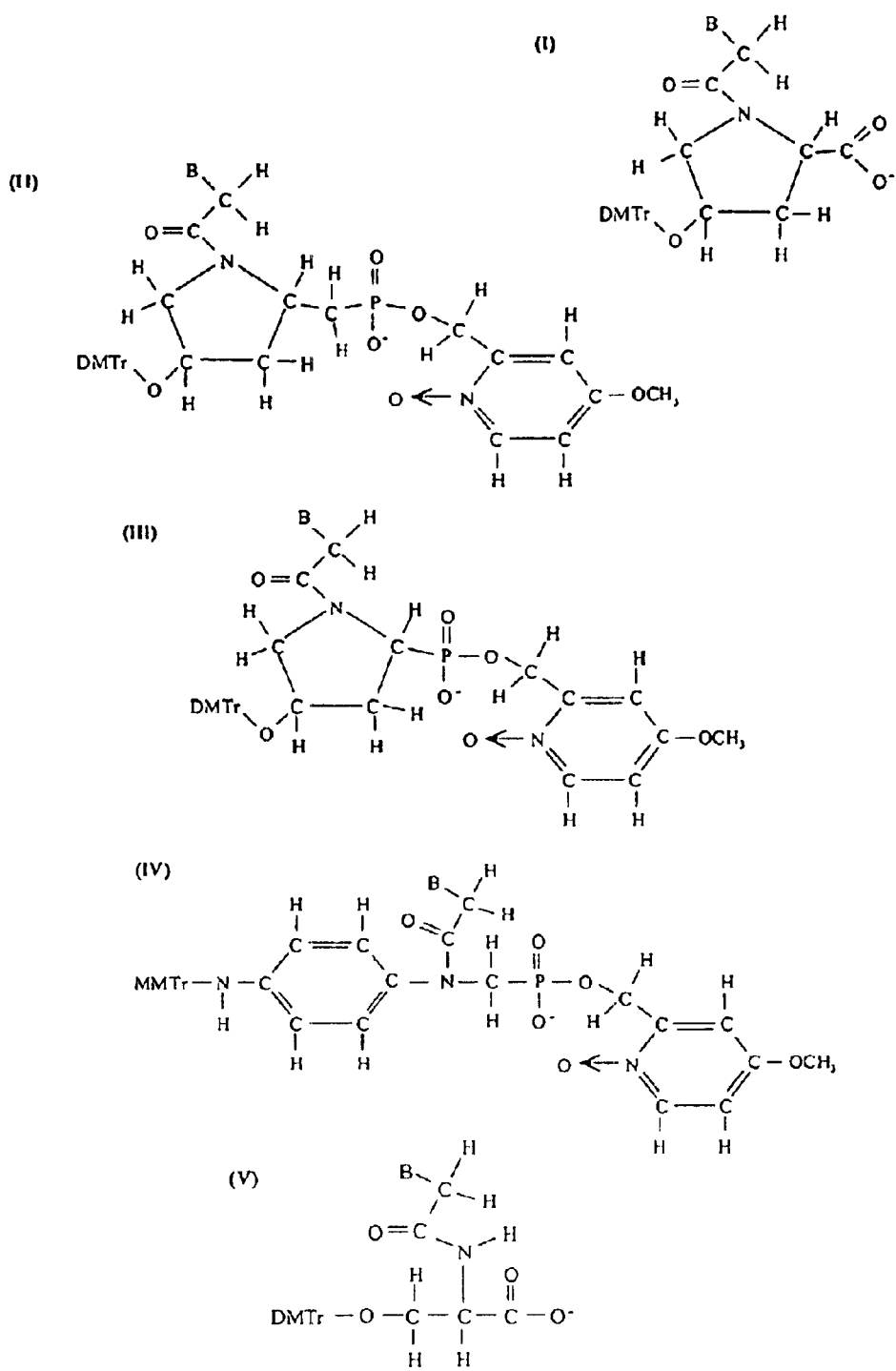
FIG. 1 depicts some preferred oligonucleotide analogue monomers of the present invention: a HypNA monomer (I) carrying the DMTr hydroxyl protecting group, a Hyp-1NA monomer (II) carrying the DMTr hydroxyl protecting group and the catalytic 1-oxydo-4-methoxy-2-picolyloyl phosphonate protecting group, a Hyp-2NA monomer (III) carrying the DMTr hydroxyl protecting group and the catalytic 1-oxydo-4-methoxy-2-picolyloyl phosphonate protecting group, a pPNA-Ar1 monomer (IV) carrying the MMTr amino protecting group and the catalytic 1-oxydo-4-methoxy-2-picolyloyl phosphonate protecting group, and a SerNA monomer (V), carrying the DMTr hydroxyl protecting group.
Figure 2:
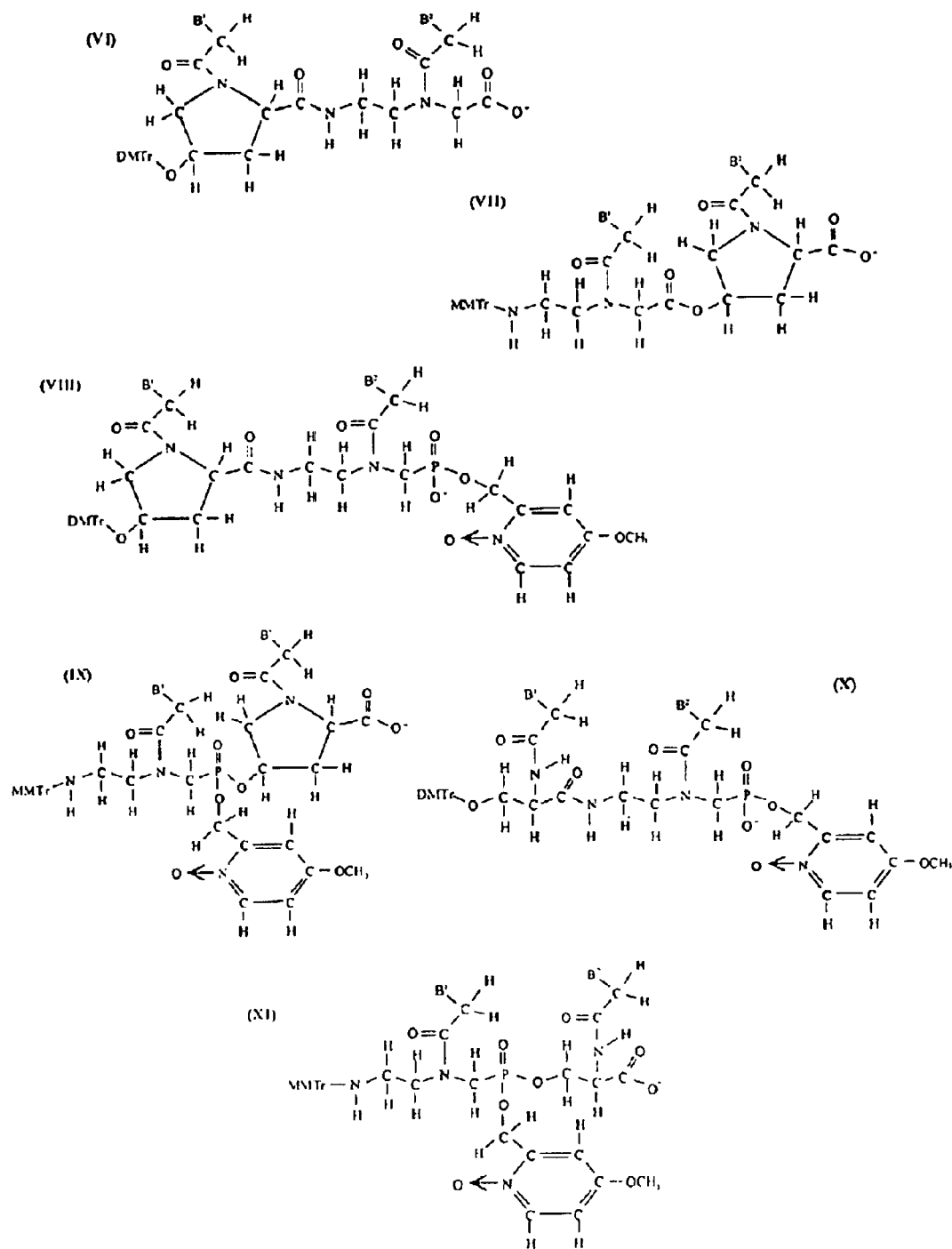
FIG. 2 depicts some preferred oligonucleotide analogue dimers of the present invention: a HypNA-PNA dimer (VI) carrying the DMTr hydroxyl protecting group, a PNA-HypNA dimer (VII) carrying the MMTr amino protecting group, a HypNA-pPNA dimer (VIII) carrying the DMTr hydroxyl protecting group and the catalytic 1-oxydo-4- methoxy-2-picolyloyl phosphonate protecting group, a pPNA-HypNA dimer (IX) carrying the MMTr amino protecting group and the catalytic 1-oxydo-4-methoxy-2-picolyloyl phosphonate protecting group, a SerNA-pPNA dimer (X) carrying the DMTr hydroxyl protecting group and the catalytic 1-oxydo-4-methoxy-2-picolyloyl phosphonate protecting group, and a pPNA-SerNA dimer (XI) carrying the MMTr amino protecting group and the catalytic 1-oxydo-4-methoxy-2-picolyloyl phosphonate protecting group.
Figure 3A:
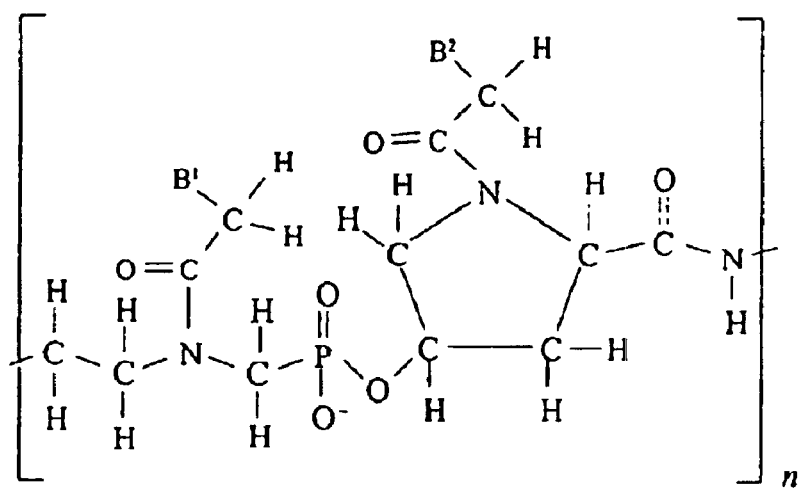
Figure 3A:
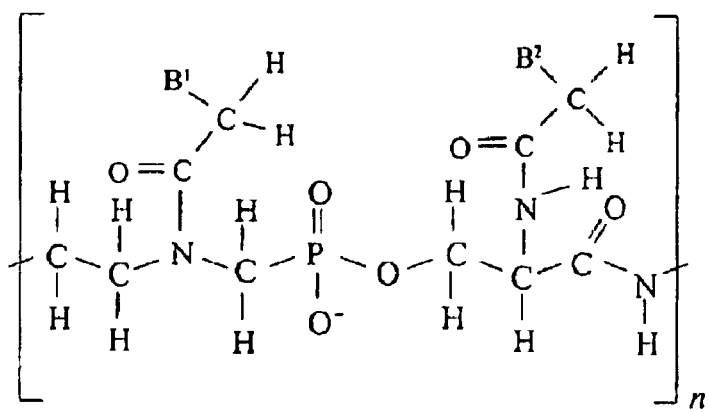
Figure 3B:
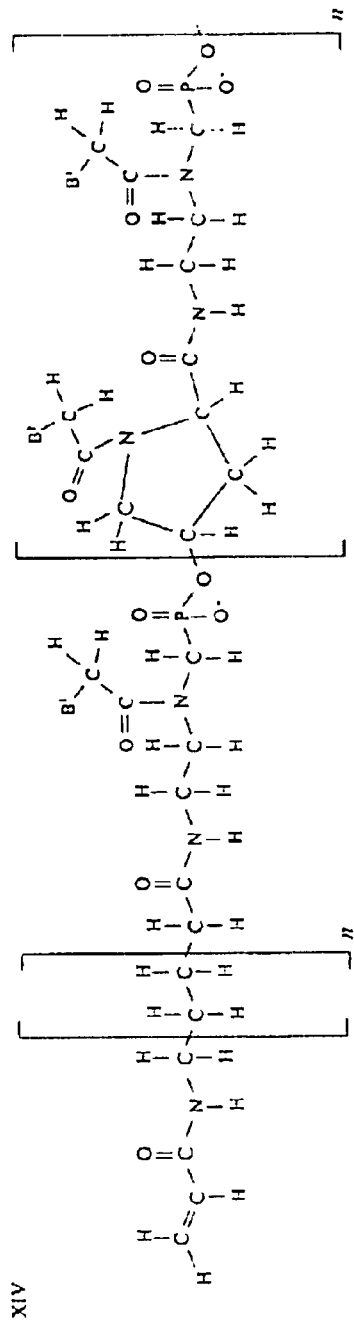
Figure 3B:
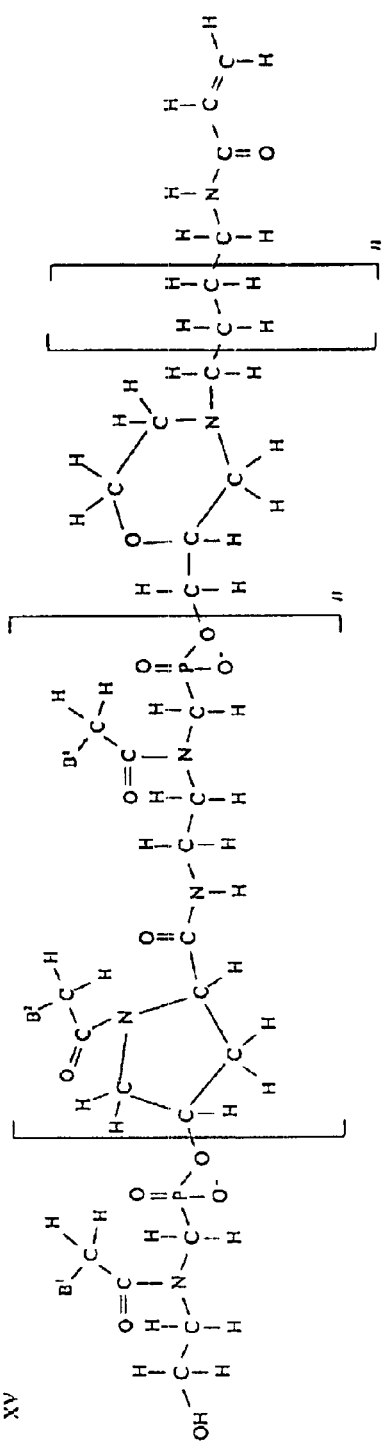

All sequences in Table 1 are poly T (thy) and have the structures of HypNAs, SerNAs, pPNAs, and PNAs depicted in FIG. 2: $T^N$ is a classical PNA monomer. T* is a classical PNA monomer in which the terminal carboxyl group has been replace with a hydroxyl. $T^O$ is a classical PNA monomer in which the terminal amino has been replaced with a hydroxyl group. $P^N$ is a phosphono PNA monomer. $P^O$ is a phosphono PNA monomer in which the terminal amino has been replaced with a hydroxyl group. $P^{Ph}$ is a phosphono PNA monomer in which the terminal phosphate carries a phenyl group. hT is a HypNA monomer. sT is a SerNA monomer. PyrN is a classical PNA in which the base position comprises a pyrene molecule.

Example 18

Synthesis of Oligonucleotide Analogues Coupled at the 3' end to Acrylamide and Oligonucleotide Analogue-Acrylamide Polymers Synthesis of oligonucleotide analogue oligomers used solid phase synthesis and the methods disclosed herein and known in the art (Efimov et al., Nucleic Acids Res. 26: 566–575 (1998) and Efimov et al., Russian Journal of Bioorganic Chemistry 25: 545–555 (1999)). An LCAA CPG solid support was derivatized by acylation of the LCAA amino groups with the 3' succinate of 2'-O-benzoyl-5'-O-dimethoxy-trityl-1-deoxy-D-ribofuranose. Oligonucleotides and oligonucleotide analogues were elongated on the deprotected ribofuranose moiety. When the oligomer was complete the terminal protecting group was removed using 3% trichloracetic acid in DCM for 3 min. The catalytic phosphonate protecting groups were removed by treatment with 2 ml of a solution 1:2:2 v/v/v thiophenol-triethylamine-dioxane for 3 h. at room temperature. The support was treated for 5 h. (55 degrees C.) with concentrated ammonia to remove any N-protecting group from nucleobases and to cleave the oligomer from the support.

Released oligomers carrying 3' ribofuranose units were resuspended in 0.5 ml $H_2O$, and their ribofuranose units were oxidized to generate dialdehydes using 0.1 ml 0.1 M $NaIO_4$. After a 15 min incubation, 0.1 mL 0.2 M sodium hypophosphite was added and the mixture was incubated for 20 min to reduce excess $NaIO_4$. After adding sodium acetate, pH 4, to a final concentration of 50 mM, 0.3 mL of 50 mM N-(2-amino-ethyl)acrylamide hydrochloride was added. 0.15 mL of $NaCNBH_3$ in acetonitrile was added and the mixture was incubated at 20 degrees C. for 30 min. Water was then added to bring the volume to 1.5 mL, and the oligomers comprising attached acrylamide monomers were purified on a Pharmacia NAP-25 column.

To synthesize an acrylamide polymer comprising oligonucleotide analogues, the 3'-acrylamide-oligomer conjugates were copolymerized with acrylamide by making a solution of 100 mM acrylamide and 0.5 mM oligonucleotide analogue-acrylamide conjugates and adding TEMED to 0.1% and ammonium persulfate to 0.1%. The mixture was stirred at room temperature for 16 hours, and then the acrylamide polymer was precipitated with 5 volumes of ethanol and dissolved in water. The preparation was fractionated by gel filtration using a 0.5 Bio-Gel A (BioRad) column and fractions were collected by UV absorption indicating the presence of the acrylamide-conjugated oligonucleotide analogues. The collected fractions were lyophilized.

Example 19

Synthesis of Oligonucleotide Analogues Coupled at the 5' end to Acrylamide and Oligonucleotide Analogue-Acrylamide Polymers Synthesis of oligonucleotide analogue oligomers used solid phase synthesis and the methods disclosed herein and known in the art (Efimov et al., Nucleic Acids Res. 26: 566–575 (1998) and Efimov et al., Russian Journal of Bioorganic Chemistry 25: 545–555 (1999)). An LCAA CPG solid support was derivatized by acylation of the LCAA amino groups with the 3' succinate of 2'-O-benzoyl-5'-O-dimethoxy-trityl-1-deoxy-D-ribofuranose. Oligonucleotides and oligonucleotide analogues were elongated on the deprotected ribofuranose moiety.

When the oligomer was complete an acrylamide residue was added to the 5' terminus of the support-coupled oligomer by adding a 0.3 M solution of acrylic acid anhydride, 0.3 M triethylamine in puridine acetonitrile (1:3, v/v) and allowing the reaction to proceed for 15 min, after which the support was washed with acetonitrile. After allowing the support to dry, the oligomers were deprotected and released from the solid support as described in the previous example. The terminal protecting group was removed using 3% trichloracetic acid in DCM for 3 min. The catalytic phosphonate protecting groups were removed by treatment of the support with piperidine. The support was treated for 5 h. (55 degrees C.) with concentrated ammonia to remove any N-protecting group from nucleobases and to cleave the oligomer from the support.

Acrylamide polymers comprising oligonucleotide analogues were synthesized as described in the previous example.

Example 20

Hybridization of Support-Bound Polyacrylamide-Oligonucleotide Co-Polymers and Polyacrylamide-Oligonucleotide Analogue Co-Polymers to Nucleic Acids Oligonucleotides were made by standard solid phase synthesis using the phosphramidite method and a 5'-amino group was added to the oligonucleotides using an N-MMT-aminolinker phosphramidite (Cruachem) as the 5'-terminal unit. The oligomers synthsized comprised pairs of oligomers that differed by a single nucleobase. Acrylamide polymers comprising oligonucleotides were synthesized in the same way as described for polymers comprising oligonucleotide analogues in Example 18.

For the attachment of acrylamide polymers comprising oligonucleotides or oligonucleotide analogues (polyacrylamide-oligomer co-polymers) to a glass solid support, oligomers coupled to acrylamide monomers were co-polymerized with acrylamide and N-bromoacetyl-6-aminohexyl acrylamide hydrochloride. 95 mM acrylamide was mixed with 5 mM of derivatized acrylamide and 0.5 mM of oligomer-coupled acrylamide in 50% aqueous dimethylformadide, 0.05% TEMED and 0.1% ammonium persulfate. The mixture was stirred for 16 hr under nitrogen at room temperature. The resulting polymers were precipitated with ethanol and fractionated by gel filtration using a 0.5 Bio-Gel A (BioRad) column.

Glass microscope slides were treated with 3-mercaptopropyltrimethoxysilane using methods known in the art. Polyacrylamide-NHCOCH$_2$Br acrylamide-oligomer acrylamide co-polymers were attached to the aldehyde functionalized glass slides by adding 2 microliters of a 1 mg/mL copolymer solution in 0.1 M triethylammonium phosphate (pH 9) to the surface of the mercapto-silane coated glass slide. After a 6 hour incubation under nitrogen at room temperature, excess beta mercaptoethanol was added to cap unreacted bromacetamide groups. The slide was then washed with 0.1 sodium phosphate (pH 7) and water.

Oligonucleotide probes labeled with $^{32}$P were added at a concentration of 200 nM to a hybridization solution containing 0.1 M NaCl, 10 mM sodium phosphate (pH 7), 5 mM EDTA, 10 mM MgCl2, and 0.1% sodium dodecyl sulfate. The hybridization solution (0.5 mL) was added to the matrix on the glass slide comprising the attached polyacrylamide-oligonucleotide analogues and the slide was incubated for 1–2 hours at a temperature 10–20 degrees below the Td (determined by solution hybridization/denaturation experiments).

A series of washes was performed at increasing temperatures (an increase of 5 degrees per wash) and aliquots of the wash solution were removed for scintillation counting. The melting temperature for each oligomer was determined by the amount of labeled oligonucleotide probe removed by washing. Table 2 shows that a single nucleobase mismatch between the 15-mer DNA probe and a HypNA-pPNA oligomer causes a twenty degree drop in melting temperature, indicating a high degree of binding specificity.

TABLE 2

Effect of Single-base Mismatches on Tm's of Oligonucleotides and Oligonucleotide Analogues

| Oligomer No. | Oligomer Type | Sequence | Tm (degr. C.) | Td (degr. C.) |
|---|---|---|---|---|
| 1 | PNA | t$_{15}$ | 85 | |
| 2 | PNA | t-t-t-t-t-c-t-t-t-c-t-t-t-t-T' | 27 | |
| 3 | PNA | t-t-t-t-t-t-c-t-t-t-t-t-t-T' | 64 | |
| 4 | PNA-pPNA | t*tttT' t*tttT' t*tttT' | 76 | |
| 5 | PNA-pPNA | t*tttT' c*tttC' t*tttT' | 20 | |
| 6 | PNA-pPNA | t*tttT' t*tctT' t*tttT' | 52 | |
| 7 | HypNA-pPNA | T t$^h$T t$^h$T t$^h$T t$^h$T t$^h$T t$^h$T t$^h$T | 81 | |
| 8 | HypNA-pPNA | T t$^h$T t$^h$T c$^h$T t$^h$T c$^h$T t$^h$T t$^h$T | 24 | |
| 9 | HypNA-pPNA | T t$^h$T t$^h$T t$^h$T c$^h$T t$^h$T t$^h$T t$^h$T | 59 | |
| 10 | DNA | T$^{15}$(SEQ ID NO: 10) | 36 | |
| 11 | DNA | T$_5$-C-T$_3$-C-T$_5$(SEQ ID NO: 11) | <10 | |
| 12 | DNA | T$_7$-C-T$_7$(SEQ ID NO: 11) | 24 | |
| 13 | PNA | ctgcaaaggacaccatga | 72 | 74 |
| 14 | PNA | ctgcaaagcacaccatga | 54 | 55 |
| 15 | PNA-pPNA | C*t*gcaA'a*ggaC'a*ccaT'g*A* | 67 | 68 |
| 16 | PNA-pPNA | C*t*gcaA'a*gcaC'a*ccaT'g*A* | 50 | 51 |
| 17 | HypNA-pPNA | C*t$^h$G'c$^h$A'a$^h$A'g$^h$G'a$^h$C'a$^h$C'c$^h$A t$^h$G'A* | 69 | 71 |
| 18 | HypNA-pPNA | C*t$^h$G'c$^h$A'a$^h$A'g$^h$C a$^h$C'c$^h$A't$^h$G'A* | 49 | 50 |
| 19 | DNA | CTGCAAAGGACACCATGA (SEQ ID NO: 13) | 54 | 55 |
| 20 | DNA | CTGCAAAGCACACCATGA (SEQ ID NO: 14) | 40 | 41 |

T, A, C, and G are DNA monomers. T*, A*, C*, and G* are pPNA monomers (N-(2-hydroxyethyl)glycine backbone). T', A', C', and G' are pPNA monomers (N-(2-aminoethyl)glycine backbone). t, a, c, and g are PNA monomers (N-(2-aminoethyl)glycine backbone). t*, a*, c*, and g* are PNA monomers (N-(2-hydroxyethyl)glycine backbone). t$^h$, a$^h$, c$^h$, and g$^h$ are HypNA monomers (trans-4-hydroxy-L-proline backbone). Single base mismatches are underlined.

Example 21

Sandwich Hybridization of Oligonucleotides and Oligonucleotide Analogues of Different Compositions to Nucleic Acids Fifteen nucleobase long capture oligonucleotides and oligonucleotide analogues (PNA oligomers, pPNA-PNA (1:1) oligomers, and HypNA-pPNA (1:1) oligomers) were synthesized with the sequence: CTGGAGGAAGATCTG (SEQ ID NO: 1), ATGGAACCGAAATCT (SEQ ID NO: 2), and AAACRCACACCTGC (SEQ ID NO: 3), such that they were complementary to bases −21 to −7, 1–15, and 22–36 of a target double-stranded DNA molecule representing a 720 bp XhoI-BamHI fragment of a cloned artificial gene for the Fc domain of human IgG1 (Efimov et al., Biorg. Khim. 22: 168–174 (1996)) using methods known in the art and disclosed herein. The capture oligonucleotides and oligonucleotide analogues were coupled to acrylamide monomers and incorporated into acrylamide polymers using methods detailed in Example 19 and fixed to derivatized glass slides as described in Example 20.

Oligonucleotide or oligonucleotide analogue (PNA oligomers, pPNA-PNA (1:1) oligomers, and HypNA-pPNA (1:1) oligomers) detection probes were synthesized with the sequences: TCCGTTATGCACGAA (SEQ ID NO: 4), AAC-CACTACACCCAG (SEQ ID NO: 5), and GGGAAATAAGGATCC (SEQ ID NO: 6), such that they were complementary to the target DNA molecule, using methods known in the art and disclosed herein.

Oligonucleotide or oligonucleotide analogue (PNA oligomers, pPNA-PNA (1:1) oligomers, and HypNA-pPNA (1:1) oligomers) amplification probes were synthesized with the sequence: ACTACTACTACTACT (SEQ ID NO: 7), using methods known in the art and disclosed herein.

An oligonucleotide signal probe was synthesized with the sequence: AGTAGTAGTAGTAGTAGT (SEQ ID NO: 8), using methods known in the art, and was 5' labeled with $^{32}$P The detection and amplification probes were coupled to acrylamide monomers and incorporated into polymers using the methods described in Example 18.

Prior to hybridization, the target DNA molecule was denatured by treatment with 0.05 M NaOH for 5 min at room temperature, chilled on ice and neutralized with acetic acid. The target was added to a hybridization solution containing 150 mM NaCl, 60 mM Na citrate (pH 7), 1 mg/ml sonicated salmon sperm DNA, 5 mM EDTA, and 0.1% SDS for 2 hours. The matrix-coated glass slide was washed in 150 mM NaCl, 60 mM Na citrate (pH 7), and 0.1% SDS for 30 minutes, after which a polyacrylamide-oligonucleotide or polyacrylamide-oligonucleotide analogue co-polymer was added that comprised detection probes (complementary to the target) and amplification probes (complementary to the signal probe) such that the ratio of detection probe to target DNA was 10:1. The ratio of detection probes to amplification probes in the co-polymer was 1:10. After washing in 150 mM NaCl, 60 mM Na citrate (pH 7), and 0.1% SDS for 30 minutes, the $^{32}$P-labeled signal probe was hybridized to the slide, in the same hybridization buffer used earlier, and the slide was washed as before.

TABLE 3

Sandwich hybridization using oligonucleotide and oligonucleotide analogue detection and amplification probes.

| Target DNA Conc. (amol) | Probe signal (cpm) (signal/noise) DNA | Probe signal (cpm) (signal/noise) PNA-pPNA | Probe signal (cpm) (signal/noise) HypNA-pPNA | Probe signal (cpm) (signal/ noise) PNA |
|---|---|---|---|---|
| 0 | 13 | 15 | 11 | 12 |
| 5 | 18 (1.0) | 44 (2.9) | 50 (3.3) | 49 (3.3) |
| 10 | 65 (2.3) | 124 (6.3) | 131 (5.1) | 134 (5.8) |
| 20 | 232 (9.2) | 340 (19.6) | 354 (17.6) | 315 (18.4) |
| 100 | 961 (19.4) | 1380 (37.4) | 1405 (40.5) | 1410 (40.3) |
| 500 | 6180 (40.5) | 8395 (94.5) | 9421 (92.5) | |
| 1000 | 17847 (89.8) | 19324 (92.8) | 19537 (100.9) | |

Example 22

Use of HypNA-pPNA Oligonucleotides in the Detection of Nucleic Acids

Fourteen sequences derived from genes encoding transcription factors, each 18 nucleotides in length, are selected for their similarity in predicted Tm. These sequences are used to design HypNA-pPNA oligomers. The oligomers are synthesized on an Applied Biosystems DNA Synthesizer, using the phosphotriester method as illustrated in Example 13. The oligonucleotide analogue oligomers are synthesized with a linker having a 3'-amino functional group to allow for attachment to the glass slide. The oligonucleotides are attached to a phenylisothiocyanate-activated glass slide by a flexible linker (Guo et al., Nucl. Acids Res. 22: 5456–5465). Each oligomer is spotted at a distinct locus on one half of the glass slide to form an array.

As a control, the same fourteen sequences are used to synthesize DNA oligomers. The DNA oligomers are synthesized using the phosphoramide method and spotted on the other half of the same array.

Nucleic acid RNA samples are generated by in vitro transcription of cloned amplified segments of genes corresponding to the oligomer sequences. These RNAs are reverse transcribed into cDNA. The cDNA is hybridized to the glass slide under conditions that favor HypNA-pPNA hybridization to nucleic acids. The slides are washed, and then the slide is stained with SYBR Green II (Molecular Probes, Eugene, Oreg.). The slide is illuminated with 254 nm epi-illumination and photographed with Polaroid 667 film using a SYBR Green photographic filter.

Example 23

Isolation of mRNA Using a HypNA-pPNA PolyT 12-mer, and a "Clamping" HypNA-pPNA Poly T23-mer HeLa cells ($10^8$ mammalian cells) grown in tissue culture and collected by centrifugation were lysed by vortexing the cells in 15 mls of a solution containing 200 mM Tris, pH 7.5, 200 mM NaCl, 500 mM Guanidine thiocyanate, 25 mM $MgCl_2$, and a mixture of nonionic, anionic, and cationic detergents, such as Triton X-100, sodium dodecyl sulfate, and cetyldimethylaethylammonium bromide, and the cell lysate was incubated at 45° C. for 15–60 minutes. The lystate was passed through a sterile plastic syringe attached to an 18–21 gauge needle 4–5 times. A mixture of biotinylated HypNA-pPNA mixture (100 μl of 22.5 μM) was added to the cell lysate. The mixture consisted a 2:1 mixture of a 'linear' poly T 12-mer HypNA-pPNA, with the HypNA to pPNA in a 1:3 ratio and a "clamping" poly T 23-mer HypNA-pPNA, again with the HypNA to pPNA in a 1:3 ratio.

The clamping poly T 24-mer was synthesized according to methods disclosed herein, and described in Efimov et al., Nucleic Acids Res. 26: 566–575 (1998) and Efimov et al., Russian Journal of Bioorganic Chemistry 25: 545–555 (1999), by alternating coupling of HypNA-pPNA dimers and pPNA monomers to the growing oligomer on an Applied Biosytems dT-LCAA-CPG solid support using the phosphotriester synthesis. The hydroxyl group of the HypNA moiety of the Thy HypNA-pPNA dimer was protected with DMTr and the phosphonate of the pPNA moiety of the Thy HypNA-pPNA dimer carried the 1-oxido-4-alkoxy-2-picolyl catalytic protecting group. Thy pPNA monomers carried the 1-oxido-4-alkoxy-2-picolyl catalytic protecting group on the phosphonate and the DMTr hydroxyl protecting group. In this was a poly T oligomer was synthesized with the structure: 3'-dT(pPNA-pPNA-pPNA-HypNA)$_3$- . A hexa(ethylene glycol) linker (formula 1) was added in the middle of the sequence like a regular monomer by forming a phosphate bond between the linker and the hydroxyl group of the HypNA using 2,4,6-triisopropylbenzenesulfonyl chloride (TPSCI) (Aldrich) as a coupling reagent. A Thy pPNA monomer with an DMTr-protected hydroxyl group was then coupled to the free terminus of the linker by forming a phosphonate bond. Thy-Thy HypNA-pPNA dimers (in which the hydroxyl group of the HypNA moiety was protected with DMTr and the phosphonate of the pPNA moiety carried the 1-oxido-4-alkoxy-2-picolyl catalytic protecting group) and Thy pPNA monomers (carrying the 1-oxido-4-alkoxy-2-picolyl catalytic protecting group on the phosphonate) were added alternately by forming phosphonate bonds using TPSCI to form the second arm of the clamping oligo. For biotinylation of the clamping oligo, a biotin linker (formula 2) was added like a regular monomer to the terminal HypNA residue of the clamping oligo to form the sequence: 3'-dT-(pPNA-pNA-pPNA-HypNA)$_3$-linker1-(pPNA-pPNA-pPNA-HypNA)$_3$-linker2-5' while the oligo was still attached to the solid support followed by coupling with biotin (biotin was previously treated with DBU and diphenylphosphoryl azide (Aldrich)) to the terminal amino group of the biotin linker. The 1-oxido-4-alkoxy-2-picolyl catalytic protecting groups were removed by treatment of the oligomer with thiophenol-triethylamine-dioxane (1:2:2 v/v/v; 2 ml/30 mg of the support for 3 h at room temperature). To release the oligomers from the support, the support was treated with aqueous concentrated ammonia. The clamping biotinylated oligomers were purified by PAGE.

The linear poly Thy 12-mer HypNA-pPNA, with HypNA to pPNA monomers in a 1:3 ratio, was synthesized on a dT-LCAA-CPG solid Support (Applied Biosystems) using the phosphotriester synthesis as disclosed herein and described by Efimov et al., Nucleic Acids Res. 26: 566–575 (1998) and Efimov, et al. Russian Journal of Bioorganic Chemistry 25: 545-555 (1999), by alternating coupling of HypNA-pPNA dimers and pPNA monomers to the growing oligomer. The linear poly Thy 12-mer HypNA-pPNA was biotinylated as described above for the clamping oligomer.

The cell lysate/HypNA-pPNA mixture was incubated at 37° C., with gentle shaking, for 45-60 minutes. Streptavidin coated magnetic beads (binding capacity of approx. 10 pmol of probe/µl of particles) were added directly to the cell lysate/HypNA-pPNA mixture, and the mixture was incubated at room temperature on a rocking platform for 1 hour.

Using a magnet, the streptavidin beads with the HypNA-pPNA-analog with mRNA attached was separated from the remaining cell lysate material. The lysate supernatant was carefully removed with a pipet. The beads were washed once with High Salt Buffer (10 mM Tris, pH 7.5, 500 mM NaCl), once with Super Wash Buffer (10 mM Tris, pH 7.5, 250 mM NaCl, 0.1% Tween 20), and three times with Low Salt Buffer (10 mM Tris, pH 7.5, 250 mM NaCl).

Following the Super Wash Buffer wash, the HypNA-pPNA captured material was subjected to DNAse treatment. Similar to oligo dT, oligo T HypNA-pPNA will hybridize to some genomic DNA at A-rich regions. PNAs, including HypNA-pPNAs, are resistant to nucleases. Therefore, it is possible to perform a DNase digest of the captured nucleic acid while it is attached to the streptavidin beads, although this treatment is optional. DNAse digestions were performed by adding 1 ml of Low Salt Buffer (10 mM Tris, pH 7.5, 250 mM NaCl) to the beads after removal of the Super Wash Buffer. The beads were resuspended in this buffer using a micro pipet tip. Three units of RNase-free Dnase were added. The resuspended beads were incubated with Dnase at room temperature for 10 minutes. The streptavidin beads bound to the HypNA-pPNA-analog with the mRNA attached were then separated from the remaining degraded DNA using a magnet. The beads were then washed in low salt buffer, as above.

The washed streptavidin beads were resuspended in 150 µl of DEPC-treated water. The beads were allowed to sit in the DEPC-treated water for 5 minutes at room temperature to allow the mRNA to fall off the HypNA-pPNA oligomers attached to the beads. Using a magnet, the beads were separated from the mRNA. The eluted mRNA was collected. A second elution was performed by adding 150 µl of DEPC-treated water to the beads and, after 5 minutes at room temperature, collecting the beads with a magnet and removing the eluate, which was pooled with the first eluate.

The eluted RNA was diluted 1:25 in 10 mM Tris-HCl, pH 7.5 and the absorbance at 260 was 0.24 and the absorbance at 280 nm was 0.125, giving a 260:280 ration of 1.92 and a yield of 72 micrograms of polyA RNA. Gel electrophoresis in the presence of formaldehyde showed the preparation was substantially free of ribosomal RNA.

Example 24

Normalization of a cDNA Libraries Using Oligonucleotide Analogues

A HypNA-pPNA oligomer of sequence: N-term-CTGGTCTCAAGTCAG-C-term, complementary to the 3' untranslated region of the β-actin mRNA, and having a HypNA to pPNA of 1:1, 1:2, or 1:3 is synthesized using the methods of the present invention. The HypNA-pPNA oligomer will be also comprises a poly-histidine moiety for binding to $Ni^{2+}$-NTA resins. The attachment of the 6-His peptide can be through the synthesis of an amide bond between carboxy terminal of the His peptide and the amino terminus of a pPNA residue of the HypNA-pPNA oligomer.

In one experiment, polyadenylated (poly A) RNA is prepared from HeLa according to methods described in Example 23, or by other methods known in the art. One nanomole of the HypNA-pPNA oligomer is added to a preparation of 0.5 micrograms of HeLa mRNA in 50 mM Tris-HCl, pH 8.3, 30 mM KCl, 8 mM $MgCl_2$, and 10 mM dithiothreitol and the mixture (10 microliters) is heated to 70 degrees C. for 10 min. and then cooled on ice. Oligo dT primer obtained commercially is added to the mixture, which is again heated to 70 degrees C. for 10 min. and then cooled on ice. cDNA synthesis is then performed using reverse transcription standard techniques. A control reverse transcription (RT) reaction without the HypNA-pPNA oligomer is also performed.

First-strand cDNA from the above RT reactions is used to amplify a region of the actin gene. Glyceraldehyde-3-Phosphate Dehydrogenase (GAPDH), (a second abundant gene) is reverse transcribed and PCR amplified from both mRNA populations to show that HypNA-pPNA oligomer hybridization to one gene does not affect the RT of a second gene.

In another approach, termed the "subtracting" approach, uses a specific binding member on the HypNA-pPNA oligomer to pull out the HypNA-pPNA/RNA. In this case nickel-NTA-coated beads are added to the hybridization reaction and used to pull out HypNA-pPNA/abundant message heteroduplexes. As with the first approach, the subtracted mRNA and a normal mRNA control sample are reverse transcribed and PCR-amplified with actin primers to determine the representation of β-actin in the two mRNA populations. These two mRNA samples are also reverse transcribed and PCR amplified with the GAPDH primers as positive controls. The primers used in this study are outlined in Table 4.

TABLE 4

Primers used in PCR reactions for the β-actin and GAPDH genes.

| Gene name | Sequence | Size of PCR Product |
|---|---|---|
| Actin | 5'-GCTCACCATGGATGATGATATCGC-3' (SEQ ID NO: 15) 5'-GGAGGAGCAATGATCTTGATCTTC-3' (SEQ ID NO: 16) | 1000 bp |
| GAPDH | 5'-TTAGCACCCCTGGCCAAGG-3' (SEQ ID NO: 17) 5'-CTTACTCCTTGGAGGCCATG-3' (SEQ ID NO: 18) | 540 bp | cDNA libraries can be constructed from RNA population that have been normalized by the specific binding of HypNA-pPNA oligonucleotide analogues to one or more abundant messages and the removal of the abundant messages from the RNA population, as described above. Screening a normalized library (such as by filter hybridization) can demonstrate an increased representation of less abundant genes in the cDNA library, relative to the representation of less abundant genes in cDNA libraries that have not been normalized.

Example 25

Synthesis of 4-O-4,4'-Dimethoxytrityl-N-($N^4$-benzoylcytosin-9-ylacetyl)-L-hydroxyproline [monomer (I)]

4-O-4,4'-Dimethoxytrityl-N-($N^4$-benzoylcytosin-9-ylacetyl)-L-hydroxyproline was made by dissolving 4-hydroxyproline methyl ester hydrochloride (1.82 g, 10 mmol) in 40 ml of a 1:1 mixture of pyridine-acetonitrile containing 1.4 ml (10 mmol) of triethylamine. $N^4$-Benzoylcytosin-9-ylacetic acid (3.55 g, 13 mmol) and N,N'-dicyclohexylcarbodiimide (DCC) (2.88 g, 14 mmol) were added. The reaction was terminated after 3 hours stirring by the addition of 2 ml water and incubated overnight at room temperature.

The mixture was then filtered to remove precipitated dicyclohexyl urea. The filtrate was dried by evaporation and coevaporated with pyridine (2×30 ml) and then dissolved in pyridine (40 ml). 4,4'-Dimethoxytrityl chloride (DMTrCl) (4.41 g, 13 mmol) was added and the mixture was incubated at 50° C. for 30 min., cooled to room temperature followed by addition 5% $NaHCO_3$ (60 ml). The product was extracted with methylene chloride (DCM) (2×80 ml), organic layers were dried over $Na_2SO_4$ then solvent was removed by evaporation. The residue was dissolved in pyridine (60 ml) and LiI (30 mmol, 4.05 g) was added and the solution was heated at 90° C. for 6 hrs. The reaction mixture was evaporated 70 ml of 1M TEAB solution was added and the product was extracted with DCM (3×80 ml). The combined organic phase was washed once with 0.5M TEAB (100 ml), dried over $Na_2SO_4$ then solvent was removed by evaporation and co-evaporated with toluene (3×50 ml).

The resulting product was chromatographed on silica gel in a gradient of 0–8% methanol in DCM containing 1% triethylamine to give 4.6 mmol (3.48 g, 46%) triethylammonium salt of the title compound.

Example 26

Synthesis of 4-O-4,4'-Dimethoxytrityl-N-($N^2$-isobutyrylguanin-9-ylacetyl)-L-hydroxyproline [monomer (I)]

4-O-4,4'-Dimethoxytrityl-N-($N^2$-isobutyrylguanin-9-ylacetyl)-L-hydroxyproline was made by dissolving 4-hydroxyproline methyl ester hydrochloride (1.82 g, 10 mmol) in 40 ml of a 1:1 mixture of pyridine-acetonitrile containing 1.4 ml (10 mmol) of triethylamine. $N^2$-Isobutyrylguanin-9-ylacetic acid (3.62 g, 13 mmol) and DCC (2.88 g, 14 mmol) were added. The reaction was terminated after 3 hours stirring by the addition of 2 ml water and incubated overnight at room temperature.

The mixture was then filtered to remove precipitated dicyclohexyl urea. The filtrate was dried by evaporation and coevaporated with pyridine (2×30 ml) and then dissolved in pyridine (40 ml). 4,4'-Dimethoxytrityl chloride (DMTrCl) (4.41 g, 13 mmol) was added and the mixture was incubated at 50° C. for 30 min., cooled to room temperature followed by addition 5% $NaHCO_3$ (60 ml). The product was extracted with methylene chloride (DCM) (2×80 ml), organic layers were dried over $Na_2SO_4$ then solvent was removed by evaporation. The residue was dissolved in pyridine (50 ml) and LiI (30 mmol, 4.05 g) was added and the solution was heated at 90° C. for 6 hrs. The reaction mixture was evaporated 70 ml of 1M TEAB solution was added and the product was extracted with DCM (3×80 ml). The combined organic phase was washed once with 0.5M TEAB (100 ml), dried over $Na_2SO_4$, and then solvent was removed by evaporation and co-evaporated with toluene (3×50 ml).

The resulting product was chromatographed on silica gel in a gradient of 0–10% methanol in DCM containing 1% triethylamine to give 4.1 mmol (3.26 g, 41%) triethylammonium salt of the title compound.

Example 27

Mismatch Discrimination of Oligonucleotides and Oligonucleotide Analogues in Moderate Salt Conditions A HypNA-pPNA 16-mer was synthesized using HypNA-pPNA dimer synthons and phosphotriester synthesis as in Example 13. The sequence of the HypNA-pPNA oligomer was: $T_h$-$G_p$-$G_h$-$T_p$-$C_h$-$T_p$-$C_h$-$A_p$-$A_h$-$G_p$-$T_h$-$C_p$-$A_h$-$G_p$-$T_h$-$G_p$-dT, where the subscript h denotes a "HypNA" monomeric unit and the subscript p denotes a "pPNA" monomeric unit.

DNA oligomers were synthesized using standard methods having sequences complementary to the HypNA-pPNA sequence, either totally complementary, or having one or two mismatches with respect to the HypNA-pPNA sequence (see Table 5). For performing DNA-DNA control hybridizations, a DNA oligomer with a sequence identical to that of the HypNA-pPNA oligomer, 5'-TGGTCTCACGTCAGTG-3' (SEQ ID NO: 19) was also synthesized.

To perform the melting curve analysis, the DNA oligomers and HypNA-pPNA oligomers were mixed at a 1:1 in a volume of 400 microliters. For nucleic acid hybridization controls, DNA oligomers and complementary (or partially complementary) DNA oligomers, were mixed at a 1:1 ratio in a volume of 400 microliters. The hybridization solutions contained 20 millimolar Tris-HCl, pH 7.5, 150 millimolar NaCl, and 10 millimolar $MgCl_2$.

The mixtures of DNA oligomers or DNA oligomers with HypNA-pPNA oligomers were then incubated at 90 degrees C. for 3 minutes and allowed to cool gradually to room temperature overnight. The samples were then heated at a rate of 1 degree C. per minute from 20 degrees C. to 100 degrees C. using a thermal control unit linked to a spectrophotometer. Changes in the absorbance at 260 nanometers were recorded, and a Tm was calculated for each combination of oligomers.

In some cases, there was no discernible Tm, which we interpret to be the result of the inability of particular oligomer pairs to form stable complexes.

TABLE 5

Mismatch Discrimination of HypNA-pPNA Oligonucleotide Analogues and DNA Oligomers Hybridized to DNA

| Tm, ° C. DNA/DNA (ΔTm) | Tm, ° C. PNA/DNA (ΔTm) | Probe Sequence |
|---|---|---|
| 61.6 | 58.2 | No mismatches: 5'-CAC TGA CTT GAG ACC A -3' (SEQ ID NO: 20) |
| 61.7 | 57.9 | No mismatches |
| 51.7 (9.9) | 45.1 (13.1) | Mismatch A: 5'-CAC TGA G̲TT GAG ACC A -3' (SEQ ID NO: 21) |
| 51.8 (9.9) | 45.4 (12.5) | Mismatch A |
| 42.6 (19) | No Tm | Mismatch B: 5'-CAC TGA G̲TG̲ GAG ACC A -3' (SEQ ID NO: 22) |
| 42.6 (18.9) | 50.7* | Mismatch B |
|  | 60.4* | Mismatch B |
| 51.6 (10) | 48.3 (9.9) | Mismatch C: 5'-CAC TGA CTT GAG T̲CC A -3' (SEQ ID NO: 23) |
| 53.8 (7.9) | 49.2 (8.7) | Mismatch C |
| 52.7 (8.9) | No Tm | Mismatch E: 5'-CG̲G̲ TGA CTT GAG ACC A -3' (SEQ ID NO: 25) |
| 55.1 (6.6) | 53.8* | Mismatch E |
|  | 48.4* | Mismatch E |
|  | 47.4* | Mismatch E |
| 52.6 (9) | 43.7 (14.5) | Mismatch F: 5'-CAC TGA CG̲T GAG ACC A -3' (SEQ ID NO: 26) |

TABLE 5-continued

Mismatch Discrimination of HypNA-pPNA Oligonucleotide Analogues and DNA Oligomers Hybridized to DNA

| Tm, °C. DNA/DNA (ΔTm) | Tm, °C. PNA/DNA (ΔTm) | Probe Sequence |
|---|---|---|
| 55.6 (6.1) | 43.7 (14.2) | Mismatch F: |
| 52.2 (9.4) | 47.3 (10.9) | Mismatch G: 5'-CAC TGA CT<u>G</u> GAG ACC A -3' (SEQ ID NO: 27) |
| 52.6 (9.1) | 53.4 (4.5) | Mismatch G |
| 50.0 (11.6) | 52.7 (5.5) | Mismatch H: 5'-CAC TGA C<u>A</u>T GAG ACC A -3' (SEQ ID NO: 28) |
| 53.4 (8.3) | 51.8 (6.1) | Mismatch H |
| 33.3 (28.3) | No Tm | Mismatch K: 5'-CAC TGA <u>G</u>TT <u>C</u>AG ACC A -3' (SEQ ID NO: 29) |
| 36.2 (25.5) | 50.9 (7)* | Mismatch K |
| 52.3 (9.3) | 43.1 (15.1) | Mismatch J: 5'-CAC TGA <u>A</u>TT GAG ACC A -3' (SEQ ID NO: 30) |
| 52.5 (9.2) | 48.5 (9.4) | Mismatch J |
| 47.4 (14.2) | No Tm | Mismatch L: 5'-CAC TGA <u>G</u>TT <u>G</u>GG ACC A -3' (SEQ ID NO: 31) |
| 50.0 (11.7) | 33.6 (24.3)* | Mismatch L |
| 50.2 (11.5) | No Tm | Mismatch M: 5'-CAC <u>GG</u>A <u>G</u>TT GAG ACC A -3' (SEQ ID NO: 32) |
| 45.2 (16.4) | 60.5* | Mismatch M |

*Tms not reliable, complex probably unstable.

Example 28

Mismatch Discrimination of Oligonucleotides and Oligonucleotide Analogues in High Salt Conditions A HypNA-pPNA 16-mer was synthesized using HypNA-pPNA dimer synthons and phosphotriester synthesis as in Example 13. The sequence of the HypNA-pPNA oligomer was: $T_h$-$G_p$-$G_h$-$T_p$-$C_h$-$T_p$-$C_h$-$A_p$-$A_h$-$G_p$-$T_h$-$C_p$-$A_h$-$G_p$-$T_h$-$G_p$-.

DNA oligomers were synthesized using standard methods having sequences complementary to the HypNA-pPNA sequence, either completely complementary, or having one or two mismatches with respect to the HypNA-pPNA sequence (see Table 5). For performing DNA-DNA control hybridizations, a DNA oligomer with a sequence identical to that of the HypNA-pPNA oligomer was also synthesized.

To perform the melting curve analysis, the DNA oligomers and HypNA-pPNA oligomers were mixed at a 1:1 ratio in a volume of 400 microliters. For nucleic acid hybridization controls, DNA oligomers and complementary (or nearly complementary) DNA oligomers, were mixed at a 1:1 ratio in a volume of 400 microliters. The hybridization solutions contained 20 millimolar Tris-HCl, pH 7.5, 500 millimolar NaCl, and 10 millimolar $MgCl_2$.

The mixtures of DNA oligomers or DNA oligomers with HypNA-pPNA oligomers were then incubated at 90 degrees C. for 3 minutes and allowed to cool gradually to room temperature overnight. The samples were then heated at a rate of 1 degree C. per minute from 20 degrees C. to 100 degrees C. using a thermal control unit linked to a spectrophotometer. Changes in the absorbance at 260 nanometers were recorded, and a Tm was calculated for each combination of oligomers.

In some cases, there was no discernible Tm, which we interpret to be the result of the inability of particular oligomer pairs to form stable complexes.

TABLE 6

Thermal Stability of Duplexes Comprising DNA and HypNA-pPNA Oligomers

| Tm, °C. DNA/DNA (ΔTm) | Tm, °C. PNA/DNA (ΔTm) | Probe Sequence |
|---|---|---|
| 64.0 | 58.0 | No mismatches: 5'-CAC TGA CTT GAG ACC A-3' (SEQ ID NO: 20) |
| 63.8 | 59.1 | No mismatches |
| 64.5 | | No mismatches |
| 51.7 (7) | 41.4 (17) | Mismatch A: 5'-CAC TGA <u>G</u>TT GAG ACC A -3' (SEQ ID NO: 21) |
| 56.8 (7) | 41.1 (17) | Mismatch A |
| 52.6 (11) | No Tm | Mismatch B: 5'-CAC TGA <u>G</u>T<u>G</u> GAG ACC A -3' (SEQ ID NO: 22) |
| 46.8 (17) | No Tm | Mismatch B |
| 47.2 (17) | | |
| 46.1 (18) | | |
| 60.8 (3) | 54.3 (4) | Mismatch D 5'-CAC TGA CTT GAG AC<u>G</u> A -3' (SEQ ID NO: 24) |
| 62.7 (1) | 54.9 (3) | Mismatch D |
| 56.5 (7) | No Tm | Mismatch E 5'-<u>CGG</u> TGA CTT GAG ACC A -3' (SEQ ID NO: 25) |
| 56.8 (7) | No Tm | Mismatch E |
| 53.9 (10) | No Tm | Mismatch F 5'-CAC TGA C<u>GT</u> GAG ACC A -3' (SEQ ID NO: 26) |
| 55.3 (9) | No Tm | Mismatch F |
| 56.2 (8) | No Tm | Mismatch G 5'-CAC TGA CT<u>G</u> GAG ACC A -3' (SEQ ID NO: 27) |
| 56.1 (8) | No Tm | Mismatch G |
| 55.1 (9) | 41.3 (17) | Mismatch H 5'-CAC TGA C<u>A</u>T GAG ACC A -3' (SEQ ID NO: 28) |
| 53.3 (11) | 43.5 (15) | Mismatch H |

Example 29

Melting Curve Analysis of Poly T DNA and Poly T PNA Analogues Hybridized to Poly A DNA and Poly A RNA In this experiment we compared hybridized complexes of DNA/DNA, DNA/PNAs, RNA/DNA and PNA/PNAs, for the stability of the complex formed. Poly A DNA oligomers, poly T DNA oligomers, poly A RNA oligomers, and poly T RNA oligomers were synthesized by solid phase synthesis. PNA oligonucleotide analogues were synthesized by solid phase synthesis using methods disclosed herein. The classical PNA Poly T oligomer consisted of a PNA having a N-(2-aminoethyl)glycine backbone. The 1:1 Poly T PNA consisted of: biotin-linker-(HypNA-pPNA)$_7$-dT. The 1:2 Poly T PNA consisted of: biotin-linker-(HypNA-pPNA-pPNA)$_5$-dT. The 1:3 Poly T PNA consisted of: biotin-linker-[(HypNA-pPNA)-(pPNA-pPNA)]$_4$-dT.

To hybridize DNA/DNA and DNA/RNA oligomers, equal amounts of oligonucleotide were mixed in 20 mM Tris, pH 7.5, 100 mM NaCl, 10 mM $MgCl_2$, incubated at 90° C. for 3 minutes and left to cool gradually to room temperature overnight. Samples were then heated at a rate of 1° C. per minute from 20° C. to 100° C., using a spectrophotometer linked to a thermal control unit. Changes in $A_{260}$ were recorded and a Tm value was calculated for each complex.

To hybridize PNA oligonucleotide analogues to DNA and RNA oligomers, the ratio of DNA (or RNA) oligomer to PNA oligomer was 1:2. This 1:2 ratio was used to promote the formation of a triplex structure, with 2 PNA oligomers binding to each DNA oligomer.

These samples were hybridized and treated in a identical manner to the DNA/DNA and DNA/RNA complexes to obtain Tm values.

The results (Table 7) show that, unlike oligomers comprised of DNA, RNA, or classical PNAs, PNA analogues that comprise HypNA and pPNA residues differ significantly in the stability of the complexes they form with DNA and with RNA. HypNA-pPNA oligomers form more stable complexes with RNA than they form with DNA, and the difference in the stability of the HypNA-pPNA/DNA and HypNA-pPNA/RNA complexes increases with increasing proportions of pPNA residues in the HypNA-pPNA oligomer.

TABLE 7

Thermal Stability of Poly T Nucleotide and Oligonucleotide Analogue Probes Hybridized with Poly A DNA and Poly A

| Probe | Target: 16 mer poly A DNA Tm, °C. | Target: 16 mer poly A RNA Tm, °C. |
|---|---|---|
| Poly T DNA | 46.3 | 45.5 |
| Poly T DNA | 46.6 | 49.2 |
| Classical Poly T PNA | 85.0 | 82.0 |
| 1:1 Poly T PNA-analog | 81.1 | 73.0 |
| 1:1 Poly T PNA-analog | 81.9 | 72.7 |
| 1:2 Poly T PNA-analog | 74.4 | 66.1 |
| 1:2 Poly T PNA-analog | 74.0 | 66.0 |
| 1:3 Poly T PNA-analog | 60.9 | 48.9 |
| 1:3 Poly T PNA-analog | 60.8 | 47.2 |

Example 30

Detection of Complementary Target DNA and RNA Samples by Affinity PAGE and Detection with Intercalating Dyes A HypNA-pPNA capture probe with the sequence: (Ch-Tp-Gh-Cp-Ah-Ap-Ah-Gp-Gh-Ap-Ch-Ap-Ch-Cp-Ah-Tp)-dG was synthesized coupled to a 5' acrylamide residue as described in Example 19. The capture probe was co-polymerized with acrylamide as described in Example 18 in slots of an acrylamide gel as described in Rehman et al. (Nucleic Acids Research 27: 649–655 (1999)). Target oligonucleotides having the sequence:
d(TCATGGTGTCCTTTGCAGTTTTTTTGTGAGTGT-TGAG) (SEQ ID NO:33)—complementary
d(TCATGGT CTCCTTTGCAGTTTTTTTGTGAGTGTTGAG) (SEQ ID NO:34)—mismatched
r(UCAUGGUGUCCUUUGCAGUUUUUUUGUGAG-UGUUGAGUGA) (SEQ ID NO:35)—complementary
r(UCAUGGU CACCUUUGCAGUUUUUUUGUGAGUGUUGAG-UGA) (SEQ ID NO:36)—mismatched
were electrophoresed through lanes of the gel at 40° C.

Following electrophoresis, the gel was stained with ethidium bromide and photographed under UV illumination. Visual inspection of the stained gel (FIG. 8) revealed that single nucleobase mismatches did not result in the capture of a target by the capture HypNA-pPNA probe co-polymerized into the polyacrylamide gel and in fluorescence of the hybridization products (lanes 2, 4, and 6), while complementary oligonucleotide/HypNA-pPNA complexes resulted in ethidium-stained fluorescent hybrids captured by the gel layer containing the specific HypNA-pPNA probe (lanes 1, 3, and 5).

Example 31

Protocol for Large-scale (Maxi) mRNA Isolation Using Linear HypNA-pPNA Oligomers 1. Begin isolation with $1-2 \times 10^8$ cells or 0.4–1 g tissue. Tissue will need to be homogenized in 15 ml complete lysis buffer until the solution is uniformly suspended. Resuspend cell pellets in 15 ml complete lysis buffer. It may be necessary to heat the cell pellet at 42–45° C. for 2 minutes and/or vortex the cell pellet for complete resuspension.

| Lysis Buffer: | Complete Lysis Buffer: |
|---|---|
| 200 mM Tris-HCl, pH 7.5 | 150 microliters Proteinase/15 ml Lysis Buffer |
| 200 mM NaCl | Proteinase = 20 mg/ml Proteinase K |
| 500 mM GTC | |
| 25 mM $MgCl_2$ | |
| 1% Pete Jones Detergent | |

(Pete Jones Detergent is a 1:10 dilution of Bold laundry detergent (Procter and Gamble, available in the United Kingdom) that is allowed to sit at room temperature for 48 hours and then filtered.)

2. Incubate the cell lysate at 42–45° C. for 15–60 minutes. Incubation is important for complete digestion of ribonucleases and proteins. A 60 minute incubation is recommended for tissue samples, while cell material is effectively digested in 15–20 minutes. The time of incubation can be optimized for a particular sample type.
3. If insoluble material persists, particularly in the case of tissue preparations, centrifuge at 12,000× g (10,000 rpm for Sorval SS-34 rotors) for 10 minutes at room temperature and transfer the supernatant to a new tube.
4. Shear any remaining DNA by passing the lysate through a sterile plastic syringe attached to an 18–21 gauge needle 4–5 times. This will yield a cleaner mRNA preparation.
5. Add 75 microliters 1 (4.5 nanomoles) poly T 'PNA probe' (1:1 HypNA-pPNA 14-mer linear probe having the sequence: biotin-(HypNA-pPNA)$_7$-dT) to the cell lysate.
   1:1 HypNA-pPNA probe is supplied lyophilized and resuspended in ultra pure HPLC grade water to make a 60 pmol/microliter working stock.
6. Incubate the lysate containing the probe at 70° C. for 10 minutes. Centrifuge the samples at 14,000 rpm for 5 seconds. (This incubation step can open up any secondary structure on the RNA and allow the 1:1 HypNA-pPNA probe to bind more efficiently.)
7. Incubate the cell lysate/probe mixture at room temperature for 15 minutes with gentle shaking.
8. Add 470 microliters Streptavidin beads to the cell lysate/probe mixture. Incubate at room temperature for 45 minutes with gentle shaking.
   The streptavidin beads used in the kit are also magnetic. Magnetic capture can be used as an alternative method to centrifugation (steps 8, 10, and 11, below). The beads have a 9 pmol/microliter biotin binding capacity. Therefore 470 microliter streptavidin beads can capture up to 4230 pmol biotinylated probe. 4500 pmol of 1:1 HypNA-pPNA probe are added to the reaction, but only 80% of the probe (3600 pmol) is biotinylated. So our sample should contain an excess of the streptavidin beads. We found no significant differences in yield for bead incubation times ranging from 30 minutes to 1 hour.

9. Centrifuge the samples at 2,500× g (3,500 rpm for JS-4.2 and JS-3.0 rotors) for 10–15 minutes at room temperature in a table-top or similar centrifuge. Carefully remove the lysate supernatant and discard.

10. Add 10 ml Wash Buffer. Resuspend the streptavidin beads by pipetting up and down with a pipet tip. If the beads are difficult to resuspend vortex at low speeds.

Wash Buffer:
20 mM Tris-HCl, pH 7.5
250 mM NaCl
(DEPC treated)

11. Spin the samples at 2,500× g for 5 minutes at room temperature. Carefully remove and discard the Wash Buffer.

12. Repeat steps 9 and 10 one to two more times. Increasing the number of washes will reduce the amount of ribosomal RNA in the final mRNA preparation.

13. Add 500 microliters Wash Buffer. Resuspend the streptavidin beads by pipetting up and down with a pipet tip. Transfer the resuspended beads to a microcentrifuge tube.

14. Centrifuge at 14,000× g (full speed in a microcentrifuge) for 3 minutes. Carefully remove the Wash Buffer with a pipet tip.

15. Resuspend the streptavidin beads in 150 microliter DEPC-treated water. Use a sterile pipet tip to ensure the beads are evenly resuspended. Make sure to resuspend any beads that may have collected along the wall of the microcentrifuge tube.

16. Incubate the beads resuspended in DEPC-treated water for 5 minutes at 75° C. to allow the mRNA to fall off the HypNA-pPNA probe.

17. Spin at 14,000× g for 3 minutes. The mRNA is now in the eluate. DO NOT DISCARD. Transfer the eluate to a sterile microcentrifuge tube.

18. Most of the mRNA comes off in the first elution, but for individuals wanting to obtain an additional 10% mRNA a second elution can be performed by repeating steps 14–16. The two eluates can be combined into the same microcentrifuge tube.

19. The mRNA can be used directly or precipitated. We recommend precipitation of the samples.

Using the above protocol, 230 micrograms of poly A RNA were isolated from 1×108 Hela cells. The RNA had an A260/280 of 2.02.

Example 32

Protocol for Mid-Scale (Midi) mRNA Isolation Using Linear HypNA-pPNA Oligomers

1. Begin isolation with 1×10$^7$ cells or 50–200 mg tissue. Tissue will need to be homogenized in 1.5 ml complete lysis buffer until the solution is uniformly suspended. Resuspend cell pellets in 1.5 ml complete lysis buffer. It may be necessary to heat the cell pellet at 42–45° C. for 2 minutes and/or vortex the cell pellet for complete resuspension.

| Lysis Buffer: | Complete Lysis Buffer: |
|---|---|
| 200 mM Tris-HCl, pH 7.5 | 15 microliters Proteinase/1.5 ml Lysis Buffer |
| 200 mM NaCl | Proteinase = 20 mg/ml Proteinase K |
| 500 mM GTC | |
| 25 mM MgCl$_2$ | |
| 1% Pete Jones Detergent | |

(Pete Jones Detergent is a 1:10 dilution of Bold laundry detergent (Procter and Gamble, available in the United Kingdom) that is allowed to sit at room temperature for 48 hours and then filtered.)

2. Incubate the cell lysate at 42–45° C. for 15–60 minutes. Incubation is important for complete digestion of ribonucleases and proteins. A 60 minute incubation is recommended for tissue samples, while cell material is effectively digested in 15–20 minutes. The time of incubation can be optimized for a particular sample type.

3. If insoluble material persists, particularly in the case of tissue preparations, centrifuge at 14,000× g (full speed in a microcentrifuge) for 10 minutes at room temperature and transfer the supernatant to a new tube.

4. Shear any remaining DNA by passing the lysate through a sterile plastic syringe attached to an 18–21 gauge needle 4–5 times. This will yield a cleaner mRNA preparation.

5. Add 15 microliters (600 pmoles) poly T 'PNA probe' (1:1 HypNA-pPNA 14-mer linear probe having the sequence: biotin-(HypNA-pPNA)$_7$-dT) to the cell lysate.
   1:1 HypNA-pPNA probe is supplied lyophilized and resuspended in ultra pure HPLC grade water to make a 40 pmol/microliter working stock.

6. Incubate at 70° C. for 10 minutes. Centrifuge the samples at 14,000 rpm for 5 seconds. (This incubation step can open up any secondary structure on the RNA and allow the 1:1 HypNA-pPNA probe to bind more efficiently.)

7. Incubate the cell lysate/probe mixture at room temperature for 15 minutes with gentle shaking.

8. Add 60 microliters streptavidin beads to the cell lysate/probe mixture. Incubate at room temperature for 45 minutes with gentle shaking.
   The streptavidin beads used in the kit are also magnetic. Magnetic capture can be used as an alternative centrifugation centrifugation (steps 8, 10, and 11, below). The beads have 9 pmol/microliter biotin binding capacity. Therefore 60 microliter streptavidin beads can capture up to 540 pmol biotinylated probe. We added 600 pmol 1:1 HypNA-pPNA probe to our reaction, but only 80% of the probe (480 pmol) is biotinylated. So our sample should contain an excess of streptavidin beads. We found no significant differences in yield for bead incubation times ranging from 30 minutes to 1 hour.

9. Centrifuge the samples at 14,000× g for 5 minutes at room temperature. Carefully remove and discard the supernatant.

10. Add 750 microliters Wash Buffer. Resuspend the streptavidin beads by pipetting up and down. If the beads are difficult to resuspend vortex at low speeds.
    Wash Buffer:
    20 mM Tris-HCl, pH 7.5
    250 mM NaCl
    (DEPC treated)

11. Spin at 14,000× g for 3 minutes at room temperature. Carefully remove and discard the Wash Buffer.

12. Repeat steps 9 and 10 one to two more times. Increasing the number of washes will reduce the amount of ribosomal RNA in the final mRNA preparation.

13. Resuspend the streptavidin beads in 75 microliters DEPC water. Use a sterile pipet tip to ensure the beads are completely resuspended. Make sure to resuspend any beads that may have collected along the wall of the microcentrifuge tube.
14. Incubate the beads resuspended in DEPC water for 5 minutes at 75° C. to allow the mRNA to fall off the HypNA-pPNA probe.
15. Spin at 14,000× g for 3 minutes. The mRNA is now in the eluate. DO NOT DISCARD. Transfer the eluate to a sterile microcentrifuge tube.
16. Most of the mRNA comes off in the first elution, but for individuals wanting to obtain an additional 10% mRNA a second elution can be performed repeating steps 12–14. The two eluates can be combined into the same microcentrifuge tube.
17. The mRNA can be used directly or precipitated. We recommend precipitation of the samples.

Using the above protocol to isolated poly A RNA from 1×10$^7$ Hela cells, we have obtained yields of 12, 14, and 17 micrograms of poly A RNA, having A260/280 of 1.98, 1.93, and 1.95 respectively.

Example 33

Protocol for mRNA Isolation from Total RNA Using Linear HypNA-pPNA Oligomers

1. Begin isolation with up to 500 micrograms total RNA in RNase-free water. Add the total RNA to the RNase-free 2 ml microcentrifuge tube provided and mix with an equal volume of 2× Binding Buffer. The final volume of the hybridization reaction should not exceed 1.5 ml.
   2× Binding Buffer
   20 mM Tris, pH 7.5
   600 mM NaCl
   20 mM MgCl2
2. Add 15 microliters poly T 'PNA probe' (1:1 HypNA-pPNA 14-mer linear probe having the sequence: biotin-(HypNA-pPNA)$_7$-dT) to the total RNA mixture.
   1:1 HypNApPNA probe is supplied lyophilized and resuspended in ultra pure HPLC grade water to make a 40 pmol/microliter working stock. Therefore each reaction receives 600 pmol of the probe.
3. Incubate at 70° C. for 10 minutes. Centrifuge the samples at 14,000× g for 5 seconds.
4. Incubate the hybridization reaction at room temperature for 15 minutes with gentle shaking.
5. Add 60 microliters streptavidin beads to the hybridization reaction. Incubate at room temperature for 45 minutes with gentle shaking.
6. Centrifuge the samples at 14,000× g (full speed in a microcentrifuge) for 5 minutes at room temperature. Carefully remove and discard the supernatant.
7. Add 750 microliters Wash Buffer. Resuspend the streptavidin beads by pipetting up and down. If the beads are difficult to resuspend vortex at low speeds.
   Wash Buffer:
   20 mM Tris-HCl, pH 7.5
   250 mM NaCl
      (DEPC treated)
8. Spin at 14,000× g for 3 minutes at room temperature. Carefully remove and discard the Wash Buffer.
9. Repeat steps 7 and 8 one to two more times. Increasing the number of washes will reduce the amount of ribosomal RNA in the final mRNA preparation.
10. Resuspend the streptavidin beads in 75 microliters DEPC water. Use a sterile pipet tip to ensure the beads are completely resuspended. Make sure to resuspend any beads that may have collected along the wall of the microcentrifuge tube.
11. Incubate the beads resuspended in DEPC water for 5 minutes at 75° C.
12. Spin at 14,000× g for 3 minutes. The mRNA is now in the eluate. DO NOT DISCARD. Transfer the eluate to a sterile microcentrifuge tube.
13. Most of the mRNA comes off in the first elution, but for individuals wanting to obtain an additional 10% mRNA a second elution can be performed repeating steps 10–12. The two eluates can be combined into the same microcentrifuge tube.
14. The mRNA can be used directly or precipitated. We recommend precipitation of the samples.

Using the above protocol, we have isolated 8 micrograms of poly A RNA from 500 micrograms of total RNA. The final product had an A260/280 of 2.01.

Example 34

Protocol for mRNA Isolation in 96-Well Plates Using Linear HypNA-pPNA Oligomers

1. Begin isolation with 5×10$^5$ cells or 10 mg tissue. Tissue will need to be ground in a mortar and pestle under liquid nitrogen or homogenized prior to use. Cells will need to be washed with PBS prior to use.
2. Add 100 microliters lysis buffer to the cells or tissue. Incubate at 37° C. for 30 minutes.
3. Transfer the cells (contained in 100 microliters lysis buffer) from the culture plate to the 96-well Filter plate.
4. Assemble the Filter Plate on top of the Hybridization plate with the Alignment Frame holding the two together.
5. Centrifuge at 1000× g (2,200 rpm in JS-4.2 and JS-3.0 rotors) for 10 minutes at room temperature. The clarified lysate is now in the Hybridization plate. If all the wells of the Filter Plate were not used it may be placed back in the zip-lock for further use. Mark the used Filter plate wells to prevent their re-use.
6. Add 10 microliters poly T 'PNA probe' (1:1 HypNA-pPNA 14-mer linear probe having the sequence: biotin-(HypNA-pPNA)$_7$-dT) to each well being used.
   1:1 HypNA-pPNA is at 1.5 pmol/microliter working concentration.
7. Incubate for 1 hour at room temperature with gentle shaking.
8. Add 10 microliters streptavidin beads to each well being used.
   Streptavidin beads are diluted in 20% sodium azide to make a 1.5 pmol/µl working concentration.
9. Incubate for 1 hour at room temperature with gentle shaking.
10. Place the Hybridization Plate on the 96-well magnet. Let sit 5 minutes for the magnetic beads to be completely pulled back. Carefully remove and discard the supernatant.
11. Remove the Hybridization Plate from the 96-well magnet. Add 100 ill Wash Buffer. Resuspend the beads completely by pipetting up and down.
12. Place the Hybridization Plate on the 96-well magnet. Let sit 5 minutes for the magnetic beads to be completely pulled back. Carefully remove and discard the Wash buffer.
13. Repeat steps 11 and 12 one to two more times. Make sure all of the Wash Buffer has been removed from each well after the final wash.

14. Remove the Hybridization Plate from the 96-well magnet. Add 100 microliters DEPC water to each well. Resuspend the streptavidin beads by pipetting up and down.
15. Cover Hybridization plate with acetate sheet. Incubate the Hybridization plate at 75° C. for 5 minutes.
16. Centrifuge the plate at 1000× g for 2 minutes to collect all the liquid.
17. Place the Hybridization Plate on the 96-well magnet. Let sit 5 minutes for the magnetic beads to be completely pulled back. Carefully transfer the 100 microliters eluate to the UV Elution plate.
18. The eluted mRNA is now ready to be quantified in a UV plate reader.

Using the above protocol to isolate poly A RNA from samples of 0.5×10$^6$ cells, we obtained 172 nanograms and 252 nanograms of poly A RNA having A260/280's of 1.4 and 1.7, respectively.

All publications, including patent documents and scientific articles, referred to in this application, including any bibliography, are incorporated by reference in their entirety for all purposes to the same extent as if each individual publication were individually incorporated by reference.

All headings are for the convenience of the reader and should not be used to limit the meaning of the text that follows the heading, unless so specified.

BIBLIOGRAPHY

U.S. Pat. No. 5,432,272
U.S. Pat. No. 5,508,178 issued Apr. 16, 2996 to Rose et al.
U.S. Pat. No. 5,539,082 issued Jul. 23, 1996 to Nielsen et al.
U.S. Pat. No. 5,641,625 issued Jun. 24, 1997 to Ecker et al.
U.S. Pat. No. 5,656,461 issued Aug. 12, 1997 to Demers
U.S. Pat. No. 5,714,331 issued Feb. 3, 1998 to Buchardt et al.
U.S. Pat. No. 5,719,262 issued Feb. 17, 1998 to Buchardt et al.
U.S. Pat. No. 5,736,336 issued Apr. 7, 1998 to Buchardt et al.
U.S. Pat. No. 5,766,855 issued Jun. 16, 1998 to Burchardt et al.
U.S. Pat. No. 5,773,571 issued Jun. 30, 1998 to Nielsen et al.
U.S. Pat. No. 5,786,461 issued Jul. 28, 1998 to Buchardt et al.
U.S. Pat. No. 5,837,459 issued Nov. 17, 1998 to Berg et al.
U.S. Pat. No. 5,861,250 issued Jan. 19, 1999 to Stanley et al.
U.S. Pat. No. 5,864,010 issued Jan. 26, 1999 to Cook et al.
U.S. Pat. No. 5,874,553 issued Feb. 23, 1999 to Peyman et al.
U.S. Pat. No. 5,888,733 issued Mar. 30, 1999 to Hyldig-Nielsen et al.
U.S. Pat. No. 5,972,610 issued Oct. 26, 1999 to Buchardt et al.
U.S. Pat. No. 5,977,296 issued Nov. 2, 1999 to Nielsen et al.
U.S. Pat. No. 6,004,750 issued Dec. 21, 1999 to Frank-Kamenetskii et al.
U.S. Pat. No. 6,015,887 issued Jan. 18, 2000 to Teng
U.S. Pat. No. 6,020,124 issued Feb. 1, 2000 to Sorenson
U.S. Pat. No. 6,020,126 issued Feb. 1, 2000 to Carlsson et al.
U.S. Pat. No. 6,025,140 issued Feb. 15, 2000 to Langel et al.
U.S. Pat. No. 6,025,482 issued Feb. 15, 2000 to Cook et al.
U.S. Pat. No. 6,045,995 issued Apr. 9, 2000 to Cummins et al.
U.S. Pat. No. 6,060,242 issued May 9, 2000 to Nie et al.
U.S. Pat. No. 6,063,571 issued May 16, 2000 to Uhlmann et al.
U.S. Pat. No. 6,107,470 issued Aug. 22, 2000 to Nielsen et al.
U.S. Pat. No. 6,110,676 issued Aug. 29, 2000 to Coull et al.
U.S. Pat. No. 6,110,678 issued Aug. 29, 2000 to Weisburg et al.
U.S. Pat. No. 6,150,510
U.S. Pat. No. 6,165,720 issued Dec. 26, 2000 to Feigner et al.
WO 92/002258
WO 92/20702
WO 93/10820
WO 94/22892
WO 94/24144
Adams et al. *J. Am. Chem. Soc.* 105: 661–663 (1983).
Ausubel et al., *Current Protocols in Molecular Biology,* John Wiley and Sons (1998).
Beaucage and Caruthers, *Tetrahedron Lett.* 22:1859–1862 (1981).
Briepohl et al., *Bioorg. & Med. Chem. Lett.* 6: 665 (1996).
Chow et al., *Nucl. Acids Res.* 9: 2807–2817 (1981).
Coste et al., *Tetrahedron Lett.* 31: 669–672 (1990).
Crea and Horn, *Nucl. Acids Res.* 8: 2331–2348 (1980).
Efimov et al., *Nucleic Acids Res.* 11: 8369–8387 (1983).
Efimov et al., *Nucleic Acids Res.* 13: 3651–3666 (1985).
Efimov et al., *Nucleic Acids Res.* 14: 6525–6540 (1986).
Efimov et al., in Abstracts of Protein Engineering Symposium, Groningen, May 4–7, 1986, Groningen, The Netherlands, Drenth, ed. p. 9 (1986).
Efimov, et al. (1996) *Collect. Czech. Chem. Commun.* 61: S262–S264.
Efimov et al., *Bioorg. Khim.* 24: 696–709 (1998).
Efimov et al., *Nucleic Acids Res.* 26: 566–575 (1998).
Efimov et al., *Nucleic Acids Res.* 27: 4416–4426 (1999).
Efimov, et al. *Russian Journal of Bioorganic Chemistry* 25: 545–555 (1999).
Finn et al., *Nucleic Acids Res.* 24: 3357–3364 (1996).
Froehler et al. *J. Am. Chem. Soc.* 107:278–279 (1985).
Gait et al., *Nucl. Acids Res.* 8: 1081–1096 (1980).
Gait et al. *Nucl. Acids Res.* 10: 6243–6254 (1982).
Gao et al. *Tetrahedron Lett.* 32: 5477–5480 (1991).
Goodchild, J. *Bioconjugate Chemistry* 1: 165 (1990).
Harlowe and Lane, *Antibodies a Laboratory Manual,* Cold Spring Harbor Press (1988)).
Heinklein et al. in Girault and Andreu (eds.) The Peptides, 21$^{st}$ European Peptide Symposium, ESCOM, Leiden, pp. 67–77 (1990).
Koster, et al. *Tetrahedron Lett.* 24: 747–750 (1983).
Koysynkina et al. (1994) *Tetrahedron Lett.* 35: 5173–5176.
McCollum and Andrus, *Tetrahedron Lett.* 32: 4069–4072 (1991).
Orum et al. *Nucl Acids Res.* 21: 5332–5336 (1993).
Pain et al. *Cells Tissues Organs* 165: 212–219 (1999)
Sambrook et al., *Molecular Cloning: A Laboratory Manual,* 2nd edition, Cold Spring Harbor Press, Cold Spring Harbor, N.Y. (1989).
Sandler and Karo, Polymer Synthesis Vol. 1, Academic Press (1992).
Sandler and Karo, Polymer Synthesis Vol. 2, Academic Press (1994).
Sproat et al. *Nucleic Acids Res.* 14: 1811–1824 (1986).
Takeuchi et al., *Chem. Pharm. Bull.* 22: 832–840 (1974).
van der Laan et al., *Tetrahedron Lett.* 37: 7857–7860 (1996).
Will et al. (1995) *Tetrahedron* 51: 12069–12082.

What is claimed is:

1. A method for inhibiting gene expression, comprising administering an oligonucleotide analogue to at least one cell or at least one organism to inhibit expression of at least one gene that comprises a nucleotide sequence that is at least partially complementary to the oligonucleotide analogue, wherein the oligonucleotide analogue comprises the structure:

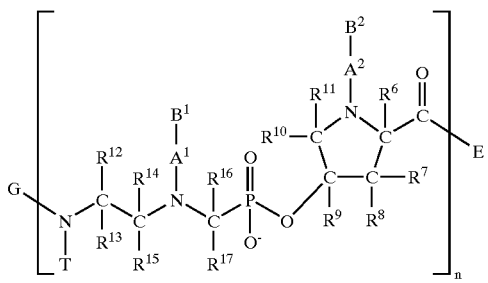

wherein G is selected from a group consisting of H and a protecting group;

wherein E is selected from a group consisting of O—, OH, a protecting group, and an activating group;

wherein n is 1 or greater;

wherein each $B^1$ and $B^2$ is independently selected from the group consisting of H, a naturally occurring nucleobase, a non-naturally occurring nucleobase, an aromatic moiety, a DNA intercalator, a heterocyclic moiety, and a reporter group, wherein amino groups, if present, are, optionally, protected by amino protecting groups;

wherein each $A^1$ and $A^2$ is independently selected from the group consisting of formula (Ia), (Ib), and (Ic):

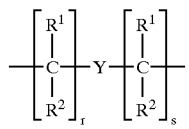 I(a)

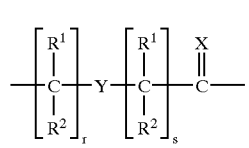 I(b)

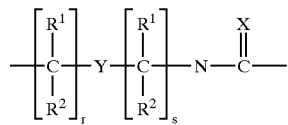 I(c)

wherein each $R^1$ and $R^2$ is independently selected from the group consisting of hydrogen; $(C_1-C_6)$alkyl; hydroxy-, alkoxy-, amino-, or alkythio-substituted $(C_1-C_6)$alkyl; hydroxy; alkoxy; alkylthio; amino; and halogen;

wherein r and s are, for I(a), I(b), and I(c) independently of one another, values from 0 to 5;

Y is a single bond, O, S, or $NR^4$;

X is O, S, Se, $NR^5$, $CH_2$, or $C(CH_3)_2$; and wherein each $R^4$ and $R^5$ is independently selected from the group of consisting of hydrogen; $(C_1-C_6)$alkyl; hydroxy-, alkoxy-, amino-, or alkythio-substituted $(C_1-C_6)$alkyl; hydroxy; alkoxy; amino; aryl; aralkyl; heteroaryl; and an amino acid side chain;

wherein each $R^6$ is independently selected from the group of consisting of hydrogen; $(C_1-C_6)$alkyl; hydroxy-, alkoxy-, amino-, or alkythio-substituted $(C_1-C_6)$alkyl; aryl; aralkyl; heteroaryl; and an amino acid side chain;

wherein each $R^7$ is independently selected from the group of consisting of hydrogen; $(C_1-C_6)$alkyl; hydroxy-, alkoxy-, amino-, or alkythio-substituted $(C_1-C_6)$alkyl; hydroxy; alkoxy; alkylthio; amino; aryl; aralkyl; and heteroaryl; and each $R^8$ is independently selected from the group of consisting of hydrogen; $(C_1-C_6)$ alkyl; hydroxy-, alkoxy-, amino-, or alkythio-substituted $(C_1-C_6)$alkyl; aryl; aralkyl; and heteroaryl; or wherein each $R^7$ is independently selected from the group of consisting of hydrogen; $(C_1-C_6)$alkyl; hydroxy-, alkoxy-, amino-, or alkythio-substituted $(C_1-C_6)$alkyl; aryl; aralkyl; and heteroaryl; and $R^8$ is independently selected from the group of consisting of hydrogen; $(C_1-C_6)$alkyl; hydroxy-, alkoxy-, amino-, or alkythio-substituted $(C_1-C_6)$alkyl; hydroxy; alkoxy; alkylthio; amino; aryl; aralkyl; heteroaryl and halogen;

wherein each $R^9$ is independently selected from the group of consisting g of hydrogen; $(C_1-C_6)$alkyl; hydroxy-, alkoxy-, amino-, or alkythio-substituted $(C_1-C_6)$alkyl; alkoxy; aryl; arylkyl; and heteroaryl;

wherein each $R^{10}$ and $R^{11}$ is independently selected from the group of consisting of hydrogen; $(C_1-C_6)$alkyl; hydroxy-, alkoxy-, amino-, or alkythio-substituted $(C_1-C_6)$alkyl; aryl; aralkyl; heteroaryl; and an amino acid side chain;

wherein each $R^{12}$, $R^{13}$, $R^{14}$, $R^{15}$, $R^{16}$, and $R^{17}$ is independently selected from the group of consisting of hydrogen; $(C_1-C_6)$alkyl; hydroxy-, alkoxy-, amino-, or alkythio-substituted $(C_1-C_6)$alkyl; hydroxy; alkoxy; alkylthio; aryl; aralkyl; heteroaryl; and an amino acid side chain; and wherein each T is independently selected from the group of consisting of hydrogen; $(C_1-C_6)$alkyl; hydroxy-, alkoxy-, amino-, or alkythio-substituted $(C_1-C_6)$alkyl; hydroxy; alkoxy; alkylthio; aryl; aralicyl; heteroaryl; and an amino acid side chain;

and salts thereof.

2. A method according to claim 1 wherein n is less than about 500.

3. A method according to claim 1 wherein n is less than about 50.

4. A method according to claim 1 wherein n is less than about 15.

5. A method according to claim 1 wherein n is selected from the group consisting of 2, 3, 4, 5, 6, 7, 8, 9, 10, 11, 12, 13, 14, and 15.

6. A method according to claim 2 wherein said oligonucleotide analogue comprises a ratio of HypNA to pPNA monomers and wherein the ratio of HypNA to pPNA monomers in the oligonucleotide analogue is from bout 2:1 to about 1:3.

7. A method according to claim 2 wherein said oligonucleotide analogue comprises a ratio of HypNA to pPNA monomers and wherein the ratio of HypNA to pPNA monomers in the oligonucleotide analogue is from bout 1:1 to about 1:2.

8. A method for inhibiting gene expression, comprising administering an oligonucleotide analogue to at least one cell or at least one organism to inhibit expression of at least one gene that comprises a nucleotide sequence that is at least partially complementary to the oligonucleotide analogue, wherein the oligonucleotide analogue comprises the structure:

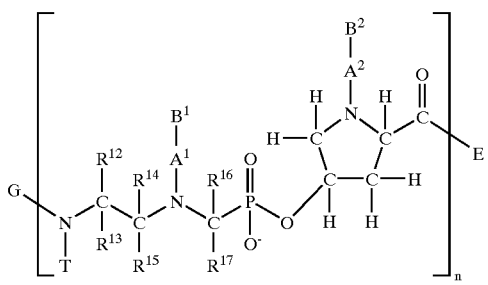

wherein G is selected from a group consisting of H and is a protecting group;

wherein E is selected from a group consisting of O—, OH, a protecting group, and an activating group;

wherein n is 1 or greater;

wherein each $B^1$ and $B^2$ is independently selected from the group consisting of H, a naturally occurring nucleobase, a non-naturally occurring nucleobase, an aromatic moiety, a DNA intercalator, a heterocyclic moiety, and a reporter group, wherein amino groups, if present, are, optionally, protected by amino protecting groups;

wherein each $A^1$ and $A^2$ is independently selected from the group of consisting of formula (Ia), (Ib), and (Ic):

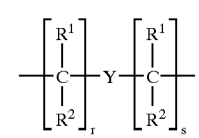 I(a)

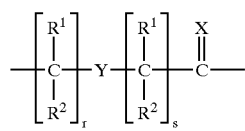 I(b)

-continued

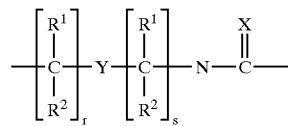 I(c)

wherein each $R^1$ and $R^2$ is independently selected from the group of consisting of hydrogen; $(C_1-C_6)$alkyl; hydroxy-, alkoxy-, amino-, or alkythio-substituted $(C_1-C_6)$alkyl; hydroxy; alkoxy; alkylthio; amino; and halogen;

wherein r and s are, for I(a), (Ib), and (Ic) independently of one another, values from 0 to 5;

Y is a single bond, O, S, or $NR^4$;

X is O, S, Se, $NR^5$, $CH_2$, or $C(CH_3)_2$; and wherein each $R^4$ and $R^5$ is independently selected from the group of consisting of hydrogen; $(C_1-C_6)$alkyl; hydroxy-, alkoxy-, amino-, or alkythio-substituted $(C_1-C_6)$alkyl; hydroxy; alkoxy; amino; aryl; aralkyl; heteroaryl; and an amino acid side chain;

wherein each $R^{12}$, $R^{13}$, $R^{14}$, $R^{15}$, $R^{16}$, and $R^{17}$ is independently selected from the group of consisting of hydrogen; $(C_1-C_6)$alkyl; hydroxy-, alkoxy-, amino-, or alkythio-substituted $(C_1-C_6)$alkyl; hydroxy; alkoxy; alkylthio; aryl; aralkyl; heteroaryl; and an amino acid side chain; and wherein each T is independently selected from the group of consisting of hydrogen; $(C_1-C_6)$alkyl; hydroxy-, alkoxy-, amino-, or alkythio-substituted $(C_1-C_6)$alkyl; hydroxy; alkoxy; alkylthio; aryl; aralkyl; heteroaryl; and an amino acid side chain;

and salts thereof.

9. A method according to claim 8 wherein n is less than about 500.

10. A method according to claim 8 wherein n is less than about 50.

11. A method according to claim 8 wherein n is less than about 15.

12. A method according to claim 8 wherein n is selected from the group consisting of 2, 3, 4, 5, 6, 7, 8, 9, 10, 11, 12, 13, 14, and 15.

13. A method according to claim 9 wherein said oligonucleotide analogue comprises a ratio of HypNA to pPNA monomers and wherein the ratio of HypNA to pPNA monomers in the oligonucleotide analogue is from about 2:1 to about 1:3.

14. A method according to claim 9 wherein said oligonucleotide analogue comprises a ratio of HypNA to pPNA monomers and wherein the ratio of HypNA to pPNA monomers in the oligonucleotide analogue is from about 1:1 to about 1:2.

15. A method for inhibiting gene expression, comprising administering an oligonucleotide analogue to at least one cell or at least one organism to inhibit expression of at least one gene that comprises a nucleotide sequence that is at least partially complementary to the oligonucleotide analogue, wherein the oligonucleotide analogue comprises the structure:

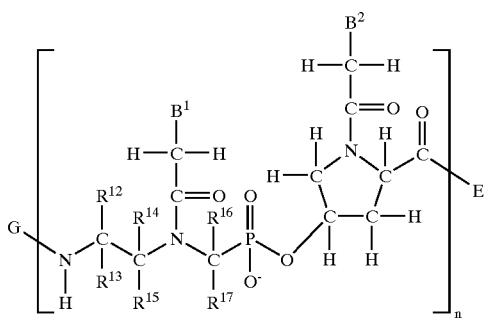

wherein G is selected from a group consisting of H and is a protecting group;

wherein E is selected from a group consisting of O—, OH, a protecting group, and an activating group;

wherein n is 1 or greater;

wherein each $B^1$ and $B^2$ is independently selected from the group consisting of H, a naturally occurring nucleobase, a non-naturally occurring nucleobase, an aromatic moiety, a DNA intercalator, a heterocyclic moiety, and a reporter group, wherein amino groups, if present, are, optionally, protected by amino protecting groups;

wherein each $R^{12}$, $R^{13}$, $R^{14}$, $R^{15}$, $R^{16}$, and $R^{17}$ is independently selected from the group consisting of hydrogen; $(C_1-C_6)$alkyl; hydroxy-, alkoxy-, amino-, or alkythio-substituted $(C_1-C_6)$alkyl; hydroxy; alkoxy; alkylthio; aryl; aralkyl; heteroaryl; and an amino acid side chain; and wherein each T is independently selected from the group of consisting of hydrogen; $(C_1-C_6)$alkyl; hydroxy-, alkoxy-, amino-, or alkythio-substituted $(C_1-C_6)$alkyl; hydroxy; alkoxy; alkylthio; aryl; aralkyl; heteroaryl; and an amino acid side chain;

and salts thereof.

16. A method according to claim 15 wherein n is less than about 500.

17. A method according to claim 15 wherein n is less than about 50.

18. A method according to claim 15 wherein n is less than about 15.

19. A method according to claim 15 wherein n is selected from the group consisting of 2, 3, 4, 5, 6, 7, 8, 9, 10, 11, 12, 13, 14, and 15.

20. A method according to claim 16 wherein said oligonucleotide analogue comprises a ratio of HypNA to pPNA monomers and wherein the ratio of HypNA to pPNA monomers in the oligonucleotide analogue is from about 2:1 to about 1:3.

21. A method according to claim 16 wherein said oligonucleotide analogue comprises a ratio of HypNA to pPNA monomers and wherein the ratio of HypNA to pPNA monomers in the oligonucleotide analogue is from about 1:1 to about 1:2.

22. A method for inhibiting gene expression, comprising administering an oligonucleotide analogue to at least one cell or at least one organism to inhibit expression of at least one gene that comprises a nucleotide sequence that is at least partially complementary to the oligonucleotide analogue, wherein the oligonucleotide analogue comprises the structure:

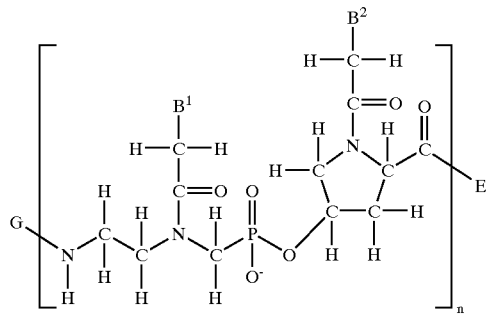

wherein G is selected from a group consisting of H and is a protecting group;

wherein E is selected from a group consisting of O—, OH, a protecting group, and an activating group;

wherein n is 1 or greater;

wherein each $B^1$ and $B^2$ is independently selected from the group consisting of H, a naturally occurring nucleobase, a non-naturally occurring nucleobase, an aromatic moiety, a DNA intercalator, a heterocyclic moiety, and a reporter group, wherein amino groups, if present, are, optionally, protected by amino protecting groups; and wherein each T is independently selected from the group of consisting of hydrogen; $(C_1-C_6)$alkyl; hydroxy-, alkoxy-, amino-, or alkythio-substituted $(C_1-C_6)$alkyl; hydroxy; alkoxy; alkylthio; aryl; aralkyl; heteroaryl; and an amino acid side chain;

and salts thereof.

23. A method according to claim 22 wherein n is less than about 500.

24. A method according to claim 22 wherein n is less than about 50.

25. A method according to claim 22 wherein n is less than about 15.

26. A method according to claim 22 wherein n is selected from the group consisting of 2, 3, 4, 5, 6, 7, 8, 9, 10, 11, 12, 13, 14, and 15.

27. A method according to claim 23 wherein said oligonucleotide analogue comprises a ratio of HypNA to pPNA monomers and wherein the ratio of HypNA to pPNA monomers in the oligonucleotide analogue is from about 2:1 to about 1:3.

28. A method according to claim 23 wherein said oligonucleotide analogue comprises a ratio of HypNA to pPNA monomers and wherein the ratio of HypNA to pPNA monomers in the oligonucleotide analogue is from about 1:1 to about 1:2.

* * * * *

SEQUENCE LISTING

<160> NUMBER OF SEQ ID NOS: 36

<210> SEQ ID NO 1
<211> LENGTH: 15
<212> TYPE: DNA
<213> ORGANISM: Artificial Sequence
<220> FEATURE:
<223> OTHER INFORMATION: Synthetic Construct
<221> NAME/KEY: misc_feature
<223> OTHER INFORMATION: Synthetic Construct

<400> SEQUENCE: 1
ctggaggaag atctg                                                    15

<210> SEQ ID NO 2
<211> LENGTH: 15
<212> TYPE: DNA
<213> ORGANISM: Artificial Sequence
<220> FEATURE:
<223> OTHER INFORMATION: Synthetic Construct
<221> NAME/KEY: misc_feature
<223> OTHER INFORMATION: Synthetic Construct

<400> SEQUENCE: 2
atggaaccga aatct                                                    15

<210> SEQ ID NO 3
<211> LENGTH: 14
<212> TYPE: DNA
<213> ORGANISM: Artificial Sequence
<220> FEATURE:
<223> OTHER INFORMATION: Synthetic Construct
<221> NAME/KEY: misc_feature
<223> OTHER INFORMATION: Synthetic Construct

<400> SEQUENCE: 3
aaactcacac ctgc                                                     14

<210> SEQ ID NO 4
<211> LENGTH: 15
<212> TYPE: DNA
<213> ORGANISM: Artificial Sequence
<220> FEATURE:
<223> OTHER INFORMATION: Synthetic Construct
<221> NAME/KEY: misc_feature
<223> OTHER INFORMATION: Synthetic Construct

<400> SEQUENCE: 4
tccgttatgc acgaa                                                    15

<210> SEQ ID NO 5
<211> LENGTH: 15
<212> TYPE: DNA
<213> ORGANISM: Artificial Sequence
<220> FEATURE:
<223> OTHER INFORMATION: Synthetic Construct
<221> NAME/KEY: misc_feature
<223> OTHER INFORMATION: Sythetic Construct

<400> SEQUENCE: 5
aaccactaca cccag                                                    15

<210> SEQ ID NO 6
<211> LENGTH: 15
<212> TYPE: DNA
<213> ORGANISM: Artificial Sequence

```
<220> FEATURE:
<223> OTHER INFORMATION: Synthetic Construct
<221> NAME/KEY: misc_feature
<223> OTHER INFORMATION: Synthetic Construct

<400> SEQUENCE: 6
gggaaataag gatcc                                                          15

<210> SEQ ID NO 7
<211> LENGTH: 15
<212> TYPE: DNA
<213> ORGANISM: Artificial Sequence
<220> FEATURE:
<223> OTHER INFORMATION: Synthetic Construct
<221> NAME/KEY: misc_feature
<223> OTHER INFORMATION: Synthetic Construct

<400> SEQUENCE: 7
actactacta ctact                                                          15

<210> SEQ ID NO 8
<211> LENGTH: 18
<212> TYPE: DNA
<213> ORGANISM: Artificial Sequence
<220> FEATURE:
<223> OTHER INFORMATION: Synthetic Construct
<221> NAME/KEY: misc_feature
<223> OTHER INFORMATION: Synthetic Construct

<400> SEQUENCE: 8
agtagtagta gtagtagt                                                       18

<210> SEQ ID NO 9
<211> LENGTH: 16
<212> TYPE: DNA
<213> ORGANISM: Artificial Sequence
<220> FEATURE:
<223> OTHER INFORMATION: Synthetic Construct
<221> NAME/KEY: misc_feature
<223> OTHER INFORMATION: Synthetic Construct

<400> SEQUENCE: 9
tttttttttt tttttt                                                         16

<210> SEQ ID NO 10
<211> LENGTH: 15
<212> TYPE: DNA
<213> ORGANISM: Artificial Sequence
<220> FEATURE:
<223> OTHER INFORMATION: Synthtic Construct
<221> NAME/KEY: misc_feature
<223> OTHER INFORMATION: SynthetiConstruct

<400> SEQUENCE: 10
tttttttttt ttttt                                                          15

<210> SEQ ID NO 11
<211> LENGTH: 15
<212> TYPE: DNA
<213> ORGANISM: Artificial Sequence
<220> FEATURE:
<223> OTHER INFORMATION: Synthetic Construct
<221> NAME/KEY: misc_feature
<223> OTHER INFORMATION: Synthetic Construct

<400> SEQUENCE: 11
tttttctttc ttttt                                                          15
```

```
<210> SEQ ID NO 12
<211> LENGTH: 15
<212> TYPE: DNA
<213> ORGANISM: Artificial Sequence
<220> FEATURE:
<223> OTHER INFORMATION: Synthetic Construct
<221> NAME/KEY: misc_feature
<223> OTHER INFORMATION: Synthetic Sequence

<400> SEQUENCE: 12
tttttttctt ttttt                                                     15

<210> SEQ ID NO 13
<211> LENGTH: 18
<212> TYPE: DNA
<213> ORGANISM: Artificial Sequence
<220> FEATURE:
<223> OTHER INFORMATION: Synthetic Construct
<221> NAME/KEY: misc_feature
<223> OTHER INFORMATION: Synthetic Construct

<400> SEQUENCE: 13
ctgcaaagga caccatga                                                  18

<210> SEQ ID NO 14
<211> LENGTH: 18
<212> TYPE: DNA
<213> ORGANISM: Artificial Sequence
<220> FEATURE:
<223> OTHER INFORMATION: Synthetic Construct
<221> NAME/KEY: misc_feature
<223> OTHER INFORMATION: Synthetic Construct

<400> SEQUENCE: 14
ctgcaaagca caccatga                                                  18

<210> SEQ ID NO 15
<211> LENGTH: 24
<212> TYPE: DNA
<213> ORGANISM: Artificial Sequence
<220> FEATURE:
<223> OTHER INFORMATION: Synthetic Construct
<221> NAME/KEY: misc_feature
<223> OTHER INFORMATION: Synthetic Construct

<400> SEQUENCE: 15
gctcaccatg gatgatgata tcgc                                           24

<210> SEQ ID NO 16
<211> LENGTH: 24
<212> TYPE: DNA
<213> ORGANISM: Artificial Sequence
<220> FEATURE:
<223> OTHER INFORMATION: Synthetic Construct
<221> NAME/KEY: misc_feature
<223> OTHER INFORMATION: Synthetic Construct

<400> SEQUENCE: 16
ggaggagcaa tgatcttgat cttc                                           24

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct
<221> NAME/KEY: misc_feature
<223> OTHER INFORMATION: Synthetic Construct
```

```
<400> SEQUENCE: 17
ttagcacccc tggccaaagg                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct
<221> NAME/KEY: misc_feature
<223> OTHER INFORMATION: Synthetic Construct

<400> SEQUENCE: 18
cttactcctt ggaggccatg                                               20

<210> SEQ ID NO 19
<211> LENGTH: 16
<212> TYPE: DNA
<213> ORGANISM: Homo sapiens

<400> SEQUENCE: 19
tggtctcacg tcagtg                                                   16

<210> SEQ ID NO 20
LENGTH: 16
<212> TYPE: DNA
<213> ORGANISM: Homo sapiens

<400> SEQUENCE: 20
cactgacttg agacca                                                   16

<210> SEQ ID NO 21
LENGTH: 16
<212> TYPE: DNA
<213> ORGANISM: Artificial Sequence
<220> FEATURE:
<223> OTHER INFORMATION: Syntheitic Construct, 1 base mismatch from
      SEQ ID NO: 20

<400> SEQUENCE: 21
cactgagttg agacca                                                   16

<210> SEQ ID NO 22
<211> LENGTH: 16
<212> TYPE: DNA
<213> ORGANISM: Artificial Sequence
<220> FEATURE:
<223> OTHER INFORMATION: Synthetic Construct, 1 base mismatch from
      SEQ ID NO: 20

<400> SEQUENCE: 22
cactgagtgg agacca                                                   16

<210> SEQ ID NO 23
<211> LENGTH: 16
<212> TYPE: DNA
<213> ORGANISM: Artificial Sequence
<220> FEATURE:
<223> OTHER INFORMATION: Synthetic Construct, 1 base mismatch from
      SEQ ID NO: 20

<400> SEQUENCE: 23
cactgacttg agtcca                                                   16
```

<210> SEQ ID NO 24
<211> LENGTH: 16
<212> TYPE: DNA
<213> ORGANISM: Artificial Sequence
<220> FEATURE:
<223> OTHER INFORMATION: Syntheitic Construct, 1 base mismatch from
      SEQ ID NO: 20

<400> SEQUENCE: 24
cactgacttg agacga                                                    16

<210> SEQ ID NO 25
<211> LENGTH: 16
<212> TYPE: DNA
<213> ORGANISM: Artificial Sequence
<220> FEATURE:
<223> OTHER INFORMATION: Synthetic Construct, 2 base mismatch from
      SEQ ID NO: 20

<400> SEQUENCE: 25
cggtgacttg agacca                                                    16

<210> SEQ ID NO 26
<211> LENGTH: 16
<212> TYPE: DNA
<213> ORGANISM: Artificial Sequence
<220> FEATURE:
<223> OTHER INFORMATION: Synthetic Construct, 1 base mismatch from
      SEQ ID NO: 20

<400> SEQUENCE: 26
cactgacgtg agacca                                                    16

<210> SEQ ID NO 27
<211> LENGTH: 16
<212> TYPE: DNA
<213> ORGANISM: Artificial Sequence
<220> FEATURE:
<223> OTHER INFORMATION: Synthetic Construct, 1 base mismatch from
      SEQ ID NO: 20

<400> SEQUENCE: 27
cactgactgg agacca                                                    16

<210> SEQ ID NO 28
<211> LENGTH: 16
<212> TYPE: DNA
<213> ORGANISM: Artificial Sequence
<220> FEATURE:
<223> OTHER INFORMATION: Synthetic Construct, 1 base mismatch from
      SEQ ID NO: 20

<400> SEQUENCE: 28
cactgacatg agacca                                                    16

<210> SEQ ID NO 29
<211> LENGTH: 16
<212> TYPE: DNA
<213> ORGANISM: Artificial Sequence
<220> FEATURE:
<223> OTHER INFORMATION: Synthetic Construct, 2 base mismatch from
      SEQ ID NO: 20

<400> SEQUENCE: 29
cactgagttc agacca                                                    16

```
<210> SEQ ID NO 30
<211> LENGTH: 16
<212> TYPE: DNA
<213> ORGANISM: Artificial Sequence
<220> FEATURE:
<223> OTHER INFORMATION: Synthetic Construct, 1 base mismatch from
      SEQ ID NO: 20

<400> SEQUENCE: 30
cactgaattg agacca                                                    16

<210> SEQ ID NO 31
<211> LENGTH: 16
<212> TYPE: DNA
<213> ORGANISM: Artificial Sequence
<220> FEATURE:
<223> OTHER INFORMATION: Synthetic Construct, 2 base mismatch from
      SEQ ID NO: 20

<400> SEQUENCE: 31
cactgagttg ggacca                                                    16

<210> SEQ ID NO 32
<211> LENGTH: 16
<212> TYPE: DNA
<213> ORGANISM: Artificial Sequence
<220> FEATURE:
<223> OTHER INFORMATION: Synthetic Construct, 2 base mismatch from
      SEQ ID NO: 20

<400> SEQUENCE: 32
cacggagttg agacca                                                    16

<210> SEQ ID NO 33
<211> LENGTH: 37
<212> TYPE: DNA
<213> ORGANISM: Artificial Sequence
<220> FEATURE:
<223> OTHER INFORMATION: Synthetic Construct

<400> SEQUENCE: 33
tcatggtgtc ctttgcagtt tttttgtgag tgttgag                             37

<210> SEQ ID NO 34
<211> LENGTH: 37
<212> TYPE: DNA
<213> ORGANISM: Artificial Sequence
<220> FEATURE:
<223> OTHER INFORMATION: Synthetic Construct

<400> SEQUENCE: 34
tcatggtctc ctttgcagtt tttttgtgag tgttgag                             37

<210> SEQ ID NO 35
<211> LENGTH: 40
<212> TYPE: RNA
<213> ORGANISM: Artificial Sequence
<220> FEATURE:
<223> OTHER INFORMATION: Synthetic Construct

<400> SEQUENCE: 35
ucaugguguc cuuugcaguu uuuuugugag uguugaguga                          40

<210> SEQ ID NO 36
<211> LENGTH: 40
<212> TYPE: RNA
<213> ORGANISM: Artificial Sequence
```

-continued

```
<220> FEATURE:
<223> OTHER INFORMATION: Synthetic Construct

<400> SEQUENCE: 36
ucaugguguc cuuugcaguu uuuuugugag uguugaguga                40
```